US 10,905,784 B2

Feb. 2, 2021

(12) United States Patent
Kelly et al.

(10) Patent No.: US 10,905,784 B2
(45) Date of Patent: Feb. 2, 2021

(54) RADIOLABELED ANTI-LAG3 ANTIBODIES FOR IMMUNO-PET IMAGING

(71) Applicant: Regeneron Pharmaceuticals, Inc., Tarrytown, NY (US)

(72) Inventors: Marcus Kelly, New York, NY (US); Dangshe Ma, Millwood, NY (US); William Olson, Yorktown Heights, NY (US); Richard Tavare, Croton-on-Hudson, NY (US); Gavin Thurston, Briarcliffe Manor, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 25 days.

(21) Appl. No.: 15/892,440

(22) Filed: Feb. 9, 2018

(65) Prior Publication Data

US 2018/0228926 A1    Aug. 16, 2018

Related U.S. Application Data

(60) Provisional application No. 62/457,287, filed on Feb. 10, 2017.

(51) Int. Cl.
*A61K 51/10* (2006.01)
*A61K 39/00* (2006.01)
*C07K 16/28* (2006.01)
*C07C 259/00* (2006.01)

(52) U.S. Cl.
CPC .......... *A61K 51/1027* (2013.01); *A61K 39/00* (2013.01); *A61K 51/1039* (2013.01); *C07C 259/00* (2013.01); *C07K 16/2803* (2013.01); *C07K 2317/21* (2013.01)

(58) Field of Classification Search
CPC ............... A61K 51/00; A61K 51/1027; A61K 51/1039; A61K 39/00; C07C 259/00; C07K 16/2803; C07K 2317/21
USPC .......... 424/1.11, 1.49, 1.65, 1.69, 1.81, 1.85, 424/1.89, 9.1, 9.2
See application file for complete search history.

(56) References Cited

U.S. PATENT DOCUMENTS

| | | | |
|---|---|---|---|
| 4,680,338 A | 7/1987 | Sundoro | |
| 5,332,567 A | 7/1994 | Goldenberg | |
| 5,639,879 A | 6/1997 | Mease et al. | |
| 5,976,877 A | 11/1999 | Hercend et al. | |
| 6,143,273 A | 11/2000 | Faure et al. | |
| 6,197,524 B1 | 3/2001 | Romagnani | |
| 6,524,802 B1 * | 2/2003 | Lee .................. | C07K 14/475 435/7.1 |
| 6,596,541 B2 | 7/2003 | Murphy et al. | |
| 7,087,411 B2 | 8/2006 | Daly et al. | |
| 7,582,298 B2 | 9/2009 | Stevens et al. | |
| 8,246,995 B2 | 8/2012 | Dai et al. | |
| 8,257,740 B1 | 9/2012 | Sung et al. | |
| 8,502,018 B2 | 8/2013 | Murphy et al. | |
| 8,551,481 B2 | 10/2013 | Pardoll et al. | |
| 8,771,966 B2 | 7/2014 | Dennis et al. | |
| 9,321,832 B2 * | 4/2016 | Tomlinson ............. | C07K 16/18 |
| 9,429,584 B2 | 8/2016 | Matsumura et al. | |
| 9,475,874 B2 | 10/2016 | Sawada et al. | |
| 9,546,206 B2 | 1/2017 | Ring et al. | |
| 2004/0018557 A1 | 1/2004 | Qu et al. | |
| 2004/0101920 A1 | 5/2004 | Radziejewski et al. | |
| 2008/0193376 A1 | 8/2008 | Tawakol et al. | |
| 2008/0260650 A1 | 10/2008 | Tawakol et al. | |
| 2009/0297439 A1 | 12/2009 | Comoglio et al. | |
| 2010/0111856 A1 | 5/2010 | Gill et al. | |
| 2010/0233183 A1 | 9/2010 | Triebel et al. | |
| 2010/0331527 A1 | 12/2010 | Davis et al. | |
| 2011/0070238 A1 | 3/2011 | Triebel et al. | |
| 2011/0150892 A1 | 6/2011 | Thudium et al. | |
| 2011/0195454 A1 | 8/2011 | McWhirter | |
| 2013/0022759 A1 | 1/2013 | Okumura et al. | |
| 2013/0095114 A1 | 4/2013 | Pardoll et al. | |
| 2014/0088295 A1 | 3/2014 | Smith et al. | |
| 2014/0093511 A1 | 4/2014 | Lonberg et al. | |
| 2014/0127226 A1 | 5/2014 | Pardoll et al. | |
| 2014/0243504 A1 | 8/2014 | Davis et al. | |
| 2014/0286935 A1 | 9/2014 | Hamblin et al. | |
| 2014/0377174 A1 | 12/2014 | Houthoff et al. | |
| 2015/0191543 A1 | 7/2015 | Wu et al. | |
| 2015/0203579 A1 | 7/2015 | Papadopoulos et al. | |
| 2015/0203580 A1 | 7/2015 | Papadopoulos et al. | |
| 2015/0299133 A1 | 10/2015 | Osterkamp et al. | |
| 2016/0000946 A1 | 1/2016 | Cheng et al. | |
| 2016/0151515 A1 | 6/2016 | Joubert et al. | |
| 2016/0222116 A1 | 8/2016 | Korman et al. | |

(Continued)

FOREIGN PATENT DOCUMENTS

| | | | |
|---|---|---|---|
| EP | 0510079 B1 | 5/1999 | |
| EP | 0758383 B1 | 1/2007 | |

(Continued)

OTHER PUBLICATIONS

Patra et al, Chem. Commun, vol. 50, pp. 11523-11525 (Year: 2014).*
Sigma-Aldrich, Amino Acid Reference Charts, 4 pages (Year: 2020).*
"NCT01968109 on Sep. 3, 2015," ClinicalTrials.gov Archive, Sep. 3, 2015, pp. 1-6, XP055328270, retrieved from the Internet: URL:https://clinicaltrials.gov/archive/NCT01968109/2015_09_03.

(Continued)

*Primary Examiner* — D. L. Jones
(74) *Attorney, Agent, or Firm* — FisherBroyles, LLP; Cara L. Crowley-Weber; Robert Chang

(57) ABSTRACT

Radiolabeled anti-LAG3 antibodies and their use in immuno-PET imaging are provided herein. Included are methods of detecting the presence of LAG3 proteins in a patient or sample.

24 Claims, 13 Drawing Sheets

Specification includes a Sequence Listing.

(56) References Cited

U.S. PATENT DOCUMENTS

| | | |
|---|---|---|
| 2016/0310570 A1 | 10/2016 | Triebel et al. |
| 2017/0022273 A1 | 1/2017 | Zhou et al. |
| 2017/0029507 A1 | 2/2017 | Ho et al. |
| 2017/0097333 A1 | 4/2017 | Bhagwat et al. |
| 2017/0119913 A1 | 5/2017 | Osterkamp et al. |
| 2017/0137517 A1 | 5/2017 | Bowman et al. |
| 2017/0258948 A1 | 9/2017 | Morin et al. |
| 2017/0267759 A1 | 9/2017 | Liang et al. |
| 2017/0283442 A1 | 10/2017 | D'Souza et al. |
| 2017/0290914 A1 | 10/2017 | Liang et al. |
| 2017/0334995 A1 | 11/2017 | Zettl et al. |
| 2018/0015154 A1 | 1/2018 | Weichert et al. |
| 2018/0043041 A1 | 2/2018 | Bansal et al. |
| 2018/0055947 A1 | 3/2018 | Van Dongen et al. |
| 2018/0078662 A1 | 3/2018 | Agnew et al. |
| 2018/0126012 A1 | 5/2018 | Weichert et al. |
| 2018/0228926 A1 | 8/2018 | Kelly et al. |

FOREIGN PATENT DOCUMENTS

| | | |
|---|---|---|
| EP | 1897548 B1 | 8/2013 |
| EP | 2320940 | 3/2015 |
| EP | 3266465 | 7/2016 |
| EP | 2142210 B1 | 8/2016 |
| WO | 1995/30750 A2 | 11/1995 |
| WO | 1997/03695 A1 | 2/1997 |
| WO | 1998/58059 A1 | 12/1998 |
| WO | 2004/078928 A2 | 9/2004 |
| WO | 2005/103081 A2 | 11/2005 |
| WO | 2008/124467 A1 | 10/2008 |
| WO | 2008/132601 A2 | 11/2008 |
| WO | 2010/019570 | 2/2010 |
| WO | 2011/056983 | 5/2011 |
| WO | 2011/153346 A1 | 12/2011 |
| WO | 2012/087962 A2 | 6/2012 |
| WO | 2013/022782 A1 | 2/2013 |
| WO | 2013/138696 A1 | 9/2013 |
| WO | 2013/149159 A1 | 10/2013 |
| WO | 2013/165940 A1 | 11/2013 |
| WO | 2013/177055 A2 | 11/2013 |
| WO | 2014/008218 A1 | 1/2014 |
| WO | 2014/140180 A1 | 9/2014 |
| WO | 2014/159087 A1 | 10/2014 |
| WO | 2014/159835 A1 | 10/2014 |
| WO | 2014/200969 A2 | 12/2014 |
| WO | 2014/210064 A1 | 12/2014 |
| WO | 2015/042246 A1 | 3/2015 |
| WO | 2015/048312 A1 | 4/2015 |
| WO | 2015/053871 A2 | 4/2015 |
| WO | 2015/061209 A1 | 4/2015 |
| WO | 2015/075445 A1 | 5/2015 |
| WO | 2015/089344 A1 | 6/2015 |
| WO | 2015/132602 A1 | 9/2015 |
| WO | 2015/138920 A1 | 9/2015 |
| WO | 2015/140212 A1 | 9/2015 |
| WO | 2015/179658 A2 | 11/2015 |
| WO | 2015/191715 A1 | 12/2015 |
| WO | 2015/200119 | 12/2015 |
| WO | 2016/020502 A1 | 2/2016 |
| WO | 2016/040723 A1 | 3/2016 |
| WO | 2016/040724 A1 | 3/2016 |
| WO | 2016/040868 A1 | 3/2016 |
| WO | 2016/058056 A1 | 4/2016 |
| WO | 2016/126858 | 8/2016 |
| WO | 2016/144873 A2 | 9/2016 |
| WO | 2016/172010 A1 | 10/2016 |
| WO | 2017/015560 A2 | 1/2017 |
| WO | 2017/059397 A1 | 4/2017 |
| WO | 2017/062888 A1 | 4/2017 |
| WO | 2017/087589 | 5/2017 |
| WO | 2017/087826 A1 | 5/2017 |
| WO | 2017/087901 | 5/2017 |
| WO | 2017/106129 | 6/2017 |
| WO | 2017/149143 | 9/2017 |
| WO | 2017/198741 | 11/2017 |
| WO | 2017/201111 A1 | 11/2017 |
| WO | 2017/213494 A1 | 12/2017 |
| WO | 2017/219995 | 12/2017 |
| WO | 2017/220569 | 12/2017 |
| WO | 2017/223565 A1 | 12/2017 |
| WO | 2018/049083 A1 | 3/2018 |
| WO | 2018/058125 A1 | 3/2018 |
| WO | 2018/083705 A1 | 5/2018 |
| WO | 2018/128664 A2 | 7/2018 |
| WO | 2018/148476 A1 | 8/2018 |

OTHER PUBLICATIONS

Abaza and Atassi (1992) "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin" Journal of Protein Chemistry 11(5):433-444.

Al-Lazikani, et al. (1997) "Standard Conformations for the Canonical Structures of Immunoglobulins," J. Mol. Biol. 273:927-948.

Altschul, et al. (1990) "Basic Local Alignment Search Tool," J. Mol. Biol. 215:403-410.

Altschul, et al. (1997) "Gapped BLAST and PSI-BLAST: a new generation of protein database search programs," Nucleic Acids Research, 25(17):3389-3402.

Alzimami et al, (2014) "Comparison of Zr-89, I-124, and F-18 Imaging Characteristics in PET Using Gate Monte Carlo Simulations: Imaging" International Journal of Radiation Oncology, 88:502.

Anderson et al. (2016) "Lag-3, Tim-3, and TIGIT: Co-inhibitory Receptorswith Specialized Functions in Immune Regulation," Immunity 44:989-1004.

Andreae, et al. (2002) "Maturation and Activation of Dendritic Cells Induced by Lymphocyte Activation Gene-3 (CD223)," J. Immunol. 168:3874-3880.

Andreae, et al. (2003) "MHC class II signal transduction in human dendritic cells induced by a natural ligand, the LAG-3 protein (CD223)," Blood 102(6):2130-2137.

Arruebo, et al. (2009) "Antibody-conjugated nanoparticles for biomedical applications," J. of Nanomaterials, vol. 2009, Article ID 439389, 24 pgs, doi:10.1155/2009/439389.

Bae, et al. (2014) "Trafficking of LAG-3 to the Surface on Activated T Cells vialts Cytoplasmic Domain and Protein Kinase C Signaling," J. Immunol. 2014; 193:3101-3112.

Barber, et al. (2006) "Restoring function in exhausted CD8 T cells during chronic viral infection," Nature 439:682-687.

Blackburn, et al. (2009) "Coregulation of CD8+ T cell exhaustion by multiple inhibitory receptors during chronic viral infection," Nature Immunology 10(1):29-37.

Brignone, et al (2010) "First-line chemoimmunotherapy in metastatic breast carcinoma: combination of paclitaxel and IMP321 (LAG-3Ig) enhances immune responses and antitumor activity," J. of Translational Medicine 8:71.

Brignone,et al. (2007) "A Soluble Form of Lymphocyte Activation Gene-3 (IMP321) Induces Activation of a Large Range of Human Effector Cytotoxic Cells," J. Immunol. 179:4202-4211.

Brignone, et al. (2007) "IMP321 (sLAG-3) safety and T cell response potentiation using an influenza vaccine as a model antigen: A single-blind phase I study," Vaccine 25:4641-4650.

Brignone, et al. (2007) "IMP321 (sLAG-3), an immunopotentiator for T cell responses against a HBsAg antigen in healthy adults: a single blind randomised controlled phase I study," Journal of Immune Based Therapies and Vaccines 5:1-15.

Brignone, et al. (2009) "A Phase I Pharmacokinetic and Biological Correlative Study of IMP321, a Novel MHC Class II Agonist, in Patients with Advanced Renal Cell Carcinoma," Clin. Cancer Res. 15(19):6225-6231.

Buisson and Triebel (2005) "LAG-3 (CD223) reduces macrophage and dendritic cell differentiation from monocyte precursors," Immunology 114:369-374.

Camisaschi, et al. (2010) "LAG-3 Expression Defines a Subset of CD4+CD25highFoxp3+ Regulatory T Cells That Are Expanded at Tumor Sites," J. Immunol. 184:6545-6551.

(56) References Cited

OTHER PUBLICATIONS

Camisaschi, et al. (2014) "Alternative Activation of Human Plasmacytoid DCs In Vitro and in Melanoma Lesions: Involvement of LAG-3," J. of Investigative Dermatology 134:1893-1902.
Casati, et al. (2006) "Soluble Human LAG-3 Molecule Amplifies the In vitro Generation of Type 1 Tumor-Specific Immunity," Cancer Res. 66(8):4450-4460.
Casati, et al. (2008) "Human Lymphocyte Activation Gene-3 Molecules Expressed by Activated T Cells Deliver Costimulation Signal for Dendritic Cell Activation1," J. Immunol. 180:3782-3788.
Chang, et al. (2015) "Metabolic Competition in the Tumor Microenvironment Is a Driver of Cancer Progression", Cell, 162:1229-1241.
Chatterjee, et al. (2016) "A humanized antibody for imaging immune checkpoint ligand PD-L1 expression in tumors", Oncotarget 7(9):10215-10227.
Chen and Chen (2014) "The effect of immune microenvironment on the progressionand prognosis of colorectal cancer," Med. Oncol. 31:82.
Chen and Flies (2013) "Molecular mechanisms of T cell co-stimulation and co-inhibition," Nature Rev. Immunol. 13:227-242.
Chen, et al. (2015) "LAG-3 Negatively Regulates the Function of Intrahepatic HCV-specific CD8+ T Cells," doi: 10.1111/jgh.13017.
Cheson, et al. (2014) "Recommendations for Initial Evaluation, Staging, and Response Assessment of Hodgkin and Non-Hodgkin Lymphoma: The Lugano Classification," J. Clin. Oncol. 32(27):3059-3068.
Chun, et al. (2004) "The effect of soluble LAG-3 (CD223) treatment in fetal thymic organ culture," Biotechnology Letters 26: 1371-1377.
Colman, et al. (1994) "Effects of amino acid sequence changes on antibody-antigen interactions", Research in Immunology 145(1):33-36.
Crawford, et al. (2014) Molecular and Transcriptional Basis of CD4+ T Cell Dysfunction during Chronic Infection, Immunity 40:289-302.
Creelan (2015) "Update on Immune Checkpoint Inhibitors in Lung Cancer," Cancer Control, J. of Moffitt Cancer Center 21(1):80-89.
De Vries "Antibody immunotherapy imaging." Department of Medical Oncology University Medical Center Groningen, The Netherlands, 16 pages.
De Vries (2015) "MPDL3280A-imaging-IST-UMCG", ClinicalTrials. gov Identifier: NCT02453984, University Medical Center Groningen, 10 pages.
Demeure et al. (2001) "T Lymphocytes infiltrating various tumour types express the MHC class II ligand lymphocyte activation gene-3 (LAG-3): role of LAG-3/MHC class II interactions in cell-cell contacts," Eur. J. of Cancer 37:1709-1718.
Deng, et al. (2016) "Preclinical pharmacokinetics, pharmacodynamics, tissue distribution, and tumor penetration of anti-PD-L1 monoclonal antibody, an immune checkpoint inhibitor", mAbs, 8(3):593-603.
Deri, et al. (2015) "p-SCN-Bn-HOPO: A Superior Bifunctional Chelator for (89)Zr ImmunoPET", Bioconjugate Chem., 26(12) 2579-2591.
Dijkers et al. (2010) "Biodistribution of 89Zr-trastuzumab and PETImaging of HER2-Positive Lesions in Patients With Metastatic Breast Cancer", Clinical Pharmacology and Therapeutics, 87(5):586-592.
Domizio, et al. (2014) "Plasmacytoid Dendritic Cells in Melanoma: Can We Revert Bad into Good?" J. of Investigative Dermatology 134, 1797-1800.
Edwards, et al. (2003) "The Remarkable Flexibility of the Human Antibody Repertoire; Isolation of Over One Thousand Different Antibodies to a Single Protein, BLyS" J. Mol. Biol. 334:103-118.
Ehring (1999) "Hydrogen Exchange/Electrospray Ionization Mass Spectrometry Studies of Structural Features of Proteins and Protein/Protein Interactions," Analytical Biochem. 267:252-259.

Eisenhauer et al. (2009) "New response evaluation criteria in solid tumours: Revised RECIST guideline (version 1.1)," Eur. J. Cancer 45:228-247.
Engen and Smith (2001) "The Basics of Ion Chromatography," Anal. Chem. 73:256A-265A.
Ferrara, et al. (2015) "Recombinant renewable polyclonal antibodies" mAbs 7(1):32-41.
Ferris et al. (2014) "Too Much of a Good Thing? Tim-3 and TCR Signaling in T Cell Exhaustion," J. Immunol. 193:1525-1530.
Flies et al (2011) "Blockade of the B7-H1/PD-1 Pathway for Cancer Immunotherapy," Yale J. Biol. Med. 84 (4):409-421.
Fougeray et al. (2006) "A soluble LAG-3 protein as an immunopotentiator for therapeutic vaccines: Preclinical evaluation of IMP321," Vaccine 24:5426-5433.
Gagliani et al. (2013) "Coexpression of CD49b and LAG-3 identifies human and mouse T regulatory type 1 cells," Nature Medicine 19(6):739-746.
Gautron, et al. (2014) "Enhanced suppressor function of TIM-3+ FoxP3+ regulatory T cells," Eur. J. Immunol. 44: 2703-2711.
Vajdos et al. (2002) "Comprehensive Functional Maps of the Antigen-binding Site of an Anti-ErbB2 Antibody Obtained with Shotgun Scanning Mutagenesis," J. Mol. Biol. 320:415-428.
Van De Watering et al. (2014) "Zirconium-89 Labeled Antibodies: A New Tool for Molecular Imaging in Cancer Patients", Biomed Research international, Article ID 203601, 2014:1-13.
Vosjan, et al. (2010) "Conjugation and radiolabeling of monoclonal antibodies with zirconium-89 for PET imaging using the bifunctional chelate p-isothiocyanatobenzyl-desferrioxamine" Nature Protocols, 5(4):739-743.
Vugts, et al. (2017) "Comparison of the octadentate bifunctional chelatorDFO*-pPhe-NCS and the clinically used hexadentate bifunctional chelator DFO-pPhe-NCS for 89Zr-immuno-PET", Eur J Nucl Med Mol Imaging, 44: 286-295.
Wang-Gillam et al. (2013) "A phase I study of IMP321 and gemcitabine as the front-line therapy in patients with advanced pancreatic adenocarcinoma," Invest New Drugs 31:707-713.
Williams et al. (2015) "LAG-3 and 4-1BB identify dysfunctional antigenspecificT cells in the tumor microenvironment and combinatorial LAG-¾-1BB targeting gives synergistic tumor control," Journal for ImmunoTherapy of Cancer; 3 (Suppl 2):p. 328.
Wolchok et al. (2009) "Guidelines for the Evaluation of Immune Therapy Activity in Solid Tumors: Immune-Related Response Criteria," Clin. Cancer Res. 15:7412-7420.
Wong, et al. (1998) "Structural Requirements for a Specificity Switch and for Maintenance of Affinity Using Mutational Analysis of a Phage-Displayed Anti-Arsonate Antibody of Fab Heavy Chain First Complementarity-Determining Region," The Journal of Immunology, 160:5990-5997.
Woo et al. (2010) "Differential subcellular localization of the regulatory T-cell protein LAG-3 and the coreceptor CD4," Eur J Immunol; 40(6): 1768-1777.
Woo et al. (2012) "Immune Inhibitory Molecules LAG-3 and PD-1 Synergistically Regulate T-cell Function to Promote Tumoral Immune Escape," Cancer Res. 72:917-927.
Workman et al. (2002) "Cutting Edge: Molecular Analysis of the Negative Regulatory Function of Lymphocyte Activation Gene-31," J. Immunol. 169:5392-5395.
Workman et al. (2009) "LAG-3 Regulates Plasmacytoid Dendritic Cell Homeostasis1," J. Immunol. 182(4):1885-1891.
Wu et al. (1987) "Receptor-mediated in vitro gene transformation by a soluble DNA carrier system," J. Biol. Chem. 262:4429-4432.
Xiao and Freeman (2015) "The Microsatellite Instable Subset of Colorectal Cancer Is a Particularly Good Candidate for Checkpoint Blockade Immunotherapy," Cancer Discovery 5:16-18.
Xu et al. (2014) "LSECtin Expressed on Melanoma Cells Promotes TumorProgression by Inhibiting Antitumor T-cell Responses," Cancer Res. 74(13):3418-3428.
Yan et al. (2015) "Targeting C-type lectin receptors for cancer immunity," Frontiers in Immunology 6:408.
Zhai, et al. (2015) "Novel Bifunctional Cyclic Chelator for 89Zr Labeling-Radiolabeling and Targeting Properties of RGD Conjugates", Mol. Pharmaceutics, 12:2142.

(56) References Cited

OTHER PUBLICATIONS

Natarajan et al. (2015) "Novel Radiotracer for ImmunoPET Imaging of PD-1 Checkpoint Expression on Tumor Infiltrating Lymphocytes", Bioconjug Chem, 26(10):2062-2069.
Needleman and Wunsch (1970) "A general method applicable to the search for similarities in the amino acid sequence of two proteins," J. Mol. Biol. 48:443-453.
Nguyen and Ohashi (2015) "Clinical blockade of PD1 and LAG3—potential mechanisms of action," Immunology 15:45-56.
Nguyen, et al. (2014) "Clinical blockade of PD1 and LAG3—potential mechanisms of action", Nature Reviews Immunology, 15(1):45-56.
Nijland et al. (2019) "Molecular Imaging Using Radiolabeled Atezolizumab to Assess Atezolizumab Biodistribution in Lymphoma Patients", University Medical Center Groningen, ClinicalTrials.gov Identifier: NCT03850028, 11 pages.
Nishino et al. (2013) "Developing a Common Language for Tumor Response to Immunotherapy: Immune-Related Response Criteria Using Unidimensional Measurements," Clin. Cancer Res. 19:3936-3943.
Norde et al. (2012) "Coinhibitory molecules in hematologic malignancies: targets for therapeutic intervention," Blood 120(4):728-736.
Okamura et al. (2009) "CD4+CD25-LAG3+ regulatory T cells controlled by the transcription factor Egr-2," PNAS 106(33):13974-13979.
Okamura et al. (2012) "Roles of LAG3 and EGR2 in regulatory T cells," Ann. Rheum. Dis. 71: i96-i100. doi:10.1136/annrheumdis-2011-200588.
Okamura et al. (2015) "TGF-b3-expressing CD4+CD25-LAG3+ regulatory T cells control humoral immune responses," Nature Communications 6:6329.
Okazaki (2010) "PD-1 and LAG-3 inhibitory co-receptors act synergistically to prevent autoimmunity in mice," J. Exp. Med. 208(2):395-407.
Oosting et al. (2015) "89Zr-Bevacizumab PET Visualizes Heterogeneous TracerAccumulation in Tumor Lesions of Renal Cell Carcinoma Patients and Differential Effects of Antiangiogenic Treatment", The Journal of Nuclear Medicine, 56(1):63-69.
Padlan et al. (1995) "Identification of specificity-determining residues in antibodies," The FASEB Journal 9:133-139.
Pandya et al. (2015) "Di-macrocyclic terephthalamide ligands as chelators for the PET radionuclide zirconium-89", Chem Commun (Camb), 51(12):2301-2303.
Pardol (2012) "Regulating the Regulators for Cancer Immunotherapy: LAG-3 Finally Catches Up," LAG-3 Presentation.
Pardoll (2012) "The blockade of immune checkpointsin cancer immunotherapy," Nature Reviews Cancer 12:252-264.
Pearson (1994) "Using the FASTA Program to Search Protein and DNA Sequence Databases," Methods in Molecular Biology 24:307-331.
Perez-Garcia (2014) "Orchestrating immune check-point blockade for cancerimmunotherapy in combinations," Current Opinion in Immunology, Tumour Immunology 27:89-97.
Perk et al. (2010) "p-Isothiocyanatobenzyl-desferrioxamine: a new bifunctional chelate for facile radiolabeling of monoclonal antibodies with zirconium-89 for immuno-PET imaging", Eur. J. Nucl. Med. Mol Imaging, 37(2):250-259.
Perk, et al. (2009) "p-Isothiocyanatobezyl-desferrioxamine: a new bifunctional chelate for facile radiolabeling of monoclonal antibodies with zirconium-89 for immuno-PET imaging", European Journal of Nuclear Medicine and Molecualr Imagining, Springer, Berlin, DE, 37(2):250-259.
Poirier, et al. (2011) "Antibody-mediated depletion of lymphocyte-activation gene-3 (LAG-3+)-activated T lymphocytes prevents delayed-type hypersensitivity in non-human primates," British Society for Immunology, Clinical and Experimental Immunology 164: 265-274.
Powell et al. (1998) "Compendium of excipients for parenteral formulations," J. Pharm. Sci. Technol. 52:238-311.

Price et al. (2014) "H6phospa-trastuzumab: bifunctional methylenephosphonate-based chelator with 89Zr, 111In and 177Lu", Dalton Trans., 43(1):119-131.
Reddy et al. (2000) "Elimination of Fc Receptor-Dependent Effector Functions of a Modified IgG4 Monoclonal Antibody to Human CD4," J. Immunol. 164:1925-1933.
Reineke (2004) "Antibody Epitope Mapping Using Arrays of Synthetic Peptides," Methods Mol. Biol. 248:443-463.
Roncarolo et al. (2014) "Tr1 Cells and the Counter-Regulation of Immunity: Natural Mechanisms and Therapeutic Applications," Curr. Top. Microbiol. Immunol. 380: 39-68.
Rouhani et al. (2015) "Roles of lymphatic endothelial cells expressing peripheral tissue antigens in CD4 T-cell tolerance induction," Nature Communications 6:6771.
Rudikoff, et al. (1982) "Single amino acid substitution altering antigen-binding specificity," Proc. Natl. Acad. Sci. 79:1979-1983.
Sega et al. (2014) "Role of Lymphocyte Activation Gene-3 (Lag-3) in Conventional and Regulatory T Cell Function in Allogeneic Transplantation," PLoS ONE 9(1):e86551.
Schumacher, et al. (2016) "Current Status: Site-Specific Antibody Drug Conjugates", J. Clin. Immunol. 36(Suppl1): S100-S107.
Shield et al. (2002) "Lack of Fucose on Human IgG1 N-Linked Oligosaccharide Improves Binding to Human Fc RIII and Antibody-dependent Cellular Toxicity," J. of Biol. Chem. 277(30):26733-26740.
Shin and Ribas (2015) "The evolution of checkpoint blockade as a cancer therapy: what's here, what's next?" Current Opinion in Immunology, Tumour Immunology 33:23-35.
Sierro et al. (2011) "The CD4-like molecule LAG-3, biology and therapeutic applications," Expert Opin. Ther. Targets 15(1):91-101.
Sittig et al. (2013) "Clonal expansion of renal cell carcinoma-infiltrating T lymphocytes," Landes Bioscience, OncoImmunology 2:9, e26014-1-10.
Slizys and Widnersson (2016) "The new "Pet" on the block: radio imaging with Zirconium-89", FPA Patent Attorneys, 5 pages.
Smith and Waterman (1981) "Identification of common molecular subsequences," J. Mol. Biol. 147:195-197.
Sun et al. (2014) "Expression regulation of co-inhibitory molecules on human natural killer cells in response to cytokine stimulations," Cytokine 65:33-41.
Taube et al. (2015) "Differential expression of immune-regulatory genes associated with PD-L1 display in melanoma: implications for PD-L1 pathway blockade," Clin Cancer Res Published Online First May 5, 2015.
Tavare et al. (2016) "An Effective Immuno-PET Imaging Method to Monitor CD8-Dependent Responses to Immunotherapy", Cancer Research, 76(1):73-82.
Thaventhiran et al. (2012) "T Cell Co-inhibitory Receptors: Functions and Signalling Mechanisms," J. Clin. Cell Immunol. S12:004. doi:10.4172/2155-9899312-004.
Van Dongen, et al. (2007) "Immuno-PET: A Navigator inMonoclonal Antibody Development and Applications", The Oncologist, 12:1379-1389.
Boerman and Oyen (2011) "Immuno-PET of Cancer: A Revival of Antibody Imaging", Journal of Nuclear Medicine, 52(8): 1171.
Tian et al. (2015) "The Upregulation of LAG-3 on T Cells Defines a Subpopulation with Functional Exhaustion and Correlates with Disease Progression in HIV-Infected Subjects," J. Immunol. 194:3873-3882.
Triebel (2003) "LAG-3: a regulator of T-cell and DC responses and its use in therapeutic vaccination," TRENDS in Immunology 24(12): 619-622.
Triebel et al. (2006) "A soluble lymphocyte activation gene-3 (sLAG-3) protein as a prognostic factor in human breast cancer expressing estrogen or progesterone receptors," Cancer Letters 235:147-153.
Turnis et al. (2012) "Combinatorial immunotherapy PD-1 may not be LAG-ing behind any more," OncoImmunology 1 (7):1172-1174.
Turnis et al. (2015) "Inhibitory receptors as targets for cancer immunotherapy," Eur. J. Immunol. 45:1892-1905.
Tutt et al. (1991) "Trispecific F(ab')3 derivatives that use cooperative signaling via the TCR/CD3 complex and CD2 to activate and rediret resting cytotoxic T cells," J. Immunol. 147:60-69.

(56) References Cited

OTHER PUBLICATIONS

Gebhart et al. (2015) "Molecular imaging as a tool to investigate heterogeneity of advanced HER2-positive breast cancer and to predict patient outcome under trastuzumab emtansine (T-DM1); the ZEPHIR trial", Annals of Oncology Advance Access, 22 pages.
GenBank Accession NP_002277.4.
GenBank Accession NP_005182.1.
Goldberg and Drake (2011) "LAG-3 in Cancer Immunotherapy," LAG-3 Biology Review, 269-278.
Goldrath et al. (1999) "Selecting and maintaining a diverse T-cell repertoire," Nature 402:255-262.
Gonnet et al. (1992) "Exhaustive Matching of the Entire Protein Sequence Database," Science 256:1443-1445.
Gros et al. (2014) "PD-1 identifies the patient-specific CD8+ tumor-reactive repertoire infiltrating human tumors," J. of Clinical Investigation 125(5):2246-2259.
Grosso (2009) "Functionally Distinct LAG-3 and PD-1 Subsets on Activatedand Chronically Stimulated CD8 T Cells1," J. Immunol. 182:6659-6669.
Grosso et al. (2007) "LAG-3 regulates CD8+ T cell accumulation and effector function in murine self- and tumor-tolerance systems," J. of Clinical Investigation 117(11):3383-3392.
Hemon et al. (2011) "MHC Class II Engagement by Its Ligand LAG-3 (CD223)Contributes to Melanoma Resistance to Apoptosis," J. Immunol. 186:5173-5183.
Herbst et al. (2014) "Predictive correlates of response to the anti-PD-L1 antibody MPDL3280A in cancer patients" Nature 515(7528):563-567.
Heskamp et al. (2015) "Noninvasive Imaging of Tumor PD-L1 Expression Using Radiolabeled Anti-PD-L1 Antibodies", Cancer Res, 75(14):2928-2936.
Higashikawa et al. (2014) "64Cu-DOTA-Anti-CTLA-4 mAb Enabled PET Visualization of CTLA-4 on the T-Cell Infiltrating Tumor Tissues", PLoS One, 9(11):e109866, 8 pages.
Hochleitner et al. (2000) "Characterization of a discontinuous epitope of the human immunodeficiency virus (HIV) core protein p24 by epitope excision and differential chemical modification followed by mass spectrometric peptide mapping analysism" Protein Sci. 9:487-496.
Huang et al. (2004) "Role of LAG-3 in Regulatory T Cells," Immunity 21:503-513.
Huang et al. (2015) "LAG3 and PD1 co-inhibitory molecules collaborate to limit CD8+ T cell signaling and dampen antitumor immunity in a murine ovarian cancer model," Oncotarget, 6(29):27359-27377.
Huard et al. (1994) "Cellular expression and tissue distribution of the humanLAG-3-encoded protein, an MHC class II ligand," Immunogenetics 39: 213-217.
Huard et al. (1996) "T cell major histocompatibility complex class II molecules down-regulate CD4+ T cell clone responses following LAG-3 binding," Eur. J. Immunol. 26:1180-1186.
Huard et al. (1997) "Characterization of the major histocompatibility complex class II binding site on LAG-3 protein," PNAS 94:5744-5749.
Huard, et al. (1995) "CD4/major histocompatibility complex class II interaction analyzed with CD4- and lymphocyte activation gene-3 (LAG-3)-Ig fusion proteins," Eur. J. Immunol. 25:2718-2721.
International Search Report and Written Opinion, PCT/US2018/017525, dated Apr. 17, 2018, 14 pages.
International Search Report and Written Opinion, received for PCT/US2016/056156, dated Mar. 10, 2017, 23 pages.
Invitation to Pay Additional Fees and, Where Applicable, Protest Fee, received for PCT/US2016/056156, on Jan. 10, 2017, 10pgs.
Jackson, et al. (1995) "In Vitro Antibody Maturation Improvement of a High Affinity, Neutralizing Antibody Against IL-1 beta," The Journal of Immunology 154:3310-3319.
Jauw et al. (2016) "Immuno-Positron Emission Tomography with Zirconium-89-Labeled Monoclonal Antibodies in Oncology: What Can We Learn from Initial Clinical Trials?", Frontiers in Pharmacology, vol. 7, Article 131, 15 pages.

Jing et al. (2015) "Combined immune checkpoint protein blockade and low dose whole body irradiation as immunotherapy for myeloma," J. for Immuno. Therapy of Cancer 3:2 pp. 1-15.
Junghans et al. (1990) "Anti-Tac-H, a Humanized Antibody to the Interleukin 2 Receptor with New Features for Immunotherapy in Malignant and Immune Disorders," Cancer Research 50:1495-1502.
Juno et al. (2015) "Elevated expression of LAG-3, but not PD-1, is associated with impaired iNKT cytokine production during chronic HIV-1 infection and treatment," Retrovirology 12:17.
Kazane, et al. (2013) "Self-Assembled Antibody Multimers through Peptide Nucleic Acid Conjugation," Journal of the American Chemical Society, 135(1):340-346.
Klein, et al. (2012) "Progress in overcoming the chain association issue in bispecific heterodimeric IgG antibodies," mAbs 4(6):653-663.
Kouo et al. (2015) "Galectin-3 shapes antitumor immune responses by suppressing CD8+ T cells via LAG-3 and inhibiting expansion of plasmacytoid dendritic cells," Cancer Immunol. Res. Published Online First Feb. 17, 2015, 42 pages.
Kufer et al. (2004) "A revival of bispecific antibodies," TRENDS in Biotech. 22(5):238-244.
Lamberts et al., (2015) "ImmunoPET with Anti-Mesothelin Antibody in Patients with Pancreatic and Ovarian Cancer Before Anti-Mesothelin Antibody-Drug Conjugate Treatment", Clinical Cancer Research, 22(7):1642-1652.
Langer (1990) "New methods of drug delivery," Science 249:1527-1533.
Lederman et al. (1991) "A Single Amino Acid Substitution in a Common African Allele of the CD4 Molecule Ablates Bidning of the Monoclonal Antibody, OKT4" Molecular Immunology 28:1171-1181.
Legat et al. (2013) "Inhibitory receptor expression depends more dominantly on differentiation and activation than 'exhaustion of human CD8 T cells," Frontiers in Immunol., Tumor Immunity 4:455.
Lerner (1982) "Tapping the immunological repertoire to produce antibodies of predetermined specificity" Nature 299:592-596.
Li et al. (2007) "Metalloproteases regulate T-cell proliferation and effector function via LAG-3," The EMBO Journal 26 (2) 494-504.
Liang et al. (2008) "Regulatory T Cells Inhibit Dendritic Cells by LymphocyteActivation Gene-3 Engagement of MHC Class II 1," J. Immunol. 180:5916-5926.
Llosa et al. (2014) "The Vigorous Immune Microenvironment of Microsatellite Instable Colon Cancer Is Balanced by Multipleultiple Counter-Inhibitory Checkpoints," Cancer Discov. 5(1):43-51.
Lloyd (1999) "The Art, Science and Technology of Pharmaceutical Compounding," 8 pages.
Macon-Lemaitre and Triebel (2005) "The negative regulatory function of the lymphocyte-activation gene-3 co-receptor (CD223) on human T cells," Immunology 115:170-178.
Mao et al. (2016) "Pathological a-synuclein transmission initiated by binding lymphocyte-activation gene 3," Science 353:6307.
Martin et al. (1989) "Modeling antibody hypervariable loops: A combined algorithm," PNAS 86:9268-9272.
Matsuzaki et al. (2010) "Tumor-infiltrating NY-ESO-1-specific CD8+ T cells are negatively regulated by LAG-3 and PD-1 in human ovarian cancer," PNAS 107(17):7875-7880.
Maute et al. (2015) "Engineering high-affinity PD-1 variants for optimized immunotherapy and immuno-PET imaging", Proc Natl Acad Sci U S A, 112(47):E6506-E6514.
Mindt et al. (2014) "Octadetante bifuntional chelating agent for Zr-89 based Imagining probes", Technology Opportunity, Ref. No. UZ-$^{15}/_{736}$,1 page.
Miyazaki et al. (1996) "Independent Modes of Natural Killing Distinguished in Mice Lacking Lag3," Science 272:405-408.
Petrik, et al. (2016) "In Vitro and In Vivo Comparison of SelectedGa-68 and Zr-89 Labelled Siderophores", Mol. Imaging Biol., 18:344-352.
NCT03780725 on Dec. 19, 2018, ClinicalTrials.gov Archive, "This Study Tests How BI 754111 is Distributed in Patients With Advanced

(56) References Cited

OTHER PUBLICATIONS

Non-small Cell Lung Cancer or Patients With Head and Neck Cancer Who Are Treated With BI754091", https://clinicaltrials.gov/ct2/show/NCT03780725.

Kabat (1991) "Sequences of Proteins of Immunological Interest" National Institutes of Health, Bethesda, Md. 147:1709-1719.

Kelly et al. (2018) "Immuno-PET detection of LAG-3 expressing intratumoral lymphocytes using the zirconium-89 radiolabeled fully human anti-LAG-3 antibody REGN3767", Abstarct in Proceedings AACR Cancer Res., 78(Suppl): Abstract No. 3033, 4pgs.

Lecocq et al. (2019) "Noninvasive Imaging of the Immune CheckpointLAG-3 Using Nanobodies, from Development to Pre-Clinical Use", Biomolecules, 9(10):1-19.

Li and Zhu (2016) "Immuno-PET imagining using 89Zr labeled PD-L1 antibody in non-small cell lung cancer Xenograft", Journal of Nuclear Medicine, 57(Suppl. 2):337.

\* cited by examiner

Statistic analysis was performed using Unpaired Mann-Whitney nonparametric T test

Sample information of melanoma tissues

| Sample ID | Sex | Age | Ethnicity | Sample type | Matrix | Diagnosis | Histological diagnosis | TNM | Stage | Clark's level of invasion | Breslow microstaging, cm | Tumor size, cm | Metastases | Date of surgery | Tumor content % | Weight, g |
|---|---|---|---|---|---|---|---|---|---|---|---|---|---|---|---|---|
| 13181ST2(3) | M | 45 | Caucasian | FF | skin | melanoma | epithelioid cell melanoma | T4bN3M0 | IIIC | V | 1 | 1.8x1x1 | 9/9 lymph nodes | 03/16/2015 | 95 | 0.9 |
| 13171912(3) | M | 58 | Caucasian | FF | skin | melanoma | spindle cell melanoma | T4bN0M0 | IIC | V | 1 | 6x5x1 | no | 09/23/2014 | 100 | 0.8 |
| 13841T2(1) | F | 51 | Caucasian | FF | skin | melanoma | mixed cell melanoma | T4aN0M0 | IIB | IV | 1.3 | 3.5x3.5x1.3 | no | 02/08/2010 | 100 | 0.8 |
| 13788T2(4) | F | 63 | Caucasian | FF | skin | melanoma | spindle cell melanoma | T4bN1bM0 | IIIC | III | 2.5 | 7 cm | 1/1 lymph nodes | 10/23/2009 | 100 | 0.7 |
| 13765T2(2) | M | 56 | Caucasian | FF | skin | melanoma | epithelioid cell melanoma | T4bN3M0 | IIIC | III | 0.7 | 2.5x1.5 | 6/6 lymph nodes | 08/26/2009 | 90 | 0.8 |
| 13177812(5) | M | 58 | Caucasian | FF | skin | melanoma | epithelioid cell melanoma | T4bN3M0 | IIIC | V | 30 mm | 5x3x3 | 11/17 lymph nodes | 12/15/2014 | 100 | 0.7 |
| 13129112(1) | F | 33 | Caucasian | FF | skin | melanoma | nevoid cell melanoma | T4bN3M0 | IIIC | III | 15 mm | 3x1.5 | 6/6 lymph nodes | 03/15/2012 | 100 | 1 |
| 13108616(1) | M | 59 | Caucasian | FF | skin | melanoma | epithelioid cell melanoma | T4aN0M0 | IIB | V | 10 mm | 2.5 cm | no | 05/12/2011 | 75 | 0.6 |
| 13547T2(1) | M | 73 | Caucasian | FF | skin and adipose tissue | melanoma | epithelioid cell melanoma | recurrent | recurrent | III | 15 mm | N/A | 1/18 lymph nodes | 05/21/2008 | 100 | 0.9 |
| 13524T2(7) | F | 44 | Caucasian | FF | skin | melanoma | epithelioid cell melanoma | T4bN2aM0 | IIIC | III | 22 mm | 2 cm | 2/12 lymph nodes | 01/24/2008 | 100 | 0.65 |

FIGURE 12

RADIOLABELED ANTI-LAG3 ANTIBODIES FOR IMMUNO-PET IMAGING

CROSS-REFERENCE TO RELATED APPLICATIONS

This application claims the benefit under 34 U.S.C. § 119(e) of U.S. Provisional Application No. 62/457,287, filed Feb. 10, 2017, which is herein specifically incorporated by reference in its entirety.

FIELD

This disclosure relates to radiolabeled anti-LAG3 antibodies and their use in immuno-PET imaging.

SEQUENCE LISTING

An official copy of the sequence listing is submitted concurrently with the specification electronically via EFS-Web as an ASCII formatted sequence listing with a file name of "10329US01_SEQ_LIST_ST25.txt", a creation date of Feb. 9, 2018, and a size of about 254 KB. The sequence listing contained in this ASCII formatted document is part of the specification and is herein incorporated by reference in its entirety.

BACKGROUND

T cell co-stimulatory and co-inhibitory molecules (collectively named co-signaling molecules) play a crucial role in regulating T cell activation, subset differentiation, effector function and survival (Chen et al 2013, Nature Rev. Immunol. 13: 227-242). Following recognition of cognate peptide-MHC complexes on antigen-presenting cells by the T cell receptor (TCR), co-signaling receptors co-localize with T cell receptors at the immune synapse, where they synergize with TCR signaling to promote or inhibit T cell activation and function (Flies et al 2011, Yale J. Biol. Med. 84: 409-421). The ultimate immune response is regulated by a balance between co-stimulatory and co-inhibitory signals ("immune checkpoints") (Pardoll 2012, Nature Reviews Cancer 12: 252-264). Lymphocyte activation gene-3 (LAG3) functions as one such 'immune checkpoint' in mediating peripheral T cell tolerance.

LAG3 (also called CD223) is a 503 amino acid transmembrane protein receptor expressed on activated CD4 and CD8 T cells, γδ T cells, natural killer T cells, B-cells, natural killer cells, plasmacytoid dendritic cells and regulatory T cells. LAG3 is a member of the immunoglobulin (Ig) superfamily. The primary function of LAG3 is to attenuate the immune response. LAG3 binding to MHC class II molecules results in delivery of a negative signal to LAG3-expressing cells and down-regulates antigen-dependent CD4 and CD8 T cell responses. LAG3 negatively regulates the ability of T cells to proliferate, produce cytokines and lyse target cells, termed as 'exhaustion' of T cells. LAG3 is also reported to play a role in enhancing T regulatory (Treg) cell function (Pardoll 2012, Nature Reviews Cancer 12: 252-264).

Immuno-positron emission tomography (PET) is a diagnostic imaging tool that utilizes monoclonal antibodies labeled with positron emitters, combining the targeting properties of an antibody with the sensitivity of positron emission tomography cameras. See, e.g., *The Oncologist,* 12: 1379 (2007); *Journal of Nuclear Medicine,* 52(8): 1171 (2011). Immuno-PET enables the visualization and quantification of antigen and antibody accumulation in vivo and, as such, can serve as an important tool for diagnostics and complementing therapy. For example, immuno-PET can aid in the selection of potential patient candidates for a particular therapy, as well as in the monitoring of treatment.

As LAG3 has emerged as a target for tumor immunotherapy and infectious immunotherapy, there is need for diagnostic tools for anti-LAG3 therapy, including, inter alia, diagnostic tools that enable the detection of suitable patient candidates for said therapy.

BRIEF SUMMARY

Included in this disclosure are radiolabeled anti-LAG3 antibody conjugates for use in immuno-PET imaging.

In one aspect, the conjugate comprises an anti-LAG3 antibody or antigen-binding fragment thereof, a chelating moiety, and a positron emitter.

Provided herein are also processes for synthesizing said conjugates and synthetic intermediates useful for the same.

Provided herein are also methods of imaging a tissue that expresses LAG3, the methods comprising administering a radiolabeled anti-LAG3 antibody conjugate described herein to the tissue; and visualizing the LAG3 expression by positron emission tomography (PET) imaging.

Provided herein are also methods of imaging a tissue comprising LAG3-expressing cells, for example, LAG3-expressing intratumoral lymphocytes, the methods comprising administering a radiolabeled anti-LAG3 antibody conjugate described herein to the tissue, and visualizing the LAG3 expression by PET imaging.

Provided herein are also methods for detecting LAG3 in a tissue, the methods comprising administering a radiolabeled anti-LAG3 antibody conjugate described herein to the tissue; and visualizing the LAG3 expression by PET imaging. In one embodiment, the tissue is present in a human subject. In certain embodiments, the subject is a non-human mammal. In certain embodiments, the subject has a disease or disorder such as cancer, an inflammatory disease, or an infection.

Provided herein are also methods for identifying a patient to be suitable for anti-tumor therapy comprising an inhibitor of LAG3, the methods comprising selecting a patient with a solid tumor, administering a radiolabeled antibody conjugate described herein, and visualizing the administered radiolabeled antibody conjugate in the tumor by PET imaging wherein presence of the radiolabeled antibody conjugate in the tumor identifies the patient as suitable for anti-tumor therapy comprising an inhibitor of LAG3.

Provided herein are also methods of treating a tumor, the methods comprising selecting a subject with a solid tumor; determining that the solid tumor is LAG3-positive; and administering an anti-tumor therapy to the subject in need thereof. In certain embodiments, the anti-tumor therapy comprises an inhibitor of LAG3. In certain embodiments, the anti-tumor therapy comprises an inhibitor of the PD-1/PD-L1 signaling axis (e.g., an anti-PD-1 antibody or an anti-PD-L1 antibody). In certain embodiments, the anti-tumor therapy comprises an inhibitor of LAG3 and/or an inhibitor of the PD-1/PD-L1 signaling axis. In certain embodiments, the subject is administered a radiolabeled anti-LAG3 antibody conjugate described herein, and localization of the radiolabeled antibody conjugate is imaged via positron emission tomography (PET) imaging to determine if the tumor is LAG3-positive. In certain embodiments, the subject is further administered a radiolabeled anti-PD-1 antibody conjugate, and localization of the radiolabeled antibody conjugate is imaged via positron emission tomography (PET) imaging to determine if the tumor is PD-1-positive.

Provided herein are also methods for monitoring the efficacy of an anti-tumor therapy in a subject, wherein the methods comprise selecting a subject with a solid tumor wherein the subject is being treated with an anti-tumor therapy; administering a radiolabeled anti-LAG3 conjugate described herein to the subject; imaging the localization of the administered radiolabeled conjugate in the tumor by PET imaging; and determining tumor growth, wherein a decrease from the baseline in uptake of the conjugate or radiolabeled signal indicates efficacy of the anti-tumor therapy. In certain embodiments, the anti-tumor therapy comprises an inhibitor of LAG3 (e.g., an anti-LAG3 antibody). In certain embodiments, the anti-tumor therapy comprises an inhibitor of LAG3 and an inhibitor of the PD-1/PD-L1 signaling axis. In certain embodiments, the anti-tumor therapy comprises a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504, as well as those disclosed in Patent Publication No. US 2015-0203580), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

Provided herein are also methods for predicting response of a patient to an anti-tumor therapy, the methods comprising selecting a patient with a solid tumor; and determining if the tumor is LAG3-positive, wherein if the tumor is LAG3-positive it predicts a positive response of the patient to an anti-tumor therapy. In certain embodiments, the tumor is determined positive by administering a radiolabeled anti-LAG3 antibody conjugate of the present disclosure and localizing the radiolabeled antibody conjugate in the tumor by PET imaging wherein presence of the radiolabeled antibody conjugate in the tumor indicates that the tumor is LAG3-positive. In some embodiments, the anti-tumor therapy is selected from a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

Provided herein are also methods for predicting response of a patient to an anti-tumor therapy comprising an inhibitor LAG3, the methods comprising selecting a patient with a solid tumor; and determining if the tumor is LAG3-positive, wherein if the tumor is LAG3-positive it indicates a positive response of the patient to an anti-tumor therapy comprising an inhibitor of LAG3. In certain embodiments, the tumor is determined positive by administering a radiolabeled anti-LAG3 antibody conjugate of the present disclosure and localizing the radiolabeled antibody conjugate in the tumor by PET imaging wherein presence of the radiolabeled antibody conjugate in the tumor indicates that the tumor is LAG3-positive.

BRIEF DESCRIPTION OF THE FIGURES

FIG. 12 provides characteristics of the melanoma samples studied in Example 7.

DETAILED DESCRIPTION

I. Definitions

Figure 1:
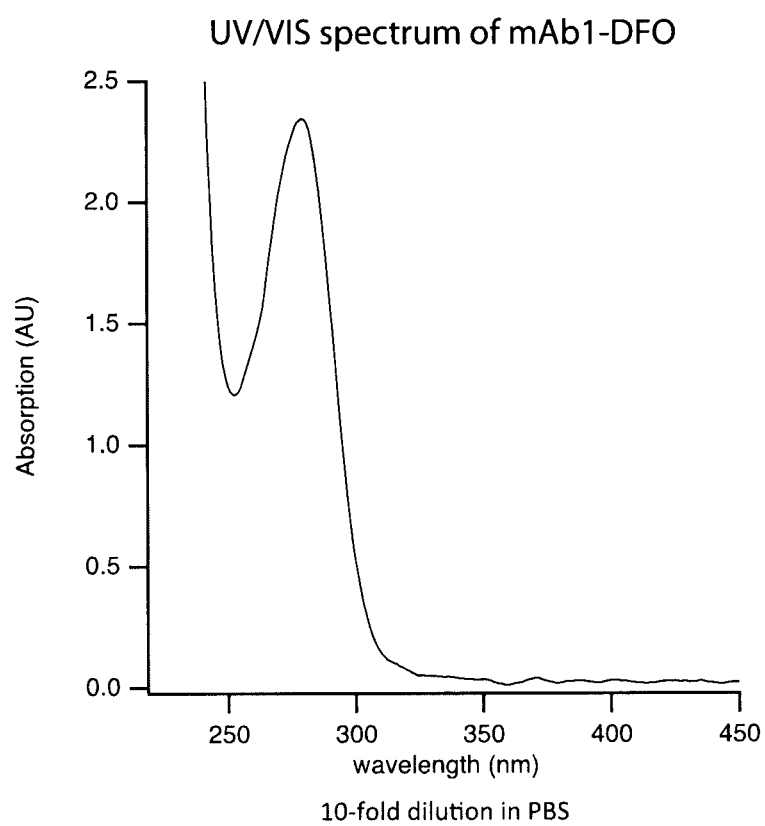
FIG. 1 depicts UV/VIS spectrum of DFO modified anti-LAG3 antibody (mAb1-DFO).

Unless defined otherwise herein, all technical and scientific terms used herein have the same meaning as commonly understood by one of ordinary skill in the art to which the disclosed subject matter belongs.

The term "LAG3" refers to the lymphocyte activation gene-3 protein, an immune checkpoint receptor or T cell co-inhibitor, also known as CD223. The amino acid sequence of full-length LAG3 is provided in GenBank as accession number NP_002277.4 and is also referred to herein as SEQ ID NO: 582. The term "LAG3" also includes protein variants of LAG3 having the amino acid sequence of SEQ ID NOs: 574, 575 or 576. The term "LAG3" includes recombinant LAG3 or a fragment thereof. The term also encompasses LAG3 or a fragment thereof coupled to, for example, histidine tag, mouse or human Fc, or a signal sequence such as the signal sequence of ROR1. For example, the term includes sequences exemplified by SEQ ID NO: 575, comprising a mouse Fc (mIgG2a) at the C-terminal, coupled to amino acid residues 29-450 of full-length ectodomain LAG3. Protein variants as exemplified by SEQ ID NO: 574 comprise a histidine tag at the C-terminal, coupled to amino acid residues 29-450 of full length ectodomain LAG3. Unless specified as being from a non-human species, the term "LAG3" means human LAG3.

LAG3 is a member of the immunoglobulin (Ig) superfamily. LAG3 is a type-1 transmembrane protein with four extracellular Ig-like domains D1 to D4 and is expressed on intratumoral lymphocytes including activated T cells, natural killer cells, B cells, plasmacytoid dendritic cells, and regulatory T cells. The LAG3 receptor binds to MHC class II molecules present on antigen presenting cells (APCs).

The term "B7-1" refers to the T-lymphocyte activation antigen, also known as costimulatory factor CD80. B7-1 is a 288 amino acid membrane receptor with an extracellular N-terminal domain which comprises IgV-like (aa 37-138) and IgC-like (aa 154-232) regions, a transmembrane domain (aa 243-263) and a C-terminal intracellular region (aa 263-288). The amino acid sequence of full-length B7-1 is provided in GenBank as accession number NP_005182.1.

As used herein, the term "T-cell co-inhibitor" refers to a ligand and/or receptor which modulates the immune response via T-cell activation or suppression. The term "T-cell co-inhibitor", also known as T-cell co-signaling molecule, includes, but is not limited to, lymphocyte activation gene 3 protein (LAG-3, also known as CD223), programmed death-1 (PD-1), cytotoxic T-lymphocyte antigen-4 (CTLA-4), B and T lymphocyte attenuator (BTLA), CD-28, 2B4, LY108, T-cell immunoglobulin and mucin-3 (TIM3), T-cell immunoreceptor with immunoglobulin and ITIM domains (TIGIT; also known as VSIG9), leucocyte associated immunoglobulin-like receptor 1 (LAIR1; also known as CD305), inducible T-cell costimulator (ICOS; also known as CD278), B7-1 (CD80), and CD160.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region "LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The anti-LAG3 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes anti-LAG3 monoclonal antibodies comprising variants of any of the HCVR, LCVR, and/or CDR amino acid sequences disclosed herein having one or more conservative substitutions. For example, the present disclosure includes anti-LAG3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present disclosure that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present disclosure, the term "multi-specific antigen-binding molecules" also includes bi-specific, tri-specific or multi-specific antibodies or antigen-binding fragments thereof. In certain embodiments, an antibody of the present disclosure is functionally linked to another antibody or antigen-binding fragment thereof to produce a bispecific antibody with a second binding specificity. Bispecific and multi-specific antibodies of the present disclosure are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to LAG3. Moreover, multi-specific antibodies that bind to one domain in LAG3 and one or more additional antigens or a bi-specific that binds to two different regions of LAG3 are nonetheless considered antibodies that "specifically bind", as used herein.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to LAG3.

An "isolated antibody", as used herein, is intended to refer to an antibody that is substantially free of other antibodies (Abs) having different antigenic specificities (e.g., an isolated antibody that specifically binds LAG3, or a fragment thereof, is substantially free of Abs that specifically bind antigens other than LAG3.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix. Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as chronic viral infection, cancer or autoimmune disease.

II. Radiolabeled Immunoconjugates of LAG3 Antibodies for Immuno-PET Imaging

Provided herein are radiolabeled antigen-binding proteins that bind LAG3. In some embodiments, the radiolabeled antigen-binding proteins comprise an antigen-binding protein covalently linked to a positron emitter. In some embodiments, the radiolabeled antigen-binding proteins comprise an antigen-binding protein covalently linked to one or more chelating moieties, which are chemical moieties that are capable of chelating a positron emitter.

In some embodiments, antigen-binding proteins that bind LAG3, e.g., antibodies, are provided, wherein said antigen-binding proteins that bind LAG3 are covalently bonded to one or more moieties having the following structure:

$$-L-M_Z$$

wherein L is a chelating moiety; M is a positron emitter; and z, independently at each occurrence, is 0 or 1; and wherein at least one of z is 1.

In some embodiments, the radiolabeled antigen-binding protein is a compound of Formula (I):

$$M-L-A-[L-M_Z]_k \qquad (I)$$

A is a protein that binds LAG3; L is a chelating moiety; M is a positron emitter; z is 0 or 1; and k is an integer from 0-30. In some embodiments, k is 1.

In certain embodiments, the radiolabeled antigen-binding protein is a compound of Formula (II):

$$A\text{-}[L\text{-}M]_k \quad (II)$$

wherein A is a protein that binds LAG3; L is a chelating moiety; M is a positron emitter; and k is an integer from 1-30.

In some embodiments, provided herein are compositions comprising a conjugate having the following structure:

$$A\text{-}L_k$$

wherein A is a protein that binds LAG3; L is a chelating moiety; and k is an integer from 1-30; wherein the conjugate is chelated with a positron emitter in an amount sufficient to provide a specific activity suitable for clinical PET imaging.

Suitable binding proteins, chelating moieties, and positron emitters are provided below.

A. LAG3 Binding Proteins

Suitable LAG3 binding protein are proteins that specifically bind to LAG3, including those described in PCT/US16/56156, incorporated herein by reference in its entirety. Exemplary anti-LAG3 antibodies of the present disclosure are listed in Table 1 of PCT/US16/56156, also presented below.

regions (LCVRs), heavy chain complementarity determining regions (HCDR1, HCDR2 and HCDR3), and light chain complementarity determining regions (LCDR1, LCDR2 and LCDR3) of the exemplary anti-LAG3 antibodies.

In some embodiments, the binding protein is an antibody or antigen binding fragment comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present disclosure provides antibodies, or antigen-binding frag-

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M14985N | 2 | 4 | 6 | 8 | 10 | 12 | 14 | 16 |
| H1M14987N | 18 | 20 | 22 | 24 | 26 | 28 | 30 | 32 |
| H2M14811N | 34 | 36 | 38 | 40 | 42 | 44 | 46 | 48 |
| H2M14885N | 50 | 52 | 54 | 56 | 58 | 60 | 62 | 64 |
| H2M14926N | 66 | 68 | 70 | 72 | 74 | 76 | 78 | 80 |
| H2M14927N | 82 | 84 | 86 | 88 | 90 | 92 | 94 | 96 |
| H2M14931N | 98 | 100 | 102 | 104 | 106 | 108 | 110 | 112 |
| H2M18336N | 114 | 116 | 118 | 120 | 122 | 124 | 126 | 128 |
| H2M18337N | 130 | 132 | 134 | 136 | 138 | 140 | 142 | 144 |
| H4H15477P | 146 | 148 | 150 | 152 | 154 | 156 | 158 | 160 |
| H4H15483P | 162 | 164 | 166 | 168 | 170 | 172 | 174 | 176 |
| H4H15484P | 178 | 180 | 182 | 184 | 186 | 188 | 190 | 192 |
| H4H15491P | 194 | 196 | 198 | 200 | 202 | 204 | 206 | 208 |
| H4H17823P | 210 | 212 | 214 | 216 | 218 | 220 | 222 | 224 |
| H4H17826P2 | 226 | 228 | 230 | 232 | 234 | 236 | 238 | 240 |
| H4H17828P2 | 242 | 244 | 246 | 248 | 250 | 252 | 254 | 256 |
| H4sH15460P | 258 | 260 | 262 | 264 | 266 | 268 | 270 | 272 |
| H4sH15462P | 274 | 276 | 278 | 280 | 282 | 284 | 286 | 288 |
| H4sH15463P | 290 | 292 | 294 | 296 | 298 | 300 | 302 | 304 |
| H4sH15464P | 306 | 308 | 310 | 312 | 314 | 316 | 318 | 320 |
| H4sH15466P | 322 | 324 | 326 | 328 | 330 | 332 | 334 | 336 |
| H4sH15467P | 338 | 340 | 342 | 344 | 346 | 348 | 350 | 352 |
| H4sH15470P | 354 | 356 | 358 | 360 | 362 | 364 | 366 | 368 |
| H4sH15475P | 370 | 372 | 374 | 376 | 378 | 380 | 382 | 384 |
| H4sH15479P | 386 | 388 | 390 | 392 | 394 | 396 | 398 | 400 |
| H4sH15480P | 402 | 404 | 406 | 408 | 410 | 412 | 414 | 416 |
| H4sH15482P | 418 | 420 | 422 | 424 | 426 | 428 | 430 | 432 |
| H4sH15488P | 434 | 436 | 438 | 440 | 442 | 444 | 446 | 448 |
| H4sH15496P2 | 450 | 452 | 454 | 456 | 522 | 524 | 526 | 528 |
| H4sH15498P2 | 458 | 460 | 462 | 464 | 522 | 524 | 526 | 528 |
| H4sH15505P2 | 466 | 468 | 470 | 472 | 522 | 524 | 526 | 528 |
| H4sH15518P2 | 474 | 476 | 478 | 480 | 522 | 524 | 526 | 528 |
| H4sH15523P2 | 482 | 484 | 486 | 488 | 522 | 524 | 526 | 528 |
| H4sH15530P2 | 490 | 492 | 494 | 496 | 522 | 524 | 526 | 528 |
| H4sH15555P2 | 498 | 500 | 502 | 504 | 530 | 532 | 534 | 536 |
| H4sH15558P2 | 506 | 508 | 510 | 512 | 530 | 532 | 534 | 536 |
| H4sH15567P2 | 514 | 516 | 518 | 520 | 530 | 532 | 534 | 536 |
| H4H14813N | 538 | 540 | 542 | 544 | 546 | 548 | 550 | 552 |
| H4H17819P | 554 | 556 | 558 | 560 | 562 | 564 | 566 | 568 |

Table 1 sets forth the amino acid sequence identifiers of the heavy chain variable regions (HCVRs), light chain variable regions, comprising an HCVR/LCVR amino acid sequence pair contained within any of the exemplary anti- LAG3 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562. In certain embodiments, the HCVR/LCVR amino acid sequence pair is selected from one of SEQ ID NOs: 386/394 (e.g., H4sH15479P), 418/426 (e.g., H4sH15482P) or 538/546 (e.g., H4sH14813N). In certain other embodiments, the HCVR/LCVR amino acid sequence pair is selected from one of SEQ ID NOs: 458/464 (e.g., H4sH15498P2), 162/170 (e.g., H4H15483P), and 579/578 (e.g., H4H15482P).

In some embodiments, the binding protein is an antibody or antigen binding fragment comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary anti-LAG3 antibodies listed in Table 1. In certain embodiments, the HCDR3/LCDR3 amino acid sequence pair is selected from the group consisting of SEQ ID NOs: 392/400 (e.g., H4sH15479P), 424/432 (e.g., H4sH15482P), and 544/552 (e.g., H4sH14813N).

In some embodiments, the binding protein is an antibody or antigen binding fragment comprising a set of six CDRs (i.e., HCDR1-HCDR2-HCDR3-LCDR1-LCDR2-LCDR3) contained within any of the exemplary anti-LAG3 antibodies listed in Table 1. In certain embodiments, the HCDR1-HCDR2-HCDR3-LCDR1-LCDR2-LCDR3 amino acid sequence set is selected from the group consisting of SEQ ID NOs: 388-390-392-396-398-400 (e.g., H4sH15479P), 420-422-424-428-430-432 (e.g., H4sH15482P), and 540-542-544-548-550-552 (e.g., H4sH14813N).

In some embodiments, the binding protein is an antibody or antigen binding fragment comprising a set of six CDRs (i.e., HCDR1-HCDR2-HCDR3-LCDR1-LCDR2-LCDR3) contained within an HCVR/LCVR amino acid sequence pair as defined by any of the exemplary anti-LAG3 antibodies listed in Table 1. For example, in some embodiments, the binding protein is an antibody or antigen binding fragment comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 386/394 (e.g., H4sH15479P), 418/426 (e.g., H4sH15482P) and 538/546 (e.g., H4sH14813N). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In some embodiments, binding proteins are antibodies and antigen-binding fragments thereof that compete for specific binding to LAG3 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

Additional exemplary anti-LAG3 antibodies useful herein include LAG525 (and other LAG3 antibodies disclosed in U.S. 20100233183), relatlimab (and other LAG3 antibodies disclosed in U.S. 20110150892), GSK2831781 (and other LAG3 antibodies disclosed in U.S. 20140286935), MGD013 (and other LAG3 antibodies disclosed in WO2015200119) and LAG3 antibodies disclosed in U.S. 20160222116, U.S. 20170022273, U.S. 20170097333, U.S. 20170137517, U.S. 20170267759, U.S. 20170290914, U.S. 20170334995, WO2016126858, WO2016200782, WO2017087589, WO2017087901, WO2017106129, WO2017149143, WO2017198741, WO2017219995, and WO2017220569.

Also provided herein are isolated antibodies and antigen-binding fragments thereof that block LAG3 binding to MHC class II. In some embodiments, the antibody or antigen-binding fragment thereof that blocks LAG3 binding may bind to the same epitope on LAG3 as MHC class II or may bind to a different epitope on LAG3 as MHC class II. In certain embodiments, the antibodies of the disclosure that block LAG3 binding to MHC class II comprise the CDRs of an HCVR having an amino acid sequence selected from the group consisting of HCVR sequences listed in Table 1; and the CDRs of a LCVR having an amino acid sequence selected from the group consisting of LCVR sequences listed in Table 1.

In alternate embodiments, the present disclosure provides antibodies and antigen-binding fragments thereof that do not block LAG3 binding to MHC class II.

In some embodiments, the binding proteins are antibodies and antigen-binding fragments thereof that bind specifically to LAG3 from human or other species. In certain embodiments, the antibodies may bind to human LAG3 and/or to cynomolgus LAG3.

In some embodiments, the binding proteins are antibodies and antigen-binding fragments thereof that cross-compete for binding to LAG3 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the binding protein is an isolated antibody or antigen-binding fragment that has one or more of the following characteristics: (a) blocks the binding of LAG3 or to MHC class II; (b) binds specifically to human LAG3 and/or cynomolgus LAG3; (c) blocks LAG3-induced impairment of T cell activation and rescues T cell signaling; and (d) suppresses tumor growth and increases survival in a subject with cancer.

In some embodiments, the antibody or antigen binding fragment thereof may bind specifically to LAG3 in an agonist manner, i.e., it may enhance or stimulate LAG3 binding and/or activity; in other embodiments, the antibody may bind specifically to LAG3 in an antagonist manner, i.e., it may block LAG3 from binding to its ligand.

In some embodiments, the antibody or antigen binding fragment thereof may bind specifically to LAG3 in an neutral manner, i.e., it binds but does not block or enhance or stimulate LAG3 binding and/or activity.

In certain embodiments, the antibodies or antigen-binding fragments are bispecific comprising a first binding specificity to LAG3 and a second binding specificity for a second target epitope. The second target epitope may be another epitope on LAG3 or on a different protein. In certain embodiments, the second target epitope may be on a different cell including a different T cell, a B-cell, a tumor cell or a virally infected cell.

In certain embodiments, an isolated antibody or antigen-binding fragment thereof is provided that binds specifically to human lymphocyte activation gene 3 (LAG3) protein, wherein the antibody or antigen-binding fragment thereof has a property selected from the group consisting of: (a) binds monomeric human LAG3 with a binding dissociation equilibrium constant ($K_D$) of less than about 10 nM as measured in a surface plasmon resonance assay at 25° C. (using the assay format as defined in Example 3 of PCT/US16/56156, or a substantially similar assay); (b) binds monomeric human LAG3 with a $K_D$ less than about 8 nM as measured in a surface plasmon resonance assay at 37° C.; (c) binds dimeric human LAG3 with a $K_D$ less than about 1.1 nM as measured in a surface plasmon resonance assay at 25° C.; (d) binds dimeric human LAG3 with a $K_D$ less than about 1 nM as measured in a surface plasmon resonance assay at 37° C.; (e) binds to a hLAG3-expressing cell with an $EC_{50}$ less than about 8 nM as measured in a flow cytometry assay; (f) binds to a mfLAG3-expressing cell with a $EC_{50}$ less than about 2.3 nM as measured in a flow cytometry assay; (g) blocks binding of hLAG3 to human MHC class II with $IC_{50}$ less than about 32 nM as determined by a cell adherence assay; (h) blocks binding of hLAG3 to mouse MHC class II with $IC_{50}$ less than about 30 nM as determined by a cell adherence assay; (i) blocks binding of hLAG3 to MHC class II by more than 90% as determined by a cell adherence assay; (j) rescues LAG3-mediated inhibition of T cell activity with $EC_{50}$ less than about 9 nM as determined in a luciferase reporter assay; and (k) binds to activated CD4+ and CD8+ T cells with $EC_{50}$ less than about 1.2 nM, as determined in a fluorescence assay.

In some embodiments, the antibodies and antigen-binding fragments thereof bind LAG3 with a dissociative half-life (t1/2) of greater than about 1.6 minutes as measured by surface plasmon resonance at 25° C. or 37° C., e.g., using an assay format as defined in Example 3 of PCT/US16/56156, or a substantially similar assay. In certain embodiments, the antibodies or antigen-binding fragments bind LAG3 with a t1/2 of greater than about 5 minutes, greater than about 10 minutes, greater than about 30 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1100 minutes, as measured by surface plasmon resonance at 25° C. or 37° C., e.g., using an assay format as defined in Example 3 of PCT/US16/56156 (e.g., mAb-capture or antigen-capture format), or a substantially similar assay.

In some embodiments, antibodies or antigen-binding fragments thereof bind to a human LAG3-expressing cell with an $EC_{50}$ less than about 8 nM as measured by a flow cytometry assay as defined in Example 5 of PCT/US16/56156, or a substantially similar assay. In certain embodiments, the antibodies or antigen-binding fragments thereof bind to a hLAG3-expressing cell with an $EC_{50}$ less than about 5 nM, less than about 2 nM, less than about 1 nM, or less than about 0.5 nM, as measured by a flow cytometry assay, e.g., using the assay format in Example 5 of PCT/US16/56156, or a substantially similar assay.

In some embodiments, antibodies or antigen-binding fragments thereof bind to a cynomolgus monkey LAG3-expressing cell with an $EC_{50}$ less than about 2.5 nM as measured by a flow cytometry assay as defined in Example 5 of PCT/US16/56156, or a substantially similar assay. In certain embodiments, the antibodies or antigen-binding fragments thereof bind to a mfLAG3-expressing cell with an $EC_{50}$ less than about 2 nM, or less than about 1 nM, as measured by a flow cytometry assay, e.g., using the assay format as defined in Example 5 of PCT/US16/56156, or a substantially similar assay.

In some embodiments, antibodies or antigen-binding fragments thereof block LAG3 binding to MHC class II (e.g., human HLA-DR2) with an $IC_{50}$ of less than about 32 nM as determined using a cell adherence assay, e.g., as shown in Example 7 of PCT/US16/56156, or a substantially similar assay. In certain embodiments, the antibodies or antigen-binding fragments thereof block LAG3 binding to human MHC class II with an $IC_5O$ less than about 25 nM, less than about 20 nM, less than about 10 nM, or less than about 5 nM, as measured by a cell adherence assay, e.g., using the assay format as defined in Example 7 of PCT/US16/56156, or a substantially similar assay.

In some embodiments, the antibodies or antigen-binding fragments thereof block LAG3 binding to MHC class II with an $IC_{50}$ of less than about 30 nM as determined using a cell adherence assay, e.g., as shown in Example 7 of PCT/US16/56156, or a substantially similar assay. In certain embodiments, the antibodies or antigen-binding fragments thereof block mouse LAG3 binding to human MHC class II with an $IC_{50}$ less than about 25 nM, less than about 20 nM, less than about 10 nM, or less than about 5 nM, as measured by a cell adherence assay, e.g., using the assay format as defined in Example 7 of PCT/US16/56156, or a substantially similar assay.

In some embodiments, the antibodies or antigen-binding fragments thereof block binding of LAG3 to human or mouse MHC class II by more than 90% as measured by a cell adherence assay as defined in Example 7 of PCT/US16/56156, or a substantially similar assay.

In some embodiments, the antibodies or antigen-binding fragments thereof block LAG-induced T cell down-regulation with an $EC_{50}$ less than 9 nM as measured by a T cell/APC luciferase reporter assay as defined in Example 8 of PCT/US16/56156, or a substantially similar assay. In certain embodiments, the antibodies or antigen-binding fragments thereof block LAG3-induced T cell down-regulation with an $EC_{50}$ less than about 5 nM, less than about 1 nM, less than about 0.5 nM, or less than about 0.1 nM, as measured by a T cell/APC luciferase reporter assay, e.g., using the assay format as defined in Example 8 of PCT/US16/56156, or a substantially similar assay.

In some embodiments, the antibodies or antigen-binding fragments thereof bind to cynomolgus activated CD4+ and CD8+ T cells with an $EC_{50}$ less than about 1.2 nM as measured by a fluorescence assay as defined in Example 9 of PCT/US16/56156, or a substantially similar assay. In certain embodiments, the antibodies or antigen-binding fragments thereof bind to cynomolgus activated CD4+ and CD8+ T cells with an $EC_{50}$ less than about 1.1 nM, less than about 1 nM, less than about 0.5 nM, less than about 0.2 nM, or less than about 0.1 nM, as measured by a fluorescence assay, e.g., using the assay format as defined in Example 9 of PCT/US16/56156, or a substantially similar assay.

In one embodiment, the antibody or fragment thereof is a monoclonal antibody or antigen-binding fragment thereof that binds to LAG3, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 464, 472, 480, 488, 496, 504, 512, 520, 544, and 560, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 528, 536, 552, and 568, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 460, 468, 476, 484, 492, 500, 508, 516, 540, and 556, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 462, 470, 478, 486, 494, 502, 510, 518, 542, and 558, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 524, 532, 548, and 564, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 526, 534, 550, and 566, or a substantially similar sequence thereof having at least 90%, at least 95%, at least 98% or at least 99% sequence identity; (v) binds monomeric human LAG3 with a binding dissociation equilibrium constant ($K_D$) of less than about 10 nM as measured in a surface plasmon resonance assay at 25° C.; (vi) binds monomeric human LAG3 with a $K_D$ less than about 8 nM as measured in a surface plasmon resonance assay at 37° C.; (vii) binds dimeric human LAG3 with a $K_D$ less than about 1.1 nM as measured in a surface plasmon resonance assay at 25° C.; (viii) binds dimeric human LAG3 with a $K_D$ less than about 1 nM as measured in a surface plasmon resonance assay at 37° C.; (ix) binds to a hLAG3-expressing cell with an $EC_{50}$ less than about 8 nM as measured in a flow cytometry assay; (x) binds to a mfLAG3-expressing cell with a $EC_{50}$ less than about 2.3 nM as measured in a flow cytometry assay; (xi) blocks binding of hLAG3 to human MHC class II with $IC_{50}$ less than about 32 nM as determined by a cell adherence assay; (xii) blocks binding of hLAG3 to mouse MHC class II with $IC_{50}$ less than about 30 nM as determined by a cell adherence assay; (xiii) blocks binding of hLAG3 to MHC class II by more than 90% as determined by a cell adherence assay; (xiv) rescues LAG3-mediated inhibition of T cell activity with $EC_{50}$ less than about 9 nM as determined in a luciferase reporter assay; (xv) binds to activated CD4+ and CD8+ T cells with $EC_{50}$ less than about 1.2 nM, as determined in a fluorescence assay; and (xvi) suppresses tumor growth and increases survival in a subject with cancer.

In one embodiment, the antibody or fragment thereof is a monoclonal antibody or antigen-binding fragment thereof that blocks LAG3 binding to MHC class II, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 464, 472, 480, 488, 496, 504, 512, 520, 544, and 560, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 528, 536, 552, and 568, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 460, 468, 476, 484, 492, 500, 508, 516, 540, and 556, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 462, 470, 478, 486, 494, 502, 510, 518, 542, and 558, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 524, 532, 548, and 564, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 526, 534, 550, and 566, or a substantially similar sequence thereof having at least 90%, at least 95%, at least 98% or at least 99% sequence identity; (v) binds monomeric human LAG3 with a binding dissociation equilibrium constant ($K_D$) of less than about 10 nM as measured in a surface plasmon resonance assay at 25° C.; (vi) binds monomeric human LAG3 with a $K_D$ less than about 8 nM as measured in a surface plasmon resonance assay at 37° C.; (vii) binds dimeric human LAG3 with a $K_D$ less than about 1.1 nM as measured in a surface plasmon resonance assay at 25° C.; (viii) binds dimeric human LAG3 with a $K_D$ less than about 1 nM as measured in a surface plasmon resonance assay at 37° C.; (ix) binds to a hLAG3-expressing cell with an $EC_{50}$ less than about 8 nM as measured in a flow cytometry assay; (x) binds to a mfLAG3-expressing cell with a $EC_{50}$ less than about 2.3 nM as measured in a flow cytometry assay; (xi) blocks binding of hLAG3 to human MHC class II with $IC_{50}$ less than about 32 nM as determined by a cell adherence assay; (xii) blocks binding of hLAG3 to mouse MHC class II with $IC_{50}$ less than about 30 nM as determined by a cell adherence assay; (xiii) blocks binding of hLAG3 to MHC class II by more than 90% as determined by a cell adherence assay; (xiv) rescues LAG3-mediated inhibition of T cell activity with $EC_{50}$ less than about 9 nM as determined in a luciferase reporter assay; (xv) binds to activated CD4+ and CD8+ T cells with $EC_{50}$ less than about 1.2 nM, as determined in a fluorescence assay; and (xvi) suppresses tumor growth and increases survival in a subject with cancer.

In certain embodiments, the antibodies may function by blocking or inhibiting the MHC class II-binding activity associated with LAG3 by binding to any other region or fragment of the full length protein, the amino acid sequence of which is shown in SEQ ID NO: 582.

In certain embodiments, the antibodies are bi-specific antibodies. The bi-specific antibodies can bind one epitope in one domain and can also bind a second epitope in a different domain of LAG3. In certain embodiments, the bi-specific antibodies bind two different epitopes in the same domain. In one embodiment, the multi-specific antigen-binding molecule comprises a first antigen-binding specificity wherein the first binding specificity comprises the extracellular domain or fragment thereof of LAG3; and a second antigen-binding specificity to another epitope of LAG3.

In certain embodiments, the anti-LAG3 antibodies or antigen-binding fragments thereof bind an epitope within any one or more of the regions exemplified in LAG3, either in natural form, as exemplified in SEQ ID NO: 582, or recombinantly produced, as exemplified in SEQ ID NOS: 574-576, or to a fragment thereof. In some embodiments, the antibodies bind to an extracellular region comprising one or more amino acids selected from the group consisting of amino acid residues 29-450 of LAG3. In some embodiments, the antibodies bind to an extracellular region comprising one or more amino acids selected from the group consisting of amino acid residues 1-533 of cynomolgus LAG3, as exemplified by SEQ ID NO: 576.

In certain embodiments, anti-LAG3 antibodies and antigen-binding fragments thereof interact with one or more epitopes found within the extracellular region of LAG3 (SEQ ID NO: 588). The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular region of LAG3. Alternatively, the epitope may consist of a plurality of non-contiguous amino acids (or amino acid sequences) located within the extracellular region of LAG3. The epitope of LAG3 with which the exemplary antibody H4sH15482P interacts is defined by the amino acid sequence LRRAGVTWQHQPDSGPPAAAPGHPLAPGPHPAAPSS-WGPRPRRY (SEQ ID NO: 589), which corresponds to amino acids 28 to 71 of SEQ ID NO: 588. Accordingly, also included are anti-LAG3 antibodies that interact with one or more amino acids contained within the region consisting of amino acids 28 to 71 of SEQ ID NO: 588 (i.e., the sequence LRRAGVTWQHQPDSGPPAAAPGHPLAPGPHPAAPSS-WGPRPRRY [SEQ ID NO: 589]).

The present disclosure includes anti-LAG3 antibodies that bind to the same epitope, or a portion of the epitope, as any of the specific exemplary antibodies described herein in Table 1, or an antibody having the CDR sequences of any of the exemplary antibodies described in Table 1. Likewise, also included are anti-LAG3 antibodies that compete for binding to LAG3 or a LAG3 fragment with any of the specific exemplary antibodies described herein in Table 1, or an antibody having the CDR sequences of any of the exemplary antibodies described in Table 1. For example, the present disclosure includes anti-LAG3 antibodies that cross-compete for binding to LAG3 with one or more antibodies provided herein (e.g., H4sH15482P, H4sH15479P, H4sH14813N, H4H14813N, H4H15479P, H4H15482P, H4H15483P, H4sH15498P, H4H15498P, H4H17828P2, H4H17819P, and H4H17823P).

The antibodies and antigen-binding fragments described herein specifically bind to LAG3 and modulate the interaction of LAG3 with MHC class II. The anti-LAG3 antibodies may bind to LAG3 with high affinity or with low affinity. In certain embodiments, the antibodies are blocking antibodies wherein the antibodies bind to LAG3 and block the interaction of LAG3 with MHC class II. In some embodiments, the blocking antibodies of the disclosure block the binding of LAG3 to MHC class II and/or stimulate or enhance T-cell activation. In some embodiments, the blocking antibodies are useful for stimulating or enhancing the immune response and/or for treating a subject suffering from cancer, or a chronic viral infection. The antibodies when administered to a subject in need thereof may reduce the chronic infection by a virus such as human immunodeficiency virus (HIV), hepatitis B virus (HBV), hepatitis C virus (HCV), human papilloma virus (HPV), lymphocytic choriomeningitis virus (LCMV), and simian immunodeficiency virus (SIV) in the subject. They may be used to inhibit the growth of tumor cells in a subject. They may be used alone or as adjunct therapy with other therapeutic moieties or modalities known in the art for treating cancer, or viral infection. In certain embodiments, the anti-LAG3 antibodies that bind to LAG3 with a low affinity are used as multi-specific antigen-binding molecules wherein the first binding specificity binds to LAG3 with a low affinity and the second binding specificity binds to an antigen selected from the group consisting of a different epitope of LAG3 and another T-cell co-inhibitor.

In some embodiments, the antibodies bind to LAG3 and reverse the anergic state of exhausted T cells. In certain embodiments, the antibodies bind to LAG3 and inhibit regulatory T cell activity. In some embodiments, the antibodies may be useful for stimulating or enhancing the immune response and/or for treating a subject suffering from cancer, a viral infection, a bacterial infection, a fungal infection, or a parasitic infection. The antibodies when administered to a subject in need thereof may reduce chronic infection by a virus such as HIV, LCMV or HBV in the subject. They may be used to inhibit the growth of tumor cells in a subject. They may be used alone or as adjunct therapy with other therapeutic moieties or modalities known in the art for treating cancer, or viral infection.

In certain embodiments, the antibodies of the present disclosure are agonist antibodies, wherein the antibodies bind to LAG3 and enhance the interaction of LAG3 and MHC class II. In some embodiments, the activating antibodies enhance binding of LAG3 to MHC class II and/or inhibit or suppress T-cell activation. The activating antibodies of the present disclosure may be useful for inhibiting the immune response in a subject and/or for treating autoimmune disease.

Certain anti-LAG3 antibodies are able to bind to and neutralize the activity of LAG3, as determined by in vitro or in vivo assays. The ability of the antibodies to bind to and neutralize the activity of LAG3 may be measured using any standard method known to those skilled in the art, including binding assays, or activity assays, as described herein.

Non-limiting, exemplary in vitro assays for measuring binding activity are illustrated in Examples provided in PCT/US16/56156: in Example 3, the binding affinities and kinetic constants of human anti-LAG3 antibodies for human LAG3 were determined by surface plasmon resonance and the measurements were conducted on a Biacore 4000 or T200 instrument; in Example 4, blocking assays were used to determine cross-competition between anti-LAG3 antibodies; Examples 5 and 6 describe the binding of the antibodies to cells overexpressing LAG3; in Example 7, binding assays were used to determine the ability of the anti-LAG3 antibodies to block MHC class II-binding ability of LAG3 in vitro; in Example 8, a luciferase assay was used to determine the ability of anti-LAG3 antibodies to antagonize LAG3 signaling in T cells; and in Example 9, a fluorescence assay was used to determine the ability of anti-LAG3 antibodies to bind to activated monkey CD4+ and CD8+ T cells.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to LAG3. An antibody fragment may include a Fab fragment, a F(ab)$_2$ fragment, a Fv fragment, a dAb fragment, a fragment containing a CDR, or an isolated CDR. In certain embodiments, the term "antigen-binding fragment" refers to a polypeptide or fragment thereof of a multi-specific antigen-binding molecule. In such embodiments, the term "antigen-binding fragment" includes, e.g., MHC class II molecule which binds specifically to LAG3. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (VI) $V_H$-$C_H2$-$C_H3$; (vii) $V_H$-$C_L$; (Viii) $V_L$-$C_H1$; (ix) $V_L$-$C_H2$; (X) $V_L$-$C_H3$; (Xi) $V_L$-$C_H1$-$C_H2$; (XII) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

The anti-LAG3 antibodies and antibody fragments of the present disclosure encompass proteins having amino acid sequences that vary from those of the described antibodies, but that retain the ability to bind LAG3. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

According to certain embodiments of the present disclosure, anti-LAG3 antibodies comprise an Fc domain comprising one or more mutations which enhance or diminish antibody binding to the FcRn receptor, e.g., at acidic pH as compared to neutral pH. For example, the present disclosure includes anti-LAG3 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present disclosure includes anti-LAG3 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present disclosure includes anti-LAG3 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present disclosure.

The present disclosure also includes anti-LAG3 antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H 2$ domain derived from a human IgG1, human IgG2 or human IgG4 molecule, combined with part or all of a $C_H 3$ domain derived from a human IgG1, human IgG2 or human IgG4 molecule. According to certain embodiments, the antibodies of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., US Patent Publication No. 20140243504, the disclosure of which is hereby incorporated by reference in its entirety). In certain embodiments, the Fc region comprises a sequence selected from the group consisting of SEQ ID NOs: 569, 570, 571, 572 and 573.

B. Positron Emitters and Chelating Moieties

Suitable positron emitters include, but are not limited to, those that form stable complexes with the chelating moiety and have physical half-lives suitable for immuno-PET imaging purposes. Illustrative positron emitters include, but are not limited to, $^{89}$Zr, $^{68}$Ga, $^{64}$Cu, $^{44}$Sc, and $^{86}$Y. Suitable positron emitters also include those that directly bond with the LAG3 binding protein, including, but not limited to, $^{76}$Br and $^{124}$I, and those that are introduced via prosthetic group, e.g., $^{18}$F.

The chelating moieties described herein are chemical moieties that are covalently linked to the LAG3 binding protein, e.g., anti-LAG3 antibody and comprise a portion capable of chelating a positron emitter, i.e., capable of reacting with a positron emitter to form a coordinated chelate complex. Suitable moieties include those that allow efficient loading of the particular metal and form metal-chelator complexes that are sufficiently stable in vivo for diagnostic uses, e.g., immuno-PET imaging. Illustrative chelating moieties include those that minimize dissociation of the positron emitter and accumulation in mineral bone, plasma proteins, and/or bone marrow depositing to an extent suitable for diagnostic uses.

Examples of chelating moieties include, but are not limited to, those that form stable complexes with positron emitters $^{89}$Zr, $^{68}$Ga, $^{64}$Cu, $^{44}$Sc, and/or $^{86}$Y. Illustrative chelating moieties include, but are not limited to, those described in Nature Protocols, 5(4): 739, 2010; Bioconjugate Chem., 26(12): 2579 (2015); Chem Commun (Camb), 51(12): 2301 (2015); Mol. Pharmaceutics, 12: 2142 (2015); Mol. Imaging Biol., 18: 344 (2015); Eur. J. Nucl. Med. Mol. Imaging, 37:250 (2010); Eur. J. Nucl. Med. Mol. Imaging (2016). doi:10.1007/s00259-016-3499-x; Bioconjugate Chem., 26(12): 2579 (2015); WO 2015/140212A1; and U.S. Pat. No. 5,639,879, incorporated by reference in their entireties.

Illustrative chelating moieties also include, but are not limited to, those that comprise desferrioxamine (DFO), 1,4,7,10-tetraacetic acid (DOTA), diethylenetriaminepentaacetic acid (DTPA), ethylenediaminetetraacetic acid (EDTA), (1,4,7,10-Tetraazacyclododecane-1,4,7,10-tetra (methylene phosphonic) acid (DOTP), 1R, 4R, 7R, 10R)-α'α''α'''-Tetramethyl-1,4,7,10-tetraazacyclododecane-1,4,7, 10-tetraacetic acid (DOTMA), 1,4,8,11-Tetraazacyclotetradecane-1,4,8, 11-tetraacetic acid (TETA), H$_4$octapa, H$_6$phospa, H$_2$dedpa, H$_5$decapa, H$_2$azapa, HOPO, DO2A, 1,4,7,10-Tetrakis(carbamoylmethyl)-1,4,7,10-tetraazacyclododecane (DOTAM), 1,4,7-triazacyclononane-N, N',N''-triacetic acid (NOTA), 1,4,7,10-Tetrakis(carbamoylmethyl)-1,4,7,10-tetraazacyclododecane (DOTAM), 1,4,8, 11-tetraazabicyclo[6.6.2]hexadecane-4, 11-dicetic acid (CB-TE2A), 1,4,7,10-Tetraazacyclododecane (Cyclen), 1,4,8,11-Tetraazacyclotetradecane (Cyclam), octadentate chelators, e.g., DFO*, which can be conjugated to the antibody via DFO*-pPhe-NCS (See Vugt et al., Eur J Nucl Med Mol Imaging (2017) 44: 286-295), hexadentate chelators, phosphonate-based chelators, macrocyclic chelators, chelators comprising macrocyclic terephthalamide ligands, bifunctional chelators, fusarinine C and fusarinine C derivative chelators, triacetylfusarinine C (TAFC), ferrioxamine E (FOXE), ferrioxamine B (FOXB), ferrichrome A (FCHA), and the like.

In some embodiments, the chelating moieties are covalently bonded to the LAG3 binding protein, e.g., antibody or antigen binding fragment thereof, via a linker moiety, which covalently attaches the chelating portion of the chelating moiety to the binding protein. In some embodiments, these linker moieties are formed from a reaction between a reactive moiety of the LAG3 binding protein, e.g., cysteine or lysine of an antibody, and reactive moiety that is attached to a chelator, including, for example, a p-isothiocyanatobenyl group and the reactive moieties provided in the conjugation methods below. In addition, such linker moieties optionally comprise chemical groups used for purposes of adjusting polarity, solubility, steric interactions, rigidity, and/or the length between the chelating portion and the LAG3 binding protein.

C. Preparation of Radiolabeled Anti-LAG3 Conjugates

The radiolabeled anti-LAG3 protein conjugates can be prepared by (1) reacting a LAG3 binding protein, e.g., antibody, with a molecule comprising a positron emitter chelator and a moiety reactive to the desirable conjugation site of the LAG3 binding protein and (2) loading the desirable positron emitter.

Suitable conjugation sites include, but are not limited to, lysine and cysteine, both of which can be, for example, native or engineered, and can be, for example, present on the heavy or light chain of an antibody. Cysteine conjugation sites include, but are not limited to, those obtained from mutation, insertion, or reduction of antibody disulfide bonds. Methods for making cysteine engineered antibodies include, but are not limited to, those disclosed in WO2011/056983. Site-specific conjugation methods can also be used to direct the conjugation reaction to specific sites of an antibody, achieve desirable stoichiometry, and/or achieve desirable chelator-to-antibody ratios. Such conjugation methods are known to those of ordinary skill in the art and include, but are not limited to cysteine engineering and enzymatic and chemo-enzymatic methods, including, but not limited to, glutamine conjugation, Q295 conjugation, and transglutaminase-mediated conjugation, as well as those described in *J. Clin. Immunol.*, 36: 100 (2016), incorporated herein by reference in its entirety. Suitable moieties reactive to the desirable conjugation site generally enable efficient and facile coupling of the LAG3 binding protein, e.g., antibody and positron emitter chelator. Moieties reactive to lysine and cysteine sites include electrophilic groups, which are known to those of ordinary skill. In certain aspects, when the desired conjugation site is lysine, the reactive moiety is an isothiocyanate, e.g., p-isothiocyanatobenyl group or reactive ester. In certain aspects, when the desired conjugation site is cysteine, the reactive moiety is a maleimide.

When the chelator is desferrioxamine (DFO), suitable reactive moieties include, but are not limited to, an isothiocyantatobenzyl group, an n-hydroxysuccinimide ester,2,3, 5,6 tetrafluorophenol ester, n-succinimidyl-S-acetylthioacetate, and those described in *BioMed Research International*, Vol 2014, Article ID 203601, incorporated herein by reference in its entirety. In certain embodiments, the LAG3 binding protein is an antibody and the molecule comprising a positron emitter chelator and moiety reactive to the conjugation site is p-isothiocyantatobenzyl-desferrioxamine (p-SCN-Bn-DFO):

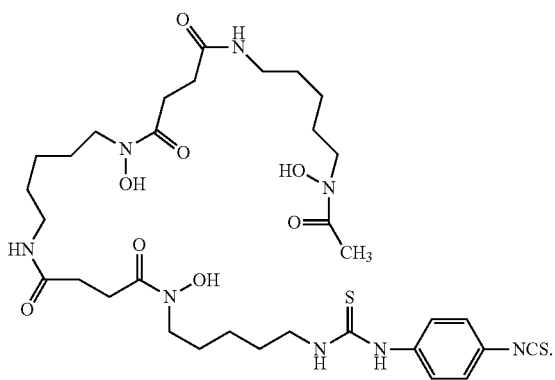

Positron emitter loading is accomplished by incubating the LAG3 binding protein chelator conjugate with the positron emitter for a time sufficient to allow coordination of said positron emitter to the chelator, e.g., by performing the methods described in the examples provided herein, or substantially similar method.

D. Illustrative Embodiments of Conjugates

Included in the instant disclosure are radiolabeled antibody conjugates comprising an antibody or antigen binding fragment thereof that binds human LAG3 and a positron emitter. Also included in the instant disclosure are radiolabeled antibody conjugates comprising an antibody or antigen binding fragment thereof that binds human LAG3, a chelating moiety, and a positron emitter.

In some embodiments, the chelating moiety comprises a chelator capable of forming a complex with $^{89}$Zr. In certain embodiments, the chelating moiety comprises desferrioxamine. In certain embodiments, the chelating moiety is p-isothiocyanatobenzyl-desferrioxamine.

In some embodiments, the positron emitter is $^{89}$Zr. In some embodiments, less than 1.0% of the anti-LAG3 antibody is conjugated with the positron emitter, less than 0.9% of the anti-LAG3 antibody is conjugated with the positron emitter, less than 0.8% of the anti-LAG3 antibody is conjugated with the positron emitter, less than 0.7% of the anti-LAG3 antibody is conjugated with the positron emitter, less than 0.6% of the anti-LAG3 antibody is conjugated with the positron emitter, less than 0.5% of the anti-LAG3 antibody is conjugated with the positron emitter, less than 0.4% of the anti-LAG3 antibody is conjugated with the positron emitter, less than 0.3% of the anti-LAG3 antibody is conjugated with the positron emitter, less than 0.2% of the anti-LAG3 antibody is conjugated with the positron emitter, or less than 0.1% of the anti-LAG3 antibody is conjugated with the positron emitter.

In some embodiments, the chelating moiety-to-antibody ratio of the conjugate is from 1 to 2.

In a particular embodiment, chelating moiety is p-isothiocyanatobenzyl-desferrioxamine and the positron emitter is $^{89}$Zr. In another particular embodiment, the chelating moiety is p-isothiocyanatobenzyl-desferrioxamine and the positron emitter is $^{89}$Zr, and the chelating moiety-to-antibody ratio of the conjugate is from 1 to 2.

In some embodiments, provided herein are antigen-binding proteins that bind LAG3, wherein said antigen-binding proteins that bind LAG3 are covalently bonded to one or more moieties having the following structure:

$$-L-M_Z$$

wherein L is a chelating moiety; M is a positron emitter; and z, independently at each occurrence, is 0 or 1; and wherein at least one of z is 1. In certain embodiments, the radiolabeled antigen-binding protein is a compound of Formula (I):

$$M-L-A-[L-M_Z]_k \qquad (I)$$

A is a protein that binds LAG3; L is a chelating moiety; M is a positron emitter; z is 0 or 1; and k is an integer from 0-30. In some embodiments, k is 1.

29

In some embodiments, L is:

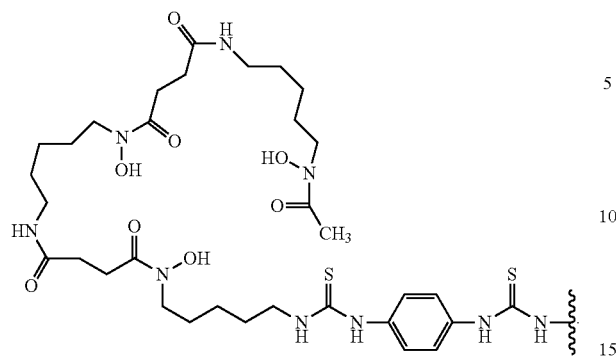

In some embodiments, M is $^{89}$Zr.

In some embodiments, k is an integer from 1 to 2. In some embodiments, k is 1.

30

In some embodiments, -L-M is

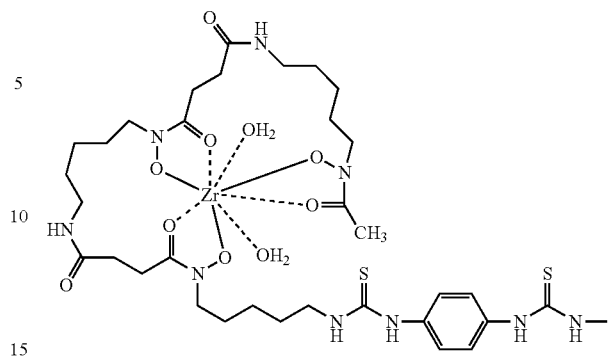

Included in the instant disclosure are also methods of synthesizing a radiolabeled antibody conjugates comprising contacting a compound of Formula (III):

(III)

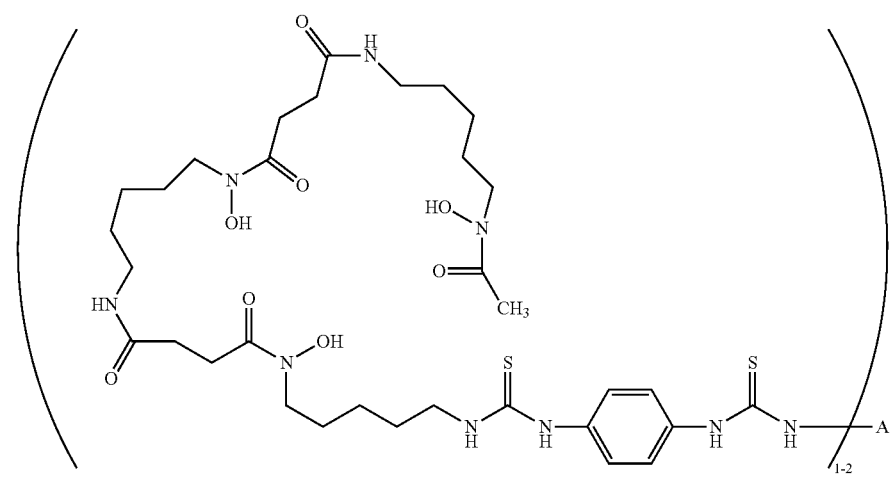

with $^{89}$Zr, wherein A is an antibody or antigen-binding fragment thereof that binds LAG3. In certain embodiments, the compound of Formula (III) is synthesized by contacting an antibody, or antigen binding fragment thereof, that binds LAG3, with p-SCN-Bn-DFO.

Provided herein is also the product of the reaction between a compound of Formula (III) with $^{89}$Zr.

Provided herein are compounds of Formula (III):

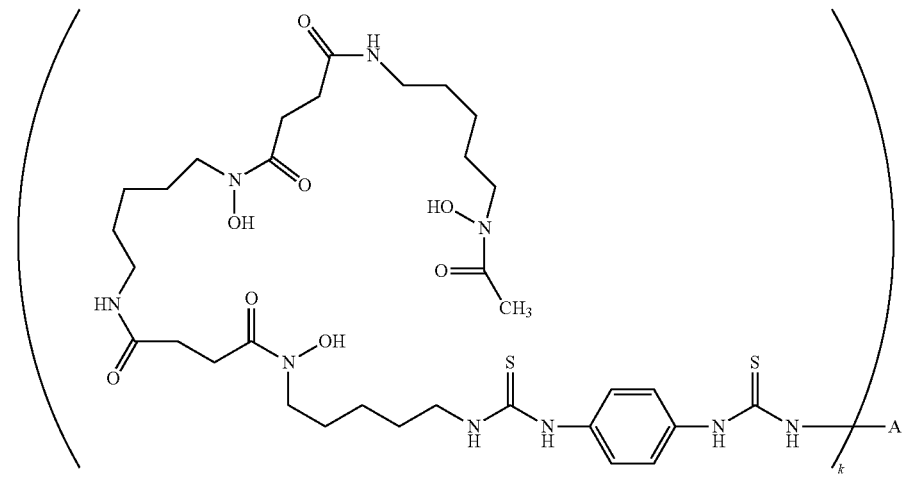

wherein A is an antibody or antigen binding fragment thereof that binds LAG3 and k is an integer from 1-30. In some embodiments, k is 1 or 2.

In some embodiments, provided herein are compositions comprising a conjugate having the following structure:

A-L$_k$ wherein A is a protein that binds LAG3; L is a chelating moiety; and k is an integer from 1-30; wherein the conjugate is chelated with a positron emitter in an amount sufficient to provide a specific activity suitable for clinical PET imaging. In some embodiments, the amount of chelated positron emitter is an amount sufficient to provide a specific activity of about 1 to about 20 mCi per 1-50 mg of the protein that binds LAG3. In some embodiments, the amount of chelated positron emitter is an amount sufficient to provide a specific activity of up to 20 mCi, up to 15 mCi, or up to 10 mCi per 1-50 mg of the protein that binds LAG3, for example, in a range of about 3 to about 20 mCi, about 5 to about 20 mCi, about 1 to about 15 mCi, about 3 to about 15 mCi, about 5 to about 15 mCi, about 1 to about 10 mCi, or about 3 to about 10 mCi.

In some embodiments, the antibody or antigen-binding fragment thereof binds monomeric human LAG3 with a binding dissociation equilibrium constant ($K_D$) of less than about 2 nM as measured in a surface plasmon resonance assay at 37° C.

In some embodiments, the antibody or antigen-binding fragment thereof binds monomeric human LAG3 with a $K_D$ less than about 1.5 nM in a surface plasmon resonance assay at 25° C.

In some embodiments, the antibody or antigen-binding fragment thereof binds dimeric human LAG3 with a $K_D$ of less than about 90 pM as measured in a surface plasmon resonance assay at 37° C.

In some embodiments, the antibody or antigen-binding fragment thereof that binds dimeric human LAG3 with a $K_D$ less than about 20 pM in a surface plasmon resonance assay at 25° C.

In some embodiments, the antibody or antigen-binding fragment thereof competes for binding to human LAG3 with a reference antibody comprising the complementarity determining regions (CDRs) of a HCVR, wherein the HCVR has an amino acid sequence selected from the group consisting of HCVR sequences listed in Table 1; and the CDRs of a LCVR, wherein the LCVR has an amino acid sequence selected from the group consisting of LCVR sequences listed in Table 1. In some embodiments, the reference antibody or antigen-binding fragment thereof comprises an HCVR/LCVR amino acid sequence pair as set forth in Table 1. In some embodiments, the reference antibody comprises an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562.

In some embodiments, the antibody or antigen-binding fragment thereof enhances LAG3 binding to MHC class II. In some embodiments, the antibody or antigen binding fragment thereof blocks LAG3 binding to MHC class II. In some embodiments, the antibody or antigen binding fragment thereof do not increase or decrease LAG3 binding to its ligands.

In some embodiments, the antibody or antigen-binding fragment thereof comprises the complementarity determining regions (CDRs) of a HCVR, wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554; and the CDRs of a LCVR, wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562. In certain embodiments, the isolated antibody comprises an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562. In certain embodiments, the isolated antibody comprises an HCVR/LCVR amino acid sequence pair selected from the group consisting of SEQ ID NOs: 386/394, 418/426, 538/546, 577/578, 579/578, and 580/581.

In some embodiments, the antibody is a human monoclonal antibody or antigen-binding fragment thereof that binds specifically to human LAG3, wherein the antibody or antigen-binding fragment thereof comprises a heavy chain variable region (HCVR) having an amino acid sequence selected from the group consisting of HCVR sequences listed in Table 1.

In some embodiments, the antibody is a human monoclonal antibody or antigen-binding fragment thereof that binds specifically to human LAG3, wherein the antibody or antigen-binding fragment thereof comprises a light chain variable region (LCVR) having an amino acid sequence selected from the group consisting of LCVR sequences listed in Table 1.

In some embodiments, the antibody a human monoclonal antibody or antigen-binding fragment thereof that binds specifically to human LAG3, wherein the antibody or antigen-binding fragment thereof comprises (a) a HCVR having an amino acid sequence selected from the group consisting of HCVR sequences listed in Table 1; and (b) a LCVR having an amino acid sequence selected from the group consisting of LCVR sequences listed in Table 1.

In some embodiments, the antibody or antigen-binding fragment thereof comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

In some embodiments, the antibody or antigen-binding fragment thereof comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 372, 388, 404, 420, 436, 452, 460, 468, 476, 484, 492, 500, 508, 516, 540, and 556;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326, 342, 358, 374, 390, 406, 422, 438, 454, 462, 470, 478, 486, 494, 502, 510, 518, 542, and 558;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, 344, 360, 376, 392, 408, 424, 440, 456, 464, 472, 480, 488, 496, 504, 512, 520, 544, and 560;

(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 380, 396, 412, 428, 444, 524, 532, 548, and 564;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 382, 398, 414, 430, 446, 526, 534, 550, and 566; and (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336, 352, 368, 384, 400, 416, 432, 448, 528, 536, 552, and 568.

In some embodiments, the antibody or antigen-binding fragment comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562. In some embodiments, the antibody or antigen-binding fragment comprises a HCVR/LCVR amino acid sequence pair selected from the group consisting of SEQ ID NOs: 386/394, 418/426, and 538/546.

E. Scaled Manufacturing for Production of Anti-LAG3 Antibody-Chelator Conjugates Included in the present disclosure are scaled-up manufacturing processes for producing anti-LAG3 antibodies conjugated to a chelator. The anti-LAG3 antibody-chelator conjugates are in a form suitable for radiolabeling.

Good manufacturing processes are adhered to in all aspects of production, including maintaining a sterile environment, practicing aseptic procedures, keeping records of all processes, and documenting product quality, purity, strength, and identity, and any deviations therefrom.

The scaled-up manufacturing process is, in some embodiments, much faster than the manufacturing process for research and development. In some embodiments, the scaled-up manufacturing process can take less than 12 hours, or less than 10 hours, or less than 8 hours, or less than 6 hours, or less than 4 hours, or less than or about 2 hours.

In some embodiments, a first step comprises ultrafiltration and diafiltration (UFDF), using a 30-50 kDa membrane, of the anti-LAG3 antibody to remove excipients, conjugation interfering species, and salts that inhibit the conjugation process. Exemplary membrane polymers include polyethersulfone (PES), cellulose acetate (CA), and regenerated cellulose (RC). In this step, the antibody is buffer exchanged in a low ionic strength and non-interfering buffer solution. The buffer pH can be between about 4.5 to about 6, or about 5 to about 6, or about 5.3 to about 5.7, or about 5.5. Buffer systems contemplated herein include any buffer system lacking a primary amine. Exemplary buffers include acetate, phosphate, or citrate buffers. The buffer provides protein stability during pre-conjugation processing. The process volume can be further reduced to concentrate the antibody, then sterile filtered.

Following the pre-conjugation UFDF, the concentrated and filtered antibody can be transferred into an amine free carbonate buffer system. The carbonate buffer system can have a pH in a range from about 8.5 to about 9.6, or from about 9.0 to about 9.6, or from about 9.2 to about 9.4, or from about 9.4 to about 9.6, or a pH of about 9.4.

A chelator, for example, DFO, in solvent is added to a target concentration into the buffer system containing the antibody, and additional solvent can be added to the solution to a desired percentage. The chelator can be added in molar excess of the antibody, for example, 3.5-5:1 chelator to antibody. The total reaction volume can be up to 5 L.

The reaction temperature and the reaction time are inversely related. For example, if the reaction temperature is higher, the reaction time is lower. If the reaction temperature is lower, the reaction time is higher. Illustratively, at a temperature above about 18° C., the reaction may take less than 2 hours; at a temperature below 18° C., the reaction may take more than 2 hours.

The conjugation reaction can be terminated by quenching, for example, by the addition of acetic acid.

In some embodiments, conjugation of the antibody with deferoxamine is performed to produce DFO-mAb conjugates. In some embodiments, conjugation of the antibody with p-SCN-Bn-deferoxamine is performed to produce DFO-mAb conjugates.

Exemplary solvents for the chelator include DMSO and DMA. Subsequent UFDF steps utilize membranes, and the membrane is chosen based on the solvent system used in the conjugation step. For example, DMA dissolves PES membranes, so the two could not be used in the same system.

Carbonate buffers are not preferred for stability of the conjugate during long term storage. Thus, once the antibody-chelator conjugates have been formed, they can be buffer exchanged into a buffer chosen specifically for long term storage and stability. Exemplary buffers include citrate, acetate, phosphate, arginine, and histidine buffers. A further UFDF step can be performed to remove residual salts and to provide a suitable concentration, excipient level, and pH of the conjugated monoclonal antibody. The resulting antibody-chelator conjugates can be sterile filtered and stored for subsequent formulation.

III. Methods of Using Radiolabeled Immunoconjugates

In certain aspects, the present disclosure provides diagnostic and therapeutic methods of use of the radiolabeled antibody conjugates of the present disclosure.

According to one aspect, the present disclosure provides methods of detecting LAG3 in a tissue, the methods comprising administering a radiolabeled anti-LAG3 antibody conjugate of the provided herein to the tissue; and visualizing the LAG3 expression by positron emission tomography (PET) imaging. In certain embodiments, the tissue comprises cells or cell lines. In certain embodiments, the tissue is present in a subject, wherein the subject is a mammal. In certain embodiments, the subject is a human subject. In certain embodiments, the subject has a disease or disorder selected from the group consisting of cancer, infectious disease and inflammatory disease. In one embodiment, the subject has cancer. In certain embodiments, the infectious disease is a bacterial infection caused by, for example, rickettsial bacteria, bacilli, *klebsiella*, meningococci and gonococci, *proteus*, pneumonococci, *pseudomonas*, streptococci, staphylococci, *serratia*, Borriella, *Bacillus anthricis, Chlamydia, Clostridium, Corynebacterium diphtheriae, Legionella, Mycobacterium leprae, Mycobacterium lepromatosis, Salmonella, Vibrio cholerae*, and *Yersinia pestis*. In certain embodiments, the infectious disease is a viral infection caused by, for example, human immunodeficiency virus (HIV), hepatitis C virus (HCV), hepatitis B virus (HBV), herpes virus (e.g., VZV, HSV-I, HAV-6, HSV-II, CMV, and Epstein Barr virus), human papilloma virus (HPV), lymphocytic choriomeningitis virus (LCMV), and simian immunodeficiency virus (SIV). In certain embodiments, the infectious disease is a parasitic infection caused by, for example, *Entamoeba* spp., *Enterobius vermicularis, Leishmania* spp., *Toxocara* spp., *Plasmodium* spp., *Schistosoma* spp., *Taenia solium, Toxoplasma gondii*, and *Trypanosoma cruzi*. In certain embodiments, the infectious disease is a fungal infection caused by, for example, *Aspergillus (fumigatus, niger*, etc.), *Blastomyces dermatitidis, Candida (albicans, krusei, glabrata, tropicalis*, etc.), *Coccidioides immitis, Cryptococcus neoformans*, Genus Mucorales (*mucor, absidia, rhizopus*, etc.), *Histoplasma capsulatum, Paracoccidioides brasiliensis*, and *Sporothrix schenkii*.

According to one aspect, the present disclosure provides methods of imaging a tissue that expresses LAG3 comprising administering a radiolabeled anti-LAG3 antibody conjugate of the present disclosure to the tissue; and visualizing the LAG3 expression by positron emission tomography (PET) imaging. In one embodiment, the tissue is comprised in a tumor. In one embodiment, the tissue is comprised in a tumor cell culture or tumor cell line. In one embodiment, the tissue is comprised in a tumor lesion in a subject. In one embodiment, the tissue is intratumoral lymphocytes in a tissue. In one embodiment, the tissue comprises LAG3-expressing cells.

According to one aspect, the present disclosure provides methods for measuring response to a therapy, wherein the response to a therapy is measured by measuring inflammation. The methods, according to this aspect, comprise administering a radiolabeled antibody conjugate provided herein to a subject in need thereof and visualizing the LAG3 expression by positron emission tomography (PET) imaging. In certain embodiments, the inflammation is present in a tumor in the subject. In certain embodiments, an increase in LAG3 expression correlates to increase in inflammation in a tumor. In certain embodiments, the inflammation is present in an infected tissue in the subject. In certain embodiments, an decrease in LAG3 expression correlates to a decrease in inflammation in an infected tissue.

According to one aspect, the present disclosure provides methods for measuring response to a therapy, wherein the response to a therapy is measured by measuring inflammation. The methods, according to this aspect, comprise (i) administering a radiolabeled antibody conjugate provided herein to a subject in need thereof and visualizing the LAG3 expression by positron emission tomography (PET) imaging, and (ii) repeating step (i) one or more times after initiation of therapy. In certain embodiments, the inflammation is present in a tissue in the subject. In certain embodiments, an increase in LAG3 expression correlates to increase in inflammation in the tissue. In certain embodiments, a decrease in LAG3 expression correlates to a decrease in inflammation in the tissue. In certain embodiments, LAG3 expression visualized in step (i) is compared to LAG3 expression visualized in step (ii).

According to one aspect, the present disclosure provides methods for determining if a patient is suitable for anti-tumor therapy comprising an inhibitor of LAG3, the methods comprising selecting a patient with a solid tumor, administering a radiolabeled antibody conjugate of the present disclosure, and localizing the administered radiolabeled antibody conjugate in the tumor by PET imaging wherein presence of the radiolabeled antibody conjugate in the tumor identifies the patient as suitable for anti-tumor therapy comprising an inhibitor of LAG3.

According to one aspect, the present disclosure provides methods for identifying a candidate for anti-tumor therapy comprising an inhibitor of LAG3 and an inhibitor of the PD-1/PD-L1 signaling axis, the methods comprising selecting a patient with a solid tumor, administering a radiolabeled antibody conjugate of the present disclosure, and localizing the administered radiolabeled antibody conjugate in the tumor by PET imaging wherein presence of the radiolabeled antibody conjugate in the tumor identifies the patient as suitable for anti-tumor therapy comprising an inhibitor of LAG3. In some embodiments, the patient is further administered a radiolabeled anti-PD-1 conjugate and the administered radiolabeled anti-PD-1 conjugate is localized in the tumor by PET imaging, wherein presence of the radiolabeled antibody conjugate in the tumor identifies the patient as suitable for anti-tumor therapy comprising an inhibitor of the PD-1/PD-L1 signaling axis.

Provided herein are also methods for predicting response of a patient to an anti-tumor therapy, the methods comprising selecting a patient with a solid tumor; and determining if the tumor is LAG3-positive, wherein if the tumor is LAG3-positive it predicts a positive response of the patient to an anti-tumor therapy. In certain embodiments, the tumor is determined positive by administering a radiolabeled anti-LAG3 antibody conjugate of the present disclosure and localizing the radiolabeled antibody conjugate in the tumor by PET imaging wherein presence of the radiolabeled antibody conjugate in the tumor indicates that the tumor is LAG3-positive.

In some embodiments, the anti-tumor therapy is selected from a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504, as well as those disclosed in Patent Publication No. US 2015-0203580), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

In some embodiments, the anti-tumor therapy is selected from the following: nivolumab, ipilimumab, pembrolizumab, and combinations thereof.

According to one aspect, the present disclosure provides methods for predicting response of a patient to an anti-tumor therapy comprising an inhibitor of LAG3, the methods comprising selecting a patient with a solid tumor, determining if the tumor is LAG3-positive, wherein a positive response of the patient is predicted if the tumor is LAG3-positive. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is LAG3-positive.

According to one aspect, the present disclosure provides methods for predicting response of a patient to an anti-tumor therapy comprising an inhibitor of LAG3 in combination with an inhibitor of the PD-1/PD-L1 signaling axis, the methods comprising selecting a patient with a solid tumor, determining if the tumor is LAG3 positive and PD-1-positive, wherein a positive response of the patient is predicted if the tumor is LAG3 positive and PD-1-positive. In certain embodiments, the tumor is determined LAG3 positive by administering a radiolabeled anti-LAG3 conjugate and localizing the radiolabeled antibody conjugate in the tumor by PET imaging wherein presence of the radiolabeled antibody conjugate in the tumor indicates that the tumor is LAG3-positive. In certain embodiments, the tumor is determined PD-1 positive by further administering a radiolabeled anti-PD-1 conjugate and localizing the radiolabeled anti-PD-1 conjugate in the tumor by PET imaging wherein presence of the radiolabeled antibody conjugate in the tumor indicates that the tumor is PD-1-positive.

According to one aspect, the present disclosure provides methods for detecting a LAG3-positive tumor in a subject. The methods, according to this aspect, comprise selecting a subject with a solid tumor; administering a radiolabeled antibody conjugate of the present disclosure to the subject; and determining localization of the radiolabeled antibody conjugate by PET imaging, wherein presence of the radiolabeled antibody conjugate in a tumor indicates that the tumor is LAG3-positive.

In some aspects, the subject in need thereof is administered a dose of about 20 mg or less, a dose of about 15 mg or less, a dose of about 10 mg or less, for example, a dose of 2 mg, or 5 mg, or 10 mg, of a radiolabeled anti-LAG3 antibody conjugate.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., colon cancer, breast cancer, lung cancer, prostate cancer, skin cancer, liver cancer, bone cancer, ovarian cancer, cervical cancer, pancreatic cancer, head and neck cancer, and brain cancer. The term includes subjects with primary or metastatic tumors (advanced malignancies). In certain embodiments, the expression "a subject in need thereof" includes patients with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes patients with a solid tumor which has been treated with one or more lines of prior therapy but which has subsequently relapsed or metastasized. In certain embodiments, the term includes subjects having an inflammatory disease or disorder including, but not limited to, cancer, rheumatoid arthritis, atherosclerosis, periodontitis, hay fever, heart disease, coronary artery disease, infectious disease, bronchitis, dermatitis, meningitis, asthma, tuberculosis, ulcerative colitis, Crohn's disease, inflammatory bowel disease, hepatitis, sinusitis, psoriasis, allergy, fibrosis, lupus, vasiculitis, ankylosing spondylitis, Graves' disease, Celiac disease, fibromyalgia, and transplant rejection.

In certain embodiments, the methods of the present disclosure are used in a subject with a solid tumor. The terms "tumor", "cancer" and "malignancy" are interchangeably used herein. As used herein, the term "solid tumor" refers to an abnormal mass of tissue that usually does not contain cysts or liquid areas. Solid tumors may be benign (not cancer) or malignant (cancer). In some embodiments, the tumor is metastatic. For the purposes of the present disclosure, the term "solid tumor" means malignant solid tumors. The term includes different types of solid tumors named for the cell types that form them, viz. sarcomas, carcinomas and lymphomas. In certain embodiments, the term "solid tumor" includes cancers including, but not limited to, colorectal cancer, ovarian cancer, prostate cancer, breast cancer, brain cancer, cervical cancer, bladder cancer, anal cancer, uterine cancer, colon cancer, liver cancer, melanoma, metastatic melanoma, pancreatic cancer, lung cancer, endometrial cancer, bone cancer, testicular cancer, skin cancer, kidney cancer, stomach cancer, esophageal cancer, head and neck cancer, salivary gland cancer, and myeloma.

In some embodiments, the methods disclosed herein can be used in a subject with cancer, for example, a subject having blood cancer, brain cancer, renal cell cancer, ovarian cancer, bladder cancer, prostate cancer, breast cancer, hepatic cell carcinoma, bone cancer, colon cancer, non-small-cell lung cancer, squamous cell carcinoma of head and neck, colorectal cancer, mesothelioma, B cell lymphoma, and melanoma. In some aspects, the cancer is metastatic, for example, metastatic melanoma.

According to one aspect, the present disclosure provides methods of treating a tumor in a subject. The methods, according to this aspect, comprise selecting a subject with a solid tumor; determining that the tumor is LAG3-positive; and administering one or more doses of an inhibitor of LAG3. In certain embodiments, the tumor is determined to be LAG3-positive by administering a radiolabeled antibody conjugate of the present disclosure to the subject; and visualizing the radiolabeled antibody conjugate in the tumor by PET imaging, wherein presence of the radiolabeled antibody conjugate in the tumor indicates that the tumor is LAG3-positive.

In a further aspect, the methods of treating comprise administering one or more doses of an inhibitor of LAG3 in combination with a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGES), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA× CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any other therapy care to treat cancer. In certain embodiments, an inhibitor of LAG3 may be used in combination with cancer vaccines including dendritic cell vaccines, oncolytic viruses, tumor cell vaccines, etc. to augment the anti-tumor response. Examples of cancer vaccines that can be used in combination with an inhibitor of LAG3 include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, an inhibitor of LAG3 may be used in combination with radiation therapy in methods to generate long-term durable anti-tumor responses and/or enhance survival of patients with cancer. In some embodiments, the inhibitor of LAG3, e.g. an anti-LAG3 antibody, may be administered prior to, concomitantly or after administering radiation therapy to a cancer patient. For example, radiation therapy may be administered in one or more doses to tumor lesions followed by administration of one or more doses of anti-LAG3 antibodies. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-LAG3 antibody. For example, intracranial radiation may be administered to a patient with brain cancer (e.g., glioblastoma multiforme) in combination with systemic administration of an anti-LAG3 antibody. In certain embodiments, the anti-LAG3 antibodies may be administered in combination with radiation therapy and a chemotherapeutic agent (e.g., temozolomide) or a VEGF antagonist (e.g., aflibercept).

In certain embodiments, an inhibitor of LAG3 may be administered in combination with one or more anti-viral drugs to treat viral infection caused by, for example, LCMV, HIV, HPV, HBV or HCV. Examples of anti-viral drugs include, but are not limited to, zidovudine, lamivudine, abacavir, ribavirin, lopinavir, efavirenz, cobicistat, tenofovir, rilpivirine and corticosteroids.

In certain embodiments, an inhibitor of LAG3 may be administered in combination with one or more anti-bacterial drugs to treat bacterial infection caused by, for example, rickettsial bacteria, bacilli, *klebsiella*, meningococci and gonococci, *proteus*, pneumonococci, *pseudomonas*, streptococci, staphylococci, *serratia*, Borriella, *Bacillus* anthricis, *Chlamydia, Clostridium, Corynebacterium diphtheriae, Legionella, Mycobacterium leprae, Mycobacterium lepromatosis, Salmonella, Vibrio cholerae,* and *Yersinia pestis*. Examples of anti-bacterial drugs include, but are not limited to, penicillins, tetracyclines, cephalosporins, quinolones, lincomycins, macrolides, ketolides, sulfonamides, glycopeptides, aminoglycosides, and carbapenems.

In certain embodiments, an inhibitor of LAG3 may be administered in combination with one or more anti-fungal drugs to treat fungal infection caused by, for example, *Aspergillus (fumigatus, niger,* etc.), *Blastomyces dermatitidis, Candida (albicans, krusei, glabrata, tropicalis,* etc.), *Coccidioides immitis, Cryptococcus neoformans,* Genus Mucorales *(mucor, absidia, rhizopus,* etc.), *Histoplasma capsulatum, Paracoccidioides brasiliensis,* and *Sporothrix schenkii*. Examples of anti-fungal drugs include, but are not limited to, amphotericin B, fluconazole, vorixonazole, posaconazole, itraconazole, voriconazole, anidulafungin, caspofungin, micafungin, and flucytosine.

In certain embodiments, an inhibitor of LAG3 may be administered in combination with one or more anti-parasitic drugs to treat parasitic infection caused by, for example, *Entamoeba* spp., *Enterobius vermicularis, Leishmania* spp., *Toxocara* spp., *Plasmodium* spp., *Schistosoma* spp., *Taenia solium, Toxoplasma gondii,* and *Trypanosoma cruzi*. Examples of anti-parasitic drugs include, but are not limited to, praziquantel, oxamniquine, metronidazole, tinidazole, nitazoxanide, dehydroemetine or chloroquine, diloxanide furoate, iodoquinoline, chloroquine, paromomycin, pyrantel pamoate, albendazole, nifurtimox, and benznidazole.

The additional therapeutically active agent(s)/component(s) may be administered prior to, concurrent with, or after the administration of the inhibitor of LAG3. For purposes of the present disclosure, such administration regimens are considered the administration of a LAG3 inhibitor "in combination with" a second therapeutically active component.

In some aspects, the methods of treating comprise selecting a subject with a bacterial infection, a viral infection, a fungal infection, or a parasitic infection; determining that an affected tissue in the subject is LAG3-positive; and administering one or more doses of a therapeutic agent appropriate to the infection. In certain embodiments, the affected tissue is determined to be LAG3-positive by administering a radiolabeled anti-LAG3 conjugate of the present disclosure to the subject; and visualizing the radiolabeled antibody conjugate in the subject by PET imaging, wherein presence of the radiolabeled antibody conjugate in a tissue indicates that the tissue is LAG3-positive. In certain embodiments, the steps of administering and visualizing are performed one or more times in order to monitor the effectiveness of the therapeutic agent in treating the infection.

In some aspects, the methods of treating comprise selecting a subject with a solid tumor; determining that the tumor is LAG3-positive and PD-1-positive; and administering one or more doses of an inhibitor of LAG3 and/or one or more doses of an inhibitor of the PD-1/PD-L1 signaling axis (e.g., an anti-PD-1 antibody or an anti-PD-L1 antibody). In certain embodiments, the tumor is determined to be LAG3-positive by administering a radiolabeled anti-LAG3 conjugate of the present disclosure to the subject; and visualizing the radiolabeled antibody conjugate in the tumor by PET imaging, wherein presence of the radiolabeled antibody conjugate in the tumor indicates that the tumor is LAG3-positive. In certain embodiments, the tumor is determined to be PD-1-positive by administering a radiolabeled anti-PD-1 conjugate of the present disclosure to the subject; and visualizing the radiolabeled anti-PD-1 conjugate in the tumor by PET imaging, wherein presence of the radiolabeled anti-PD-1 conjugate in the tumor indicates that the tumor is PD-1-positive.

Exemplary anti-PD-1 antibodies include REGN2810, BGB-A317, nivolumab, pidilizumab, and pembrolizumab.

Exemplary anti-PD-L1 antibodies include atezolizumab, avelumab, durvalumab, MDX-1105, and REGN3504, as well as those disclosed in Patent Publication No. US 2015-0203580.

The inhibitor of the PD-1/PD-L1 signaling axis may be administered prior to, concurrent with, or after the administration of the inhibitor of LAG3. For purposes of the present disclosure, such administration regimens are considered the administration of a LAG3 inhibitor "in combination with" an inhibitor of the PD-1/PD-L1 signaling axis.

As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

According to one aspect, the present disclosure provides methods for monitoring the efficacy of an anti-tumor therapy in a subject, wherein the methods comprise selecting a subject with a solid tumor wherein the subject is being treated with an anti-tumor therapy; administering a radiolabeled anti-LAG3 conjugate of the present disclosure to the subject; imaging the localization of the administered radiolabeled conjugate in the tumor by PET imaging; and determining tumor growth, wherein a decrease from the baseline in radiolabeled signal indicates efficacy of the anti-tumor therapy. In certain embodiments, the anti-tumor therapy comprises an inhibitor of LAG3. In certain embodiments, the anti-tumor therapy further comprises an inhibitor of the PD-1/PD-L1 signaling axis (e.g., an anti-PD-1 antibody or an anti-PD-L1 antibody).

In certain embodiments, the present disclosure provides methods to assess changes in the inflammatory state of a tumor, the methods comprising selecting a subject with a solid tumor wherein the subject is being treated with an anti-tumor therapy; administering a radiolabeled anti-LAG3 conjugate provided herein to the subject; and imaging the localization of the administered radiolabeled conjugate in the tumor by PET imaging, wherein an increase from the baseline in radiolabeled signal indicates increase in inflammation and efficacy of the anti-tumor therapy. In certain embodiments, the anti-tumor therapy comprises an inhibitor of LAG3 and/or an inhibitor of the PD-1/PD-L1 signaling axis (e.g., an anti-PD-1 antibody or an anti-PD-L1 antibody). In certain embodiments, the anti-tumor therapy comprises a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

As used herein, the term "baseline," with respect to LAG3 expression in the tumor, means the numerical value of uptake of the radiolabeled conjugate for a subject prior to or at the time of administration of a dose of anti-tumor therapy. The uptake of the radiolabeled conjugate is determined using methods known in the art (see, for example, Oosting et al 2015, J. Nucl. Med. 56: 63-69). In certain embodiments, the anti-tumor therapy comprises an inhibitor of LAG3.

In some embodiments, sequential iPET scanning and tumor biopsies are performed before and after treatment with standard of care immunotherapies. Such immunotherapies can be selected from the following: nivolumab, ipilimumab, pembrolizumab, and combinations thereof.

To determine whether there is efficacy in anti-tumor therapy, the uptake of the radiolabeled conjugate is quantified at baseline and at one or more time points after administration of the LAG3 inhibitor. For example, the uptake of the administered radiolabeled antibody conjugate (e.g., radiolabeled anti-LAG3 antibody conjugate) may be measured at day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the LAG3 inhibitor (e.g., an anti-LAG3 antibody). The difference between the value of the uptake at a particular time point following initiation of treatment and the value of the uptake at baseline is used to establish whether anti-tumor therapy is efficacious (tumor regression or progression).

In certain embodiments, the radiolabeled antibody conjugate is administered intravenously or subcutaneously to the subject. In certain embodiments, the radiolabeled antibody conjugate is administered intra-tumorally. Upon administration, the radiolabeled antibody conjugate is localized in the tumor. The localized radiolabeled antibody conjugate is imaged by PET imaging and the uptake of the radiolabeled antibody conjugate by the tumor is measured by methods known in the art. In certain embodiments, the imaging is carried out 1, 2, 3, 4, 5, 6 or 7 days after administration of the radiolabeled conjugate. In certain embodiments, the imaging is carried out on the same day upon administration of the radiolabeled antibody conjugate.

In certain embodiments, the antibody or antigen-binding fragment thereof that binds specifically to LAG3. In certain embodiments, the anti-LAG3 antibody comprises the CDRs of a HCVR, wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554; and the CDRs of a LCVR, wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562.

In certain embodiments, the LAG3 inhibitor comprises an antibody or antigen-binding fragment thereof that binds specifically to LAG3. In certain embodiments, the anti-LAG3 antibody is BMS986016. In certain other embodiments, the LAG3 inhibitor comprises an antibody or antigen-binding fragment thereof that binds specifically to LAG3. In one embodiment, the anti-LAG3 antibody comprises an HCVR of SEQ ID NO: 418 and a LCVR of SEQ ID NO: 426.

IV. Examples

Certain embodiments of the disclosure are illustrated by the following non-limiting examples.

Example 1: Generation of Human Antibodies to LAG3

Human antibodies to LAG3 were generated using a fragment of LAG3 that ranges from about amino acids 29-450 of GenBank Accession NP_002277.4 (SEQ ID NO: 582) genetically fused to a mouse Fc region. The immunogen was administered directly, with an adjuvant to stimulate the immune response, to a VELOCIMMUNE® mouse (i.e., an engineered mouse comprising DNA encoding human Immunoglobulin heavy and kappa light chain variable regions), as described in U.S. Pat. No. 8,502,018 B2, or to a humanized Universal Light Chain (ULC) VelocImmune® mouse, as described in WO 2013022782. The antibody immune response was monitored by a LAG3-specific immunoassay. When a desired immune response was achieved splenocytes were harvested and fused with mouse myeloma cells to preserve their viability and form hybridoma cell lines. The hybridoma cell lines were screened and selected to identify cell lines that produce LAG3-specific antibodies. Using this technique, and the immunogen described above, several anti-LAG3 chimeric antibodies (i.e., antibodies possessing human variable domains and mouse constant domains) were obtained. Fully human versions of the antibodies can be made by replacing the mouse constant region with a human constant region. Exemplary antibodies generated in this manner from the VELOCIMMUNE® mice were designated as H1M14985N, H1M14987N, H2M14811N, H2M14885N, H2M14926N, H2M14927N, H2M14931N, H2M18336N, H2M18337N and H4H14813N.

Anti-LAG3 antibodies were also isolated directly from antigen-positive B cells (from either of the immunized mice) without fusion to myeloma cells, as described in U.S. Pat. No. 7,582,298, herein specifically incorporated by reference in its entirety. Using this method, several anti-LAG3 antibodies (i.e., antibodies possessing human variable domains and human constant domains) were obtained; exemplary antibodies generated in this manner were designated as follows: H4H15477P, H4H15483P, H4H15484P, H4H15491P, H4H17823P, H4H17826P2, H4H17828P2, H4sH15460P, H4sH15462P, H4sH15463P, H4sH15464P, H4sH15466P, H4sH15467P, H4sH15470P, H4sH15475P, H4sH15479P, H4sH15480P, H4sH15482P, H4sH15488P, H4sH15496P2, H4sH15498P2, H4sH15505P2, H4sH15518P2, H4sH15523P2, H4sH15530P2, H4sH15555P2, H4sH15558P2, H4sH15567P2, and H4H17819P.

Exemplary antibodies H4sH15496P2, H4sH15498P2, H4sH15505P2, H4sH15518P2, H4sH15523P2, H4sH15530P2, H4sH15555P2, H4sH15558P2, and H4sH15567P2 were generated from B-cells from the ULC VELOCIMMUNE® mice.

The biological properties of the exemplary antibodies generated in accordance with the methods of this Example are described in detail in the Examples set forth below.

Example 2: Conjugation of Anti-LAG3 Antibody H4sH15482P with p-SCN-Bn-DFO

In order to modify the parental anti-LAG3 antibody, H4sH15482P (having an HCVR/LCVR sequence pair of SEQ ID NOs: 418/426; hereinafter referred to as mAb1), and an isotype control antibody to be suitable for Immuno-PET studies with radiolabeling, a chelator, p-SCN-bn-Deferoxamine (DFO; Macrocylics, Cat #: B-705), was attached to the antibodies.

For the modification, mAb1, was first buffer exchanged into PBS, pH 7.2 from histidine buffer by dialysis at 4° C. overnight (Slide-A-Lyzer Dialysis Cassette G2 10 k MWCO; ThermoScientific) then buffer exchanged again using a PD-10 column (GE Healthcare, Cat. #: 17-0851-01) into a buffer composed of 50 mM carbonate buffer, 150 mM NaCl, pH 9.0 (conjugation buffer). To determine the concentration following the buffer exchanges, the samples were measured on a Nanodrop 2000 UV/VIS spectrometer (Thermo Scientific) using the MacVector sequence based extinction coefficient of 223400 $M^{-1}$ $cm^{-1}$ and molecular weight 145709 g/mol (see Table 2). In 15 a mL polypropylene tube, 1485.24 uL of mAb1 (70 mg) was added to 5374.8 uL of conjugation buffer. A 139 µL solution of DFO in DMSO was added in one-quarter increments to the mAb1 solution, each time gently being mixed by pipetting up-anddown. The final solution was 10 mg/mL mAb1 in conjugation buffer, 2% DMSO with 3-fold mole-to-mole excess of DFO. This solution was allowed to incubate in a 37° C. water bath with no additional stirring.

After 30 minutes at 37° C., the solution was promptly passed through a PD-10 desalting column (GE Healthcare, Cat. #: 17-0851-01), pre-equilibrated with a buffer containing 250 mM NaAcO at pH 5.4 (formulation buffer). The volume of the solution was reduced by approximately 50% with a 10K MWCO concentrator (Amicon Ultra-15 Centrifugal Filter Unit, EMD Millipore, Cat #: UFC901024). The final solution was sterile-filtered via a syringe filter (Acrodisc 13 mm syringe filter, Pall Corporation, Cat #: 4602). The concentration and DFO-to-Antibody Ratio (DAR) was subsequently measured by UV/VIS spectroscopy. See FIG. 1. For the absorbance measurement, the DFO-conjugated antibody was measured against the formulation buffer at 252 nm (A252), 280 nm (A280) and 600 nm (A600). For the calculation, the background was corrected at each absorbance value using the equation:

$$A_\lambda' = A_\lambda - A_{600}$$

Figure 2:
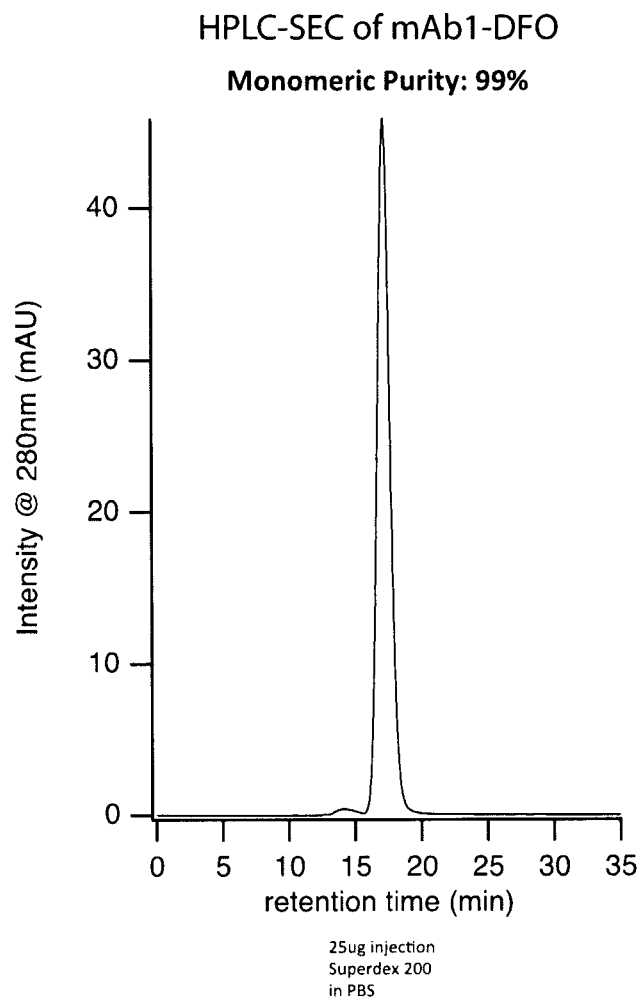
FIG. 2 depicts HPLC-SEC of DFO modified anti-LAG3 antibody.

The antibody conjugate was tested for aggregation using SEC chromatography, with 25 ug of the sample injected onto a Superdex 200 column (GE Healthcare, Cat. No. 17-5175-01) monitored at 280 nm with a PBS mobile phase (0.75 mL/min). See FIG. 2. The antibody integrity was evaluated by SDS-PAGE 4-20% Tris/Gly pre-cast gel (Novex) with 2 ug of the sample loaded. The antibody concentration, conjugate concentration, and DAR were calculated using the equations below:

Antibody Concentration Calculation $$Conc\ mAb\ (mg/mL) = \frac{A_{280}'}{\epsilon_{280}} * MW$$

Conjugate Concentration Calculation $$Conc\ conjugate\ (mg/mL) = \frac{A_{252}' - 1.53 A_{280}'}{\epsilon_{252} - 1.53\epsilon_{280}} * MW$$

DAR Calculation $$DAR = \frac{\epsilon_{252} A_{280}' - \epsilon_{280} A_{252}'}{18800 A_{252}' - 28700 A_{280}'}$$

TABLE 2

Molar extinction coefficients and molecular weight

| mAb | MW (gmol$^{-1}$) | $\epsilon_{280}$ (M$^{-1}$cm$^{-1}$) | $\epsilon_{252}$ (M$^{-1}$cm$^{-1}$) |
|---|---|---|---|
| mAb1 | 145709 | 223400 | 87077 |

TABLE 3

UV DAR, percent aggregate and concentration post DFO-attachment

| Antibody | UV DAR | Concentration (mg/mL) | % aggregate |
|---|---|---|---|
| mAb1 | 1.48 | 13.58 | 1.4% |

Example 3: $^{89}$Zr Chelation of DFO Conjugated Monoclonal Antibodies

For usage in ImmunoPET in vivo studies, the DFO-conjugated anti-LAG3 antibody, mAb1, and a DFO-conjugated isotype control antibody were radiolabeled with $^{89}$Zr.

DFO-conjugated antibody was first brought to 1.25 mg/mL in 1 M HEPES, pH 7.2. The composition of the DFO-Ab conjugate solutions for each study is listed in Table 4. Separately, $^{89}$Zr solution was prepared using the compositions for each corresponding study shown in Table 5. Stock $^{89}$Zr-oxalic acid solution was obtained from 3D Imaging. The final radioactivity of the solution was first confirmed using a Capintec CRC-25R dose calibrator (Capintec #520), then immediately combined with the DFO-Ab conjugate solution, gently mixed (pipetting up-and-down) and subsequently incubated for 45 minutes at room temperature.

After the incubation, the mixtures were transferred to desalting columns, either PD-10 (GE Healthcare, Cat. #: 17-0851-01) for study 1 or NAP-5 (GE Healthcare, Cat. #17-0853-02) for study 2, pre-equilibrated with 250 mM sodium acetate at pH 5.4 for gravity-fed desalting. For study 1, the reaction mixture was added to a PD-10 column. After the contents of the reaction entered the column bed, the flow through was discarded. The product was eluted with 250 mM sodium acetate at pH 5.4 (formulation buffer) and eluate was collected as per manufacturer's instructions. For study 2, the mixture was transferred to a NAP-5 column, and the flow through was discarded. The product was eluted with 250 mM sodium acetate at pH 5.4 (formulation buffer) and eluate was collected per the manufacturer's instructions. The Ab concentration was subsequently measured by UV/VIS spectroscopy, calculated using the appropriate extinction coefficient and the absorption at 280 nm using the equation:

Concentration in mg/mL=Absorption at 280 nm÷Extinction coefficient at 280 nm (found in Table 6)

The final mass measured in grams was recorded in Table 7. The radioactivity was measured using the dose calibrator and reported in Table 7. The final material (5 ug) was analyzed using a SEC-HPLC with UV 280 and radio-isotope detector connected in series (Agilent 1260 with Lablogic Radio-TLC/HPLC Detector, SCAN-RAM) using a Superdex 200 Increase column with PBS mobile phase at a flow rate of 0.75 mL/min. The radiotrace was used for determining radiochemical purity (100%—percent of unlabeled $^{89}$Zr) by comparing the integration of the total protein peak (~10 to 16 min) and unlabeled $^{89}$Zr peak (~25 min). The percent monomeric purity was determined by the UV 280 trace by comparing the integration of the high molecular weight (HMW) species peak (10 min to ~15 min) to the monomer (~16 min).

The specific activity and protein recovery (%) of each radiolabeled conjugate was determined using the following equations:

Mass of conjugate in mg=concentration in mg/mL× mass of solution in grams     a.

Specific activity in mCi/mg=activity of vial in mCi÷mass of conjugate in mg     b.

Protein recovery=starting conjugate mass (mg)÷Mass of conjugate in mg     c.

Figure 3:
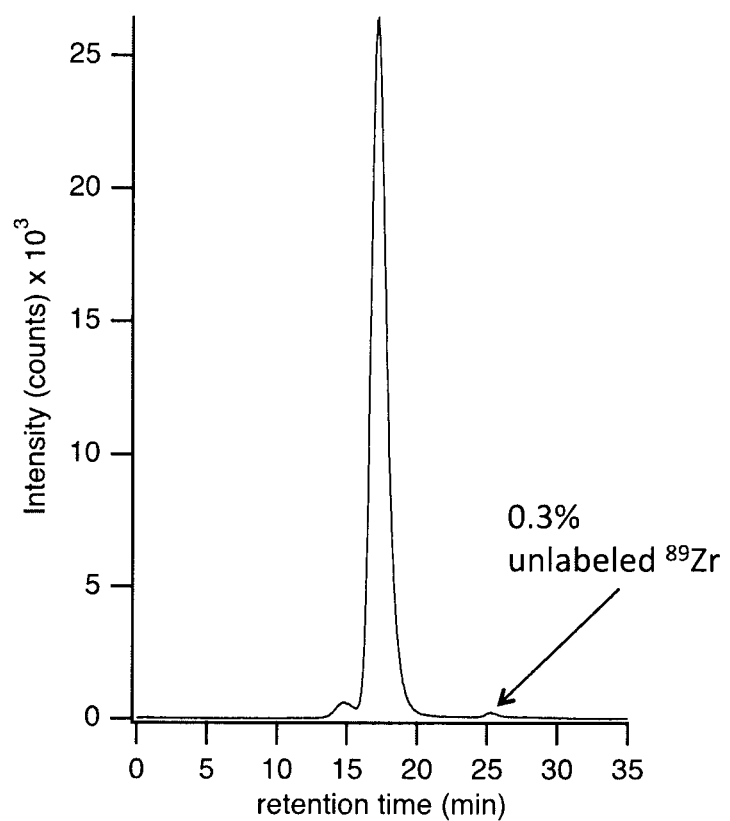
FIG. 3 depicts radio-SEC-HPLC of isotype-DFO-conjugate after $^{89}$Zr radiolabeling for Study 1.
Figure 4:
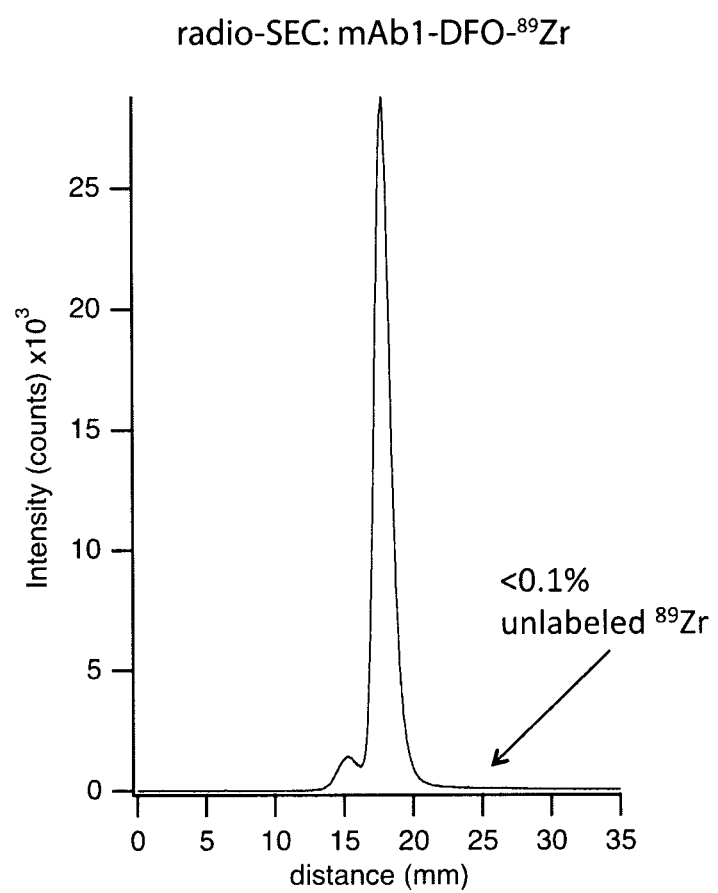
FIG. 4 depicts radio-SEC-HPLC of anti-LAG3-DFO-conjugate after $^{89}$Zr radiolabeling for Study 1.
Figure 5:
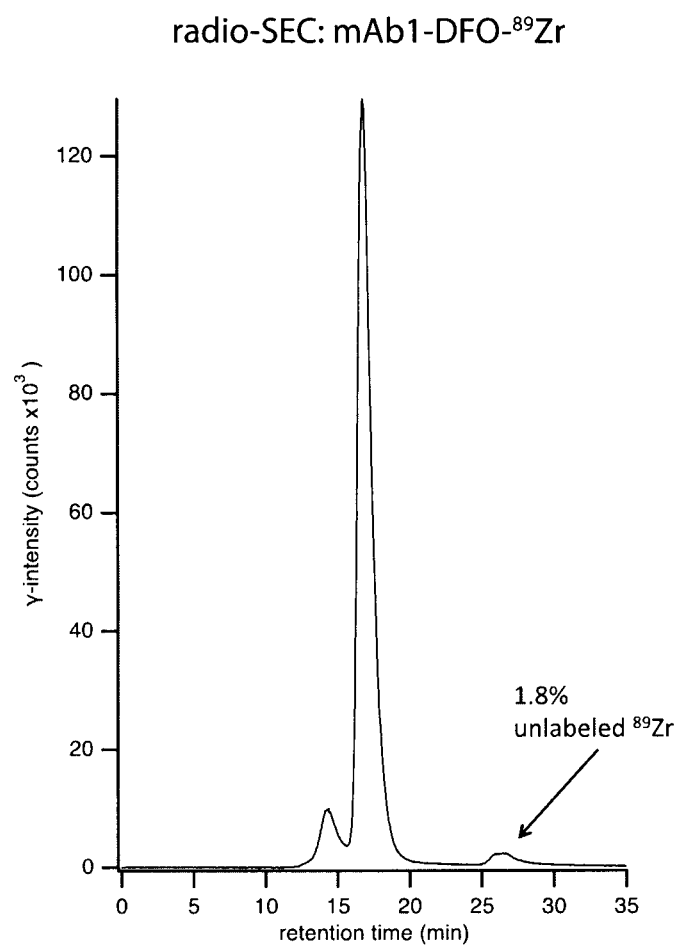
FIG. 5 depicts radio-SEC-HPLC of anti-LAG3-DFO-conjugate after $^{89}$Zr radiolabeling for Study 2.
Figure 6:
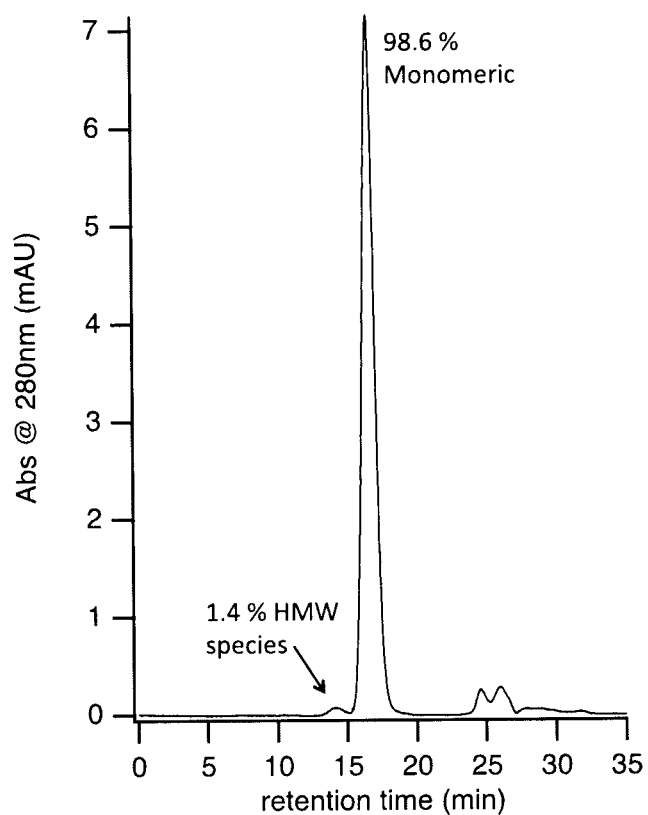
FIG. 6 depicts UV280-SEC-HPLC chromatogram and radio-iTLC trace of isotype-DFO-conjugate after $^{89}$Zr radiolabeling for Study 1.
Figure 7:
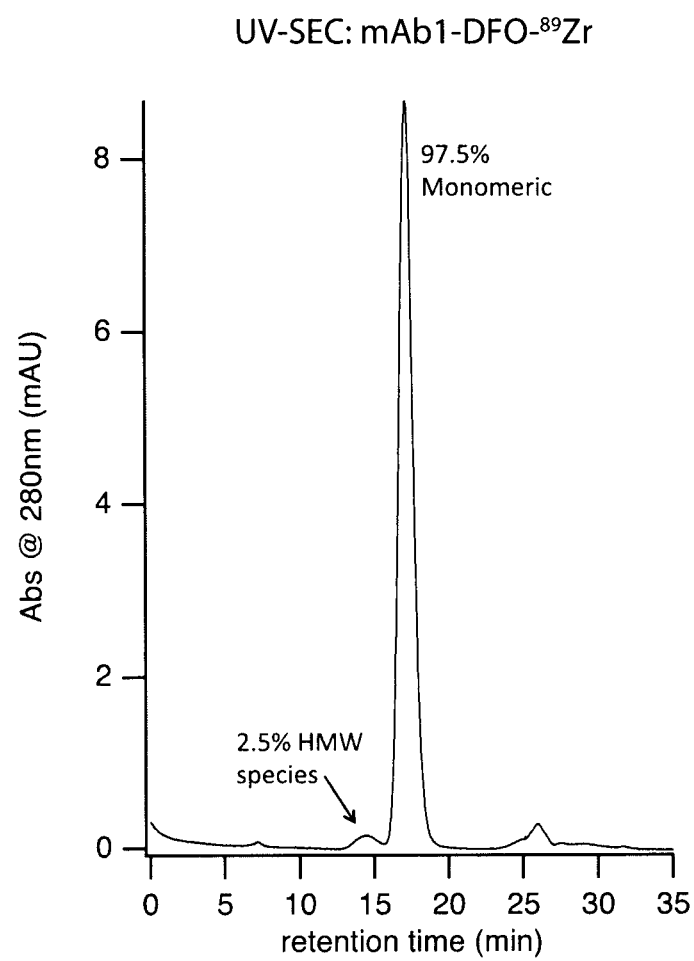
FIG. 7 depicts UV280-SEC-HPLC chromatogram and radio-iTLC trace of anti-LAG3-DFO-conjugate after $^{89}$Zr radiolabeling for Study 1.
Figure 8:
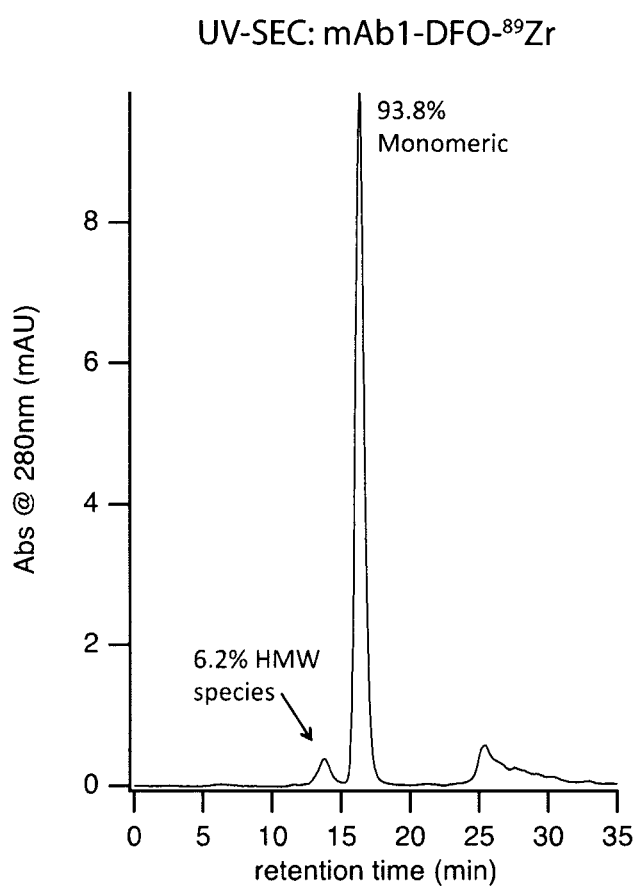
FIG. 8 depicts UV280-SEC-HPLC chromatogram and radio-iTLC trace of anti-LAG3-DFO-conjugate after $^{89}$Zr radiolabeling for Study 2.

Finally the appearance was noted and recorded in Table 7. The results are consolidated in Table 7. The radio-SEC-HPLC chromatograms, shown in FIGS. 3-5, confirm at least 98% radiochemical purity. The UV280-HPLC SEC chromatograms shown in FIGS. 6-8 confirm the highly monomeric product (>90%).

TABLE 4

DFO-antibody conjugate preparation for radiolabeling

| Radiolabeling # | Study # | Radiolabeling Lots | Concentration (mg/mL) | DAR* | Conjugate mass (mg) | Total volume (uL) | Final Concentration (mg/mL) |
|---|---|---|---|---|---|---|---|
| 1 | 1 | Isotype-DFO-$^{89}$Zr | 15.4 | 1.53 | 250 | 200 | 1.25 |
| 2 | 1 | mAb1-DFO-$^{89}$Zr | 13.6 | 1.48 | 500 | 400 | 1.25 |
| 3 | 2 | mAb1-DFO-$^{89}$Zr | 13.6 | 1.48 | 100 | 80 | 1.25 |

*DAR is defined as the DFO to Antibody Ratio

TABLE 5

$^{89}$Zr reaction solution preparation for radiolabeling

| Radiolabeling | Study # | Radiolabeling Lots | $^{89}$Zr-oxalate (uL) | 1M HEPES, pH 7.2 (uL) | Final Vol (uL) | Final Activity (uCi) | Specific Activity (uCi/uL) |
|---|---|---|---|---|---|---|---|
| 1 | 1 | Isotype-DFO-$^{89}$Zr | ~3 | 500 | 1000 | 995 | 1.0 |
| 2 | 1 | mAb1-DFO-$^{89}$Zr | ~5 | 500 | 2000 | 2060 | 1.0 |
| 3 | 2 | mAb1-DFO-$^{89}$Zr | ~6 | 394 | 400 | 2010 | 5.0 |

TABLE 6

Extinction coefficients for conjugate lots

| Radiolabeling Lot | $\varepsilon_{280}$ (AU ml mg$^{-1}$ cm$^{-1}$) |
|---|---|
| Isotype-DFO-$^{89}$Zr | 1.70 |
| mAb1-DFO-$^{89}$Zr | 1.72 |

TABLE 7

Summary of $^{89}$Zr labeled DFO-Ab conjugates for in vivo imaging and biodistribution studies

| Radiolabeling | Study # | Conjugate Lots | Appearance | Radiochemical Purity* (%) | Monomeric Purity** (%) | Protein Recovery (%) | Conc. (mg/mL) | Specific Activity (mCi/mg) |
|---|---|---|---|---|---|---|---|---|
| 1 | 1 | Isotype-DFO-$^{89}$Zr | Clear | 99.7% | 98.6% | 70% | 0.108 | 3.41 |
| 2 | 1 | mAb1-DFO-$^{89}$Zr | Clear | >99.9% | 97.5% | 70% | 0.133 | 3.58 |
| 3 | 2 | mAb1-DFO-$^{89}$Zr | Clear | 98.2% | 93.8% | 57% | 0.121 | 14.7 |

*by radio-SEC-HPLC,
** by UV-SEC-HPLC

Example 4: Immunoreactivity

The immunoreactivity (IR) of the radiolabeled anti-LAG3 antibody and isotype control antibody was measured as follows. In these assays, 20 ng of the respective $^{89}$Zr labeled antibodies were added to 15×10$^6$ MC38-cOVA/eGFP-mLAG3$^{-/-}$hLAG3$^{Tg}$ cells in a final volume of 1 mL. Samples were incubated for 45 minutes (at 37° C., 5% CO$_2$) with continuous mixing before undergoing 2 washes with media to remove any unbound antibody. The radioactivity of the test cell pellets was then counted in an automatic gamma counter (2470 Wizard2, Perkin Elmer) against 2 reference standards containing the same 20 ng of $^{89}$Zr labeled antibody. The percentage immunoreactivity was determined for the samples using the average of the standards as a measure of total activity.

As seen in Table 8, $^{89}$Zr labeled anti-LAG3 antibody retained immunoreactivity following conjugation and radiolabeling, with 86% IR.

TABLE 8

Immunoreactivity of $^{89}$Zr chelated DFO-conjugates

| Samples | Zr89 CPM |
|---|---|
| Standard 1 | 39643 |
| Standard 2 | 40134 |
| Average of Standards | 39889 |
| Cells | 34261 |
| IR | 86% |

Example 5: Selective Localization of Radiolabeled Anti-LAG3 Antibody to LAG3 Positive Tumors in Mice Implantation of Tumors and Allocation of Dosing Groups:

For in vivo imaging studies, a LAG3 positive tumor line was used. First, a murine colon carcinoma cell-line MC38-cOVA/eGFP-mLAG3$^{-/-}$hLAG3$^{Tg}$ was used. Here, cells over-express human LAG3 and full-length chicken ovalbumin fused with eGFP that was introduced by lentiviral transduction (pLVX EF1a and pLKO SSFV, respectively). For MC38-cOVA/eGFP-mLAG3$^{-/-}$hLAG3$^{Tg}$ tumor allografts, 1×10$^6$ cells were implanted subcutaneously into the left flank of male NCr nude (Taconic, Hudson N.Y.). Once tumors had reached an average volume of 100-150 mm$^3$ (~Day 7 post implantation), mice were randomized into groups of 5 and dosed with test or control $^{89}$Zr radiolabeled antibodies.

Dosing and Biodistribution of $^{89}$Zr-DFO-mAb1:

For the initial study in nude mice bearing MC38/ova/LAG3 tumors, mice received 50±1 μCi of $^{89}$Zr labeled antibody with a protein dose ~0.6 mg/kg. For the biodistribution studies, mice were euthanized 6 days post-dosing and blood was collected via cardiac puncture. Tumors and normal tissues were then excised and placed in counting tubes. Count data for $^{89}$Zr in CPM was then collected by measuring samples on an automatic gamma counter (Wizard 2470, Perkin Elmer). All tissues were also weighed and the percent-injected dose per gram (% ID/g) was calculated for each sample using standards prepared from the injected material.

Results, Summary, and Conclusion:

In this example, the NCr mice bearing MC38/ova/hLAG3 tumors received $^{89}$Zr conjugated anti-LAG3 mAb1 or non-binding antibody at a final dose of 50 μCi/mouse. Mice were subsequently left for 6 days until blood, tumor and tissues were taken and the % ID/g for the samples was calculated for all samples. The average % ID/g for each antibody is presented in Table 9. From this, the clear high uptake in MC38/ova/hLAG3 tumors is apparent over other normal tissues, with tumor uptake of 43.1% being significantly higher than the next highest uptake of 6.6% ID/g observed in the thymus. The specificity of anti-LAG3 mAb1 uptake into tumor is apparent in the significantly reduced tumor uptake of 7.8% observed for the non-binding antibody.

TABLE 9

| SAMPLE | $^{89}$Zr-mAb1 AVERAGE % ID/G | $^{89}$Zr-mAb1 STDEV % ID/G | $^{89}$Zr-non-binding Ab AVERAGE % ID/G | $^{89}$Zr-non-binding Ab STDEV % ID/G |
|---|---|---|---|---|
| LIVER | 0.5 | 6.2 | 3.9 | 0.3 |
| SPLEEN | 4.2 | 0.8 | 6.7 | 0.8 |
| KIDNEY | 5.1 | 0.8 | 6.2 | 1.2 |
| BONE | 4.3 | 2.1 | 4.9 | 1.0 |
| LUNG | 3.1 | 2.3 | 9.3 | 2.1 |
| HEART | 2.6 | 0.9 | 6.5 | 2.4 |
| BLOOD | 5.9 | 3.1 | 15.7 | 2.6 |
| THYMUS | 6.7 | 1.7 | 12.1 | 1.8 |
| MC38/ova/LAG3 | 43.1 | 9.5 | 7.8 | 0.4 |
| S. BOWEL | 1.7 | 0.5 | 2.8 | 0.5 |

Example 6: Selective Localization of Radiolabeled Anti-LAG3 Antibody to Raji/PBMC Tumors in Mice This Example describes the in vivo imaging and ex vivo biodistribution of a Zirconium-89 labeled DFO-anti-LAG3 antibody conjugate in NSG mice co-implanted with Raji cells and human PBMC.

The exemplary antibody used in this Example was MAb1, comprising HCVR/LCVR of SEQ ID NOs: 418/426.

Implantation of Tumors and Allocation of Dosing Groups:

To demonstrate specificity of the radiolabeled antibody for LAG3 targeting, 2×10$^6$ Raji cells and 5×10$^5$ human PBMC (Lot 0151029, ReachBio Research Labs) were co-implanted into the right flank of female NSG mice (8-10 weeks old, Jackson Labs). 14 days post-tumor implantation, mice were randomized into groups of 4 and injected intravenously with varying protein doses of $^{89}$Zr-DFO-mAb1.

Dosing and PET/CT Imaging of $^{89}$Zr-DFO-mAb1:

Mice bearing Raji/hPBMC tumors were injected with 5, 0.3, 0.1, or 0.03 mg/kg $^{89}$Zr-DFO-mAb1 at day 14 post-tumor implantation. Mice who received 0.1 and 0.03 mg/kg doses received ~30 or ~9 μCi of radiolabeled $^{89}$Zr-DFO-mAb1, respectively. The mice who received 5 or 0.3 mg/kg protein doses received ~30 μCi of radiolabeled $^{89}$Zr-DFO-mAb1 and additional non-DFO conjugated mAb1 (L5) as supplement to yield the final injected total protein dose.

PET imaging of antibody localization was assessed 6 days after administration of $^{89}$Zr-DFO-mAb1. A Sofie Biosciences G8 PET/CT was used to acquire PET/CT images (Sofie Biosciences and Perkin Elmer). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and subsequently co-registered with the PET images. Images were prepared using VivoQuant post-processing software (inviCRO Imaging Services).

Biodistribution of $^{89}$Zr-DFO-mAb1:

For biodistribution studies, mice were euthanized at the final time-point (6 days post-$^{89}$Zr-DFO-mAb1 administration) and blood was collected via cardiac puncture. Raji/hPBMC tumors and normal tissues were then excised, placed in counting tubes, and weighed. Count data for $^{89}$Zr in CPM was then collected by measuring samples on an automatic gamma counter (Wizard 2470, Perkin Elmer). The percent-injected dose per gram (% ID/g) was calculated for each sample using standards prepared from the injected material.

Figure 9:
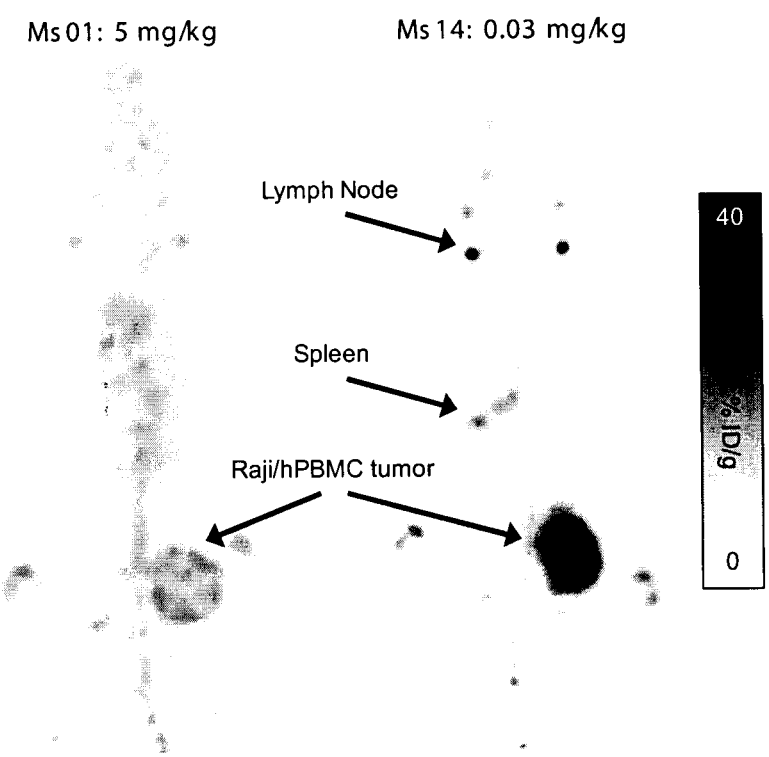
FIG. 9 provides representative images of $^{89}$Zr-DFO-mAb1 injected at a protein dose of 5 mg/kg (Ms01) or 0.03 mg/kg (Ms14) demonstrating specific targeting of $^{89}$Zr-DFO-mAb1 to Raji/hPBMC tumors using 0.03 mg/kg of $^{89}$Zr-DFO-mAb1 and blocking at 5 mg/kg of $^{89}$Zr-DFO-mAb1. Specific uptake in the spleen and lymph nodes is seen at the lower dose of 0.03 mg/kg $^{89}$Zr-DFO-mAb1.

Results, Summary, and Conclusions:

This study demonstrates antigen-specific targeting of $^{89}$Zr-DFO-mAb1 to LAG3 expressed on human lymphocytes in subcutaneous Raji/hPBMC tumors grown in NSG mice. The blocking dose of 5 mg/kg $^{89}$Zr-DFO-mAb1 showed increased blood uptake (% ID/g) and lower tumor uptake (% ID/g) in Raji/hPBMC tumors compared to the lower doses of 0.3, 0.1, and 0.03 mg/kg $^{89}$Zr-DFO-mAb1 (Table 10). Furthermore, as the protein dose decreased, the average tumor-to-blood ratio increased demonstrating specificity to Lag-3 in vivo (Table 10). In addition to targeting Lag-3 expressed in the Raji/hPBMC tumors, the lower doses of 0.3, 0.1, and 0.03 mg/kg $^{89}$Zr-DFO-mAb1 demonstrated targeting to the spleen and axillary lymph nodes of tumor bearing mice. Representative PET images (FIG. 9) at day 6 post $^{89}$Zr-DFO-mAb1 administration demonstrate higher targeting of $^{89}$Zr-DFO-mAb1 to the tumor, spleen, and axillary lymph nodes at 0.03 mg/kg compared 5 mg/kg.

TABLE 10

Ex vivo biodistribution at day 6 after administration of $^{89}$Zr-DFO-mAb1 injected at protein doses of 5. 0.3, 0.1, or 0.03 mg/kg in NSG mice bearing Raji/hPBMC tumors. Values are shown as average and standard deviations of % ID/g and tumor-to-blood ratios

| SAMPLE | $^{89}$Zr-DFO-mAb1 5 mg/kg | | $^{89}$Zr-DFO-mAb1 0.3 mg/kg | | $^{89}$Zr-DFO-mAb1 0.1 mg/kg | | $^{89}$Zr-DFO-mAb1 0.03 mg/kg | |
|---|---|---|---|---|---|---|---|---|
| | Average % ID/g | STDEV % ID/g | Average % ID/g | STDEV % ID/g | Average % ID/g | STDEV % ID/g | Average % ID/g | STDEV % ID/g |
| Blood | 18.45 | 1.69 | 12.17 | 3.20 | 8.13 | 4.28 | 7.81 | 5.37 |
| Tumor | 20.52 | 5.34 | 40.43 | 8.09 | 33.26 | 10.81 | 48.92 | 28.53 |
| Thymus | 7.78 | 0.64 | 6.57 | 2.04 | 7.98 | 4.71 | 3.22 | 2.43 |
| Heart | 5.5 | 0.45 | 3.74 | 0.57 | 2.79 | 1.14 | 2.39 | 1.47 |
| Lungs | 10.14 | 0.54 | 8.30 | 2.40 | 9.72 | 1.63 | 8.14 | 1.08 |
| Spleen | 7.74 | 0.17 | 22.32 | 13.82 | 103.68 | 126.79 | 59.20 | 40.84 |
| Intestine | 1.82 | 0.23 | 1.43 | 0.20 | 0.80 | 0.44 | 1.19 | 0.23 |
| Liver | 4.51 | 0.26 | 5.56 | 1.16 | 9.75 | 3.87 | 10.75 | 5.58 |
| Kidney | 6.73 | 0.99 | 6.17 | 1.28 | 5.77 | 1.59 | 5.49 | 1.56 |
| Bone | 8.78 | 1.75 | 8.39 | 3.10 | 8.87 | 2.64 | 9.83 | 1.54 |
| Tumor-to-blood ratio | 1.10 | 0.21 | 3.46 | 1.05 | 5.44 | 3.60 | 9.71 | 8.27 |

Example 7: LC-PRM-MS Quantitation of LAG3 in Raji/PBMC Xenografts and Clinical Samples Frozen tissue samples (Raji/PBMC tumors, mouse spleens, and melanoma tissue; see FIG. 12 for source and characteristics of melanoma tissues) were lysed with lysis buffer (8 M urea in 50 mM NH$_4$HCO$_3$ with 1% RapiGest). Tissues were cut into small pieces and were homogenized with 1 mL lysis buffer in a tight fitting dounce homogenizer. The lysate was incubated on ice for 30 mins with sonication for 30 sec every 10 mins to achieve complete protein extraction. The lysate was centrifuged at 14,000 g for 10 mins. Protein concentration was measured by BCA assay. Each sample was diluted to 1 mg/mL then was centrifuged at 14,000 g for 10 mins and was stored in aliquots at −80° C.

Unimplanted NSG mouse spleen lysate was used as the surrogate matrices to generate the standard curve for LAG3 quantitation. LAG3.Fc was spiked into each of 100 µg of mouse spleen lysate at a final concentration ranging from 0.39 to 50 ng/mg protein (1:2 serial dilution). Standards, xenografts and clinical melanoma lysates were precipitated in 900 µL of cold acetone overnight and then denatured in 90 µL of 8M Urea/TCEP buffer at 37° C. for 1 hr. Heavy labeled human LAG3 peptide (FVWSSLDTPSQR$^{13}$C6$^{15}$N4) was added to all samples as internal standard. The standards and test samples were alkylated with IAA at room temperature for 30 min and digested by lys-C (1:100 w/w) for 4 hrs then by trypsin (1:20 w/w) overnight at 37° C. Samples were quenched with 10% FA to reach a final Vol. of 100 µL.

Each processed sample (2 µL) was injected onto a pre-equilibrated nano C18 trap column and was separated by an easy nano C18 separation column. The flow rate was 250 nL/min (Mobile Phase A: water:formic acid/100:0.1 [V:V] and Mobile Phase B: acetonitrile:formic acid/100:0.1 [V:V]). Retention time and peak area were determined using Skyline software. The calibration curve was generated by plotting the peak area ratio of LAG3.Fc reference standard (unlabeled LAG3 peptide FVWSSLDTPSQR$^{12}$C6$^{14}$N4 generated by tryptic digest of hLAG3) to the internal standard (stable isotope-labeled LAG3 peptide). The concentration of LAG3 in each sample was calculated using linear regression. The lowest concentration of LAG3 reference standard (0.39 ng/mg protein) was within the dynamic range of the assay and was defined as the assay's lower limit of quantification.

Results Summary and Conclusions:

LAG3 quantitation was performed on tissue samples from 4 of PBMC/Raji xenografts from 27 days, 5 xenografts from 15 days after tumor implantation and 10 melanoma clinical samples. The tissue weights, protein amounts, extraction yield and LAG3 expression were listed in Table 11. Bmax was calculated based on the following equation with an estimation of tumor density at 1 g/mL.

$$Bmax(\text{nM}) = \frac{LAG3\ (ng/\text{mg protein}) \times \text{Total Protein Amount (mg)} \times 10E6}{5.74 * 10E4 \times \text{Tumor Weight (mg)}}$$

Figure 10:
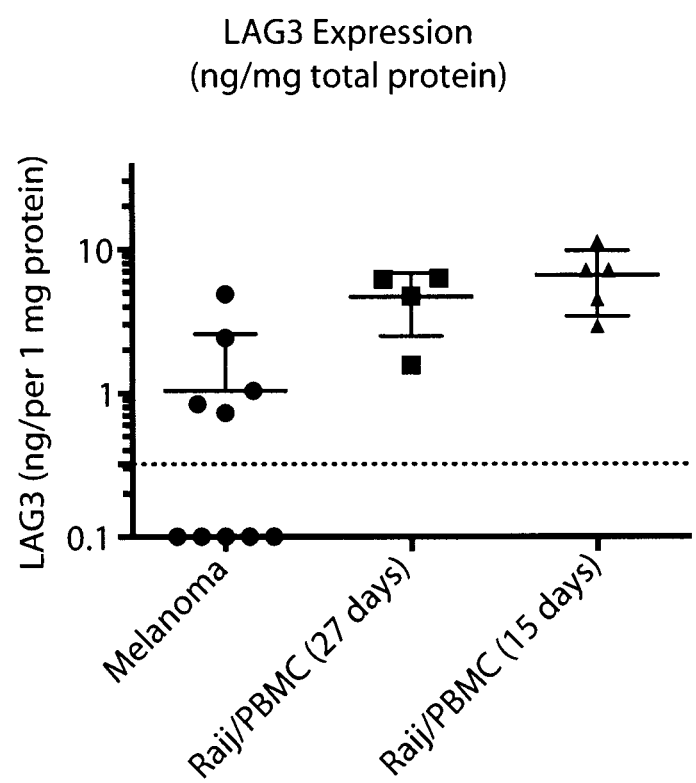
FIG. 10 shows LAG3 expression in tissue samples from PBMC/Raji xenografts (obtained at 27 days and 15 days after tumor implantation) and in melanoma clinical samples.

Five of 10 melanoma tissue samples were detected as LAG3 positive with an average expression level of 2.52±1.87 nM. This expression level is similar to Raji/PBMC model at 27 days (3.79±1.93 nM) and at 15 days (6.06±4.04 nM). See Table 11 and also FIG. 10.

TABLE 11

| | | Tissue Weight (mg) | Total Protein Amount (mg) | % protein | Lag3 (ng/mg protein) | Bmax (nM) |
|---|---|---|---|---|---|---|
| Melanoma Tissue | 131815T2(3) | 290 | 9.1 | 3.14% | BLQ | BLQ |
| | 131719T2(3) | 230 | 17.6 | 7.65% | BLQ | BLQ |
| | 13841T2(1) | 220 | 20.1 | 9.14% | 0.73 | 1.16 |
| | 13788T2(4) | 250 | 24.1 | 9.64% | 1.04 | 1.75 |
| | 13765T2(2) | 250 | 19.4 | 7.76% | BLQ | BLQ |
| | 131778T2(5) | 180 | 9.2 | 5.11% | BLQ | BLQ |
| | 131291T2(1) | 240 | 17.4 | 7.25% | 0.84 | 1.06 |
| | 131086T6(1) | 180 | 9.32 | 5.18% | BLQ | BLQ |
| | 13547T2(1) | 220 | 16.1 | 7.32% | 2.42 | 3.08 |
| | 13524T2(7) | 200 | 13 | 6.50% | 4.90 | 5.53 |
| | Mean | 226 | 15.5 | 6.87% | 1.99 | 2.52 |
| | SD | 34 | 5.2 | 1.96% | 1.76 | 1.87 |

TABLE 11-continued

| | | Tissue Weight (mg) | Total Protein Amount (mg) | % protein | Lag3 (ng/mg protein) | Bmax (nM) |
|---|---|---|---|---|---|---|
| Raji/PBMC Xenograft (27 Days) | 85100_0 | 419.5 | 20.9 | 4.98% | 4.74 | 4.10 |
| | 85101_8 | 248.9 | 10.3 | 4.14% | 1.58 | 1.14 |
| | 85104_23 | 256.5 | 9.74 | 3.80% | 6.24 | 4.12 |
| | 85103_19 | 112.5 | 5.92 | 5.26% | 6.32 | 5.78 |
| | Mean | 259 | 11.72 | 4.54% | 4.72 | 3.79 |
| | SD | 126 | 6.43 | 0.69% | 2.21 | 1.93 |
| Raji/PBMC Xenograft (15 Days) | 213_1 | 140 | 8.8 | 6.29% | 11.46 | 12.5 |
| | 213_2 | 260 | 10.14 | 3.90% | 4.54 | 3.08 |
| | 213_3 | 230 | 9.3 | 4.04% | 7.22 | 5.09 |
| | 213_4 | 160 | 7.9 | 4.94% | 2.95 | 2.54 |
| | 213_5 | 50 | 2.8 | 5.60% | 7.23 | 7.05 |
| | Mean | 168 | 7.8 | 4.95% | 6.68 | 6.06 |
| | SD | 82 | 6.43 | 0.69% | 2.21 | 1.93 |

Example 8: Up-Regulation of Human LAG-3 and PD-1 Expression on T Cells in the Tumor Microenvironment by Therapy with REGN2810 (Anti-Human PD-1 Ab) and mAb1 (Anti-Human LAG-3 Ab)

This experiment was carried out to evaluate the modulation of expression levels of human LAG-3 and PD-1 on T cells in the tumor microenvironment upon treatment with REGN2810 and mAb1 using Regeneron's proprietary PD-1$^{hu/hu}$/LAG-3$^{hu/hu}$ double humanized immune-competent mice. The tumor cell line used in this experiment is a murine colon carcinoma cell line MC38 (obtained from NCI at Frederick, Md., Laboratory of Tumor Immunology and Biology), which has been engineered in house to express full-length chicken ovalbumin fused with eGFP, thus referred here as MC38-cOVA/eGFP. The expression level of human LAG-3 was evaluated ex vivo on both CD4 and CD8 T cells from enzymatically disassociated tumors extracted from tumor bearing double humanized mice. All surface staining was performed with commercially available fluorochrome directly conjugated to antibodies (anti-human LAG-3 antibody: eBioscience, Clone 3DS223H; anti-human PD-1 antibody: BioLegend, Clone EH12.2H7), following standard protocol. Briefly, tumor cells were washed with PBS once, washed with ice cold staining buffer once, stained with commercial available fluorochrome directly conjugated anti-human PD-1 or anti-human LAG-3 antibody in staining buffer for 30 min on ice in the dark, washed with 2 ml of PBS once again. Fixable dye eFluor506 was also included following manufacturer's protocol (eBioscience). Samples were acquired on BD FACSCanto II™ IVD10 equipped with DIVA v8. Data were further analyzed with FlowJo v10.0.6 or the later version.

Results Summary and Conclusions:

Table 12 provides a schematic presentation of the therapeutic dosing regimen in preclinical tumor setting. 1×10$^6$ MC38-cOVA/eGFP cells were implanted s.c. into PD-1$^{hu/hu}$/LAG-3$^{hu/hu}$ double humanized immune-competent mice. At about Day 11, mice were randomized into four groups with average tumor volumes of ~100 mm$^3$ and started treatment as indicated. Tumor samples were collected 3 days after the second dose.

TABLE 12

Therapeutic dosing regimen.

| Group | Treatment | # Mice |
|---|---|---|
| Isotype | 25 mg/kg, 2x week, 2 doses, IP | 10 |
| REGN2810 (PD-1) | 10 mg/kg, 2x week, 3 doses, IP | 12 |
| mAb1 (anti-human LAG-3) | 25 mg/kg, 2x week, 2 doses, IP | 12 |
| REGN2810 + mAb1 | 10 mg/kg + 25 mg/kg, 2x week, 2 doses, IP | 12 |

As shown in Table 13, the combination of anti-human PD-1 (REGN2810) and anti-human LAG-3 (mAb1) significantly inhibited tumor growth in MC38-cOVA/eGFP syngeneic tumor model in double humanized mice. Tumor-bearing mice (tumor sizes of about 100 mm$^3$) were treated with an hIgG4 isotype control antibody, REGN2810 (anti-human PD-1, hIgG4), mAb1 (anti-human LAG-3, hIgG4s), and combination of REGN2810 and mAb1, twice a week for two doses, and tumor sizes were measured by caliper. Tumor volume was calculated as V=L×W$^2$/2. In the control group, tumor sizes ranged from 300 to 869 mm$^3$ with median value of 548 mm$^3$. REGN2810 treated group showed reduced tumor sizes (121 to 721 mm$^3$ with median at 466 mm$^3$), but the differences did not reach statistical significance. Whereas mAb1-treated group showed no difference from the isotype control group either (203 to 721 mm$^3$ with median at 592 mm$^3$), the combination treatment significantly delayed tumor growth (113 to 621 mm$^3$ with median at 289 mm$^3$, p<0.01).

TABLE 13

Anti-human PD-1 (REGN2810) and anti-Human LAG-3 (mAb1) significantly inhibited tumor growth in MC38-cOVA/GFP syngeneic tumor model in double humanized mice

| | Iso** | αhPD-1 | αhLAG-3** | Combo |
|---|---|---|---|---|
| Mice/group | 10 | 12 | 12 | 12 |
| Minimum | 299.9 | 120.9 | 202.6 | 113.4 |
| 25% Percentile | 437.6 | 321.3 | 426.9 | 192.6 |
| Median | 548.4 | 465.5 | 592.1 | 289.1 |
| 75% Percentile | 617.6 | 597.8 | 631.1 | 349.7 |
| Maximum | 868.7 | 710.6 | 760.7 | 631.4 |

Figure 11:
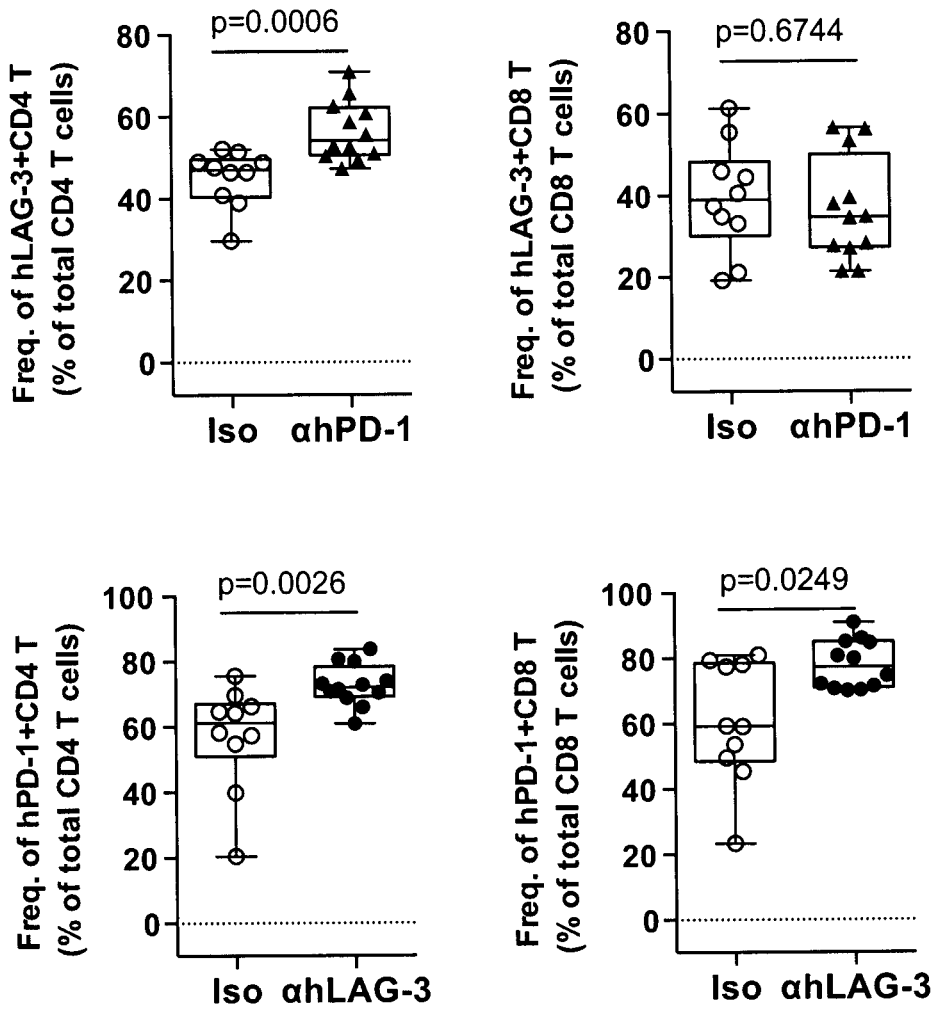
FIG. 11 provides data demonstrating REGN2810 anti-human PD-1 Ab and mAb1 anti-human LAG-3 respectively increase LAG-3+ T cells and PD-1+ T cells in tumor microenvironment.
Figure 13:
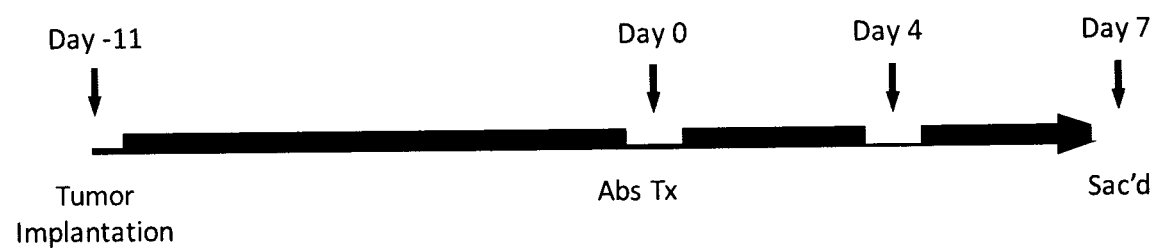
FIG. 13 provides a schematic presentation of the therapeutic dosing regimen used in Example 8.

REGN2810 anti-human PD-1 Ab and mAb1 anti-human LAG-3 respectively increased LAG-3+ T cells and PD-1+ T cells in tumor microenvironment, as can be seen in FIG. 11. Tumors from individual mice were dissociated by GentalMACs (Miltenyi Biotech) according to the Manufacturer's protocol. Samples were stained with a panel of Abs and analyzed by flow cytometer. Data presented were pre-gated on FSC/SSC, viability, singlets, CD45+CD3+ cells, then further gated on CD4 or CD8 T cells. The expression of human LAG-3 and human PD-1 were evaluated between different groups. To eliminate the possible Ab cross-competition, REGN2810- and combination-treated groups were excluded from human PD-1 analysis. Similarly, mAb1- and combination-treated groups were also excluded from human LAG-3 analysis. After two therapeutic doses, REGN2810 significantly increased the frequency of human LAG-3+ CD4 T cells in tumor microenvironment by ~24% (p=0.0006), though it did seem to have a direct modulatory role for LAG-3 expression on CD8 T cells with the dosing regimen tested. Interestingly, mAb1 also increased the frequency of human PD-1+ CD4 (p=0.0026) and CD8 T cells (p=0.0249) in tumor microenvironment by ~28%, respectively. See FIG. 11.

The results from the studies performed here clearly demonstrate that anti-LAG3 antibody labeled with $^{89}$Zr can significantly and specifically localize to tumors. One may envision a scenario where the anti-LAG3 antibody is used in the selection of patients with LAG3 positive tumors for subsequent treatment with LAG3 inhibitors, alone or in combination with other anti-cancer therapeutics including inhibitors of the PD-1/PD-L1 signaling axis.

Example 9: Scaled-Up Manufacturing Process for Producing DFO-Anti-LAG3 Antibody Conjugates This example details the scaled-up manufacturing process for preparing the anti-LAG3 antibody to be suitable for radiolabeling by attaching p-SCN-bn-Deferoxamine (DFO) to the anti-LAG3 antibody (mAb, H4sH15482P) described herein: (1) ultrafiltration and diafiltration (UFDF) processes prior to mAb conjugation removes excipients that inhibit the conjugation process; (2) following the pre-conjugation UFDF, conjugation of the mAb with p-SCN-Bn-deferoxamine is performed to produce DFO-mAb conjugates; and (3) a post-conjugation UFDF to remove residual salts provides a suitable concentration, excipient level, and pH of the conjugated monoclonal antibody. The resulting DFO-mAb conjugates are then provided in a buffered state with improved stability for subsequent formulation.

(1) Pre-Conjugation Ultrafiltration and Diafiltration (UFDF)

100 g mAb was buffer exchanged into a 5 mM acetate buffer solution having a pH of 5.50 using a Sius Prostream (TangenX Technology Corporation) membrane (membrane capacity of ≤500 g/m$^2$) to remove residual salts prior to conjugation. The process volume was reduced to further concentrate the antibody, then the antibody was sterile filtered using a Sartopore 2 (Sartorius) membrane having a 0.45/0.2 µm (heterogeneous PES double layer) or equivalent pore size. The acetate buffer temperature was kept at a target temperature of 20±5° C. The solutions were well mixed.

(2) Conjugation

The concentrated and filtered antibody (20 g) was transferred into a conjugation vessel containing an amine free carbonate buffer system (56 mM Carbonate, 167 mM Sodium Chloride, pH 9.40) resulting in negligible levels of residual acetate. DFO (25 mM p-SCN-Bn-Deferoxamine) was solubilized in DMSO and added to the conjugation vessel, along with additional DMSO such that the DMSO was present in a final amount of 5%. DFO was added in molar excess at a ratio of 4.5:1 DFO to mAb. The total reaction volume equaled 2.0 L. The buffer system was mixed throughout the addition of the reaction ingredients and throughout the reaction time.

The reaction temperature was controlled for specific time by using an equation which relates temperature to reaction time. In this instance, the reaction temperature was held at 20±2° C. for 180 minutes. The reaction was quenched by the addition of 2M acetic acid (23 mL/L), resulting in the solution having a pH of 6.

(3) Post-Conjugation UFDF

After the conjugation step, the quenched DFO-mAb conjugation solution was buffer exchanged into histidine buffer (10 mM Histidine, pH 5.50 with 0.0005% (w/v) super refined polysorbate 80 added as a shear protectant) to remove residual process salts, DMSO, and unreacted DFO. Once diafiltered, the solution was then concentrated and subsequently formulated. The histidine buffer was selected for long term storage of protein at −80° C. The same Sius Prostream membrane mentioned in step (1) was used in the final UFDF step. The resulting concentrated DFO-mAb conjugate solution was sterile filtered using the Sartopore 2 filter mentioned above.

UV-DAR (target of 1.5) and protein concentration determination was performed as described in Example 2.

TABLE 14

Molar Extinction Coefficients and Molecular Weight

| Antibody | MW (g mol$^{-1}$) | ε280 (L g$^{-1}$cm$^{-1}$) | ε252 (L g$^{-1}$cm$^{-1}$) |
|---|---|---|---|
| H4sH15482P | 145709 | 223400 | 87077 |

Example 10: ImmunoPET Imaging of LAG3 in Tumors Using an $^{89}$Zr-DFO-Anti-LAG3 Antibody Conjugate in Patients with Metastatic Melanoma The primary objective of this study is to determine the safety and tolerability of $^{89}$Zr-DFO-anti-LAG3 antibody conjugate, in which the anti-LAG3 antibody used in the radiolabeled conjugate is H4sH15482P. Outcome measures monitor adverse events and routine laboratory tests for safety.

The secondary objectives of the study are:

Study part A: To qualify $^{89}$Zr-DFO-anti-LAG3 PET as a biomarker for the evaluation of LAG3 expression in tumors. This will be accomplished by evaluating the safety of the $^{89}$Zr-DFO-anti-LAG3 PET tracer, determining optimal tracer mass dose and optimal post-injection imaging time, establishing the relationship of tumor PET signal with LAG3 tissue-based expression, and evaluating dosimetry in patients. Part A comprises a sequential tracer dose escalation design, with tumor biopsy. Imaging and blood draws at days 1, 4, and 7 post tracer injection permit blood poos SUV with subsequent calculation of tumor: blood ratios at the time of imaging; clinical dosimetry based on tissue radiation absorbed dose and effective dose calculated from PET image acquisition data and tracer activity concentration in blood; standardized uptake values (SUVs—decay-corrected activity concentration in target tissue divided by the mean activity concentration in the body at the time of injection) across the tumor regions of interest; maximal SUVs within tumor regions of interest (ROIs) (SUV$_{max}$); and plasma tracer activity concentration, with calculation of area under the curve (AUC$_{0-7\ days}$).

Study part B: To explore the construct and criterion validity of $^{89}$Zr-DFO-anti-LAG3 PET by correlating the PET signal with tissue-based LAG3 expression and clinical outcome (objective response rate and progression-free survival) after 10 therapy. Sequential iPET scanning and tumor biopsies are performed before and after treatment with standard of care immunotherapies selected from the following: nivolumab, ipilimumab, pembrolizumab, and combinations as allowed by label.

The utility of the immune-PET (iPET) tracer can be initially assessed by testing for ability to detect the presence of LAG3 tumors, as well as changes in LAG3 signal induced by an established immunotherapy, and by exploring the correlation of the iPET signal with clinical outcomes (criterion validation: against biologically and clinically meaningful outcomes).

A safe, optimal mass dose of $^{89}$Zr-DFO-anti-LAG3 can be identified that shows adequate tumor uptake by PET, tracer PK, and dosimetry. Selection of three tracer mass dose levels is based on preclinical mouse xenograft imaging and biodistribution studies, and on clinical and preclinical data using unlabeled anti-LAG3 therapeutic antibodies. The planned mass dose escalation is 2 mg, 5 mg, and 10 mg. The approach is to use doses that are sub-therapeutic or pharmacologically inert, so as not to interfere with prospective anti-tumor therapy.

The optimal mass dose will demonstrate tumor SUV, maximal SUV ($SUV_{max}$) within the tumor lesion region of interest (ROI) and tumor:blood ratio all >1 (and ideally a tumor-blood ratio of 3-4) in at least one lesion (ideally in >1 lesion, in patients with several metastases).

Tracer activity in plasma (or serum) and/or blood pool SUV (the activity PK measures for this study) will be detectable throughout the 7-day imaging window, following dosing, suggesting adequate availability of tracer to compartmentalize into tumor lesions. Ratios of tumor and blood signal will be based on SUVs, although other activity concentration units may be used. The same applies to measurements of blood activity concentration, which could be reported in terms of absolute units or normalized units.

LAG3 PET signal intensity in a biopsied lesion will covary with degree of LAG3 expression in the tissue biopsy using semi-quantitative measures.

The autoradiographic LAG3 PET signal will correlate spatially with LAG3 expression in tissue biopsy samples.

LAG3 PET signal intensity will increase following treatment with an immunotherapy.

LAG3 PET signal intensity increase will correlate with response following treatment with an immunotherapy.

Additionally, exploratory objectives and outcome measures include determining expression of LAG3 in tissue biopsies in correlation with tumor $^{89}$Zr-DFO-anti-LAG3 uptake using immunohistochemistry, RNAscope, liquid chromatography mass spectrometry (LC/MS), and autoradiography. For part B only, exploratory objectives include measuring changes in $^{89}$Zr-DFO-anti-LAG3 signal after treatment and correlation of $^{89}$Zr-DFO-anti-LAG3 signal with clinical outcome after treatment. The outcome measures include SUV, SUVmax, tumor:blood ratio, and clinical outcome following immunotherapy treatment (serial CT for the purpose of calculation of responder status using RECIST 1.1 and tumor volume), objective response rate, and progression-free survival.

Patient Target Population

The target population will consist of patients 18 years of age or older with advanced metastatic melanoma, histologically or cytologically confirmed diagnosis, with at least one lesion amendable to biopsy. The patient must have an ECOG performance status of less than or equal to 2, an anticipated life expectancy of at least 3 months, and adequate organ and bone marrow function.

Inclusion of patients with an indication that has a high prevalence of the target will support assessment of LAG3 iPET tumor localization which is a key outcome of the study. Detection and correlation of post-immunotherapy LAG3 expression with clinical outcomes requires a patient population with well characterized clinical response rates to immunotherapies. Metastatic melanoma patients represent a patient population with established response rates to checkpoint inhibitors as well as the high levels of prevalence and expression of LAG3.

Study Design

The study comprises part A (construct validation) and part B (criterion validation). Duration of the study is 9 weeks for Part A (4 weeks screening, 1 week tracer dosing, scans and biopsy, 4 weeks safety follow up), and 18 weeks for Part B (4 weeks screening, 1 week tracer dosing, scans and biopsy, up to 8 weeks on immunotherapy, 1 week second tracer dose and scan, 4 weeks safety follow up).

Part A

Part A is a dose finding study in which patients receive a single tracer dose, followed by serial scans and a biopsy over a 7 day period. Once the scanning sequence and biopsy are completed, subjects can immediately be treated with a standard of care immunotherapy regime (anti-PD-1 alone or in combination with anti-CTLA4 according to labeled indication).

Dose Cohorts in Part A

Part A comprises three sequential dose cohorts, consisting of 3 patients, with potential to expand the cohort to a total of 6 patients (3+3 design). Dose escalation decisions will be informed by a) safety and b) evaluation of iPET positivity. Dose limiting toxicity (DLT) is defined as a Grade 3 or higher (NTCAE) adverse event (AE) related to or possibly related to $^{89}$Zr-DFO-anti-LAG3, one week following tracer administration. For hematologic lab AEs, DLT is defined as Grade 4 or higher. Tumor uptake positivity/tumor localization is defined by a tumor:blood ratio greater than 1. Adequate PK is defined by SUV in blood in the range of 1-5 at optimum imaging time (4 or 7 days post-injection).

Cohort expansion to 6 patients will occur if any of the following conditions are met: (a) exactly 1 patient experiences a DLT or (b) at least 1 patient out of 3 shows tumor localization and adequate PK and no more than 1 patient experiences a DLT.

At the completion of a cohort of either 3 or 6 subjects, dose escalation will occur to a higher available dose if fewer than 3 patients in an expanded cohort experience a DLT.

Part A of study will stop if any of the following conditions are met (Part A stopping rules): more than 1 patient in a cohort experiences a DLT; more than 3 patients show visual tumor localization and adequate PK in each of two consecutive expanded cohorts; or no higher doses are available for escalation.

Upon reaching a Part A stopping rule, Part B dose will be selected as follows: a) if two or three expanded cohorts show more than 3 patients with tumor localization and adequate PK, then the dose cohort with tumor localization in more patients, or the highest tumor: blood ratios, will be chosen. When these are similar between cohorts, the lower dose will be chosen. b) if one cohort shows more than 3 patients with tumor localization and adequate PK, this dose will be chosen. c) if no cohorts show more than 3 patients with tumor localization and adequate PK, the study will terminate without progression to Part B.

Part B

Part B will measure LAG3 iPET signal at the defined tracer dose and post-injection time point (determined in part A), both pre- and post-immunotherapy to assess the hypotheses surrounding the role of LAG3 as an indicator of tumor inflammatory response (exploratory objectives). All patients in Part B will receive the optimal tracer mass dose and post-injection imaging timing as identified in Part A.

Part B patients will receive LAG3 iPET scanning at baseline as well as a biopsy prior to therapy. Patients will then receive a standard of care immunotherapy (currently these are monoclonal antibody-based PD-1 and CTLA-4 pathway blockers), according to the label. Four to eight weeks later an additional iPET scan will be undertaken followed by a second biopsy if feasible.

Patients in Part A who received the optimal tracer mass dose and achieved adequate scan quality may be eligible for Part B and receive a total of two iPET tracer injections. The total number of subjects in Part B (including those that enter from Part A) will not exceed 20.

Biopsy Considerations

Lesions will be selected for biopsy on the basis of accessibility and size (typically at least 20 mm diameter). All patients will undergo a baseline biopsy on the last day of the first set of iPET scans, regardless of whether the iPET study is positive or not. In this way, tissues from patients with a wide range of LAG3 tissue expression will be collected for correlation with LAG3 signal, including negative patients. The biopsy will be scheduled no later than 7 days from date of injection in order to minimize delay of therapy to the patient.

A sequence of assessments that starts with a biopsy followed by the tracer dosing and scans, and then the initiation of therapy may be preferable for practical reasons.

For Part B, a second biopsy after the second scan may be undertaken if feasible and will be optional. Sequential biopsies will be taken from the same site if practicable.

Autoradiography studies will be performed in a subset of biopsied tumors that are positive on iPET scan, with adjacent slices stained against LAG3.

Study Interventions

Part A

Following screening, each subject will receive a dose of $^{89}$Zr-DFO-anti-LAG3 followed by three sequential iPET scans over 6-7 days. Starting dose will be 2 mg, as determined from animal studies and modeling. No later than 1 day after the last iPET scan, the subject will undergo radiology-guided biopsy. If available, archived biopsy tumor tissue will also be analyzed by IHC for LAG3 expression.

For Part A, biopsy is optional, since not all subjects will receive the eventually identified optimal tracer dose.

Decision to progress to Part B will be made on the basis of Part A data and recruitment rate.

Part B

Following screening, each melanoma patient will receive a $^{89}$Zr-DFO-anti-LAG3 at the optimized mass dose (from Part A) followed by PET scanning at the optimal post-injection time point (from Part A). Then, no later than 1 day after iPET imaging, the subject will undergo radiology guided biopsy of a lesion. Subsequently, the patient will be treated, open-label, with available approved immunotherapy regimens (dosed as per label). Subjects will receive a second scan 4-8 weeks after commencement of immunotherapy. A second biopsy after the second scan may be undertaken if feasible and will be optional.

All patients will be screened by an $^{18}$F-FDG PET/CT scan. CT portion of the PET/CT scan must be of diagnostic quality or a diagnostic CT scan acquired during the screening period must be available to assess location and dimension of lesions. These scans will be used to evaluate the lesions for metabolic activity/viability and appropriate dimensions.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A radiolabeled antibody conjugate comprising an antibody or antigen binding fragment thereof that binds lymphocyte activation gene-3 (LAG3) and a positron emitter, wherein the antibody or antigen-binding fragment thereof comprises three heavy chain complementarity determining regions (HCDRs) and three light chain complementarity determining regions (LCDRs) within the heavy chain variable region (HCVR) and light chain variable region (LCVR) amino acid sequence pair selected from the group consisting of SEQ ID NOs: 2/10, 210/218, 226/234, 354/362, 418/426, 458/522, 474/522, and 554/562.

2. The conjugate of claim 1, further comprising a chelating moiety.

3. The conjugate of claim 1, wherein said antibody or antigen-binding fragment thereof is covalently bonded to one or more moieties of Formula (A):

$$-L-M_z \qquad (A)$$

wherein L is a chelating moiety; M is a positron emitter; and z, independently at each occurrence, is 0 or 1; and wherein at least one of z is 1.

4. The conjugate of claim 2, wherein the chelating moiety comprises desferrioxamine.

5. The conjugate of claim 1, wherein the positron emitter is $^{89}$Zr.

6. The conjugate of claim 3, wherein -L-M is

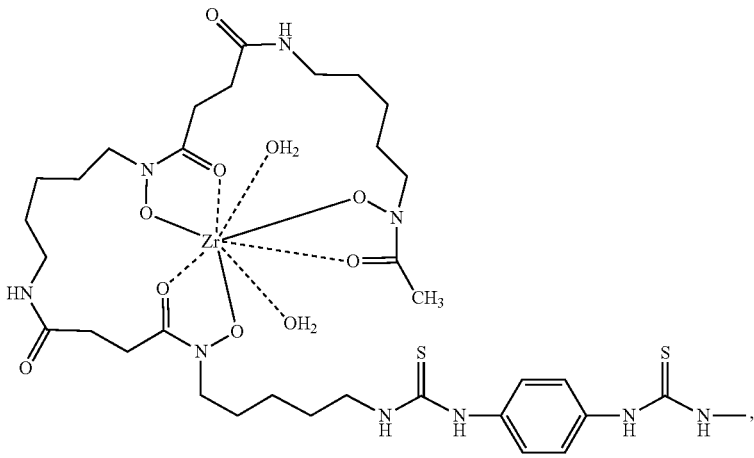

wherein Zr is the positron emitter, $^{89}$Zr.

7. The conjugate of claim 3, wherein the antibody or antigen-binding fragment thereof is covalently bonded to one, two, or three moieties of Formula (A).

8. The conjugate of claim 1, wherein the antibody or antigen-binding fragment thereof comprises three heavy chain complementarity determining regions (HCDRs) in a heavy chain variable region (HCVR), wherein the HCVR has an amino acid sequence of SEQ ID NO: 418; and three light chain complementarity determining regions (LCDRs) in a light chain variable region (LCVR), wherein the LCVR has an amino acid sequence of SEQ ID NO: 426.

9. The conjugate of claim 1, wherein the antibody or antigen-binding fragment thereof comprises within the HCVR/LCVR amino acid sequence pair of SEQ ID NOs: 418/426 a heavy chain complementarity determining region (HCDR)-1 comprising SEQ ID NO: 420; an HCDR2 comprising SEQ ID NO: 422; and an HCDR3 comprising SEQ ID NO: 424; a light chain complementarity determining region (LCDR)-1 comprising SEQ ID NO: 428; an LCDR2 comprising SEQ ID NO: 430; and an LCDR3 comprising SEQ ID NO: 432.

10. The conjugate of claim 1, wherein the antibody comprises an HCVR of SEQ ID NO: 418; and an LCVR of SEQ ID NO: 426.

11. A method of imaging a tissue that expresses LAG3 comprising administering a radiolabeled antibody conjugate of claim 1 to the tissue; and visualizing LAG3 expression by positron emission tomography (PET) imaging.

12. A method for treating a tumor comprising:
(a) selecting a subject with a solid tumor;
(b) determining that the solid tumor comprises LAG3-positive cells, comprising (i) administering a radiolabeled antibody conjugate of claim 1 to the subject in need thereof; and (ii) imaging localization of the radiolabeled antibody conjugate in the tumor by positron emission tomography (PET) imaging, wherein presence of the radiolabeled antibody conjugate in the tumor indicates that the tumor comprises LAG3-positive cells; and
(c) administering one or more doses of an anti-tumor therapy to the subject in need thereof.

13. The method of claim 12, wherein the anti-tumor therapy is selected from the group consisting of an inhibitor of LAG3, an inhibitor of the PD-1/PD-L1 signaling axis, a CTLA-4 inhibitor, a TIM3 inhibitor, a BTLA inhibitor, a TIGIT inhibitor, a CD47 inhibitor, a GITR inhibitor, an antagonist of another T cell co-inhibitor or ligand, an indoleamine-2,3-dioxygenase (IDO) inhibitor, a vascular endothelial growth factor (VEGF) antagonist, an Ang2 inhibitor, a transforming growth factor beta (TGFβ) inhibitor, an epidermal growth factor receptor (EGFR) inhibitor, a CD20 inhibitor, an antibody to a tumor-specific antigen, a cancer vaccine, a bispecific antibody, a cytotoxin, a chemotherapeutic agent, cyclophosphamide, radiotherapy, an IL-6R inhibitor, an IL-4R inhibitor, an IL-10 inhibitor, IL-2, IL-7, IL-21, IL-15, and an antibody-drug conjugate (ADC).

14. The method of claim 12, wherein the anti-tumor therapy is selected from the group consisting of an anti-LAG3 antibody, REGN2810, BGB-A317, nivolumab, pidilizumab, pembrolizumab, atezolizumab, avelumab, durvalumab, MDX-1105, REGN3504, ipilimumab, an anti-CD-28 antibody, an anti-2B4 antibody, an anti-LY108 antibody, an anti-LAIR1 antibody, an anti-ICOS antibody, an anti-CD160 antibody, an anti-VISTA antibody, aflibercept, bevacizumab, ranibizumab, sunitinib, sorafenib, pazopanib, nesvacumab, erlotinib, cetuximab, rituximab, an anti-CA9 antibody, an anti-CA125 antibody, an anti-melanoma-associated antigen 3 (MAGE3) antibody, an anti-carcinoembryonic antigen (CEA) antibody, an anti-vimentin antibody, an anti-tumor-M2-PK antibody, an anti-prostate-specific antigen (PSA) antibody, an anti-mucin-1 antibody, an anti-MART-1 antibody, an anti-CA19-9 antibody, Bacillus Calmette-Guerin, a CD3×CD20 bispecific antibody, a PSMA×CD3 bispecific antibody, dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, vincristine, cyclophosphamide, radiotherapy, sarilumab, dupilumab, anti-CD19-DM4 ADC, and anti-DS6-DM4 ADC.

15. The method of claim 12, wherein the anti-tumor therapy is selected from the group consisting of an anti-LAG3 antibody or antigen-binding fragment thereof, an anti-PD-1 antibody or antigen-binding fragment thereof, and an anti-PD-L1 antibody or antigen-binding fragment thereof.

16. The method of claim 15, wherein the anti-tumor therapy is an anti-LAG3 antibody or antigen-binding fragment thereof comprising three heavy chain complementarity determining regions (HCDRs) and three light chain complementarity determining regions (LCDRs) within the heavy chain variable region (HCVR)/light chain variable region (LCVR) sequence pair selected from the group consisting of SEQ ID NOs: 2/10, 210/218, 226/234, 354/362, 418/426, 458/522, 474/522, and 554/562.

17. The method of claim 16, wherein the anti-LAG3 antibody or antigen-binding fragment thereof comprises:
(i) three HCDRs and three LCDRs within the HCVR/LCVR amino acid sequence pair of SEQ ID NOs: 2/10, wherein the three HCDRs consist of SEQ ID NOs: 4, 6, and 8, respectively, and the three LCDRs consist of SEQ ID NOs: 12, 14, and 16, respectively,
(ii) three HCDRs and three LCDRs within the HCVR/LCVR amino acid sequence pair of SEQ ID NOs: 210/218, wherein the three HCDRs consist of SEQ ID NOs: 212, 214, and 216, respectively, and the three LCDRs consist of SEQ ID NOs: 220, 222, and 224, respectively,
(iii) three HCDRs and three LCDRs within the HCVR/LCVR amino acid sequence pair of SEQ ID NOs: 226/234, wherein the three HCDRs consist of SEQ ID NOs: 228, 230, and 232, respectively, and the three LCDRs consist of SEQ ID NOs: 236, 238, and 240, respectively,
(iv) three HCDRs and three LCDRs within the HCVR/LCVR amino acid sequence pair of SEQ ID NOs: 354/362, wherein the three HCDRs consist of SEQ ID NOs: 356, 358, and 360, respectively, and the three LCDRs consist of SEQ ID NOs: 364, 366, and 368, respectively,
(v) three HCDRs and three LCDRs within the HCVR/LCVR amino acid sequence pair of SEQ ID NOs: 418/426, wherein the three HCDRs consist of SEQ ID NOs: 420, 422, and 424, respectively, and the three LCDRs consist of SEQ ID NOs: 428, 430, and 432, respectively,
(vi) three HCDRs and three LCDRs within the HCVR/LCVR amino acid sequence pair of SEQ ID NOs: 458/522, wherein the three HCDRs consist of SEQ ID NOs: 460, 462, and 464, respectively, and the three LCDRs consist of SEQ ID NOs: 524, 526, and 528, respectively,
(vii) three HCDRs and three LCDRs within the HCVR/LCVR amino acid sequence pair of SEQ ID NOs: 474/522, wherein the three HCDRs consist of SEQ ID NOs: 476, 478, and 480, respectively, and the three LCDRs consist of SEQ ID NOs: 524, 526, and 528, respectively, and
(viii) three HCDRs and three LCDRs within the HCVR/LCVR amino acid sequence pair of SEQ ID NOs: 554/562, wherein the three HCDRs consist of SEQ ID NOs: 556, 558, and 560, respectively, and the three LCDRs consist of SEQ ID NOs: 564, 566, and 568, respectively.

18. The method of claim 16, wherein the anti-LAG3 antibody or antigen-binding fragment thereof comprises three HCDRs in a HCVR of SEQ ID NO: 418; and three LCDRs in a LCVR of SEQ ID NO: 426.

19. The method of claim 15, wherein the anti-tumor therapy is an anti-PD-1 antibody or antigen-binding fragment thereof selected from the group consisting of REGN2810, nivolumab, and pembrolizumab.

20. The method of claim 15, wherein the anti-tumor therapy is an anti-PD-L1 antibody or antigen-binding fragment thereof selected from the group consisting of atezolizumab, avelumab, and durvalumab.

21. The method of claim 18, wherein the anti-LAG3 antibody is administered in combination with a second anti-tumor therapy.

22. The method of claim 21, wherein the second anti-tumor therapy is selected from the group consisting of an inhibitor of the PD-1/PD-L1 signaling axis, a CTLA-4 inhibitor, a TIM3 inhibitor, a BTLA inhibitor, a TIGIT inhibitor, a CD47 inhibitor, a GITR inhibitor, an antagonist of another T cell co-inhibitor or ligand, an indoleamine-2,3-dioxygenase (IDO) inhibitor, a vascular endothelial growth factor (VEGF) antagonist, an Ang2 inhibitor, a transforming growth factor beta (TGFβ) inhibitor, an epidermal growth factor receptor (EGFR) inhibitor, a CD20 inhibitor, an antibody to a tumor-specific antigen, a cancer vaccine, a bispecific antibody, a cytotoxin, a chemotherapeutic agent, cyclophosphamide, radiotherapy, an IL-6R inhibitor, an IL-4R inhibitor, an IL-10 inhibitor, IL-2, IL-7, IL-21, IL-15, and an antibody-drug conjugate (ADC).

23. The method of claim 21, wherein the second anti-tumor therapy is selected from the group consisting of an anti-LAG3 antibody, REGN2810, BGB-A317, nivolumab, pidilizumab, pembrolizumab, atezolizumab, avelumab, durvalumab, MDX-1105, REGN3504, ipilimumab, an anti-CD-28 antibody, an anti-2B4 antibody, an anti-LY108 antibody, an anti-LAIR1 antibody, an anti-ICOS antibody, an anti-CD160 antibody, an anti-VISTA antibody, aflibercept, bevacizumab, ranibizumab, sunitinib, sorafenib, pazopanib, nesvacumab, erlotinib, cetuximab, rituximab, an anti-CA9 antibody, an anti-CA125 antibody, an anti-melanoma-associated antigen 3 (MAGE3) antibody, an anti-carcinoembryonic antigen (CEA) antibody, an anti-vimentin antibody, an anti-tumor-M2-PK antibody, an anti-prostate-specific antigen (PSA) antibody, an anti-mucin-1 antibody, an anti-MART-1 antibody, an anti-CA19-9 antibody, Bacillus Calmette-Guerin, a CD3×CD20 bispecific antibody, a PSMA×CD3 bispecific antibody, dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, vincristine, cyclophosphamide, radiotherapy, sarilumab, dupilumab, anti-CD19-DM4 ADC, and anti-DS6-DM4 ADC.

24. The method of claim 12, wherein the tumor is selected from the group consisting of blood cancer, brain cancer, renal cell cancer, ovarian cancer, bladder cancer, prostate cancer, breast cancer, hepatic cell carcinoma, bone cancer, colon cancer, non-small-cell lung cancer, squamous cell carcinoma of head and neck, colorectal cancer, mesothelioma, B cell lymphoma, and melanoma.

* * * * *

SEQUENCE LISTING

```
<160> NUMBER OF SEQ ID NOS: 589

<210> SEQ ID NO 1
<211> LENGTH: 372
<212> TYPE: DNA
<213> ORGANISM: Artificial Sequence
<220> FEATURE:
<223> OTHER INFORMATION: synthetic

<400> SEQUENCE: 1
gaggtgcagc tgttggagtc tgggggaggc ttggtacagc ctgggggtc cctgagactc      60 tcctgtgtgg cctctggatt caccttagc acctatgcca tgagttgggt ccgccaggct     120
ccagggatgg ggctggagtg ggtctcaagt attagtggta gtggtcgtaa cacatactat     180
gcagactccg tgaagggccg gttcaccatc tccagagaca attccaagaa cacgctgttt     240
cttcaaatga acagcctgag agccgaggac acggccgttt attactgtgc gaaagagtcc     300
gtaactggaa cttcgtccta ctactacggt gtggacgtct ggggccaagg gaccacggtc     360
accgtctcct cg                                                        372

<210> SEQ ID NO 2
<211> LENGTH: 124
<212> TYPE: PRT
<213> ORGANISM: Artificial Sequence
<220> FEATURE:
<223> OTHER INFORMATION: synthetic

<400> SEQUENCE: 2

Glu Val Gln Leu Leu Glu Ser Gly Gly Gly Leu Val Gln Pro Gly Gly
```

```
                1               5                  10                  15
            Ser Leu Arg Leu Ser Cys Val Ala Ser Gly Phe Thr Phe Ser Thr Tyr
                            20                  25                  30

Ala Met Ser Trp Val Arg Gln Ala Pro Gly Met Gly Leu Glu Trp Val
                            35                  40                  45

Ser Ser Ile Ser Gly Ser Gly Arg Asn Thr Tyr Tyr Ala Asp Ser Val
                            50                  55                  60

Lys Gly Arg Phe Thr Ile Ser Arg Asp Asn Ser Lys Asn Thr Leu Phe
             65                 70                  75                  80

Leu Gln Met Asn Ser Leu Arg Ala Glu Asp Thr Ala Val Tyr Tyr Cys
                            85                  90                  95

Ala Lys Glu Ser Val Thr Gly Thr Ser Ser Tyr Tyr Gly Val Asp
                            100                 105                 110

Val Trp Gly Gln Gly Thr Thr Val Thr Val Ser Ser
                            115                 120
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct ttagcaccta tgcc                                              24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Thr Tyr Ala
 1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
attagtggta gtggtcgtaa caca                                              24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Gly Ser Gly Arg Asn Thr
 1               5

<210> SEQ ID NO 7
<211> LENGTH: 51
<212> TYPE: DNA
<213> ORGANISM: Artificial Sequence
<220> FEATURE:

<223> OTHER INFORMATION: synthetic

<400> SEQUENCE: 7
gcgaaagagt ccgtaactgg aacttcgtcc tactactacg gtgtggacgt c    51

<210> SEQ ID NO 8
<211> LENGTH: 17
<212> TYPE: PRT
<213> ORGANISM: Artificial Sequence
<220> FEATURE:
<223> OTHER INFORMATION: synthetic

<400> SEQUENCE: 8

Ala Lys Glu Ser Val Thr Gly Thr Ser Ser Tyr Tyr Tyr Gly Val Asp
1               5                   10                  15

Val

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc    60
atcacttgcc gggcaagtca gagcattagc agttatttaa attggtatca tcagaaacca   120
gggaaagccc caaagctcct gatctatgct gcatccagtt tgcaaaatgg ggtcccatca   180
aggttcagtg gcagtggatc tgggacagat ttcactctca ccatcagcag tctgcaacct   240
gaagattttg catcttacta ctgtcaacag agttacagaa ccccgctcac tttcggcgga   300
gggaccaagg tggagatcaa a                                             321

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr His Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Arg Thr Pro Leu
                85                  90                  95

Thr Phe Gly Gly Gly Thr Lys Val Glu Ile Lys
            100                 105

<210> SEQ ID NO 11
<211> LENGTH: 18
<212> TYPE: DNA
<213> ORGANISM: Artificial Sequence

```
<220> FEATURE:
<223> OTHER INFORMATION: synthetic

<400> SEQUENCE: 11
cagagcatta gcagttat                                                    18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                               9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagagtt acagaacccc gctcact                                          27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Ser Tyr Arg Thr Pro Leu Thr
1               5

<210> SEQ ID NO 17
<211> LENGTH: 387
<212> TYPE: DNA
<213> ORGANISM: Artificial Sequence
<220> FEATURE:
<223> OTHER INFORMATION: synthetic

<400> SEQUENCE: 17
```

```
caggtgcagc tggaggagtc tgggggaggc gtggtccagc ctgggaggtc cctgagactc      60
tcctgtgcag cgtctggatt caccttcagt tggtatggca tgcactgggt ccgccaggct     120
ccaggcaagg gctggagtg gtggcactt atatggtatg atggaactaa taaaaagtat       180
ggagactccg tgaagggccg attcaccatt tccagagaca attccaagaa cacggtgtat    240
ctgcaaatga acagcctgag agccgaggac acggctgtgt attactgtgc gagagattgt    300
ggacatagtg gcaacgatcg ggggacttac tattactact acggtatgga cgtctggggc    360
caagggacca cggtcaccgt ctcctca                                         387
```

<210> SEQ ID NO 18
<211> LENGTH: 129
<212> TYPE: PRT
<213> ORGANISM: Artificial Sequence
<220> FEATURE:
<223> OTHER INFORMATION: synthetic

<400> SEQUENCE: 18

```
Gln Val Gln Leu Glu Glu Ser Gly Gly Gly Val Val Gln Pro Gly Arg
1               5                   10                  15

Ser Leu Arg Leu Ser Cys Ala Ala Ser Gly Phe Thr Phe Ser Trp Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Thr Asn Lys Lys Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Cys Gly His Ser Gly Asn Asp Arg Gly Thr Tyr Tyr Tyr
            100                 105                 110

Tyr Tyr Gly Met Asp Val Trp Gly Gln Gly Thr Thr Val Thr Val Ser
        115                 120                 125

Ser
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19

```
ggattcacct tcagttggta tggc                                             24
```

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Ser Trp Tyr Gly
1               5
```

<210> SEQ ID NO 21
<211> LENGTH: 24

<212> TYPE: DNA
<213> ORGANISM: Artificial Sequence
<220> FEATURE:
<223> OTHER INFORMATION: synthetic

<400> SEQUENCE: 21
atatggtatg atggaactaa taaa                                        24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Trp Tyr Asp Gly Thr Asn Lys
1               5

<210> SEQ ID NO 23
<211> LENGTH: 66
<212> TYPE: DNA
<213> ORGANISM: Artificial Sequence
<220> FEATURE:
<223> OTHER INFORMATION: synthetic

<400> SEQUENCE: 23
gcgagagatt gtggacatag tggcaacgat cgggggactt actattacta ctacggtatg    60
gacgtc                                                                66

<210> SEQ ID NO 24
<211> LENGTH: 22
<212> TYPE: PRT
<213> ORGANISM: Artificial Sequence
<220> FEATURE:
<223> OTHER INFORMATION: synthetic

<400> SEQUENCE: 24

Ala Arg Asp Cys Gly His Ser Gly Asn Asp Arg Gly Thr Tyr Tyr Tyr
1               5                   10                  15

Tyr Tyr Gly Met Asp Val
            20

<210> SEQ ID NO 25
<211> LENGTH: 324
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                           324

<210> SEQ ID NO 26
<211> LENGTH: 108
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagagcatta gcagctat                                              18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Ser Ile Ser Ser Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                         9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Ser
1

<210> SEQ ID NO 31
<211> LENGTH: 30

-continued

<212> TYPE: DNA
<213> ORGANISM: Artificial Sequence
<220> FEATURE:
<223> OTHER INFORMATION: synthetic

<400> SEQUENCE: 31
caacagagtt acagtacccc tccgatcacc                                            30

<210> SEQ ID NO 32
<211> LENGTH: 10
<212> TYPE: PRT
<213> ORGANISM: Artificial Sequence
<220> FEATURE:
<223> OTHER INFORMATION: synthetic

<400> SEQUENCE: 32

Gln Gln Ser Tyr Ser Thr Pro Pro Ile Thr
1               5                   10

<210> SEQ ID NO 33
<211> LENGTH: 357
<212> TYPE: DNA
<213> ORGANISM: Artificial Sequence
<220> FEATURE:
<223> OTHER INFORMATION: synthetic

<400> SEQUENCE: 33
caggtgcagc tacagcagtg gggcgcagga ctgttgaagc cttcggagac cctgtccctc      60
acctgcgctg tctatggtgg gtccttcagt ggttactact ggaactggat ccgccagccc     120
ccagggaagg gctggagtg ggttggggaa atcagtcata gaggaaccac caactacaac     180
ccgtccctca agagtcgagt caccatatca ctggacacgt ccaagaacca gttctccctg     240
aaactgacct ctgtgaccgc cgcggacacg gctgtgtatt actgttcgag agacgaggaa     300
ctggaattcc gtttctttga ctactggggc cagggaaccc tggtcaccgt ctcctca       357

<210> SEQ ID NO 34
<211> LENGTH: 119
<212> TYPE: PRT
<213> ORGANISM: Artificial Sequence
<220> FEATURE:
<223> OTHER INFORMATION: synthetic

<400> SEQUENCE: 34

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Val
        35                  40                  45

Gly Glu Ile Ser His Arg Gly Thr Thr Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Leu Thr Ser Val Thr Ala Ala Asp Thr Ala Val Tyr Tyr Cys Ser
                85                  90                  95

Arg Asp Glu Glu Leu Glu Phe Arg Phe Phe Asp Tyr Trp Gly Gln Gly
            100                 105                 110

Thr Leu Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggtgggtcct tcagtggtta ctac                                          24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Gly Ser Phe Ser Gly Tyr Tyr
1               5

<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
atcagtcata gaggaaccac c                                             21

<210> SEQ ID NO 38
<211> LENGTH: 7
<212> TYPE: PRT
<213> ORGANISM: Artificial Sequence
<220> FEATURE:
<223> OTHER INFORMATION: synthetic

<400> SEQUENCE: 38

Ile Ser His Arg Gly Thr Thr
1               5

<210> SEQ ID NO 39
<211> LENGTH: 39
<212> TYPE: DNA
<213> ORGANISM: Artificial Sequence
<220> FEATURE:
<223> OTHER INFORMATION: synthetic

<400> SEQUENCE: 39
tcgagagacg aggaactgga attccgtttc tttgactac                          39

<210> SEQ ID NO 40
<211> LENGTH: 13
<212> TYPE: PRT
<213> ORGANISM: Artificial Sequence
<220> FEATURE:
<223> OTHER INFORMATION: synthetic

<400> SEQUENCE: 40

Ser Arg Asp Glu Glu Leu Glu Phe Arg Phe Phe Asp Tyr
1               5                   10

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41

```
gaaattgtgt tgacacagtc tccagccacc ctgtctttgt ctccagggga aagagccacc    60
ctctcctgca gggccagtca gagtgttagc agctatttag cctggtacca acaaaaacct   120
ggccaggctc ccaggctcct cgtctatggt gcatccaaca gggccactgg catcccagcc   180
aggttcagtg gcagtgggtc tgggacagac ttcactctca ccatcagcag cctagagcct   240
gaagattttg catttttatta ctgtcagcag cgtagcaact ggccgctcac tttcggcgga   300
gggaccaagg tggagatcaa a                                             321
```

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Val
        35                  40                  45
Tyr Gly Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Phe Tyr Tyr Cys Gln Gln Arg Ser Asn Trp Pro Leu
                85                  90                  95
Thr Phe Gly Gly Gly Thr Lys Val Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43

```
cagagtgtta gcagctat                                                  18
```

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

```
Gln Ser Val Ser Ser Tyr
1               5
```

<210> SEQ ID NO 45
<211> LENGTH: 9
<212> TYPE: DNA
<213> ORGANISM: Artificial Sequence
<220> FEATURE:

<223> OTHER INFORMATION: synthetic

<400> SEQUENCE: 45 ggtgcatcc                                                                                        9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Gly Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
cagcagcgta gcaactggcc gctcact                                                                   27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Arg Ser Asn Trp Pro Leu Thr
1               5

<210> SEQ ID NO 49
<211> LENGTH: 357
<212> TYPE: DNA
<213> ORGANISM: Artificial Sequence
<220> FEATURE:
<223> OTHER INFORMATION: synthetic

<400> SEQUENCE: 49
cagctgcagc tgcaggagtc gggcccagga ctggtgaagc cttcggagac cctgtccctc      60
acctgcactg tctctggtga ctccatcatc agtaatagtt attactgggg ctggatccgc     120
cagcccccag ggaaggggct ggagtggatt ggcaatttct tttatactgg ggccacctac     180
tacaacccgt ccctcaagag tcgagtcacc atatccgctg acacgtccaa gaatcagttc     240
tccctgaagc tgagctctgt gaccgccgca gacacggctc tgtattattg tgcgagttat     300
aataggaatt accggttcga ccccctgggc cagggaaccc tggtcaccgt ctcctca       357

<210> SEQ ID NO 50
<211> LENGTH: 119
<212> TYPE: PRT
<213> ORGANISM: Artificial Sequence
<220> FEATURE:
<223> OTHER INFORMATION: synthetic

<400> SEQUENCE: 50

Gln Leu Gln Leu Gln Glu Ser Gly Pro Gly Leu Val Lys Pro Ser Glu
1               5                   10                  15

```
Thr Leu Ser Leu Thr Cys Thr Val Ser Gly Asp Ser Ile Ile Ser Asn
            20                  25                  30

Ser Tyr Tyr Trp Gly Trp Ile Arg Gln Pro Pro Gly Lys Gly Leu Glu
        35                  40                  45

Trp Ile Gly Asn Phe Phe Tyr Thr Gly Ala Thr Tyr Tyr Asn Pro Ser
 50                  55                  60

Leu Lys Ser Arg Val Thr Ile Ser Ala Asp Thr Ser Lys Asn Gln Phe
65                  70                  75                  80

Ser Leu Lys Leu Ser Ser Val Thr Ala Ala Asp Thr Ala Leu Tyr Tyr
                85                  90                  95

Cys Ala Ser Tyr Asn Arg Asn Tyr Arg Phe Asp Pro Trp Gly Gln Gly
            100                 105                 110

Thr Leu Val Thr Val Ser Ser
        115

<210> SEQ ID NO 51
<211> LENGTH: 30
<212> TYPE: DNA
<213> ORGANISM: Artificial Sequence
<220> FEATURE:
<223> OTHER INFORMATION: synthetic

<400> SEQUENCE: 51
ggtgactcca tcatcagtaa tagttattac                                    30

<210> SEQ ID NO 52
<211> LENGTH: 10
<212> TYPE: PRT
<213> ORGANISM: Artificial Sequence
<220> FEATURE:
<223> OTHER INFORMATION: synthetic

<400> SEQUENCE: 52

Gly Asp Ser Ile Ile Ser Asn Ser Tyr Tyr
1               5                   10

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
ttcttttata ctggggccac c                                             21

<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Phe Phe Tyr Thr Gly Ala Thr
1               5

<210> SEQ ID NO 55
<211> LENGTH: 33
<212> TYPE: DNA
<213> ORGANISM: Artificial Sequence
<220> FEATURE:
<223> OTHER INFORMATION: synthetic
```

<400> SEQUENCE: 55
gcgagttata ataggaatta ccggttcgac ccc                                    33

<210> SEQ ID NO 56
<211> LENGTH: 11
<212> TYPE: PRT
<213> ORGANISM: Artificial Sequence
<220> FEATURE:
<223> OTHER INFORMATION: synthetic

<400> SEQUENCE: 56

Ala Ser Tyr Asn Arg Asn Tyr Arg Phe Asp Pro
1               5                   10

<210> SEQ ID NO 57
<211> LENGTH: 324
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttactt ctgtcaacag agttacagta cccctccgat caccttcggc      300
caagggacac gactggagat taaa                                             324

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59

```
cagagcatta gcagctat                                                  18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Ser Ile Ser Ser Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                             9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
1

<210> SEQ ID NO 63
<211> LENGTH: 30
<212> TYPE: DNA
<213> ORGANISM: Artificial Sequence
<220> FEATURE:
<223> OTHER INFORMATION: synthetic

<400> SEQUENCE: 63
caacagagtt acagtacccc tccgatcacc                                     30

<210> SEQ ID NO 64
<211> LENGTH: 10
<212> TYPE: PRT
<213> ORGANISM: Artificial Sequence
<220> FEATURE:
<223> OTHER INFORMATION: synthetic

<400> SEQUENCE: 64

Gln Gln Ser Tyr Ser Thr Pro Pro Ile Thr
1               5                   10

<210> SEQ ID NO 65
<211> LENGTH: 381
<212> TYPE: DNA
<213> ORGANISM: Artificial Sequence
<220> FEATURE:
<223> OTHER INFORMATION: synthetic

<400> SEQUENCE: 65
caggtgcagc tacagcagtg gggcgcagga ctgttgaagc cttcggagac cctgtccctc    60
acctgcgctg tctatggtgg gtccttcagt acttactact ggagctggat ccgccagccc   120
```

```
ccagggaagg ggctggagtg gattggagag atcaatcata gtggaaacgc cgactacaac      180
ccgtccctca agagtcgagt ctccatatca gtggacacgt ccaagaacca gttctccctg      240
aggctgagct ctgtgaccgc cgcggacacg gctatttatt actgtgcgag agcgggctat      300
tgtagtagtc ccacctgcta ttcctactac tacttcggta tggacgtctg gggccaaggg      360
accacggtca ccgtctcctc a                                                381
```

<210> SEQ ID NO 66
<211> LENGTH: 127
<212> TYPE: PRT
<213> ORGANISM: Artificial Sequence
<220> FEATURE:
<223> OTHER INFORMATION: synthetic

<400> SEQUENCE: 66

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Thr Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Ala Asp Tyr Asn Pro Ser Leu Lys
    50                  55                  60

Ser Arg Val Ser Ile Ser Val Asp Thr Ser Lys Asn Gln Phe Ser Leu
65                  70                  75                  80

Arg Leu Ser Ser Val Thr Ala Ala Asp Thr Ala Ile Tyr Tyr Cys Ala
                85                  90                  95

Arg Ala Gly Tyr Cys Ser Ser Pro Thr Cys Tyr Ser Tyr Tyr Tyr Phe
            100                 105                 110

Gly Met Asp Val Trp Gly Gln Gly Thr Thr Val Thr Val Ser Ser
        115                 120                 125
```

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67

```
ggtgggtcct tcagtactta ctac                                              24
```

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

```
Gly Gly Ser Phe Ser Thr Tyr Tyr
1               5
```

<210> SEQ ID NO 69
<211> LENGTH: 21
<212> TYPE: DNA
<213> ORGANISM: Artificial Sequence
<220> FEATURE:
<223> OTHER INFORMATION: synthetic

<400> SEQUENCE: 69
atcaatcata gtggaaacgc c                                                    21

<210> SEQ ID NO 70
<211> LENGTH: 7
<212> TYPE: PRT
<213> ORGANISM: Artificial Sequence
<220> FEATURE:
<223> OTHER INFORMATION: synthetic

<400> SEQUENCE: 70

Ile Asn His Ser Gly Asn Ala
1               5

<210> SEQ ID NO 71
<211> LENGTH: 63
<212> TYPE: DNA
<213> ORGANISM: Artificial Sequence
<220> FEATURE:
<223> OTHER INFORMATION: synthetic

<400> SEQUENCE: 71
gcgagagcgg gctattgtag tagtcccacc tgctattcct actactactt cggtatggac      60
gtc                                                                    63

<210> SEQ ID NO 72
<211> LENGTH: 21
<212> TYPE: PRT
<213> ORGANISM: Artificial Sequence
<220> FEATURE:
<223> OTHER INFORMATION: synthetic

<400> SEQUENCE: 72

Ala Arg Ala Gly Tyr Cys Ser Ser Pro Thr Cys Tyr Ser Tyr Tyr Tyr
1               5                   10                  15

Phe Gly Met Asp Val
            20

<210> SEQ ID NO 73
<211> LENGTH: 324
<212> TYPE: DNA
<213> ORGANISM: Artificial Sequence
<220> FEATURE:
<223> OTHER INFORMATION: synthetic

<400> SEQUENCE: 73
gaaattgtgt tgacgcagtc tccaggcacc ctgtctttgt ctctagggga aagagccacc      60
ctctcctgca gggccagtca gagtgttatc agcagcttct tagcctggta ccagcagaaa     120
cctggccagg ctcccaggct cctcatctat ggtgcatcca gcagggccac tggcttccca     180
gacaggttca gtggcagtgg gtctgggaca gacttcactc tcaccatccg cagactggag     240
cctgaagatt ttgcagtgta ttactgtcag cagtatggta actcaccttg gacgttcggc     300
caagggacca aggtggagat caaa                                            324

<210> SEQ ID NO 74
<211> LENGTH: 108
<212> TYPE: PRT
<213> ORGANISM: Artificial Sequence
<220> FEATURE:
<223> OTHER INFORMATION: synthetic

<400> SEQUENCE: 74

Glu Ile Val Leu Thr Gln Ser Pro Gly Thr Leu Ser Leu Ser Leu Gly

```
            1               5                  10                 15
          Glu Arg Ala Thr Leu Ser Cys Arg Ala Ser Gln Ser Val Ile Ser Ser
                          20                  25                  30

Phe Leu Ala Trp Tyr Gln Gln Lys Pro Gly Gln Ala Pro Arg Leu Leu
                          35                  40                  45

Ile Tyr Gly Ala Ser Ser Arg Ala Thr Gly Phe Pro Asp Arg Phe Ser
                  50                  55                  60

Gly Ser Gly Ser Gly Thr Asp Phe Thr Leu Thr Ile Arg Arg Leu Glu
          65                  70                  75                  80

Pro Glu Asp Phe Ala Val Tyr Tyr Cys Gln Gln Tyr Gly Asn Ser Pro
                          85                  90                  95

Trp Thr Phe Gly Gln Gly Thr Lys Val Glu Ile Lys
                          100                 105
```

<210> SEQ ID NO 75
<211> LENGTH: 21
<212> TYPE: DNA
<213> ORGANISM: Artificial Sequence
<220> FEATURE:
<223> OTHER INFORMATION: synthetic

<400> SEQUENCE: 75
cagagtgtta tcagcagctt c                                                  21

<210> SEQ ID NO 76
<211> LENGTH: 7
<212> TYPE: PRT
<213> ORGANISM: Artificial Sequence
<220> FEATURE:
<223> OTHER INFORMATION: synthetic

<400> SEQUENCE: 76

Gln Ser Val Ile Ser Ser Phe
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 ggtgcatcc                                                                 9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Gly Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
cagcagtatg gtaactcacc ttggacg                                              27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Tyr Gly Asn Ser Pro Trp Thr
1               5

<210> SEQ ID NO 81
<211> LENGTH: 387
<212> TYPE: DNA
<213> ORGANISM: Artificial Sequence
<220> FEATURE:
<223> OTHER INFORMATION: synthetic

<400> SEQUENCE: 81
caggtcacct tgaaggagtc tggtcctgtg ctggtgaaac ccacagagac cctcacgctg      60
acctgcaccg tctctgggtt ctcactcagc aatgctggga tgggtgtgag ctgggtccgt     120 cagcccctg ggaaggccct ggagtggctt gcacacattt tttcgaatga cgagaagtcc     180
tacagcacat ctctgaggac cagactcacc atctccaagg acacctccaa agccaggtg     240 gtccttaccg tgaccaactt ggaccctgtg gacacagcca catatttctg tgcacggata     300
ccagagttta ccagctcgtc gtgggctctc tactacttct acggtatgga cgtctggggc     360
caagggacca cggtcaccgt ctcctca                                          387

<210> SEQ ID NO 82
<211> LENGTH: 129
<212> TYPE: PRT
<213> ORGANISM: Artificial Sequence
<220> FEATURE:
<223> OTHER INFORMATION: synthetic

<400> SEQUENCE: 82

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Gly Met Gly Val Ser Trp Val Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Arg Thr Arg Leu Thr Ile Ser Lys Asp Thr Ser Lys Ser Gln Val
65                  70                  75                  80

Val Leu Thr Val Thr Asn Leu Asp Pro Val Asp Thr Ala Thr Tyr Phe
                85                  90                  95

Cys Ala Arg Ile Pro Glu Phe Thr Ser Ser Ser Trp Ala Leu Tyr Tyr
            100                 105                 110

Phe Tyr Gly Met Asp Val Trp Gly Gln Gly Thr Thr Val Thr Val Ser
        115                 120                 125

Ser

<210> SEQ ID NO 83
<211> LENGTH: 30

<212> TYPE: DNA
<213> ORGANISM: Artificial Sequence
<220> FEATURE:
<223> OTHER INFORMATION: synthetic

<400> SEQUENCE: 83
gggttctcac tcagcaatgc tgggatgggt                30

<210> SEQ ID NO 84
<211> LENGTH: 10
<212> TYPE: PRT
<213> ORGANISM: Artificial Sequence
<220> FEATURE:
<223> OTHER INFORMATION: synthetic

<400> SEQUENCE: 84

Gly Phe Ser Leu Ser Asn Ala Gly Met Gly
1               5                   10

<210> SEQ ID NO 85
<211> LENGTH: 21
<212> TYPE: DNA
<213> ORGANISM: Artificial Sequence
<220> FEATURE:
<223> OTHER INFORMATION: synthetic

<400> SEQUENCE: 85 atttttcga atgacgagaa g                21

<210> SEQ ID NO 86
<211> LENGTH: 7
<212> TYPE: PRT
<213> ORGANISM: Artificial Sequence
<220> FEATURE:
<223> OTHER INFORMATION: synthetic

<400> SEQUENCE: 86

Ile Phe Ser Asn Asp Glu Lys
1               5

<210> SEQ ID NO 87
<211> LENGTH: 63
<212> TYPE: DNA
<213> ORGANISM: Artificial Sequence
<220> FEATURE:
<223> OTHER INFORMATION: synthetic

<400> SEQUENCE: 87
gcacggatac cagagtttac cagctcgtcg tgggctctct actacttcta cggtatggac      60
gtc      63

<210> SEQ ID NO 88
<211> LENGTH: 21
<212> TYPE: PRT
<213> ORGANISM: Artificial Sequence
<220> FEATURE:
<223> OTHER INFORMATION: synthetic

<400> SEQUENCE: 88

Ala Arg Ile Pro Glu Phe Thr Ser Ser Ser Trp Ala Leu Tyr Tyr Phe
1               5                   10                  15

Tyr Gly Met Asp Val
            20

<210> SEQ ID NO 89

<211> LENGTH: 324
<212> TYPE: DNA
<213> ORGANISM: Artificial Sequence
<220> FEATURE:
<223> OTHER INFORMATION: synthetic

<400> SEQUENCE: 89

```
gaaattgtgt tgacgcagtc tccaggcacc ctgtctttgt ctccagggga aagcgccacc      60
ctctcctgca gggccagtca gagtattacc agcacctact tcgcctggta ccagcagaaa     120
cctggccagg ctcccaggct cctcatctat gctacatcca gcagggccac tggcgtccca     180
gacaggttca gtggcagtgg gtctgggacg gacttcactc tcaccatcag cagactggag     240
cctgatgatt ttgcagtgta ttactgtcag caatatggta ggtcaccttg gacgttcggc     300
caagggacca aggtggaagt caaa                                            324
```

<210> SEQ ID NO 90
<211> LENGTH: 108
<212> TYPE: PRT
<213> ORGANISM: Artificial Sequence
<220> FEATURE:
<223> OTHER INFORMATION: synthetic

<400> SEQUENCE: 90

```
Glu Ile Val Leu Thr Gln Ser Pro Gly Thr Leu Ser Leu Ser Pro Gly
1               5                   10                  15
Glu Ser Ala Thr Leu Ser Cys Arg Ala Ser Gln Ser Ile Thr Ser Thr
            20                  25                  30
Tyr Phe Ala Trp Tyr Gln Gln Lys Pro Gly Gln Ala Pro Arg Leu Leu
        35                  40                  45
Ile Tyr Ala Thr Ser Ser Arg Ala Thr Gly Val Pro Asp Arg Phe Ser
    50                  55                  60
Gly Ser Gly Ser Gly Thr Asp Phe Thr Leu Thr Ile Ser Arg Leu Glu
65                  70                  75                  80
Pro Asp Asp Phe Ala Val Tyr Tyr Cys Gln Gln Tyr Gly Arg Ser Pro
                85                  90                  95
Trp Thr Phe Gly Gln Gly Thr Lys Val Glu Val Lys
            100                 105
```

<210> SEQ ID NO 91
<211> LENGTH: 21
<212> TYPE: DNA
<213> ORGANISM: Artificial Sequence
<220> FEATURE:
<223> OTHER INFORMATION: synthetic

<400> SEQUENCE: 91

```
cagagtatta ccagcaccta c                                                21
```

<210> SEQ ID NO 92
<211> LENGTH: 7
<212> TYPE: PRT
<213> ORGANISM: Artificial Sequence
<220> FEATURE:
<223> OTHER INFORMATION: synthetic

<400> SEQUENCE: 92

```
Gln Ser Ile Thr Ser Thr Tyr
1               5
```

<210> SEQ ID NO 93
<211> LENGTH: 9

<212> TYPE: DNA
<213> ORGANISM: Artificial Sequence
<220> FEATURE:
<223> OTHER INFORMATION: synthetic

<400> SEQUENCE: 93 gctacatcc                                                                    9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ala Thr Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
cagcaatatg gtaggtcacc ttggacg                                               27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Tyr Gly Arg Ser Pro Trp Thr
1               5

<210> SEQ ID NO 97
<211> LENGTH: 363
<212> TYPE: DNA
<213> ORGANISM: Artificial Sequence
<220> FEATURE:
<223> OTHER INFORMATION: synthetic

<400> SEQUENCE: 97
caggttcagc tggtgcagtc tggagctgag gtgaagaagc ctggggcctc agtgaaggtc            60
tcctgcaagg cttctggtta caccttacc agttatggta tcagctgggt gcgacaggcc           120
cctggacaag gcttgagtg gatgggatgg atcagcgctt acaatgataa cacaaactat           180
gcacagaagc tccagggcag agtcaccatg accgcagaca catccacgaa tacagcctac           240
atggagctaa ggagcctgag atctgacgac acggccattt attactgtgt gcgatggaat           300
tggggttccg tctactggta cttcgatctc tggggccgtg gcaccctggt cactgtctcc           360
tca                                                                        363

<210> SEQ ID NO 98
<211> LENGTH: 121
<212> TYPE: PRT
<213> ORGANISM: Artificial Sequence
<220> FEATURE:
<223> OTHER INFORMATION: synthetic -continued

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asn Thr Asn Tyr Ala Gln Lys Leu
    50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Ile Tyr Tyr Cys
                85                  90                  95

Val Arg Trp Asn Trp Gly Ser Val Tyr Trp Tyr Phe Asp Leu Trp Gly
            100                 105                 110

Arg Gly Thr Leu Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99 ggttacaccct ttaccagtta tggt                                    24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Tyr Thr Phe Thr Ser Tyr Gly
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atcagcgctt acaatgataa caca                                     24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Ala Tyr Asn Asp Asn Thr
1               5

<210> SEQ ID NO 103
<211> LENGTH: 42

```
<212> TYPE: DNA
<213> ORGANISM: Artificial Sequence
<220> FEATURE:
<223> OTHER INFORMATION: synthetic

<400> SEQUENCE: 103
gtgcgatgga attggggttc cgtctactgg tacttcgatc tc                              42

<210> SEQ ID NO 104
<211> LENGTH: 14
<212> TYPE: PRT
<213> ORGANISM: Artificial Sequence
<220> FEATURE:
<223> OTHER INFORMATION: synthetic

<400> SEQUENCE: 104

Val Arg Trp Asn Trp Gly Ser Val Tyr Trp Tyr Phe Asp Leu
1               5                  10

<210> SEQ ID NO 105
<211> LENGTH: 324
<212> TYPE: DNA
<213> ORGANISM: Artificial Sequence
<220> FEATURE:
<223> OTHER INFORMATION: synthetic

<400> SEQUENCE: 105
gaaattgtgt tgacgcagtc tccaggcacc ctgtctttgt ctccagggga aagagccacc           60
ctctcctgca gggccagtca gattattagc agcagctact ttgcctggta ccagcagaaa          120
cctggccagg ctcccaggct cctcatctat ggtgcgtcca gcagggccac tggcatccca          180
gacaggttca gtggcagtgt gtctgggaca gacttcactc tcaccatcag cagactggag          240
cctgaagatt ttgcaatgta tttctgtcag cagtatggta actcaccttg gacgttcggc          300
caagggacca aggtggaaat caaa                                                 324

<210> SEQ ID NO 106
<211> LENGTH: 108
<212> TYPE: PRT
<213> ORGANISM: Artificial Sequence
<220> FEATURE:
<223> OTHER INFORMATION: synthetic

<400> SEQUENCE: 106

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ile Ile Ser Ser Ser
            20                  25                  30

Tyr Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Val Ser Gly Thr Asp Phe Thr Leu Thr Ile Ser Arg Leu Glu
65                  70                  75                  80

Pro Glu Asp Phe Ala Met Tyr Phe Cys Gln Gln Tyr Gly Asn Ser Pro
                85                  90                  95

Trp Thr Phe Gly Gln Gly Thr Lys Val Glu Ile Lys
            100                 105

<210> SEQ ID NO 107
<211> LENGTH: 21
<212> TYPE: DNA
```

```
<213> ORGANISM: Artificial Sequence
<220> FEATURE:
<223> OTHER INFORMATION: synthetic

<400> SEQUENCE: 107
cagattatta gcagcagcta c                                              21

<210> SEQ ID NO 108
<211> LENGTH: 7
<212> TYPE: PRT
<213> ORGANISM: Artificial Sequence
<220> FEATURE:
<223> OTHER INFORMATION: synthetic

<400> SEQUENCE: 108

Gln Ile Ile Ser Ser Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 ggtgcgtcc                                                             9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Gly Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
cagcagtatg gtaactcacc ttggacg                                        27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Tyr Gly Asn Ser Pro Trp Thr
1               5

<210> SEQ ID NO 113
<211> LENGTH: 351
<212> TYPE: DNA
<213> ORGANISM: Artificial Sequence
<220> FEATURE:
<223> OTHER INFORMATION: synthetic
```

```
<400> SEQUENCE: 113
cagatcacct tgaaggagtc tggtcctacg ctggtgaaac ccacacagac cctcacgctg    60
acttgcacct tctctgggtt ctcactcaac actcatagag tgggtgtagg ctggatccgg   120
cagcccccag gaaaggccct ggagtggctt gcactcattt atgggaatga tgttaagaac   180
tacagcccat ctctggagac caggctcacc atcgccaagg acacctccaa aaaccaggtg   240
gtccttacaa tgaccaacat ggaccctgtg gacacagcca catatttctg ttcgtacata   300 acggggaag gaatgtactg gggccaggga accctggtca ccgtctcctc a             351

<210> SEQ ID NO 114
<211> LENGTH: 117
<212> TYPE: PRT
<213> ORGANISM: Artificial Sequence
<220> FEATURE:
<223> OTHER INFORMATION: synthetic

<400> SEQUENCE: 114

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr His
            20                  25                  30

Arg Val Gly Val Gly Trp Ile Arg Gln Pro Pro Gly Lys Ala Leu Glu
        35                  40                  45

Trp Leu Ala Leu Ile Tyr Gly Asn Asp Val Lys Asn Tyr Ser Pro Ser
    50                  55                  60

Leu Glu Thr Arg Leu Thr Ile Ala Lys Asp Thr Ser Lys Asn Gln Val
65                  70                  75                  80

Val Leu Thr Met Thr Asn Met Asp Pro Val Asp Thr Ala Thr Tyr Phe
                85                  90                  95

Cys Ser Tyr Ile Thr Gly Glu Gly Met Tyr Trp Gly Gln Gly Thr Leu
            100                 105                 110

Val Thr Val Ser Ser
        115

<210> SEQ ID NO 115
<211> LENGTH: 30
<212> TYPE: DNA
<213> ORGANISM: Artificial Sequence
<220> FEATURE:
<223> OTHER INFORMATION: synthetic

<400> SEQUENCE: 115
gggttctcac tcaacactca tagagtgggt                                     30

<210> SEQ ID NO 116
<211> LENGTH: 10
<212> TYPE: PRT
<213> ORGANISM: Artificial Sequence
<220> FEATURE:
<223> OTHER INFORMATION: synthetic

<400> SEQUENCE: 116

Gly Phe Ser Leu Asn Thr His Arg Val Gly
1               5                   10

<210> SEQ ID NO 117
<211> LENGTH: 21
<212> TYPE: DNA
<213> ORGANISM: Artificial Sequence
<220> FEATURE:
```

<223> OTHER INFORMATION: synthetic

<400> SEQUENCE: 117
atttatggga atgatgttaa g                                              21

<210> SEQ ID NO 118
<211> LENGTH: 7
<212> TYPE: PRT
<213> ORGANISM: Artificial Sequence
<220> FEATURE:
<223> OTHER INFORMATION: synthetic

<400> SEQUENCE: 118

Ile Tyr Gly Asn Asp Val Lys
1               5

<210> SEQ ID NO 119
<211> LENGTH: 27
<212> TYPE: DNA
<213> ORGANISM: Artificial Sequence
<220> FEATURE:
<223> OTHER INFORMATION: synthetic

<400> SEQUENCE: 119
tcgtacataa cgggggaagg aatgtac                                        27

<210> SEQ ID NO 120
<211> LENGTH: 9
<212> TYPE: PRT
<213> ORGANISM: Artificial Sequence
<220> FEATURE:
<223> OTHER INFORMATION: synthetic

<400> SEQUENCE: 120

Ser Tyr Ile Thr Gly Glu Gly Met Tyr
1               5

<210> SEQ ID NO 121
<211> LENGTH: 333
<212> TYPE: DNA
<213> ORGANISM: Artificial Sequence
<220> FEATURE:
<223> OTHER INFORMATION: synthetic

<400> SEQUENCE: 121
gatgttgtga tgactcagtc tccactctcc ctgtccgtca cccttggaca gccggcctcc     60
atttcctgta ggtctagtca aaacctcatg tacagtgatg aaacaccta cttgaattgg    120 tttcaccaga ggccaggcca atctccaagg cgtctaattt ataaggtttc taaccgggac    180
tctggggtcc cagacagatt cagcggcagt gggtcaggca ctgatttcac actgaaaatc    240
agcagggtgg aggctgagga tgttgggggtt tattactgca tgcaaggtac acactggtac    300
acatttggcc aggggaccaa gctggagatc aaa                                 333

<210> SEQ ID NO 122
<211> LENGTH: 111
<212> TYPE: PRT
<213> ORGANISM: Artificial Sequence
<220> FEATURE:
<223> OTHER INFORMATION: synthetic

<400> SEQUENCE: 122

Asp Val Val Met Thr Gln Ser Pro Leu Ser Leu Ser Val Thr Leu Gly
1               5                   10                  15

```
Gln Pro Ala Ser Ile Ser Cys Arg Ser Ser Gln Asn Leu Met Tyr Ser
                20                  25                  30

Asp Gly Asn Thr Tyr Leu Asn Trp Phe His Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Tyr Thr Phe Gly Gln Gly Thr Lys Leu Glu Ile Lys
                100                 105                 110
```

<210> SEQ ID NO 123
<211> LENGTH: 33
<212> TYPE: DNA
<213> ORGANISM: Artificial Sequence
<220> FEATURE:
<223> OTHER INFORMATION: synthetic

<400> SEQUENCE: 123
caaaacctca tgtacagtga tggaaacacc tac                                   33

<210> SEQ ID NO 124
<211> LENGTH: 11
<212> TYPE: PRT
<213> ORGANISM: Artificial Sequence
<220> FEATURE:
<223> OTHER INFORMATION: synthetic

<400> SEQUENCE: 124

```
Gln Asn Leu Met Tyr Ser Asp Gly Asn Thr Tyr
1               5                   10
```

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 aaggtttct                                                               9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

```
Lys Val Ser
1
```

<210> SEQ ID NO 127
<211> LENGTH: 24
<212> TYPE: DNA
<213> ORGANISM: Artificial Sequence
<220> FEATURE:
<223> OTHER INFORMATION: synthetic

<400> SEQUENCE: 127
atgcaaggta cacactggta caca                                             24

<210> SEQ ID NO 128
<211> LENGTH: 8
<212> TYPE: PRT
<213> ORGANISM: Artificial Sequence
<220> FEATURE:
<223> OTHER INFORMATION: synthetic

<400> SEQUENCE: 128

Met Gln Gly Thr His Trp Tyr Thr
1               5

<210> SEQ ID NO 129
<211> LENGTH: 357
<212> TYPE: DNA
<213> ORGANISM: Artificial Sequence
<220> FEATURE:
<223> OTHER INFORMATION: synthetic

<400> SEQUENCE: 129
caggtgcagc tgcagcagtg gggcgcagga ctattgaagc cttcggagac cctgtccctc     60
acctgcgctg tctatggtgg gtctttcagt ggttattact ggagctggat ccgccagccc    120
ccagggaagg gtctggaatg gattggggaa atcaatcata aggaaacac caactacaac    180 ccgtccctca agagtcgagt caccatatca ctcgacacgt ccaagaaaca gttctccctg    240
aacctgagtt ctgtgaccgc cgcggacacg gctatgtatt actgtacgag agacgaagaa    300
caggaactac gtttccttga ctactggggc cagggaaccc tggtcaccgt ctcctca       357

<210> SEQ ID NO 130
<211> LENGTH: 119
<212> TYPE: PRT
<213> ORGANISM: Artificial Sequence
<220> FEATURE:
<223> OTHER INFORMATION: synthetic

<400> SEQUENCE: 130

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Tyr Asn Pro Ser Leu Lys
    50                  55                  60

Ser Arg Val Thr Ile Ser Leu Asp Thr Ser Lys Lys Gln Phe Ser Leu
65                  70                  75                  80

Asn Leu Ser Ser Val Thr Ala Ala Asp Thr Ala Met Tyr Tyr Cys Thr
                85                  90                  95

Arg Asp Glu Glu Gln Glu Leu Arg Phe Leu Asp Tyr Trp Gly Gln Gly
            100                 105                 110

Thr Leu Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131

```
ggtgggtctt tcagtggtta ttac                                            24
```

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Gly Ser Phe Ser Gly Tyr Tyr
1               5

<210> SEQ ID NO 133
<211> LENGTH: 21
<212> TYPE: DNA
<213> ORGANISM: Artificial Sequence
<220> FEATURE:
<223> OTHER INFORMATION: synthetic

<400> SEQUENCE: 133

```
atcaatcata gaggaaacac c                                               21
```

<210> SEQ ID NO 134
<211> LENGTH: 7
<212> TYPE: PRT
<213> ORGANISM: Artificial Sequence
<220> FEATURE:
<223> OTHER INFORMATION: synthetic

<400> SEQUENCE: 134

Ile Asn His Arg Gly Asn Thr
1               5

<210> SEQ ID NO 135
<211> LENGTH: 39
<212> TYPE: DNA
<213> ORGANISM: Artificial Sequence
<220> FEATURE:
<223> OTHER INFORMATION: synthetic

<400> SEQUENCE: 135

```
acgagagacg aagaacagga actacgtttc cttgactac                            39
```

<210> SEQ ID NO 136
<211> LENGTH: 13
<212> TYPE: PRT
<213> ORGANISM: Artificial Sequence
<220> FEATURE:
<223> OTHER INFORMATION: synthetic

<400> SEQUENCE: 136

Thr Arg Asp Glu Glu Gln Glu Leu Arg Phe Leu Asp Tyr
1               5                   10

<210> SEQ ID NO 137
<211> LENGTH: 321
<212> TYPE: DNA
<213> ORGANISM: Artificial Sequence
<220> FEATURE:
<223> OTHER INFORMATION: synthetic

<400> SEQUENCE: 137

```
gagattgtgt tgacacagtc tccagccacc ctgtctttgt ctccagggga aagagccacc     60
ctctcctgca gggccagtca ggatattagc acctacttag cctggtacca acagagagct    120
```

```
ggccaggctc ccaggctcct catctatggt gcttccaaca gggccactgg catcccagcc    180
aggttcagtg gcagtgggtc tgggacagac ttcactctca ccatcagcag cctagagcct    240
gaagattttg cattttatta ctgtcaacag cgcagcaact ggccgctcac tttcggcgga    300
gggaccgagg tggagatcaa a                                              321
```

<210> SEQ ID NO 138
<211> LENGTH: 107
<212> TYPE: PRT
<213> ORGANISM: Artificial Sequence
<220> FEATURE:
<223> OTHER INFORMATION: synthetic

<400> SEQUENCE: 138

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Thr Tyr
            20                  25                  30

Leu Ala Trp Tyr Gln Gln Arg Ala Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Glu Val Glu Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139

```
caggatatta gcacctac                                                  18
```

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

```
Gln Asp Ile Ser Thr Tyr
1               5
```

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141

```
ggtgcttcc                                                             9
```

<210> SEQ ID NO 142

```
<211> LENGTH: 3
<212> TYPE: PRT
<213> ORGANISM: Artificial Sequence
<220> FEATURE:
<223> OTHER INFORMATION: synthetic

<400> SEQUENCE: 142

Gly Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: synthetic

<400> SEQUENCE: 143
caacagcgca gcaactggcc gctcact                                         27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Gln Gln Arg Ser Asn Trp Pro Leu Thr
1               5

<210> SEQ ID NO 145
<211> LENGTH: 366
<212> TYPE: DNA
<213> ORGANISM: Artificial Sequence
<220> FEATURE:
<223> OTHER INFORMATION: synthetic

<400> SEQUENCE: 145
caggtgcagc tacagcagtg gggcgcagga ctgttgaagc cttcggagac cctgtccctc     60
acctgcgttg tccatggtgg gtccttcagt ggttactact ggaactggat ccgccagccc   120
ccagggaagg gctggagtg gattggggaa atcaatcata gaggaaacac caactacaac    180
ccgtccctca gagtcgagt caccgtatca gaagacacgt ccaagaacca gttctccctg    240
aagctgagct ctttgaccgc cgcggacacg gctgtgtatt actgtgtgag aggagaggat   300
tacgattttt ggagtgatta ttataatgac tactggggcc agggaaccct ggtcaccgtc   360
tcctca                                                              366

<210> SEQ ID NO 146
<211> LENGTH: 122
<212> TYPE: PRT
<213> ORGANISM: Artificial Sequence
<220> FEATURE:
<223> OTHER INFORMATION: synthetic

<400> SEQUENCE: 146

Gln Val Gln Leu Gln Gln Trp Gly Ala Gly Leu Leu Lys Pro Ser Glu
1               5                   10                  15

Thr Leu Ser Leu Thr Cys Val Val His Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45
```

Gly Glu Ile Asn His Arg Gly Asn Thr Asn Tyr Asn Pro Ser Leu Lys
    50                  55                  60

Ser Arg Val Thr Val Ser Glu Asp Thr Ser Lys Asn Gln Phe Ser Leu
65                  70                  75                  80

Lys Leu Ser Ser Leu Thr Ala Ala Asp Thr Ala Val Tyr Tyr Cys Val
                85                  90                  95

Arg Gly Glu Asp Tyr Asp Phe Trp Ser Asp Tyr Tyr Asn Asp Tyr Trp
            100                 105                 110

Gly Gln Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggtgggtcct tcagtggtta ctac                                              24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Gly Ser Phe Ser Gly Tyr Tyr
1               5

<210> SEQ ID NO 149
<211> LENGTH: 21
<212> TYPE: DNA
<213> ORGANISM: Artificial Sequence
<220> FEATURE:
<223> OTHER INFORMATION: synthetic

<400> SEQUENCE: 149
atcaatcata gaggaaacac c                                                 21

<210> SEQ ID NO 150
<211> LENGTH: 7
<212> TYPE: PRT
<213> ORGANISM: Artificial Sequence
<220> FEATURE:
<223> OTHER INFORMATION: synthetic

<400> SEQUENCE: 150

Ile Asn His Arg Gly Asn Thr
1               5

<210> SEQ ID NO 151
<211> LENGTH: 48
<212> TYPE: DNA
<213> ORGANISM: Artificial Sequence
<220> FEATURE:
<223> OTHER INFORMATION: synthetic

<400> SEQUENCE: 151
gtgagaggag aggattacga tttttggagt gattattata atgactac                    48

<210> SEQ ID NO 152

<211> LENGTH: 16
<212> TYPE: PRT
<213> ORGANISM: Artificial Sequence
<220> FEATURE:
<223> OTHER INFORMATION: synthetic

<400> SEQUENCE: 152

Val Arg Gly Glu Asp Tyr Asp Phe Trp Ser Asp Tyr Tyr Asn Asp Tyr
1               5                   10                  15

<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gaaattgtgt tgacacagtc tccagccacc ctgtctttgt ctccagggga aagagccacc      60
ctctcctgca gggccagtca gactattagc agctacttag cctggcacca acagaaacct     120
ggccaggctc ccaggctcct catctatgat gcatccaaaa gggccacggg catcccagcc     180
aggttcagtg gcagtgggtc tgggacagac ttcactctca ccatcaccag cctagagcct     240
gaagattttg cagtttatta ctgtcagcag cgtagcaact ggcctctcac tttcggcgga     300
gggaccaagg tggagatcaa a                                                321

<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Ser Tyr
            20                  25                  30

Leu Ala Trp His Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagactatta gcagctac                                                    18

<210> SEQ ID NO 156
<211> LENGTH: 6

```
<212> TYPE: PRT
<213> ORGANISM: Artificial Sequence
<220> FEATURE:
<223> OTHER INFORMATION: synthetic

<400> SEQUENCE: 156

Gln Thr Ile Ser Ser Tyr
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gatgcatcc                                                                  9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Asp Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
cagcagcgta gcaactggcc tctcact                                             27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Arg Ser Asn Trp Pro Leu Thr
1               5

<210> SEQ ID NO 161
<211> LENGTH: 372
<212> TYPE: DNA
<213> ORGANISM: Artificial Sequence
<220> FEATURE:
<223> OTHER INFORMATION: synthetic

<400> SEQUENCE: 161
caggtgcagc tacagcagtg gggcgcagga ctgttgccgc cttcggagac cctgtccctc         60
atctgcgctg tctatggtgg gtccttcagt ggttactact ggagctggat ccgccagccc        120
ccagggaagg ggctggagtg gattggggaa atcaatcata gaggaagcac caactacaac        180
ccgtccctca gagtcgagc caccatatca gttgacacgt ccaagaacca gttctccctg        240
aagctgagct ctgtgaccgc cgcggacacg gctgtgtatt actgttcgag aggcgaggat        300
```

```
tactatgata gtagtggtta ctcgtactac tttgactact ggggccaggg aaccctggtc    360
accgtctcct ca                                                        372
```

<210> SEQ ID NO 162
<211> LENGTH: 124
<212> TYPE: PRT
<213> ORGANISM: Artificial Sequence
<220> FEATURE:
<223> OTHER INFORMATION: synthetic

<400> SEQUENCE: 162

```
Gln Val Gln Leu Gln Gln Trp Gly Ala Gly Leu Leu Pro Pro Ser Glu
1               5                   10                  15

Thr Leu Ser Leu Ile Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Arg Gly Glu Asp Tyr Tyr Asp Ser Ser Gly Tyr Ser Tyr Tyr Phe Asp
            100                 105                 110

Tyr Trp Gly Gln Gly Thr Leu Val Thr Val Ser Ser
        115                 120
```

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163

```
ggtgggtcct tcagtggtta ctac                                           24
```

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

```
Gly Gly Ser Phe Ser Gly Tyr Tyr
1               5
```

<210> SEQ ID NO 165
<211> LENGTH: 21
<212> TYPE: DNA
<213> ORGANISM: Artificial Sequence
<220> FEATURE:
<223> OTHER INFORMATION: synthetic

<400> SEQUENCE: 165

```
atcaatcata gaggaagcac c                                              21
```

<210> SEQ ID NO 166
<211> LENGTH: 7

```
<212> TYPE: PRT
<213> ORGANISM: Artificial Sequence
<220> FEATURE:
<223> OTHER INFORMATION: synthetic

<400> SEQUENCE: 166

Ile Asn His Arg Gly Ser Thr
1               5

<210> SEQ ID NO 167
<211> LENGTH: 54
<212> TYPE: DNA
<213> ORGANISM: Artificial Sequence
<220> FEATURE:
<223> OTHER INFORMATION: synthetic

<400> SEQUENCE: 167
tcgagaggcg aggattacta tgatagtagt ggttactcgt actactttga ctac            54

<210> SEQ ID NO 168
<211> LENGTH: 18
<212> TYPE: PRT
<213> ORGANISM: Artificial Sequence
<220> FEATURE:
<223> OTHER INFORMATION: synthetic

<400> SEQUENCE: 168

Ser Arg Gly Glu Asp Tyr Tyr Asp Ser Ser Gly Tyr Ser Tyr Tyr Phe
1               5                   10                  15

Asp Tyr

<210> SEQ ID NO 169
<211> LENGTH: 321
<212> TYPE: DNA
<213> ORGANISM: Artificial Sequence
<220> FEATURE:
<223> OTHER INFORMATION: synthetic

<400> SEQUENCE: 169
gaaattgtgt tgacacagtc tccagccacc ctgtctttgt ctccagggga aagagccacc      60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggccgctcac tttcggcgga    300
gggaccaagg tggagatcaa a                                              321

<210> SEQ ID NO 170
<211> LENGTH: 107
<212> TYPE: PRT
<213> ORGANISM: Artificial Sequence
<220> FEATURE:
<223> OTHER INFORMATION: synthetic

<400> SEQUENCE: 170

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
```

```
            50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171
cagagtgtta gcagctac                                                       18

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

```
Gln Ser Val Ser Ser Tyr
 1               5
```

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 gatgcatcc                                                                  9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

```
Asp Ala Ser
 1
```

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
cagcagcgta gcaactggcc gctcact                                              27

<210> SEQ ID NO 176
<211> LENGTH: 9
<212> TYPE: PRT
<213> ORGANISM: Artificial Sequence
<220> FEATURE:

<223> OTHER INFORMATION: synthetic

<400> SEQUENCE: 176

Gln Gln Arg Ser Asn Trp Pro Leu Thr
1               5

<210> SEQ ID NO 177
<211> LENGTH: 366
<212> TYPE: DNA
<213> ORGANISM: Artificial Sequence
<220> FEATURE:
<223> OTHER INFORMATION: synthetic

<400> SEQUENCE: 177
caggtgcagc tacagcagtg gggcgcagga ctgttgaggc cttcggagac cctgtccctc     60
acctgcgctg tctatggtgg gtccttcagt ggttactact ggaattggat ccgccagtcc    120
ccagggacgg ggctggagtg gattggggaa atcaatcata gagggaacat caacttcaac    180
ccgtccctca agagtcgagt caccatatca gaggacacgt ccaaaaacca attctccctg    240
aggctgaact ctgtgaccgc cgcggacacg gctgtgtatt actgtgcgag aggagaggat    300
tacgatattt ggagtggtta ttatagggag tactggggcc agggaaccct ggtcaccgtc    360
tcctca                                                              366

<210> SEQ ID NO 178
<211> LENGTH: 122
<212> TYPE: PRT
<213> ORGANISM: Artificial Sequence
<220> FEATURE:
<223> OTHER INFORMATION: synthetic

<400> SEQUENCE: 178

Gln Val Gln Leu Gln Gln Trp Gly Ala Gly Leu Leu Arg Pro Ser Glu
1               5                   10                  15
Thr Leu Ser Leu Thr Cys Ala Val Tyr Gly Gly Ser Phe Ser Gly Tyr
            20                  25                  30
Tyr Trp Asn Trp Ile Arg Gln Ser Pro Gly Thr Gly Leu Glu Trp Ile
        35                  40                  45
Gly Glu Ile Asn His Arg Gly Asn Ile Asn Phe Asn Pro Ser Leu Lys
    50                  55                  60
Ser Arg Val Thr Ile Ser Glu Asp Thr Ser Lys Asn Gln Phe Ser Leu
65                  70                  75                  80
Arg Leu Asn Ser Val Thr Ala Ala Asp Thr Ala Val Tyr Tyr Cys Ala
                85                  90                  95
Arg Gly Glu Asp Tyr Asp Ile Trp Ser Gly Tyr Tyr Arg Glu Tyr Trp
            100                 105                 110
Gly Gln Gly Thr Leu Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggtgggtcct tcagtggtta ctac                                           24

<210> SEQ ID NO 180

```
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Gly Ser Phe Ser Gly Tyr Tyr
1               5

<210> SEQ ID NO 181
<211> LENGTH: 21
<212> TYPE: DNA
<213> ORGANISM: Artificial Sequence
<220> FEATURE:
<223> OTHER INFORMATION: synthetic

<400> SEQUENCE: 181
atcaatcata gagggaacat c                                             21

<210> SEQ ID NO 182
<211> LENGTH: 7
<212> TYPE: PRT
<213> ORGANISM: Artificial Sequence
<220> FEATURE:
<223> OTHER INFORMATION: synthetic

<400> SEQUENCE: 182

Ile Asn His Arg Gly Asn Ile
1               5

<210> SEQ ID NO 183
<211> LENGTH: 48
<212> TYPE: DNA
<213> ORGANISM: Artificial Sequence
<220> FEATURE:
<223> OTHER INFORMATION: synthetic

<400> SEQUENCE: 183
gcgagaggag aggattacga tatttggagt ggttattata gggagtac                48

<210> SEQ ID NO 184
<211> LENGTH: 16
<212> TYPE: PRT
<213> ORGANISM: Artificial Sequence
<220> FEATURE:
<223> OTHER INFORMATION: synthetic

<400> SEQUENCE: 184

Ala Arg Gly Glu Asp Tyr Asp Ile Trp Ser Gly Tyr Tyr Arg Glu Tyr
1               5                   10                  15

<210> SEQ ID NO 185
<211> LENGTH: 321
<212> TYPE: DNA
<213> ORGANISM: Artificial Sequence
<220> FEATURE:
<223> OTHER INFORMATION: synthetic

<400> SEQUENCE: 185
gaaattgtgt tgacacagtc tccagccacc ctgtctttgt ctccagggga aagagccact    60
ctctcctgca gggccagtca gagtgttagc agctacttag cctggtacca gcagaaacct   120
ggccaggctc ccaggctcct catctatgat gcatccaaga gggccactgg catcccagcc   180
aggttcagtg gcagtgggtc tgggacagac ttcactctca ccatcagcag cctagagcct   240
```

```
gaagattttg ctgtttatta ctgtcagcag cgtagcaact ggcctctcgc tttcggcgga    300
gggaccaagg tggagatcaa a                                              321
```

<210> SEQ ID NO 186
<211> LENGTH: 107
<212> TYPE: PRT
<213> ORGANISM: Artificial Sequence
<220> FEATURE:
<223> OTHER INFORMATION: synthetic

<400> SEQUENCE: 186

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Ala Phe Gly Gly Gly Thr Lys Val Glu Ile Lys
            100                 105
```

<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187

```
cagagtgtta gcagctac                                                  18
```

<210> SEQ ID NO 188
<211> LENGTH: 6
<212> TYPE: PRT
<213> ORGANISM: Artificial Sequence
<220> FEATURE:
<223> OTHER INFORMATION: synthetic

<400> SEQUENCE: 188

```
Gln Ser Val Ser Ser Tyr
1               5
```

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189

```
gatgcatcc                                                             9
```

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Asp Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
cagcagcgta gcaactggcc tctcgct                                             27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Arg Ser Asn Trp Pro Leu Ala
1               5

<210> SEQ ID NO 193
<211> LENGTH: 357
<212> TYPE: DNA
<213> ORGANISM: Artificial Sequence
<220> FEATURE:
<223> OTHER INFORMATION: synthetic

<400> SEQUENCE: 193
caggtgcagc tacagcagtg gggcgcagga ctgttgaagc cttcggagac cctgtccctc         60
acctgcgctg tctatggtgg gtccttcagt gagttctact ggaactggat ccgccagccc        120
ccagagaagg gcctggagtg gattgggaa atcaatcatc gtggaaacac caactacaac        180
ccgtccctca gagtcgagt caccatatca gtagacatgt ccaagaacca gttctccctg        240
cagctgaact ctgtgaccgt cgcggacacg gctctgtatt actgtgcgtt tggctacgat        300
tttcggagtt cttatgagga cgtctggggc caagggacca cggtcaccgt ctcctca          357

<210> SEQ ID NO 194
<211> LENGTH: 119
<212> TYPE: PRT
<213> ORGANISM: Artificial Sequence
<220> FEATURE:
<223> OTHER INFORMATION: synthetic

<400> SEQUENCE: 194

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Glu Phe
            20                  25                  30

Tyr Trp Asn Trp Ile Arg Gln Pro Pro Glu Lys Gly Leu Glu Trp Ile
        35                  40                  45

Gly Glu Ile Asn His Arg Gly Asn Thr Asn Tyr Asn Pro Ser Leu Lys
    50                  55                  60

Ser Arg Val Thr Ile Ser Val Asp Met Ser Lys Asn Gln Phe Ser Leu
65                  70                  75                  80

Gln Leu Asn Ser Val Thr Val Ala Asp Thr Ala Leu Tyr Tyr Cys Ala 85                  90                  95
Phe Gly Tyr Asp Phe Arg Ser Ser Tyr Glu Asp Val Trp Gly Gln Gly
                100                 105                 110

Thr Thr Val Thr Val Ser Ser
        115

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195
ggtgggtcct tcagtgagtt ctac                                          24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

Gly Gly Ser Phe Ser Glu Phe Tyr
1               5

<210> SEQ ID NO 197
<211> LENGTH: 21
<212> TYPE: DNA
<213> ORGANISM: Artificial Sequence
<220> FEATURE:
<223> OTHER INFORMATION: synthetic

<400> SEQUENCE: 197
atcaatcatc gtggaaacac c                                             21

<210> SEQ ID NO 198
<211> LENGTH: 7
<212> TYPE: PRT
<213> ORGANISM: Artificial Sequence
<220> FEATURE:
<223> OTHER INFORMATION: synthetic

<400> SEQUENCE: 198

Ile Asn His Arg Gly Asn Thr
1               5

<210> SEQ ID NO 199
<211> LENGTH: 39
<212> TYPE: DNA
<213> ORGANISM: Artificial Sequence
<220> FEATURE:
<223> OTHER INFORMATION: synthetic

<400> SEQUENCE: 199
gcgtttggct acgattttcg gagttcttat gaggacgtc                          39

<210> SEQ ID NO 200
<211> LENGTH: 13
<212> TYPE: PRT
<213> ORGANISM: Artificial Sequence
<220> FEATURE:
<223> OTHER INFORMATION: synthetic

<400> SEQUENCE: 200

Ala Phe Gly Tyr Asp Phe Arg Ser Ser Tyr Glu Asp Val
1               5                   10

<210> SEQ ID NO 201
<211> LENGTH: 321
<212> TYPE: DNA
<213> ORGANISM: Artificial Sequence
<220> FEATURE:
<223> OTHER INFORMATION: synthetic

<400> SEQUENCE: 201
gaaattgtgt tgacacagtc tccagccacc ctgtctttgt ctccagggga aagagccacc    60
ctctcctgca gggccagtca ggatattagc acctacttag cctggcacca acagaaacct   120
ggccagcctc ccaggctcct catctatggt tcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggcgga   300
gggaccaagg tggagatcaa a                                             321

<210> SEQ ID NO 202
<211> LENGTH: 107
<212> TYPE: PRT
<213> ORGANISM: Artificial Sequence
<220> FEATURE:
<223> OTHER INFORMATION: synthetic

<400> SEQUENCE: 202

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Thr Tyr
            20                  25                  30

Leu Ala Trp His Gln Gln Lys Pro Gly Gln Pro Pro Arg Leu Leu Ile
        35                  40                  45

Tyr Gly Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
caggatatta gcacctac                                                  18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

Gln Asp Ile Ser Thr Tyr
1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 ggttcatcc                                                                9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Gly Ser Ser
1

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
cagcagcgta gcaactggcc tctcact                                            27

<210> SEQ ID NO 208
<211> LENGTH: 9
<212> TYPE: PRT
<213> ORGANISM: Artificial Sequence
<220> FEATURE:
<223> OTHER INFORMATION: synthetic

<400> SEQUENCE: 208

Gln Gln Arg Ser Asn Trp Pro Leu Thr
1               5

<210> SEQ ID NO 209
<211> LENGTH: 372
<212> TYPE: DNA
<213> ORGANISM: Artificial Sequence
<220> FEATURE:
<223> OTHER INFORMATION: synthetic

<400> SEQUENCE: 209
gaggtgcagc tgttggagtc tgggggaggc ttggtacagc cggggggtc cctgagactc          60 tcctgtgcag cctctggatt caccttcaga agctatgcca tgagttgggt ccgccaggct        120
ccagggaagg ggctggagtg gtctcagtt attagtggtg gtggtggtag acatactac          180 acagactccg tgaagggccg gttcaccatc tccagagaca attccaagag catgctgtat        240
ctgcaaatga acagcctgag agccgaggac acggccattt attactgtgc gaaagagagg        300
gtaactggaa tagaccacta ctactacggt gtggacgtct ggggccaagg gaccacggtc        360
accgtctcct ca                                                           372

<210> SEQ ID NO 210

```
<211> LENGTH: 124
<212> TYPE: PRT
<213> ORGANISM: Artificial Sequence
<220> FEATURE:
<223> OTHER INFORMATION: synthetic

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Val Ile Ser Gly Gly Gly Arg Thr Tyr Tyr Thr Asp Ser Val
    50                  55                  60

Lys Gly Arg Phe Thr Ile Ser Arg Asp Asn Ser Lys Ser Met Leu Tyr
65                  70                  75                  80

Leu Gln Met Asn Ser Leu Arg Ala Glu Asp Thr Ala Ile Tyr Tyr Cys
                85                  90                  95

Ala Lys Glu Arg Val Thr Gly Ile Asp His Tyr Tyr Tyr Gly Val Asp
            100                 105                 110

Val Trp Gly Gln Gly Thr Thr Val Thr Val Ser Ser
            115                 120

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
ggattcacct tcagaagcta tgcc                                      24

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

Gly Phe Thr Phe Arg Ser Tyr Ala
1               5

<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
attagtggtg gtggtggtag gaca                                      24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214
```

Ile Ser Gly Gly Gly Gly Arg Thr
1               5

<210> SEQ ID NO 215
<211> LENGTH: 51
<212> TYPE: DNA
<213> ORGANISM: Artificial Sequence
<220> FEATURE:
<223> OTHER INFORMATION: synthetic

<400> SEQUENCE: 215
gcgaaagaga gggtaactgg aatagaccac tactactacg gtgtggacgt c        51

<210> SEQ ID NO 216
<211> LENGTH: 17
<212> TYPE: PRT
<213> ORGANISM: Artificial Sequence
<220> FEATURE:
<223> OTHER INFORMATION: synthetic

<400> SEQUENCE: 216

Ala Lys Glu Arg Val Thr Gly Ile Asp His Tyr Tyr Tyr Gly Val Asp
1               5                   10                  15

Val

<210> SEQ ID NO 217
<211> LENGTH: 321
<212> TYPE: DNA
<213> ORGANISM: Artificial Sequence
<220> FEATURE:
<223> OTHER INFORMATION: synthetic

<400> SEQUENCE: 217
gacatccaga tgacccagtc tccatcctcc ctgtctgcat ctgtaggaga cagagtcacc    60
atcacttgcc gggcaagtca gagcattagt agctatttaa attggtatca gcagaaacca   120
gggaaagccc ctaagctcct gatctatgct acatccagtt tgcaaagtgg ggtcccatca   180
cggttcagtg gcagtgcatc tggaacagat ttcactctcg ccatcagcag tctgcaacct   240
gaagattttg caacttacta ctgtcaacag agttacacta ccccccctcac tttcggcgga   300 gggaccaagg tggagatcaa a                                             321

<210> SEQ ID NO 218
<211> LENGTH: 107
<212> TYPE: PRT
<213> ORGANISM: Artificial Sequence
<220> FEATURE:
<223> OTHER INFORMATION: synthetic

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Ala Ser Gly Thr Asp Phe Thr Leu Ala Ile Ser Ser Leu Gln Pro
65                  70                  75                  80

Glu Asp Phe Ala Thr Tyr Tyr Cys Gln Gln Ser Tyr Thr Thr Pro Leu
                85                  90                  95

Thr Phe Gly Gly Gly Thr Lys Val Glu Ile Lys
            100                 105

<210> SEQ ID NO 219
<211> LENGTH: 18
<212> TYPE: DNA
<213> ORGANISM: Artificial Sequence
<220> FEATURE:
<223> OTHER INFORMATION: synthetic

<400> SEQUENCE: 219
cagagcatta gtagctat                                                 18

<210> SEQ ID NO 220
<211> LENGTH: 6
<212> TYPE: PRT
<213> ORGANISM: Artificial Sequence
<220> FEATURE:
<223> OTHER INFORMATION: synthetic

<400> SEQUENCE: 220

Gln Ser Ile Ser Ser Tyr
1               5

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 gctacatcc                                                            9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Ala Thr Ser
1

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
caacagagtt acactacccc cctcact                                       27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Gln Gln Ser Tyr Thr Thr Pro Leu Thr
1               5

<210> SEQ ID NO 225
<211> LENGTH: 390
<212> TYPE: DNA
<213> ORGANISM: Artificial Sequence
<220> FEATURE:
<223> OTHER INFORMATION: synthetic

<400> SEQUENCE: 225

```
gaggtgcagc tggtggagtc tgggggaggc ttggtacaac ctggagggtc cctgagactt      60
tcctgtgcag cctctggatt tacattcagc agttatgaaa tgaactgggt ccgccaggct     120
ccagggaagg ggctggagtg ggtttcatat atcagtagta gtggtaatac caaagactac     180
gcaggctctg tgaagggccg agtcaccatc tccagagaca cgccaagaa cttactgtat      240 ctgcaaatga acagcctgag agccgaggac acggctgttt atcactgtgc gagagatgga     300
gggcattacg atattttgac tggttccatg tcctactact actacgcttt ggacgtctgg     360
ggccaaggga ccacggtcac cgtctcctca                                      390
```

<210> SEQ ID NO 226
<211> LENGTH: 130
<212> TYPE: PRT
<213> ORGANISM: Artificial Sequence
<220> FEATURE:
<223> OTHER INFORMATION: synthetic

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Asn Thr Lys Asp Tyr Ala Gly Ser Val
    50                  55                  60

Lys Gly Arg Val Thr Ile Ser Arg Asp Asn Ala Lys Asn Leu Leu Tyr
65                  70                  75                  80

Leu Gln Met Asn Ser Leu Arg Ala Glu Asp Thr Ala Val Tyr His Cys
                85                  90                  95

Ala Arg Asp Gly Gly His Tyr Asp Ile Leu Thr Gly Ser Met Ser Tyr
            100                 105                 110

Tyr Tyr Tyr Ala Leu Asp Val Trp Gly Gln Gly Thr Thr Val Thr Val
        115                 120                 125

Ser Ser
    130

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227

```
ggatttacat tcagcagtta tgaa                                             24
```

<210> SEQ ID NO 228
<211> LENGTH: 8
<212> TYPE: PRT
<213> ORGANISM: Artificial Sequence
<220> FEATURE:

<223> OTHER INFORMATION: synthetic

<400> SEQUENCE: 228

Gly Phe Thr Phe Ser Ser Tyr Glu
1               5

<210> SEQ ID NO 229
<211> LENGTH: 24
<212> TYPE: DNA
<213> ORGANISM: Artificial Sequence
<220> FEATURE:
<223> OTHER INFORMATION: synthetic

<400> SEQUENCE: 229
atcagtagta gtggtaatac caaa                                          24

<210> SEQ ID NO 230
<211> LENGTH: 8
<212> TYPE: PRT
<213> ORGANISM: Artificial Sequence
<220> FEATURE:
<223> OTHER INFORMATION: synthetic

<400> SEQUENCE: 230

Ile Ser Ser Ser Gly Asn Thr Lys
1               5

<210> SEQ ID NO 231
<211> LENGTH: 69
<212> TYPE: DNA
<213> ORGANISM: Artificial Sequence
<220> FEATURE:
<223> OTHER INFORMATION: synthetic

<400> SEQUENCE: 231
gcgagagatg gagggcatta cgatattttg actggttcca tgtcctacta ctactacgct   60
ttggacgtc                                                           69

<210> SEQ ID NO 232
<211> LENGTH: 23
<212> TYPE: PRT
<213> ORGANISM: Artificial Sequence
<220> FEATURE:
<223> OTHER INFORMATION: synthetic

<400> SEQUENCE: 232

Ala Arg Asp Gly Gly His Tyr Asp Ile Leu Thr Gly Ser Met Ser Tyr
1               5                   10                  15

Tyr Tyr Tyr Ala Leu Asp Val
            20

<210> SEQ ID NO 233
<211> LENGTH: 324
<212> TYPE: DNA
<213> ORGANISM: Artificial Sequence
<220> FEATURE:
<223> OTHER INFORMATION: synthetic

<400> SEQUENCE: 233
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240

```
gaagattttg caacttacta ctgtcaacag agttacagta cccctccgat caccttcggc    300
caagggacac gactggagat taaa                                          324
```

<210> SEQ ID NO 234
<211> LENGTH: 108
<212> TYPE: PRT
<213> ORGANISM: Artificial Sequence
<220> FEATURE:
<223> OTHER INFORMATION: synthetic

<400> SEQUENCE: 234

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235

```
cagagcatta gcagctat                                                  18
```

<210> SEQ ID NO 236
<211> LENGTH: 6
<212> TYPE: PRT
<213> ORGANISM: Artificial Sequence
<220> FEATURE:
<223> OTHER INFORMATION: synthetic

<400> SEQUENCE: 236

```
Gln Ser Ile Ser Ser Tyr
1               5
```

<210> SEQ ID NO 237
<211> LENGTH: 9
<212> TYPE: DNA
<213> ORGANISM: Artificial Sequence
<220> FEATURE:
<223> OTHER INFORMATION: synthetic

<400> SEQUENCE: 237

```
gctgcatcc                                                             9
```

<210> SEQ ID NO 238
<211> LENGTH: 3
<212> TYPE: PRT
<213> ORGANISM: Artificial Sequence
<220> FEATURE:

<223> OTHER INFORMATION: synthetic

<400> SEQUENCE: 238

Ala Ala Ser
1

<210> SEQ ID NO 239
<211> LENGTH: 30
<212> TYPE: DNA
<213> ORGANISM: Artificial Sequence
<220> FEATURE:
<223> OTHER INFORMATION: synthetic

<400> SEQUENCE: 239
caacagagtt acagtacccc tccgatcacc                                       30

<210> SEQ ID NO 240
<211> LENGTH: 10
<212> TYPE: PRT
<213> ORGANISM: Artificial Sequence
<220> FEATURE:
<223> OTHER INFORMATION: synthetic

<400> SEQUENCE: 240

Gln Gln Ser Tyr Ser Thr Pro Pro Ile Thr
1               5                   10

<210> SEQ ID NO 241
<211> LENGTH: 363
<212> TYPE: DNA
<213> ORGANISM: Artificial Sequence
<220> FEATURE:
<223> OTHER INFORMATION: synthetic

<400> SEQUENCE: 241
gaggtgcagc tggtggagtc tgggggaggc ttggtacagc ctgggggtc cctgagactc       60 tcctgtgcag cctctggatt cacctttaaa acctatgcca tgagctgggt ccgccaggct     120
ccagggaggg gctggagtg gtctcaggt attagtggta gtggtagtac ctcatactac      180
gcagactccg tgaagggccg gttcaccatc tccagagaca attacaagaa gacgctgtct    240
ctgcaaatga acagtctgag agccgaggac acggccgttt attactgtgc gctggatata    300
atggcaacgg taggaggtct ctttaacaac tggggccagg gaaccctggt caccgtctcc    360
tca                                                                  363

<210> SEQ ID NO 242
<211> LENGTH: 121
<212> TYPE: PRT
<213> ORGANISM: Artificial Sequence
<220> FEATURE:
<223> OTHER INFORMATION: synthetic

<400> SEQUENCE: 242

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Thr Tyr
            20                  25                  30

Ala Met Ser Trp Val Arg Gln Ala Pro Gly Arg Gly Leu Glu Trp Val
        35                  40                  45

Ser Gly Ile Ser Gly Ser Gly Ser Thr Ser Tyr Tyr Ala Asp Ser Val
    50                  55                  60

Lys Gly Arg Phe Thr Ile Ser Arg Asp Asn Tyr Lys Lys Thr Leu Ser

```
                65                  70                  75                  80
Leu Gln Met Asn Ser Leu Arg Ala Glu Asp Thr Ala Val Tyr Tyr Cys
                    85                  90                  95

Ala Leu Asp Ile Met Ala Thr Val Gly Gly Leu Phe Asn Asn Trp Gly
            100                 105                 110

Gln Gly Thr Leu Val Thr Val Ser Ser
        115                 120
```

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggattcacct ttaaaaccta tgcc                                          24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

```
Gly Phe Thr Phe Lys Thr Tyr Ala
1               5
```

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
attagtggta gtggtagtac ctca                                          24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

```
Ile Ser Gly Ser Gly Ser Thr Ser
1               5
```

<210> SEQ ID NO 247
<211> LENGTH: 42
<212> TYPE: DNA
<213> ORGANISM: Artificial Sequence
<220> FEATURE:
<223> OTHER INFORMATION: synthetic

<400> SEQUENCE: 247
gcgctggata taatggcaac ggtaggaggt ctctttaaca ac                      42

<210> SEQ ID NO 248
<211> LENGTH: 14
<212> TYPE: PRT
<213> ORGANISM: Artificial Sequence
<220> FEATURE:

<223> OTHER INFORMATION: synthetic

<400> SEQUENCE: 248

Ala Leu Asp Ile Met Ala Thr Val Gly Gly Leu Phe Asn Asn
1               5                   10

<210> SEQ ID NO 249
<211> LENGTH: 324
<212> TYPE: DNA
<213> ORGANISM: Artificial Sequence
<220> FEATURE:
<223> OTHER INFORMATION: synthetic

<400> SEQUENCE: 249

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccttg gacgttcggc     300
caagggacca aggtggaaat caaa                                             324
```

<210> SEQ ID NO 250
<211> LENGTH: 108
<212> TYPE: PRT
<213> ORGANISM: Artificial Sequence
<220> FEATURE:
<223> OTHER INFORMATION: synthetic

<400> SEQUENCE: 250

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 251
<211> LENGTH: 21
<212> TYPE: DNA
<213> ORGANISM: Artificial Sequence
<220> FEATURE:
<223> OTHER INFORMATION: synthetic

<400> SEQUENCE: 251
cagagtgtta gcagcagcta c                                                 21

<210> SEQ ID NO 252
<211> LENGTH: 7
<212> TYPE: PRT
<213> ORGANISM: Artificial Sequence
<220> FEATURE:
<223> OTHER INFORMATION: synthetic

<400> SEQUENCE: 252

Gln Ser Val Ser Ser Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 ggtgcatcc                                                                  9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Gly Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
cagcagtatg gtagctcacc ttggacg                                             27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Gln Gln Tyr Gly Ser Ser Pro Trp Thr
1               5

<210> SEQ ID NO 257
<211> LENGTH: 360
<212> TYPE: DNA
<213> ORGANISM: Artificial Sequence
<220> FEATURE:
<223> OTHER INFORMATION: synthetic

<400> SEQUENCE: 257
caggtgcagc tggtgcagtc tggggctgag gtgaagaagc ctgggtcctc ggtgaaggtc         60
tcctgcaagg cttctggagg caccttcagc agacatacta tcagctgggt gcgacaggcc        120
cctggacaag gcttgagtg gatgggaggg atcatcccta tctttggtac agcaaactac         180
gcacacaagt tccagggcag agtcacgatt accacggacg aatccacgag cacagcctac        240
atggagctga gcagcctgag atctgaggac acggccgtat attattgtgc gagagcccct        300
tatacccgac aggggtactt cgatctctgg ggccgtggca ccctggtcac cgtctcctca        360

```
<210> SEQ ID NO 258
<211> LENGTH: 120
<212> TYPE: PRT
<213> ORGANISM: Artificial Sequence
<220> FEATURE:
<223> OTHER INFORMATION: synthetic

<400> SEQUENCE: 258
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg His
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala His Lys Phe
50                  55                  60

Gln Gly Arg Val Thr Ile Thr Thr Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Tyr Thr Arg Gln Gly Tyr Phe Asp Leu Trp Gly Arg
            100                 105                 110

Gly Thr Leu Val Thr Val Ser Ser
        115                 120

```
<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259
ggaggcacct tcagcagaca tact                                         24

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260
```

Gly Gly Thr Phe Ser Arg His Thr
1               5

```
<210> SEQ ID NO 261
<211> LENGTH: 24
<212> TYPE: DNA
<213> ORGANISM: Artificial Sequence
<220> FEATURE:
<223> OTHER INFORMATION: synthetic

<400> SEQUENCE: 261
atcatcccta tctttggtac agca                                         24

<210> SEQ ID NO 262
<211> LENGTH: 8
<212> TYPE: PRT
<213> ORGANISM: Artificial Sequence
<220> FEATURE:
<223> OTHER INFORMATION: synthetic

<400> SEQUENCE: 262
```

Ile Ile Pro Ile Phe Gly Thr Ala
1               5

<210> SEQ ID NO 263
<211> LENGTH: 39
<212> TYPE: DNA
<213> ORGANISM: Artificial Sequence
<220> FEATURE:
<223> OTHER INFORMATION: synthetic

<400> SEQUENCE: 263
gcgagagccc cttatacccg acaggggtac ttcgatctc                                39

<210> SEQ ID NO 264
<211> LENGTH: 13
<212> TYPE: PRT
<213> ORGANISM: Artificial Sequence
<220> FEATURE:
<223> OTHER INFORMATION: synthetic

<400> SEQUENCE: 264

Ala Arg Ala Pro Tyr Thr Arg Gln Gly Tyr Phe Asp Leu
1               5                   10

<210> SEQ ID NO 265
<211> LENGTH: 339
<212> TYPE: DNA
<213> ORGANISM: Artificial Sequence
<220> FEATURE:
<223> OTHER INFORMATION: synthetic

<400> SEQUENCE: 265
gacatcgtga tgacccagtc tccagactcc ctggctgtgt ctctgggcga gagggccacc          60
atcaactgca agtccagcca gagtgtttta tacagctcca acaataagaa ctacttagct         120
tggtaccagc agaaaccagg acagcctcct aagctactca tttactgggc atctacccgg         180
gaatccgggg tccctgaccg attcagtggc agcgggtctg ggacagattt cactctcacc         240
atcagcagcc tgcaggctga agatgtggca gtttattact gtcagcaaga ttatagtact         300
ccgtggacgt tcggccaagg gaccaaggtg gaaatcaaa                                339

<210> SEQ ID NO 266
<211> LENGTH: 113
<212> TYPE: PRT
<213> ORGANISM: Artificial Sequence
<220> FEATURE:
<223> OTHER INFORMATION: synthetic

<400> SEQUENCE: 266

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asp Tyr Ser Thr Pro Trp Thr Phe Gly Gln Gly Thr Lys Val Glu Ile
            100                 105                 110
Lys

<210> SEQ ID NO 267
<211> LENGTH: 36
<212> TYPE: DNA
<213> ORGANISM: Artificial Sequence
<220> FEATURE:
<223> OTHER INFORMATION: synthetic

<400> SEQUENCE: 267
cagagtgttt tatacagctc caacaataag aactac                             36

<210> SEQ ID NO 268
<211> LENGTH: 12
<212> TYPE: PRT
<213> ORGANISM: Artificial Sequence
<220> FEATURE:
<223> OTHER INFORMATION: synthetic

<400> SEQUENCE: 268

Gln Ser Val Leu Tyr Ser Ser Asn Asn Lys Asn Tyr
1               5                   10

<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 tgggcatct                                                            9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Trp Ala Ser
1

<210> SEQ ID NO 271
<211> LENGTH: 27
<212> TYPE: DNA
<213> ORGANISM: Artificial Sequence
<220> FEATURE:
<223> OTHER INFORMATION: synthetic

<400> SEQUENCE: 271
cagcaagatt atagtactcc gtggacg                                       27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Gln Gln Asp Tyr Ser Thr Pro Trp Thr
1               5

<210> SEQ ID NO 273
<211> LENGTH: 354
<212> TYPE: DNA
<213> ORGANISM: Artificial Sequence
<220> FEATURE:
<223> OTHER INFORMATION: synthetic

<400> SEQUENCE: 273

```
caggtgcagc tggtgcagtc tggggctgag gtgaagaagc ctggggcctc agtgaaggtt    60
tcctgcaagg catctggata caccttcacc aactactata tacactgggt gcgacaggcc   120
cctggacaag gcttgactg gatgggaatt atcaaccctg gtggtggtaa cacaaactac    180
gcacagaagt tcctgggcag agtcaccatg accagggaca cgtccacgac cacagtctac   240
atggagctga gcagcctgag atctgaggac acggccatat attactgtgc gagagaaaac   300
tggaactctt actttgacaa ctggggccag ggaaccctgg tcaccgtctc ctca          354
```

<210> SEQ ID NO 274
<211> LENGTH: 118
<212> TYPE: PRT
<213> ORGANISM: Artificial Sequence
<220> FEATURE:
<223> OTHER INFORMATION: synthetic

<400> SEQUENCE: 274

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Asp Trp Met
        35                  40                  45

Gly Ile Ile Asn Pro Gly Gly Gly Asn Thr Asn Tyr Ala Gln Lys Phe
    50                  55                  60

Leu Gly Arg Val Thr Met Thr Arg Asp Thr Ser Thr Thr Thr Val Tyr
65                  70                  75                  80

Met Glu Leu Ser Ser Leu Arg Ser Glu Asp Thr Ala Ile Tyr Tyr Cys
                85                  90                  95

Ala Arg Glu Asn Trp Asn Ser Tyr Phe Asp Asn Trp Gly Gln Gly Thr
            100                 105                 110

Leu Val Thr Val Ser Ser
        115
```

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275

```
ggatacacct tcaccaacta ctat                                            24
```

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

-continued

Gly Tyr Thr Phe Thr Asn Tyr Tyr
1               5

<210> SEQ ID NO 277
<211> LENGTH: 24
<212> TYPE: DNA
<213> ORGANISM: Artificial Sequence
<220> FEATURE:
<223> OTHER INFORMATION: synthetic

<400> SEQUENCE: 277
atcaaccctg gtggtggtaa caca                                          24

<210> SEQ ID NO 278
<211> LENGTH: 8
<212> TYPE: PRT
<213> ORGANISM: Artificial Sequence
<220> FEATURE:
<223> OTHER INFORMATION: synthetic

<400> SEQUENCE: 278

Ile Asn Pro Gly Gly Gly Asn Thr
1               5

<210> SEQ ID NO 279
<211> LENGTH: 33
<212> TYPE: DNA
<213> ORGANISM: Artificial Sequence
<220> FEATURE:
<223> OTHER INFORMATION: synthetic

<400> SEQUENCE: 279
gcgagagaaa actggaactc ttactttgac aac                                33

<210> SEQ ID NO 280
<211> LENGTH: 11
<212> TYPE: PRT
<213> ORGANISM: Artificial Sequence
<220> FEATURE:
<223> OTHER INFORMATION: synthetic

<400> SEQUENCE: 280

Ala Arg Glu Asn Trp Asn Ser Tyr Phe Asp Asn
1               5                   10

<210> SEQ ID NO 281
<211> LENGTH: 339
<212> TYPE: DNA
<213> ORGANISM: Artificial Sequence
<220> FEATURE:
<223> OTHER INFORMATION: synthetic

<400> SEQUENCE: 281
gacatcgtga tgacccagtc tccagactcc ctggctgtgt ctctgggcga gagggccacc    60
atcaactgca gtccagccag gagtgtttta tacagctcca acaataagaa cttcttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca ctttattact gtcagcaata ttatggtgct   300
ccgtggacgt tcggccaagg gaccaaggtg gaaatcaaa                          339

<210> SEQ ID NO 282
<211> LENGTH: 113
<212> TYPE: PRT

<213> ORGANISM: Artificial Sequence
<220> FEATURE:
<223> OTHER INFORMATION: synthetic

<400> SEQUENCE: 282

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Phe Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Leu Tyr Tyr Cys Gln Gln
                85                  90                  95
Tyr Tyr Gly Ala Pro Trp Thr Phe Gly Gln Gly Thr Lys Val Glu Ile
            100                 105                 110
Lys
```

<210> SEQ ID NO 283
<211> LENGTH: 36
<212> TYPE: DNA
<213> ORGANISM: Artificial Sequence
<220> FEATURE:
<223> OTHER INFORMATION: synthetic

<400> SEQUENCE: 283
cagagtgttt tatacagctc caacaataag aacttc       36

<210> SEQ ID NO 284
<211> LENGTH: 12
<212> TYPE: PRT
<213> ORGANISM: Artificial Sequence
<220> FEATURE:
<223> OTHER INFORMATION: synthetic

<400> SEQUENCE: 284

```
Gln Ser Val Leu Tyr Ser Ser Asn Asn Lys Asn Phe
1               5                   10
```

<210> SEQ ID NO 285
<211> LENGTH: 9
<212> TYPE: DNA
<213> ORGANISM: Artificial Sequence
<220> FEATURE:
<223> OTHER INFORMATION: synthetic

<400> SEQUENCE: 285 tgggcatct       9

<210> SEQ ID NO 286
<211> LENGTH: 3
<212> TYPE: PRT
<213> ORGANISM: Artificial Sequence
<220> FEATURE:
<223> OTHER INFORMATION: synthetic

<400> SEQUENCE: 286

```
Trp Ala Ser
1
```

<210> SEQ ID NO 287
<211> LENGTH: 27
<212> TYPE: DNA
<213> ORGANISM: Artificial Sequence
<220> FEATURE:
<223> OTHER INFORMATION: synthetic

<400> SEQUENCE: 287
cagcaatatt atggtgctcc gtggacg                                          27

<210> SEQ ID NO 288
<211> LENGTH: 9
<212> TYPE: PRT
<213> ORGANISM: Artificial Sequence
<220> FEATURE:
<223> OTHER INFORMATION: synthetic

<400> SEQUENCE: 288

Gln Gln Tyr Tyr Gly Ala Pro Trp Thr
1               5

<210> SEQ ID NO 289
<211> LENGTH: 357
<212> TYPE: DNA
<213> ORGANISM: Artificial Sequence
<220> FEATURE:
<223> OTHER INFORMATION: synthetic

<400> SEQUENCE: 289
caggtccagc tggtgcagtc tggggctgag gtgaagaagc ctgggtcctc ggtgaaggtc      60
tcctgcaagg cttctggagg caccttcagc agctatacta tcaactgggt gcgacaggcc    120
cctggacaag gcttgagtg gatgggaggg atcatcccta tctttggtat agcaaactac     180
gcacagaagt tccagggcag agtcacgatt accacggacg aatccacgaa cacagcctac    240
atggagctga gcagcctgag atctgaggac acggccattt attactgtgc gagagcgaga    300
tatggttcgg ggagttatga ctactggggc cagggaaccc tggtcaccgt ctcctca       357

<210> SEQ ID NO 290
<211> LENGTH: 119
<212> TYPE: PRT
<213> ORGANISM: Artificial Sequence
<220> FEATURE:
<223> OTHER INFORMATION: synthetic

<400> SEQUENCE: 290

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Thr Asp Glu Ser Thr Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Ala Arg Tyr Gly Ser Gly Ser Tyr Asp Tyr Trp Gly Gln Gly
            100                 105                 110

Thr Leu Val Thr Val Ser Ser

```
<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggaggcacct tcagcagcta tact                                           24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Gly Thr Phe Ser Ser Tyr Thr
1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
atcatcccta tctttggtat agca                                           24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Ile Pro Ile Phe Gly Ile Ala
1               5

<210> SEQ ID NO 295
<211> LENGTH: 36
<212> TYPE: DNA
<213> ORGANISM: Artificial Sequence
<220> FEATURE:
<223> OTHER INFORMATION: synthetic

<400> SEQUENCE: 295
gcgagagcga gatatggttc ggggagttat gactac                              36

<210> SEQ ID NO 296
<211> LENGTH: 12
<212> TYPE: PRT
<213> ORGANISM: Artificial Sequence
<220> FEATURE:
<223> OTHER INFORMATION: synthetic

<400> SEQUENCE: 296

Ala Arg Ala Arg Tyr Gly Ser Gly Ser Tyr Asp Tyr
1               5                   10

<210> SEQ ID NO 297
```

```
<211> LENGTH: 339
<212> TYPE: DNA
<213> ORGANISM: Artificial Sequence
<220> FEATURE:
<223> OTHER INFORMATION: synthetic

<400> SEQUENCE: 297
gacatcgtga tgacccagtc tccagactcc ctggctgtgt ctctgggcga gagggccacc      60
atcaactgca gtccagcca gagtgtttta tacacctcca acaataagaa ctacttagct     120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttataatact    300
ccatggacgt tcggccaagg gaccaaggtg gaaatcaaa                           339

<210> SEQ ID NO 298
<211> LENGTH: 113
<212> TYPE: PRT
<213> ORGANISM: Artificial Sequence
<220> FEATURE:
<223> OTHER INFORMATION: synthetic

<400> SEQUENCE: 298

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Val Leu Tyr Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Thr Pro Trp Thr Phe Gly Gln Gly Thr Lys Val Glu Ile
            100                 105                 110

Lys

<210> SEQ ID NO 299
<211> LENGTH: 36
<212> TYPE: DNA
<213> ORGANISM: Artificial Sequence
<220> FEATURE:
<223> OTHER INFORMATION: synthetic

<400> SEQUENCE: 299
cagagtgttt tatacacctc caacaataag aactac                              36

<210> SEQ ID NO 300
<211> LENGTH: 12
<212> TYPE: PRT
<213> ORGANISM: Artificial Sequence
<220> FEATURE:
<223> OTHER INFORMATION: synthetic

<400> SEQUENCE: 300

Gln Ser Val Leu Tyr Thr Ser Asn Asn Lys Asn Tyr
1               5                  10
```

```
<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 tgggcatct                                                                9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Trp Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
cagcaatatt ataatactcc atggacg                                           27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Gln Gln Tyr Tyr Asn Thr Pro Trp Thr
1               5

<210> SEQ ID NO 305
<211> LENGTH: 360
<212> TYPE: DNA
<213> ORGANISM: Artificial Sequence
<220> FEATURE:
<223> OTHER INFORMATION: synthetic

<400> SEQUENCE: 305
cagatcacct tgaaggagtc tggtcctacg ctggtgaaac ccacacagac cctcacgctg        60
acctgcacct tctctgggtt ctcactcagc actaatggag tgggtgtggg ctggatccgt       120
cagcccccag gaaaggccct ggagtggctt ggaatcattt attggaatga tgataagcgc       180
tacagcccat ctctgaggag cagactcacc atcaccaagg acacctccaa aaaccaggtg       240
gtccttacaa tgaccaacat ggaccctgtg gacacagcca catattactg tgcacacaga       300
ggcctcttcg gaggttggtt cgaccctgg ggccagggaa ccctggtcac cgtctcctca        360

<210> SEQ ID NO 306
<211> LENGTH: 120
<212> TYPE: PRT
<213> ORGANISM: Artificial Sequence
<220> FEATURE:
<223> OTHER INFORMATION: synthetic
```

-continued

<400> SEQUENCE: 306

Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser Thr Asn
            20                  25                  30
Gly Val Gly Val Gly Trp Ile Arg Gln Pro Pro Gly Lys Ala Leu Glu
        35                  40                  45
Trp Leu Gly Ile Ile Tyr Trp Asn Asp Asp Lys Arg Tyr Ser Pro Ser
    50                  55                  60
Leu Arg Ser Arg Leu Thr Ile Thr Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala His Arg Gly Leu Phe Gly Gly Trp Phe Asp Pro Trp Gly Gln
            100                 105                 110
Gly Thr Leu Val Thr Val Ser Ser
        115                 120

<210> SEQ ID NO 307
<211> LENGTH: 30
<212> TYPE: DNA
<213> ORGANISM: Artificial Sequence
<220> FEATURE:
<223> OTHER INFORMATION: synthetic

<400> SEQUENCE: 307
gggttctcac tcagcactaa tggagtgggt                                              30

<210> SEQ ID NO 308
<211> LENGTH: 10
<212> TYPE: PRT
<213> ORGANISM: Artificial Sequence
<220> FEATURE:
<223> OTHER INFORMATION: synthetic

<400> SEQUENCE: 308

Gly Phe Ser Leu Ser Thr Asn Gly Val Gly
1               5                   10

<210> SEQ ID NO 309
<211> LENGTH: 21
<212> TYPE: DNA
<213> ORGANISM: Artificial Sequence
<220> FEATURE:
<223> OTHER INFORMATION: synthetic

<400> SEQUENCE: 309
atttattgga atgatgataa g                                                       21

<210> SEQ ID NO 310
<211> LENGTH: 7
<212> TYPE: PRT
<213> ORGANISM: Artificial Sequence
<220> FEATURE:
<223> OTHER INFORMATION: synthetic

<400> SEQUENCE: 310

Ile Tyr Trp Asn Asp Asp Lys
1               5

<210> SEQ ID NO 311
<211> LENGTH: 36

<212> TYPE: DNA
<213> ORGANISM: Artificial Sequence
<220> FEATURE:
<223> OTHER INFORMATION: synthetic

<400> SEQUENCE: 311
gcacacagag gcctcttcgg aggttggttc gacccc                                36

<210> SEQ ID NO 312
<211> LENGTH: 12
<212> TYPE: PRT
<213> ORGANISM: Artificial Sequence
<220> FEATURE:
<223> OTHER INFORMATION: synthetic

<400> SEQUENCE: 312

Ala His Arg Gly Leu Phe Gly Gly Trp Phe Asp Pro
 1               5                  10

<210> SEQ ID NO 313
<211> LENGTH: 321
<212> TYPE: DNA
<213> ORGANISM: Artificial Sequence
<220> FEATURE:
<223> OTHER INFORMATION: synthetic

<400> SEQUENCE: 313
gacatccaga tgacccagtc tccatcctcc ctgtctgcat ctgtaggaga cagagtcacc        60
atcacttgcc gggcaagtca gagcattagc aggtatttaa attggtatca gcagaaacca       120
gggaaagccc ctaacctcct gatctttgct gcatccagtt tgcaaagtgg ggtcccatca       180
aggttcagtg gcagtggatc tgggacagat ttcactctca ccatcagcag tctgcaacct       240
gaagattttg caacttactt ctgtcaacag agttacaata ccccgctcac tttcggcgga       300
gggaccaagg tggagatcaa a                                                 321

<210> SEQ ID NO 314
<211> LENGTH: 107
<212> TYPE: PRT
<213> ORGANISM: Artificial Sequence
<220> FEATURE:
<223> OTHER INFORMATION: synthetic

<400> SEQUENCE: 314

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Arg Tyr
             20                  25                  30

Leu Asn Trp Tyr Gln Gln Lys Pro Gly Lys Ala Pro Asn Leu Leu Ile
         35                  40                  45

Phe Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Ser Tyr Asn Thr Pro Leu
                 85                  90                  95

Thr Phe Gly Gly Gly Thr Lys Val Glu Ile Lys
            100                 105

<210> SEQ ID NO 315
<211> LENGTH: 18
<212> TYPE: DNA

<213> ORGANISM: Artificial Sequence
<220> FEATURE:
<223> OTHER INFORMATION: synthetic

<400> SEQUENCE: 315
cagagcatta gcaggtat                                                 18

<210> SEQ ID NO 316
<211> LENGTH: 6
<212> TYPE: PRT
<213> ORGANISM: Artificial Sequence
<220> FEATURE:
<223> OTHER INFORMATION: synthetic

<400> SEQUENCE: 316

Gln Ser Ile Ser Arg Tyr
1               5

<210> SEQ ID NO 317
<211> LENGTH: 9
<212> TYPE: DNA
<213> ORGANISM: Artificial Sequence
<220> FEATURE:
<223> OTHER INFORMATION: synthetic

<400> SEQUENCE: 317 gctgcatcc                                                            9

<210> SEQ ID NO 318
<211> LENGTH: 3
<212> TYPE: PRT
<213> ORGANISM: Artificial Sequence
<220> FEATURE:
<223> OTHER INFORMATION: synthetic

<400> SEQUENCE: 318

Ala Ala Ser
1

<210> SEQ ID NO 319
<211> LENGTH: 27
<212> TYPE: DNA
<213> ORGANISM: Artificial Sequence
<220> FEATURE:
<223> OTHER INFORMATION: synthetic

<400> SEQUENCE: 319
caacagagtt acaataccccc gctcact                                      27

<210> SEQ ID NO 320
<211> LENGTH: 9
<212> TYPE: PRT
<213> ORGANISM: Artificial Sequence
<220> FEATURE:
<223> OTHER INFORMATION: synthetic

<400> SEQUENCE: 320

Gln Gln Ser Tyr Asn Thr Pro Leu Thr
1               5

<210> SEQ ID NO 321
<211> LENGTH: 366
<212> TYPE: DNA
<213> ORGANISM: Artificial Sequence
<220> FEATURE:
<223> OTHER INFORMATION: synthetic

<400> SEQUENCE: 321

```
gaggtgcagc tggtggagtc tgggggaggc ttggtacagc cggggggtc cctgagactc      60
tcctgtgcaa tctctggatt cacctttagg agttatgcca tgacctgggt ccgccaggct    120
ccagggaagg cgctggagtg gtctcagtt attagtggta gcggtggtaa cacatactac    180
gcagactccg tgaagggccg gttcaccgtc tccagagaca attccaggaa cacgctgtat    240
ctgcaaatga acagcctgag agccgaggac acggccgtat atttctgttc gaaagttgca    300
gcagctaata attactatta cgctttggac gtctggggcc aagggaccac ggtcaccgtc    360
tcctca                                                                366
```

<210> SEQ ID NO 322
<211> LENGTH: 122
<212> TYPE: PRT
<213> ORGANISM: Artificial Sequence
<220> FEATURE:
<223> OTHER INFORMATION: synthetic

<400> SEQUENCE: 322

```
Glu Val Gln Leu Val Glu Ser Gly Gly Gly Leu Val Gln Pro Gly Gly
1               5                   10                  15
Ser Leu Arg Leu Ser Cys Ala Ile Ser Gly Phe Thr Phe Arg Ser Tyr
            20                  25                  30
Ala Met Thr Trp Val Arg Gln Ala Pro Gly Lys Ala Leu Glu Trp Val
        35                  40                  45
Ser Val Ile Ser Gly Ser Gly Gly Asn Thr Tyr Tyr Ala Asp Ser Val
    50                  55                  60
Lys Gly Arg Phe Thr Val Ser Arg Asp Asn Ser Arg Asn Thr Leu Tyr
65                  70                  75                  80
Leu Gln Met Asn Ser Leu Arg Ala Glu Asp Thr Ala Val Tyr Phe Cys
                85                  90                  95
Ser Lys Val Ala Ala Ala Asn Asn Tyr Tyr Tyr Ala Leu Asp Val Trp
            100                 105                 110
Gly Gln Gly Thr Thr Val Thr Val Ser Ser
        115                 120
```

<210> SEQ ID NO 323
<211> LENGTH: 24
<212> TYPE: DNA
<213> ORGANISM: Artificial Sequence
<220> FEATURE:
<223> OTHER INFORMATION: synthetic

<400> SEQUENCE: 323

```
ggattcacct ttaggagtta tgcc                                             24
```

<210> SEQ ID NO 324
<211> LENGTH: 8
<212> TYPE: PRT
<213> ORGANISM: Artificial Sequence
<220> FEATURE:
<223> OTHER INFORMATION: synthetic

<400> SEQUENCE: 324

```
Gly Phe Thr Phe Arg Ser Tyr Ala
1               5
```

<210> SEQ ID NO 325
<211> LENGTH: 24
<212> TYPE: DNA

```
<213> ORGANISM: Artificial Sequence
<220> FEATURE:
<223> OTHER INFORMATION: synthetic

<400> SEQUENCE: 325
attagtggta gcggtggtaa caca                                                24

<210> SEQ ID NO 326
<211> LENGTH: 8
<212> TYPE: PRT
<213> ORGANISM: Artificial Sequence
<220> FEATURE:
<223> OTHER INFORMATION: synthetic

<400> SEQUENCE: 326

Ile Ser Gly Ser Gly Gly Asn Thr
1               5

<210> SEQ ID NO 327
<211> LENGTH: 45
<212> TYPE: DNA
<213> ORGANISM: Artificial Sequence
<220> FEATURE:
<223> OTHER INFORMATION: synthetic

<400> SEQUENCE: 327
tcgaaagttg cagcagctaa taattactat tacgctttgg acgtc                         45

<210> SEQ ID NO 328
<211> LENGTH: 15
<212> TYPE: PRT
<213> ORGANISM: Artificial Sequence
<220> FEATURE:
<223> OTHER INFORMATION: synthetic

<400> SEQUENCE: 328

Ser Lys Val Ala Ala Ala Asn Asn Tyr Tyr Tyr Ala Leu Asp Val
1               5                   10                  15

<210> SEQ ID NO 329
<211> LENGTH: 336
<212> TYPE: DNA
<213> ORGANISM: Artificial Sequence
<220> FEATURE:
<223> OTHER INFORMATION: synthetic

<400> SEQUENCE: 329
gatattgtga tgactcagtc tccactctcc ctgcccgtca cccctggaga gccggcctcc         60
atctcctgca ggtctagtca gagcctcctg catagtaatg gatacaagta tttggattgg        120
tacctgcaga agccagggca gtctccacaa ctcctgatct atttggtttc taatcgggcc        180
tccggggtcc ctgacaggtt cagtggcagt ggatcaggca cagattttac actgaaaatc        240
agcagagtgg aggctgagga tgttggggtt tattattgca tgcaagctct acaaactccg        300
tacacttttg gccaggggac caagctggag atcaaa                                  336

<210> SEQ ID NO 330
<211> LENGTH: 112
<212> TYPE: PRT
<213> ORGANISM: Artificial Sequence
<220> FEATURE:
<223> OTHER INFORMATION: synthetic

<400> SEQUENCE: 330

Asp Ile Val Met Thr Gln Ser Pro Leu Ser Leu Pro Val Thr Pro Gly
```

```
1               5                   10                  15
Glu Pro Ala Ser Ile Ser Cys Arg Ser Ser Gln Ser Leu Leu His Ser
                20                  25                  30

Asn Gly Tyr Lys Tyr Leu Asp Trp Tyr Leu Gln Lys Pro Gly Gln Ser
            35                  40                  45

Pro Gln Leu Leu Ile Tyr Leu Val Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 331
<211> LENGTH: 33
<212> TYPE: DNA
<213> ORGANISM: Artificial Sequence
<220> FEATURE:
<223> OTHER INFORMATION: synthetic

<400> SEQUENCE: 331
cagagcctcc tgcatagtaa tggatacaag tat         33

<210> SEQ ID NO 332
<211> LENGTH: 11
<212> TYPE: PRT
<213> ORGANISM: Artificial Sequence
<220> FEATURE:
<223> OTHER INFORMATION: synthetic

<400> SEQUENCE: 332

```
Gln Ser Leu Leu His Ser Asn Gly Tyr Lys Tyr
1               5                   10
```

<210> SEQ ID NO 333
<211> LENGTH: 9
<212> TYPE: DNA
<213> ORGANISM: Artificial Sequence
<220> FEATURE:
<223> OTHER INFORMATION: synthetic

<400> SEQUENCE: 333 ttggtttct         9

<210> SEQ ID NO 334
<211> LENGTH: 3
<212> TYPE: PRT
<213> ORGANISM: Artificial Sequence
<220> FEATURE:
<223> OTHER INFORMATION: synthetic

<400> SEQUENCE: 334

```
Leu Val Ser
1
```

<210> SEQ ID NO 335
<211> LENGTH: 27
<212> TYPE: DNA
<213> ORGANISM: Artificial Sequence
<220> FEATURE:
<223> OTHER INFORMATION: synthetic

<400> SEQUENCE: 335

```
atgcaagctc tacaaactcc gtacact                                        27
```

<210> SEQ ID NO 336
<211> LENGTH: 9
<212> TYPE: PRT
<213> ORGANISM: Artificial Sequence
<220> FEATURE:
<223> OTHER INFORMATION: synthetic

<400> SEQUENCE: 336

```
Met Gln Ala Leu Gln Thr Pro Tyr Thr
1               5
```

<210> SEQ ID NO 337
<211> LENGTH: 381
<212> TYPE: DNA
<213> ORGANISM: Artificial Sequence
<220> FEATURE:
<223> OTHER INFORMATION: synthetic

<400> SEQUENCE: 337

```
caggtgcagc tggtggagtc tgggggaggc gtggtccagc ctgggaggtc cctgagactc     60
tcctgtgtag cgtctggatt caccttcagt aactatggca tgcactgggt ccgccaggct    120
ccaggcaagg ggctggagtg ggtggcagtt atatggaatg atggaagtaa taaatactat    180
gcagactccg tgaagggccg attcaccatc tccagagaca attccaagaa cacgctgtat    240
ctccaagtga gcagcctgag agccgatgac acggctgtat attactgtgc gagggacgga    300
gaggtcgaat atagcagctc gaattacaac tactacggtc tggatgtctg gggccaaggg    360
accacggtca ccgtctcctc a                                              381
```

<210> SEQ ID NO 338
<211> LENGTH: 127
<212> TYPE: PRT
<213> ORGANISM: Artificial Sequence
<220> FEATURE:
<223> OTHER INFORMATION: synthetic

<400> SEQUENCE: 338

```
Gln Val Gln Leu Val Glu Ser Gly Gly Gly Val Val Gln Pro Gly Arg
1               5                   10                  15
Ser Leu Arg Leu Ser Cys Val Ala Ser Gly Phe Thr Phe Ser Asn Tyr
            20                  25                  30
Gly Met His Trp Val Arg Gln Ala Pro Gly Lys Gly Leu Glu Trp Val
        35                  40                  45
Ala Val Ile Trp Asn Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Val Ser Ser Leu Arg Ala Asp Asp Thr Ala Val Tyr Tyr Cys
                85                  90                  95
Ala Arg Asp Gly Glu Val Glu Tyr Ser Ser Ser Asn Tyr Asn Tyr Tyr
            100                 105                 110
Gly Leu Asp Val Trp Gly Gln Gly Thr Thr Val Thr Val Ser Ser
        115                 120                 125
```

<210> SEQ ID NO 339
<211> LENGTH: 24
<212> TYPE: DNA
<213> ORGANISM: Artificial Sequence

```
<220> FEATURE:
<223> OTHER INFORMATION: synthetic

<400> SEQUENCE: 339
ggattcacct tcagtaacta tggc                                    24

<210> SEQ ID NO 340
<211> LENGTH: 8
<212> TYPE: PRT
<213> ORGANISM: Artificial Sequence
<220> FEATURE:
<223> OTHER INFORMATION: synthetic

<400> SEQUENCE: 340

Gly Phe Thr Phe Ser Asn Tyr Gly
1               5

<210> SEQ ID NO 341
<211> LENGTH: 24
<212> TYPE: DNA
<213> ORGANISM: Artificial Sequence
<220> FEATURE:
<223> OTHER INFORMATION: synthetic

<400> SEQUENCE: 341
atatggaatg atggaagtaa taaa                                    24

<210> SEQ ID NO 342
<211> LENGTH: 8
<212> TYPE: PRT
<213> ORGANISM: Artificial Sequence
<220> FEATURE:
<223> OTHER INFORMATION: synthetic

<400> SEQUENCE: 342

Ile Trp Asn Asp Gly Ser Asn Lys
1               5

<210> SEQ ID NO 343
<211> LENGTH: 60
<212> TYPE: DNA
<213> ORGANISM: Artificial Sequence
<220> FEATURE:
<223> OTHER INFORMATION: synthetic

<400> SEQUENCE: 343
gcgagggacg gagaggtcga atatagcagc tcgaattaca actactacgg tctggatgtc    60

<210> SEQ ID NO 344
<211> LENGTH: 20
<212> TYPE: PRT
<213> ORGANISM: Artificial Sequence
<220> FEATURE:
<223> OTHER INFORMATION: synthetic

<400> SEQUENCE: 344

Ala Arg Asp Gly Glu Val Glu Tyr Ser Ser Ser Asn Tyr Asn Tyr Tyr
1               5                   10                  15
Gly Leu Asp Val
            20

<210> SEQ ID NO 345
<211> LENGTH: 321
<212> TYPE: DNA
<213> ORGANISM: Artificial Sequence
<220> FEATURE:
```

<223> OTHER INFORMATION: synthetic

<400> SEQUENCE: 345

```
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaaactcct gatctacgat gcatccaatt tggaaacagg ggtcccatca   180
aggttcagtg aagtggatc tgggacagat tttactttca ccatcagcag cctgcagcct   240
gaagatattg taacatatta ctgtcaacag tatgatgatc tcccgatcac cttcggccaa   300
gggacacgac tggagattaa a                                              321
```

<210> SEQ ID NO 346
<211> LENGTH: 107
<212> TYPE: PRT
<213> ORGANISM: Artificial Sequence
<220> FEATURE:
<223> OTHER INFORMATION: synthetic

<400> SEQUENCE: 346

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Leu Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Val Thr Tyr Tyr Cys Gln Gln Tyr Asp Asp Leu Pro Ile
                85                  90                  95

Thr Phe Gly Gln Gly Thr Arg Leu Glu Ile Lys
            100                 105
```

<210> SEQ ID NO 347
<211> LENGTH: 18
<212> TYPE: DNA
<213> ORGANISM: Artificial Sequence
<220> FEATURE:
<223> OTHER INFORMATION: synthetic

<400> SEQUENCE: 347

```
caggacatta gcaactat                                                  18
```

<210> SEQ ID NO 348
<211> LENGTH: 6
<212> TYPE: PRT
<213> ORGANISM: Artificial Sequence
<220> FEATURE:
<223> OTHER INFORMATION: synthetic

<400> SEQUENCE: 348

```
Gln Asp Ile Ser Asn Tyr
1               5
```

<210> SEQ ID NO 349
<211> LENGTH: 9
<212> TYPE: DNA
<213> ORGANISM: Artificial Sequence
<220> FEATURE:
<223> OTHER INFORMATION: synthetic

<400> SEQUENCE: 349 gatgcatcc                                                                  9

<210> SEQ ID NO 350
<211> LENGTH: 3
<212> TYPE: PRT
<213> ORGANISM: Artificial Sequence
<220> FEATURE:
<223> OTHER INFORMATION: synthetic

<400> SEQUENCE: 350

Asp Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: synthetic

<400> SEQUENCE: 351
caacagtatg atgatctccc gatcacc                                             27

<210> SEQ ID NO 352
<211> LENGTH: 9
<212> TYPE: PRT
<213> ORGANISM: Artificial Sequence
<220> FEATURE:
<223> OTHER INFORMATION: synthetic

<400> SEQUENCE: 352

Gln Gln Tyr Asp Asp Leu Pro Ile Thr
1               5

<210> SEQ ID NO 353
<211> LENGTH: 375
<212> TYPE: DNA
<213> ORGANISM: Artificial Sequence
<220> FEATURE:
<223> OTHER INFORMATION: synthetic

<400> SEQUENCE: 353
gaggtgcagc tggtggagtc tgggggaggc ttggtacagc ctggggggtc cctgagactc         60
tcctgtgcag cctctggatt ctcctttcat aattttgcca tgaactgggt ccgccaggct        120
ccagggaagg ggctggagtg gtctcagtt attactggta gtggtactag cacacactac         180
gcagactccg tgaagggccg gttcaccatc tccagagaca attccaagaa aacgctatat        240
ctgcaaatga atagcctgag agccgaggac acggccgtat attactgtgc gaaagatcgg        300
ggctatgatt atagtggttc ttactacaac tggttcgacc cctggggcca gggaaccctg        360
gtcaccgtct cctca                                                         375

<210> SEQ ID NO 354
<211> LENGTH: 125
<212> TYPE: PRT
<213> ORGANISM: Artificial Sequence
<220> FEATURE:
<223> OTHER INFORMATION: synthetic

<400> SEQUENCE: 354

Glu Val Gln Leu Val Glu Ser Gly Gly Gly Leu Val Gln Pro Gly Gly
1               5                   10                  15

-continued

```
Ser Leu Arg Leu Ser Cys Ala Ala Ser Gly Phe Ser Phe His Asn Phe
             20                  25                  30

Ala Met Asn Trp Val Arg Gln Ala Pro Gly Lys Gly Leu Glu Trp Val
         35                  40                  45

Ser Val Ile Thr Gly Ser Gly Thr Ser Thr His Tyr Ala Asp Ser Val
     50                  55                  60

Lys Gly Arg Phe Thr Ile Ser Arg Asp Asn Ser Lys Lys Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Gly Tyr Asp Tyr Ser Gly Ser Tyr Tyr Asn Trp Phe
            100                 105                 110

Asp Pro Trp Gly Gln Gly Thr Leu Val Thr Val Ser Ser
            115                 120                 125

<210> SEQ ID NO 355
<211> LENGTH: 24
<212> TYPE: DNA
<213> ORGANISM: Artificial Sequence
<220> FEATURE:
<223> OTHER INFORMATION: synthetic

<400> SEQUENCE: 355
ggattctcct ttcataattt tgcc                                            24

<210> SEQ ID NO 356
<211> LENGTH: 8
<212> TYPE: PRT
<213> ORGANISM: Artificial Sequence
<220> FEATURE:
<223> OTHER INFORMATION: synthetic

<400> SEQUENCE: 356

Gly Phe Ser Phe His Asn Phe Ala
1               5

<210> SEQ ID NO 357
<211> LENGTH: 24
<212> TYPE: DNA
<213> ORGANISM: Artificial Sequence
<220> FEATURE:
<223> OTHER INFORMATION: synthetic

<400> SEQUENCE: 357
attactggta gtggtactag caca                                            24

<210> SEQ ID NO 358
<211> LENGTH: 8
<212> TYPE: PRT
<213> ORGANISM: Artificial Sequence
<220> FEATURE:
<223> OTHER INFORMATION: synthetic

<400> SEQUENCE: 358

Ile Thr Gly Ser Gly Thr Ser Thr
1               5

<210> SEQ ID NO 359
<211> LENGTH: 54
<212> TYPE: DNA
<213> ORGANISM: Artificial Sequence
<220> FEATURE:
<223> OTHER INFORMATION: synthetic
```

<400> SEQUENCE: 359
gcgaaagatc ggggctatga ttatagtggt tcttactaca actggttcga cccc    54

<210> SEQ ID NO 360
<211> LENGTH: 18
<212> TYPE: PRT
<213> ORGANISM: Artificial Sequence
<220> FEATURE:
<223> OTHER INFORMATION: synthetic

<400> SEQUENCE: 360

Ala Lys Asp Arg Gly Tyr Asp Tyr Ser Gly Ser Tyr Tyr Asn Trp Phe
 1               5                  10                  15

Asp Pro

<210> SEQ ID NO 361
<211> LENGTH: 327
<212> TYPE: DNA
<213> ORGANISM: Artificial Sequence
<220> FEATURE:
<223> OTHER INFORMATION: synthetic

<400> SEQUENCE: 361
gacatccaga tgacccagtc tccatcctcc ctgtctgcat ctgtaggaga cagaatcacc     60
atcacttgcc gggcaagtca gagtattagc agctatttaa attggtatca gcagaaacca    120
gggaaagccc ctaaactcct gatctttgct gcatcaaatt tgcaaagtgg ggtcccatca    180
aggttcagtg gcagtggatc tgggacagat ttcactctca ccatcagtag tctgcaacct    240
gaagattttg caacttacta ctgtcaacag agttacagta ccccatcctt attcactttc    300
ggccctggga ccaaagtgga tatcaaa                                       327

<210> SEQ ID NO 362
<211> LENGTH: 109
<212> TYPE: PRT
<213> ORGANISM: Artificial Sequence
<220> FEATURE:
<223> OTHER INFORMATION: synthetic

<400> SEQUENCE: 362

Asp Ile Gln Met Thr Gln Ser Pro Ser Ser Leu Ser Ala Ser Val Gly
 1               5                  10                  15

Asp Arg Ile Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Phe Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ser
                85                  90                  95

Leu Phe Thr Phe Gly Pro Gly Thr Lys Val Asp Ile Lys
            100                 105

<210> SEQ ID NO 363
<211> LENGTH: 18
<212> TYPE: DNA
<213> ORGANISM: Artificial Sequence
<220> FEATURE:

<223> OTHER INFORMATION: synthetic

<400> SEQUENCE: 363
cagagtatta gcagctat                                          18

<210> SEQ ID NO 364
<211> LENGTH: 6
<212> TYPE: PRT
<213> ORGANISM: Artificial Sequence
<220> FEATURE:
<223> OTHER INFORMATION: synthetic

<400> SEQUENCE: 364

Gln Ser Ile Ser Ser Tyr
1               5

<210> SEQ ID NO 365
<211> LENGTH: 9
<212> TYPE: DNA
<213> ORGANISM: Artificial Sequence
<220> FEATURE:
<223> OTHER INFORMATION: synthetic

<400> SEQUENCE: 365 gctgcatca                                                     9

<210> SEQ ID NO 366
<211> LENGTH: 3
<212> TYPE: PRT
<213> ORGANISM: Artificial Sequence
<220> FEATURE:
<223> OTHER INFORMATION: synthetic

<400> SEQUENCE: 366

Ala Ala Ser
1

<210> SEQ ID NO 367
<211> LENGTH: 33
<212> TYPE: DNA
<213> ORGANISM: Artificial Sequence
<220> FEATURE:
<223> OTHER INFORMATION: synthetic

<400> SEQUENCE: 367
caacagagtt acagtacccc atccttattc act                         33

<210> SEQ ID NO 368
<211> LENGTH: 11
<212> TYPE: PRT
<213> ORGANISM: Artificial Sequence
<220> FEATURE:
<223> OTHER INFORMATION: synthetic

<400> SEQUENCE: 368

Gln Gln Ser Tyr Ser Thr Pro Ser Leu Phe Thr
1               5                   10

<210> SEQ ID NO 369
<211> LENGTH: 384
<212> TYPE: DNA
<213> ORGANISM: Artificial Sequence
<220> FEATURE:
<223> OTHER INFORMATION: synthetic

<400> SEQUENCE: 369

```
gaggtgcagc tggtggagtc tgggggaggc ttggtacagc ctggagggtc cctgagactc    60
tcctgtgcag tctctggatt caccttcagt agttacgaga tgaactgggt ccgccaggct   120
ccagggaagg ggctggaatg ggtttcacac attagtagta gtggaagtac catatactac   180
gcagactctg tgaagggccg attcaccatg tccagagaca acgccaagaa ctcactgtat   240
ctgcaaatga acagcctgag agccgaggac acggctgttt attactgtgc gagagatggg   300
aatatctgga gtggttatta tgccgcctac tacttctacg gtatggacgt ctggggccaa   360
gggaccacgg tcaccgtctc ctca                                          384
```

<210> SEQ ID NO 370
<211> LENGTH: 128
<212> TYPE: PRT
<213> ORGANISM: Artificial Sequence
<220> FEATURE:
<223> OTHER INFORMATION: synthetic

<400> SEQUENCE: 370

```
Glu Val Gln Leu Val Glu Ser Gly Gly Gly Leu Val Gln Pro Gly Gly
  1               5                  10                  15

Ser Leu Arg Leu Ser Cys Ala Val Ser Gly Phe Thr Phe Ser Ser Tyr
             20                  25                  30

Glu Met Asn Trp Val Arg Gln Ala Pro Gly Lys Gly Leu Glu Trp Val
         35                  40                  45

Ser His Ile Ser Ser Ser Gly Ser Thr Ile Tyr Tyr Ala Asp Ser Val
     50                  55                  60

Lys Gly Arg Phe Thr Met Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Asn Ile Trp Ser Gly Tyr Tyr Ala Ala Tyr Tyr Phe
            100                 105                 110

Tyr Gly Met Asp Val Trp Gly Gln Gly Thr Thr Val Thr Val Ser Ser
        115                 120                 125
```

<210> SEQ ID NO 371
<211> LENGTH: 24
<212> TYPE: DNA
<213> ORGANISM: Artificial Sequence
<220> FEATURE:
<223> OTHER INFORMATION: synthetic

<400> SEQUENCE: 371

```
ggattcacct tcagtagtta cgag                                           24
```

<210> SEQ ID NO 372
<211> LENGTH: 8
<212> TYPE: PRT
<213> ORGANISM: Artificial Sequence
<220> FEATURE:
<223> OTHER INFORMATION: synthetic

<400> SEQUENCE: 372

```
Gly Phe Thr Phe Ser Ser Tyr Glu
  1               5
```

<210> SEQ ID NO 373
<211> LENGTH: 24
<212> TYPE: DNA
<213> ORGANISM: Artificial Sequence
<220> FEATURE:

<223> OTHER INFORMATION: synthetic

<400> SEQUENCE: 373
attagtagta gtggaagtac cata                                          24

<210> SEQ ID NO 374
<211> LENGTH: 8
<212> TYPE: PRT
<213> ORGANISM: Artificial Sequence
<220> FEATURE:
<223> OTHER INFORMATION: synthetic

<400> SEQUENCE: 374

Ile Ser Ser Ser Gly Ser Thr Ile
1               5

<210> SEQ ID NO 375
<211> LENGTH: 63
<212> TYPE: DNA
<213> ORGANISM: Artificial Sequence
<220> FEATURE:
<223> OTHER INFORMATION: synthetic

<400> SEQUENCE: 375
gcgagagatg ggaatatctg agtggttat tatgccgcct actacttcta cggtatggac    60
gtc                                                                 63

<210> SEQ ID NO 376
<211> LENGTH: 21
<212> TYPE: PRT
<213> ORGANISM: Artificial Sequence
<220> FEATURE:
<223> OTHER INFORMATION: synthetic

<400> SEQUENCE: 376

Ala Arg Asp Gly Asn Ile Trp Ser Gly Tyr Tyr Ala Ala Tyr Tyr Phe
1               5                   10                  15

Tyr Gly Met Asp Val
            20

<210> SEQ ID NO 377
<211> LENGTH: 336
<212> TYPE: DNA
<213> ORGANISM: Artificial Sequence
<220> FEATURE:
<223> OTHER INFORMATION: synthetic

<400> SEQUENCE: 377
gatattgtga tgacccagac tccactctcc tcacctgtca cccttggaca gccggcctcc    60
atctcctgca ggtctagtca aagcctcgta cacagtgatg gaaaaaccta cttgagttgg   120
cttcagcaga ggccaggcca gcctccaaga ctcctaattt ataagatttc taaccggttc   180
tctggggtcc cagacagaat cagtggcagt ggggcaggga cagatttcac actgaaaatc   240
agcagggtgg aagctgagga tgtcggggtt tattactgca tgcaagctgt acaatttcct   300
cggacgttcg gccaagggac caaggtggaa atcaaa                             336

<210> SEQ ID NO 378
<211> LENGTH: 112
<212> TYPE: PRT
<213> ORGANISM: Artificial Sequence
<220> FEATURE:
<223> OTHER INFORMATION: synthetic -continued

<400> SEQUENCE: 378

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Lys Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Ile Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Val Gln Phe Pro Arg Thr Phe Gly Gln Gly Thr Lys Val Glu Ile Lys
            100                 105                 110

<210> SEQ ID NO 379
<211> LENGTH: 33
<212> TYPE: DNA
<213> ORGANISM: Artificial Sequence
<220> FEATURE:
<223> OTHER INFORMATION: synthetic

<400> SEQUENCE: 379
caaagcctcg tacacagtga tggaaaaacc tac        33

<210> SEQ ID NO 380
<211> LENGTH: 11
<212> TYPE: PRT
<213> ORGANISM: Artificial Sequence
<220> FEATURE:
<223> OTHER INFORMATION: synthetic

<400> SEQUENCE: 380

Gln Ser Leu Val His Ser Asp Gly Lys Thr Tyr
1               5                   10

<210> SEQ ID NO 381
<211> LENGTH: 9
<212> TYPE: DNA
<213> ORGANISM: Artificial Sequence
<220> FEATURE:
<223> OTHER INFORMATION: synthetic

<400> SEQUENCE: 381 aagatttct        9

<210> SEQ ID NO 382
<211> LENGTH: 3
<212> TYPE: PRT
<213> ORGANISM: Artificial Sequence
<220> FEATURE:
<223> OTHER INFORMATION: synthetic

<400> SEQUENCE: 382

Lys Ile Ser
1

<210> SEQ ID NO 383
<211> LENGTH: 27
<212> TYPE: DNA
<213> ORGANISM: Artificial Sequence
<220> FEATURE:

<223> OTHER INFORMATION: synthetic

<400> SEQUENCE: 383
atgcaagctg tacaatttcc tcggacg         27

<210> SEQ ID NO 384
<211> LENGTH: 9
<212> TYPE: PRT
<213> ORGANISM: Artificial Sequence
<220> FEATURE:
<223> OTHER INFORMATION: synthetic

<400> SEQUENCE: 384

Met Gln Ala Val Gln Phe Pro Arg Thr
1               5

<210> SEQ ID NO 385
<211> LENGTH: 366
<212> TYPE: DNA
<213> ORGANISM: Artificial Sequence
<220> FEATURE:
<223> OTHER INFORMATION: synthetic

<400> SEQUENCE: 385
caggtgcagc tacagcagtg gggcgcagga ctgttgaacc cttcggagac cctgtccctc         60
acctgcgctg tctatggtgg ggccttcagt gattactact ggaattggat ccgccagccc        120
ccagggaagg ggctggagtg gattggggaa atcaatcatc gcggaagcac caactacaac        180
ccgtccctca agagtcgtgt caccatttca gttgacacgt ccaagaacca gttctccctg        240
aggatgagct ctgtgaccgc cgcggacgcg gctgtgtatt actgtgcgag aggagaggat        300
tacgatattt ggaatggtta ttatcaggaa aaatggggcc agggaaccct ggtcaccgtc        360
tcctca        366

<210> SEQ ID NO 386
<211> LENGTH: 122
<212> TYPE: PRT
<213> ORGANISM: Artificial Sequence
<220> FEATURE:
<223> OTHER INFORMATION: synthetic

<400> SEQUENCE: 386

Gln Val Gln Leu Gln Gln Trp Gly Ala Gly Leu Leu Asn Pro Ser Glu
1               5                   10                  15

Thr Leu Ser Leu Thr Cys Ala Val Tyr Gly Gly Ala Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Met Ser Ser Val Thr Ala Ala Asp Ala Ala Val Tyr Tyr Cys Ala
                85                  90                  95

Arg Gly Glu Asp Tyr Asp Ile Trp Asn Gly Tyr Tyr Gln Glu Lys Trp
            100                 105                 110

Gly Gln Gly Thr Leu Val Thr Val Ser Ser
        115                 120

<210> SEQ ID NO 387

```
<211> LENGTH: 24
<212> TYPE: DNA
<213> ORGANISM: Artificial Sequence
<220> FEATURE:
<223> OTHER INFORMATION: synthetic

<400> SEQUENCE: 387
ggtggggcct tcagtgatta ctac                                       24

<210> SEQ ID NO 388
<211> LENGTH: 8
<212> TYPE: PRT
<213> ORGANISM: Artificial Sequence
<220> FEATURE:
<223> OTHER INFORMATION: synthetic

<400> SEQUENCE: 388

Gly Gly Ala Phe Ser Asp Tyr Tyr
1               5

<210> SEQ ID NO 389
<211> LENGTH: 21
<212> TYPE: DNA
<213> ORGANISM: Artificial Sequence
<220> FEATURE:
<223> OTHER INFORMATION: synthetic

<400> SEQUENCE: 389
atcaatcatc gcggaagcac c                                          21

<210> SEQ ID NO 390
<211> LENGTH: 7
<212> TYPE: PRT
<213> ORGANISM: Artificial Sequence
<220> FEATURE:
<223> OTHER INFORMATION: synthetic

<400> SEQUENCE: 390

Ile Asn His Arg Gly Ser Thr
1               5

<210> SEQ ID NO 391
<211> LENGTH: 48
<212> TYPE: DNA
<213> ORGANISM: Artificial Sequence
<220> FEATURE:
<223> OTHER INFORMATION: synthetic

<400> SEQUENCE: 391
gcgagaggag aggattacga tatttggaat ggttattatc aggaaaaa             48

<210> SEQ ID NO 392
<211> LENGTH: 16
<212> TYPE: PRT
<213> ORGANISM: Artificial Sequence
<220> FEATURE:
<223> OTHER INFORMATION: synthetic

<400> SEQUENCE: 392

Ala Arg Gly Glu Asp Tyr Asp Ile Trp Asn Gly Tyr Tyr Gln Glu Lys
1               5                   10                  15

<210> SEQ ID NO 393
<211> LENGTH: 321
<212> TYPE: DNA
<213> ORGANISM: Artificial Sequence
<220> FEATURE:
```

<223> OTHER INFORMATION: synthetic

<400> SEQUENCE: 393

```
gaaattgtgt tgacacagtc tccagccacc ctgtctttgt ctccagggga aagagccacc    60
ctctcctgca gggccagtca gagtattagc acctacttag cctggtacca acagaagcct   120
ggccaggctc ccaggctcct catctatgat gcatccaaga gggccactgg catcccagcc   180
aggttcagtg gcagtgggtc tgggacagac ttcactctca ccatcagcag cctagagcct   240
gaagattttg tagtttatta ctgtcaccag cgtagcaact ggcctctcac tttcggcgga   300
gggaccaagg tggagatcaa a                                             321
```

<210> SEQ ID NO 394
<211> LENGTH: 107
<212> TYPE: PRT
<213> ORGANISM: Artificial Sequence
<220> FEATURE:
<223> OTHER INFORMATION: synthetic

<400> SEQUENCE: 394

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Ile Ser Thr Tyr
            20                  25                  30
Leu Ala Trp Tyr Gln Gln Lys Pro Gly Gln Ala Pro Arg Leu Leu Ile
        35                  40                  45
Tyr Asp Ala Ser Lys Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Val Val Tyr Tyr Cys His Gln Arg Ser Asn Trp Pro Leu
                85                  90                  95
Thr Phe Gly Gly Gly Thr Lys Val Glu Ile Lys
            100                 105
```

<210> SEQ ID NO 395
<211> LENGTH: 18
<212> TYPE: DNA
<213> ORGANISM: Artificial Sequence
<220> FEATURE:
<223> OTHER INFORMATION: synthetic

<400> SEQUENCE: 395

```
cagagtatta gcacctac                                                  18
```

<210> SEQ ID NO 396
<211> LENGTH: 6
<212> TYPE: PRT
<213> ORGANISM: Artificial Sequence
<220> FEATURE:
<223> OTHER INFORMATION: synthetic

<400> SEQUENCE: 396

```
Gln Ser Ile Ser Thr Tyr
1               5
```

<210> SEQ ID NO 397
<211> LENGTH: 9
<212> TYPE: DNA
<213> ORGANISM: Artificial Sequence
<220> FEATURE:
<223> OTHER INFORMATION: synthetic
```

<400> SEQUENCE: 397 gatgcatcc                                                                9

<210> SEQ ID NO 398
<211> LENGTH: 3
<212> TYPE: PRT
<213> ORGANISM: Artificial Sequence
<220> FEATURE:
<223> OTHER INFORMATION: synthetic

<400> SEQUENCE: 398

Asp Ala Ser
1

<210> SEQ ID NO 399
<211> LENGTH: 27
<212> TYPE: DNA
<213> ORGANISM: Artificial Sequence
<220> FEATURE:
<223> OTHER INFORMATION: synthetic

<400> SEQUENCE: 399
caccagcgta gcaactggcc tctcact                                            27

<210> SEQ ID NO 400
<211> LENGTH: 9
<212> TYPE: PRT
<213> ORGANISM: Artificial Sequence
<220> FEATURE:
<223> OTHER INFORMATION: synthetic

<400> SEQUENCE: 400

His Gln Arg Ser Asn Trp Pro Leu Thr
1               5

<210> SEQ ID NO 401
<211> LENGTH: 351
<212> TYPE: DNA
<213> ORGANISM: Artificial Sequence
<220> FEATURE:
<223> OTHER INFORMATION: synthetic

<400> SEQUENCE: 401
caggtgcagc tgcaggagtc gggggccagga ctggtgaagc cttcggagac cctgtccctc       60
acctgcactg tctctggtgg ttccttcagt agttactact ggagttggct ccggcagccc      120
ccaggaaagg ggctggagtg gattggatat atctttttaca gtgggagtac cgactacaac     180
ccctccctca agagtcgagt caccatttca gtagacacgt ccaagaagca gttctccctg      240
aagctgacct ctgtgaccgc tgcggacacg gccgtctatt actgtgcgcg aacaataagt      300
acgtggtggt tcgcccccctg gggccaggga accctggtca ccgtctcctc a              351

<210> SEQ ID NO 402
<211> LENGTH: 117
<212> TYPE: PRT
<213> ORGANISM: Artificial Sequence
<220> FEATURE:
<223> OTHER INFORMATION: synthetic

<400> SEQUENCE: 402

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Tyr

```
                    20                  25                  30
Tyr Trp Ser Trp Leu Arg Gln Pro Pro Gly Lys Gly Leu Glu Trp Ile
        35                  40                  45

Gly Tyr Ile Phe Tyr Ser Gly Ser Thr Asp Tyr Asn Pro Ser Leu Lys
    50                  55                  60

Ser Arg Val Thr Ile Ser Val Asp Thr Ser Lys Lys Gln Phe Ser Leu
65                  70                  75                  80

Lys Leu Thr Ser Val Thr Ala Ala Asp Thr Ala Val Tyr Tyr Cys Ala
                85                  90                  95

Arg Thr Ile Ser Thr Trp Trp Phe Ala Pro Trp Gly Gln Gly Thr Leu
            100                 105                 110

Val Thr Val Ser Ser
        115

<210> SEQ ID NO 403
<211> LENGTH: 24
<212> TYPE: DNA
<213> ORGANISM: Artificial Sequence
<220> FEATURE:
<223> OTHER INFORMATION: synthetic

<400> SEQUENCE: 403
ggtggttcct tcagtagtta ctac                                              24

<210> SEQ ID NO 404
<211> LENGTH: 8
<212> TYPE: PRT
<213> ORGANISM: Artificial Sequence
<220> FEATURE:
<223> OTHER INFORMATION: synthetic

<400> SEQUENCE: 404

Gly Gly Ser Phe Ser Ser Tyr Tyr
1               5

<210> SEQ ID NO 405
<211> LENGTH: 21
<212> TYPE: DNA
<213> ORGANISM: Artificial Sequence
<220> FEATURE:
<223> OTHER INFORMATION: synthetic

<400> SEQUENCE: 405
atcttttaca gtgggagtac c                                                 21

<210> SEQ ID NO 406
<211> LENGTH: 7
<212> TYPE: PRT
<213> ORGANISM: Artificial Sequence
<220> FEATURE:
<223> OTHER INFORMATION: synthetic

<400> SEQUENCE: 406

Ile Phe Tyr Ser Gly Ser Thr
1               5

<210> SEQ ID NO 407
<211> LENGTH: 33
<212> TYPE: DNA
<213> ORGANISM: Artificial Sequence
<220> FEATURE:
<223> OTHER INFORMATION: synthetic

<400> SEQUENCE: 407
```
gcgcgaacaa taagtacgtg gtggttcgcc ccc          33

<210> SEQ ID NO 408
<211> LENGTH: 11
<212> TYPE: PRT
<213> ORGANISM: Artificial Sequence
<220> FEATURE:
<223> OTHER INFORMATION: synthetic

<400> SEQUENCE: 408

Ala Arg Thr Ile Ser Thr Trp Trp Phe Ala Pro
1               5                   10

<210> SEQ ID NO 409
<211> LENGTH: 318
<212> TYPE: DNA
<213> ORGANISM: Artificial Sequence
<220> FEATURE:
<223> OTHER INFORMATION: synthetic

<400> SEQUENCE: 409
gaaatagtga tgacacagtc tccagccacc ctgtctgtgt ctccagggggg aagagccacc    60 ctctcctgca gggccagtca gagtgttagc aacaacgtag cctggtacca gcagaaacct   120
ggccaggctc ccaggctcct catctatggt gcatccacca gggccactgg tatcccaggc   180
aggttcagtg gcagtgggtc tggaacagag ttcactctca ccatcagcag cctgcagtct   240
gaagattttg cagtttattc ctgtcagcag tataataact ggctcacttt cggcggaggg   300
accaaggtgg agatcaaa                                                 318

<210> SEQ ID NO 410
<211> LENGTH: 106
<212> TYPE: PRT
<213> ORGANISM: Artificial Sequence
<220> FEATURE:
<223> OTHER INFORMATION: synthetic

<400> SEQUENCE: 410

Glu Ile Val Met Thr Gln Ser Pro Ala Thr Leu Ser Val Ser Pro Gly
1               5                   10                  15

Gly Arg Ala Thr Leu Ser Cys Arg Ala Ser Gln Ser Val Ser Asn Asn
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Gly Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Asn Asn Trp Leu Thr
                85                  90                  95

Phe Gly Gly Gly Thr Lys Val Glu Ile Lys
            100                 105

<210> SEQ ID NO 411
<211> LENGTH: 18
<212> TYPE: DNA
<213> ORGANISM: Artificial Sequence
<220> FEATURE:
<223> OTHER INFORMATION: synthetic

<400> SEQUENCE: 411
cagagtgtta gcaacaac                                                18

<210> SEQ ID NO 412
<211> LENGTH: 6
<212> TYPE: PRT
<213> ORGANISM: Artificial Sequence
<220> FEATURE:
<223> OTHER INFORMATION: synthetic

<400> SEQUENCE: 412

Gln Ser Val Ser Asn Asn
1               5

<210> SEQ ID NO 413
<211> LENGTH: 9
<212> TYPE: DNA
<213> ORGANISM: Artificial Sequence
<220> FEATURE:
<223> OTHER INFORMATION: synthetic

<400> SEQUENCE: 413 ggtgcatcc                                                           9

<210> SEQ ID NO 414
<211> LENGTH: 3
<212> TYPE: PRT
<213> ORGANISM: Artificial Sequence
<220> FEATURE:
<223> OTHER INFORMATION: synthetic

<400> SEQUENCE: 414

Gly Ala Ser
1

<210> SEQ ID NO 415
<211> LENGTH: 24
<212> TYPE: DNA
<213> ORGANISM: Artificial Sequence
<220> FEATURE:
<223> OTHER INFORMATION: synthetic

<400> SEQUENCE: 415
cagcagtata ataactggct cact                                          24

<210> SEQ ID NO 416
<211> LENGTH: 8
<212> TYPE: PRT
<213> ORGANISM: Artificial Sequence
<220> FEATURE:
<223> OTHER INFORMATION: synthetic

<400> SEQUENCE: 416

Gln Gln Tyr Asn Asn Trp Leu Thr
1               5

<210> SEQ ID NO 417
<211> LENGTH: 369
<212> TYPE: DNA
<213> ORGANISM: Artificial Sequence
<220> FEATURE:
<223> OTHER INFORMATION: synthetic

<400> SEQUENCE: 417
caggtgcagc tggtggagtc tgggggaggc gtggtccagc ctgggaggtc cctgagactc     60
tcctgtgtag cgtctggatt cactttcagt agttatggca tgcactgggt ccgccaggct    120

```
ccaggcaagg ggctggagtg ggtggcaatt atatggtatg atggaagtaa taaatactat    180
gcagactccg tgaagggccg attcaccata tccagagaca attccaagaa cacacagtat    240
ctgcaaatga acagcctgag agccgaggac acggctgtgt attactgtgc gtcagtagct    300
acgtctgggg acttcgacta ctacggtatg gacgtctggg gccaagggac cacggtcacc    360
gtctcctca                                                            369
```

```
<210> SEQ ID NO 418
<211> LENGTH: 123
<212> TYPE: PRT
<213> ORGANISM: Artificial Sequence
<220> FEATURE:
<223> OTHER INFORMATION: synthetic

<400> SEQUENCE: 418
```

Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Ser Val Ala Thr Ser Gly Asp Phe Asp Tyr Tyr Gly Met Asp Val
            100                 105                 110

Trp Gly Gln Gly Thr Thr Val Thr Val Ser Ser
        115                 120

```
<210> SEQ ID NO 419
<211> LENGTH: 24
<212> TYPE: DNA
<213> ORGANISM: Artificial Sequence
<220> FEATURE:
<223> OTHER INFORMATION: synthetic

<400> SEQUENCE: 419
ggattcactt tcagtagtta tggc                                           24
```

```
<210> SEQ ID NO 420
<211> LENGTH: 8
<212> TYPE: PRT
<213> ORGANISM: Artificial Sequence
<220> FEATURE:
<223> OTHER INFORMATION: synthetic

<400> SEQUENCE: 420
```

Gly Phe Thr Phe Ser Ser Tyr Gly
1               5

```
<210> SEQ ID NO 421
<211> LENGTH: 24
<212> TYPE: DNA
<213> ORGANISM: Artificial Sequence
<220> FEATURE:
<223> OTHER INFORMATION: synthetic

<400> SEQUENCE: 421
```

```
atatggtatg atggaagtaa taaa                                           24
```

<210> SEQ ID NO 422
<211> LENGTH: 8
<212> TYPE: PRT
<213> ORGANISM: Artificial Sequence
<220> FEATURE:
<223> OTHER INFORMATION: synthetic

<400> SEQUENCE: 422

Ile Trp Tyr Asp Gly Ser Asn Lys
1               5

<210> SEQ ID NO 423
<211> LENGTH: 48
<212> TYPE: DNA
<213> ORGANISM: Artificial Sequence
<220> FEATURE:
<223> OTHER INFORMATION: synthetic

<400> SEQUENCE: 423

```
gcgtcagtag ctacgtctgg ggacttcgac tactacggta tggacgtc               48
```

<210> SEQ ID NO 424
<211> LENGTH: 16
<212> TYPE: PRT
<213> ORGANISM: Artificial Sequence
<220> FEATURE:
<223> OTHER INFORMATION: synthetic

<400> SEQUENCE: 424

Ala Ser Val Ala Thr Ser Gly Asp Phe Asp Tyr Tyr Gly Met Asp Val
1               5                   10                  15

<210> SEQ ID NO 425
<211> LENGTH: 321
<212> TYPE: DNA
<213> ORGANISM: Artificial Sequence
<220> FEATURE:
<223> OTHER INFORMATION: synthetic

<400> SEQUENCE: 425

```
gaaattgtgt tgacacagtc tccagccacc ctgtctttgt ctccagggga agaaccacc    60 ctctcctgca gggccagtca gagaattagc acctacttag cctggtatca acagaaacct  120
ggccaggctc ccaggctcct catctatgat gcatccaaaa gggccactgg catcccagcc  180
aggttcagtg gtagtgggtc tgggacaggc ttcactctca ccatcagcag cctagagcct  240
gaagattttg cagtttatta ctgtcagcag cgtagtaact ggcctctcac tttcggcgga  300
gggaccaagg tggagatcaa a                                            321
```

<210> SEQ ID NO 426
<211> LENGTH: 107
<212> TYPE: PRT
<213> ORGANISM: Artificial Sequence
<220> FEATURE:
<223> OTHER INFORMATION: synthetic

<400> SEQUENCE: 426

Glu Ile Val Leu Thr Gln Ser Pro Ala Thr Leu Ser Leu Ser Pro Gly
1               5                   10                  15

Glu Arg Thr Thr Leu Ser Cys Arg Ala Ser Gln Arg Ile Ser Thr Tyr
            20                  25                  30

Leu Ala Trp Tyr Gln Gln Lys Pro Gly Gln Ala Pro Arg Leu Leu Ile

```
                35                  40                  45
Tyr Asp Ala Ser Lys Arg Ala Thr Gly Ile Pro Ala Arg Phe Ser Gly
         50                  55                  60
Ser Gly Ser Gly Thr Gly Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Leu
                 85                  90                  95
Thr Phe Gly Gly Gly Thr Lys Val Glu Ile Lys
            100                 105
```

<210> SEQ ID NO 427
<211> LENGTH: 18
<212> TYPE: DNA
<213> ORGANISM: Artificial Sequence
<220> FEATURE:
<223> OTHER INFORMATION: synthetic

<400> SEQUENCE: 427
cagagaatta gcacctac                                                 18

<210> SEQ ID NO 428
<211> LENGTH: 6
<212> TYPE: PRT
<213> ORGANISM: Artificial Sequence
<220> FEATURE:
<223> OTHER INFORMATION: synthetic

<400> SEQUENCE: 428

```
Gln Arg Ile Ser Thr Tyr
 1               5
```

<210> SEQ ID NO 429
<211> LENGTH: 9
<212> TYPE: DNA
<213> ORGANISM: Artificial Sequence
<220> FEATURE:
<223> OTHER INFORMATION: synthetic

<400> SEQUENCE: 429 gatgcatcc                                                            9

<210> SEQ ID NO 430
<211> LENGTH: 3
<212> TYPE: PRT
<213> ORGANISM: Artificial Sequence
<220> FEATURE:
<223> OTHER INFORMATION: synthetic

<400> SEQUENCE: 430

```
Asp Ala Ser
 1
```

<210> SEQ ID NO 431
<211> LENGTH: 27
<212> TYPE: DNA
<213> ORGANISM: Artificial Sequence
<220> FEATURE:
<223> OTHER INFORMATION: synthetic

<400> SEQUENCE: 431
cagcagcgta gtaactggcc tctcact                                       27

<210> SEQ ID NO 432
<211> LENGTH: 9

<212> TYPE: PRT
<213> ORGANISM: Artificial Sequence
<220> FEATURE:
<223> OTHER INFORMATION: synthetic

<400> SEQUENCE: 432

Gln Gln Arg Ser Asn Trp Pro Leu Thr
1               5

<210> SEQ ID NO 433
<211> LENGTH: 357
<212> TYPE: DNA
<213> ORGANISM: Artificial Sequence
<220> FEATURE:
<223> OTHER INFORMATION: synthetic

<400> SEQUENCE: 433
gaggtgcagc tggtgcagtc tggagcagag gtgagaaagc ccggggagtc tctgaagatc    60
tcctgtaagg gttctggata cagctttact aactactgga tcgtctgggt gcgccagatg   120
cccgggaaag gcctggagtg gatggggatc atctatcctg gtgactctga taccagatac   180
agcccgtcct tccaaggcca ggtcaccatc tcagccgaca gtccatcag caccgcctac   240 ctgcagtgga gcagcctgaa ggcctcggac accgccatgt attactgtgc gagacgggat   300 acgatttttcc cttcctatcc cctctggggc cagggaaccc tggtcaccgt ctcctca     357

<210> SEQ ID NO 434
<211> LENGTH: 119
<212> TYPE: PRT
<213> ORGANISM: Artificial Sequence
<220> FEATURE:
<223> OTHER INFORMATION: synthetic

<400> SEQUENCE: 434

Glu Val Gln Leu Val Gln Ser Gly Ala Glu Val Arg Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Val Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asp Thr Ile Phe Pro Ser Tyr Pro Leu Trp Gly Gln Gly
            100                 105                 110

Thr Leu Val Thr Val Ser Ser
        115

<210> SEQ ID NO 435
<211> LENGTH: 24
<212> TYPE: DNA
<213> ORGANISM: Artificial Sequence
<220> FEATURE:
<223> OTHER INFORMATION: synthetic

<400> SEQUENCE: 435
ggatacagct ttactaacta ctgg                                            24

```
<210> SEQ ID NO 436
<211> LENGTH: 8
<212> TYPE: PRT
<213> ORGANISM: Artificial Sequence
<220> FEATURE:
<223> OTHER INFORMATION: synthetic

<400> SEQUENCE: 436

Gly Tyr Ser Phe Thr Asn Tyr Trp
1               5

<210> SEQ ID NO 437
<211> LENGTH: 24
<212> TYPE: DNA
<213> ORGANISM: Artificial Sequence
<220> FEATURE:
<223> OTHER INFORMATION: synthetic

<400> SEQUENCE: 437
atctatcctg gtgactctga tacc                                           24

<210> SEQ ID NO 438
<211> LENGTH: 8
<212> TYPE: PRT
<213> ORGANISM: Artificial Sequence
<220> FEATURE:
<223> OTHER INFORMATION: synthetic

<400> SEQUENCE: 438

Ile Tyr Pro Gly Asp Ser Asp Thr
1               5

<210> SEQ ID NO 439
<211> LENGTH: 36
<212> TYPE: DNA
<213> ORGANISM: Artificial Sequence
<220> FEATURE:
<223> OTHER INFORMATION: synthetic

<400> SEQUENCE: 439
gcgagacggg atacgatttt cccttcctat cccctc                              36

<210> SEQ ID NO 440
<211> LENGTH: 12
<212> TYPE: PRT
<213> ORGANISM: Artificial Sequence
<220> FEATURE:
<223> OTHER INFORMATION: synthetic

<400> SEQUENCE: 440

Ala Arg Arg Asp Thr Ile Phe Pro Ser Tyr Pro Leu
1               5                   10

<210> SEQ ID NO 441
<211> LENGTH: 336
<212> TYPE: DNA
<213> ORGANISM: Artificial Sequence
<220> FEATURE:
<223> OTHER INFORMATION: synthetic

<400> SEQUENCE: 441
gatattgtga tgactcagtc tcctctctcc ctgcccgtca cccctggaga gccggcctcc    60
atctcctgca ggtctagtca gagcctcctg aatagtaatg gatacaactt tttggattgg   120
tacctgcaga agccagggca gtctccacaa ctcctgatct atttggtttc taatcgggcc   180
tccggggtcc ctgacaggtt cagtggcagt ggatcaggca cagatttac actgaaaatc    240
```

```
agcagagtgg aggctgagga tattggggtt tattactgca tgcaagctct ccaaactccg    300
atcaccttcg gccaagggac acgactggag attaaa                             336
```

<210> SEQ ID NO 442
<211> LENGTH: 112
<212> TYPE: PRT
<213> ORGANISM: Artificial Sequence
<220> FEATURE:
<223> OTHER INFORMATION: synthetic

<400> SEQUENCE: 442

```
Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu Asn Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Ile Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110
```

<210> SEQ ID NO 443
<211> LENGTH: 33
<212> TYPE: DNA
<213> ORGANISM: Artificial Sequence
<220> FEATURE:
<223> OTHER INFORMATION: synthetic

<400> SEQUENCE: 443

```
cagagcctcc tgaatagtaa tggatacaac ttt                                 33
```

<210> SEQ ID NO 444
<211> LENGTH: 11
<212> TYPE: PRT
<213> ORGANISM: Artificial Sequence
<220> FEATURE:
<223> OTHER INFORMATION: synthetic

<400> SEQUENCE: 444

```
Gln Ser Leu Leu Asn Ser Asn Gly Tyr Asn Phe
1               5                   10
```

<210> SEQ ID NO 445
<211> LENGTH: 9
<212> TYPE: DNA
<213> ORGANISM: Artificial Sequence
<220> FEATURE:
<223> OTHER INFORMATION: synthetic

<400> SEQUENCE: 445

```
ttggtttct                                                             9
```

<210> SEQ ID NO 446
<211> LENGTH: 3
<212> TYPE: PRT
<213> ORGANISM: Artificial Sequence
<220> FEATURE:

<223> OTHER INFORMATION: synthetic

<400> SEQUENCE: 446

Leu Val Ser
1

<210> SEQ ID NO 447
<211> LENGTH: 27
<212> TYPE: DNA
<213> ORGANISM: Artificial Sequence
<220> FEATURE:
<223> OTHER INFORMATION: synthetic

<400> SEQUENCE: 447
atgcaagctc tccaaactcc gatcacc					27

<210> SEQ ID NO 448
<211> LENGTH: 9
<212> TYPE: PRT
<213> ORGANISM: Artificial Sequence
<220> FEATURE:
<223> OTHER INFORMATION: synthetic

<400> SEQUENCE: 448

Met Gln Ala Leu Gln Thr Pro Ile Thr
1               5

<210> SEQ ID NO 449
<211> LENGTH: 360
<212> TYPE: DNA
<213> ORGANISM: Artificial Sequence
<220> FEATURE:
<223> OTHER INFORMATION: synthetic

<400> SEQUENCE: 449
cagatcacct tgaaggagtc tggtcctacg ctggtgaaac ccacacagac cctcacgctg     60
acctgcacct ctctgggtt ctcactcagc actaatggag tgggtgtggg ctggatccgt    120
cagcccccag gaaaggccct ggagtggctt acactcattt attggaatga aaataagcac    180
tacagcccat ctctgaaaaa caggatcacc atcaccaagg acacctccaa aaaccaggtg    240
gtccttacaa tgaccaactt ggaccctgtg gacacagcca cttattactg tgtacacagg    300
ggatggttgg gagcaatctt tgcctactgg ggccagggaa ccctggtcac cgtctcctca    360

<210> SEQ ID NO 450
<211> LENGTH: 120
<212> TYPE: PRT
<213> ORGANISM: Artificial Sequence
<220> FEATURE:
<223> OTHER INFORMATION: synthetic

<400> SEQUENCE: 450

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Asn
            20                  25                  30

Gly Val Gly Val Gly Trp Ile Arg Gln Pro Pro Gly Lys Ala Leu Glu
        35                  40                  45

Trp Leu Thr Leu Ile Tyr Trp Asn Glu Asn Lys His Tyr Ser Pro Ser
    50                  55                  60

Leu Lys Asn Arg Ile Thr Ile Thr Lys Asp Thr Ser Lys Asn Gln Val
65                  70                  75                  80

Val Leu Thr Met Thr Asn Leu Asp Pro Val Asp Thr Ala Thr Tyr Tyr
            85                  90                  95

Cys Val His Arg Gly Trp Leu Gly Ala Ile Phe Ala Tyr Trp Gly Gln
        100                 105                 110

Gly Thr Leu Val Thr Val Ser Ser
        115                 120

<210> SEQ ID NO 451
<211> LENGTH: 30
<212> TYPE: DNA
<213> ORGANISM: Artificial Sequence
<220> FEATURE:
<223> OTHER INFORMATION: synthetic

<400> SEQUENCE: 451
gggttctcac tcagcactaa tggagtgggt                                     30

<210> SEQ ID NO 452
<211> LENGTH: 10
<212> TYPE: PRT
<213> ORGANISM: Artificial Sequence
<220> FEATURE:
<223> OTHER INFORMATION: synthetic

<400> SEQUENCE: 452

Gly Phe Ser Leu Ser Thr Asn Gly Val Gly
1               5                   10

<210> SEQ ID NO 453
<211> LENGTH: 21
<212> TYPE: DNA
<213> ORGANISM: Artificial Sequence
<220> FEATURE:
<223> OTHER INFORMATION: synthetic

<400> SEQUENCE: 453
atttattgga atgaaaataa g                                              21

<210> SEQ ID NO 454
<211> LENGTH: 7
<212> TYPE: PRT
<213> ORGANISM: Artificial Sequence
<220> FEATURE:
<223> OTHER INFORMATION: synthetic

<400> SEQUENCE: 454

Ile Tyr Trp Asn Glu Asn Lys
1               5

<210> SEQ ID NO 455
<211> LENGTH: 36
<212> TYPE: DNA
<213> ORGANISM: Artificial Sequence
<220> FEATURE:
<223> OTHER INFORMATION: synthetic

<400> SEQUENCE: 455
gtacacaggg gatggttggg agcaatcttt gcctac                              36

<210> SEQ ID NO 456
<211> LENGTH: 12
<212> TYPE: PRT
<213> ORGANISM: Artificial Sequence
<220> FEATURE:
<223> OTHER INFORMATION: synthetic

<400> SEQUENCE: 456

Val His Arg Gly Trp Leu Gly Ala Ile Phe Ala Tyr
1               5                   10

<210> SEQ ID NO 457
<211> LENGTH: 378
<212> TYPE: DNA
<213> ORGANISM: Artificial Sequence
<220> FEATURE:
<223> OTHER INFORMATION: synthetic

<400> SEQUENCE: 457

```
gaggtgcagc tggtggagtc tgggggaggc ttggtacagc ctgggggtc cctgagactc     60
tcctgtgcag cctctggatt cacctttact agttatgcca tgacctgggt ccgccaggct    120
ccagggaagg gctggagtg gtctcagat attagtggta gtggtggtag aacatattac      180
gcagactccg tgaagggccg gttcaccatc tccagagaca attccaagaa tatgctgtat    240
ctgcaaatga acatcctgag agccgaagac acggccgtat atcattgtgc gaagggaaca    300
ggccagcagg tggacctta caactactac tatgctttgg acgtctgggg ccaagggacc    360
acggtcaccg tctcctca                                                  378
```

<210> SEQ ID NO 458
<211> LENGTH: 126
<212> TYPE: PRT
<213> ORGANISM: Artificial Sequence
<220> FEATURE:
<223> OTHER INFORMATION: synthetic

<400> SEQUENCE: 458

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Thr Trp Val Arg Gln Ala Pro Gly Lys Gly Leu Glu Trp Val
        35                  40                  45

Ser Asp Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ile Leu Arg Ala Glu Asp Thr Ala Val Tyr His Cys
                85                  90                  95

Ala Lys Gly Thr Gly Gln Gln Val Asp Leu Tyr Asn Tyr Tyr Tyr Ala
            100                 105                 110

Leu Asp Val Trp Gly Gln Gly Thr Thr Val Thr Val Ser Ser
        115                 120                 125

<210> SEQ ID NO 459
<211> LENGTH: 24
<212> TYPE: DNA
<213> ORGANISM: Artificial Sequence
<220> FEATURE:
<223> OTHER INFORMATION: synthetic

<400> SEQUENCE: 459

```
ggattcacct ttactagtta tgcc                                            24
```

<210> SEQ ID NO 460
<211> LENGTH: 8
<212> TYPE: PRT

<213> ORGANISM: Artificial Sequence
<220> FEATURE:
<223> OTHER INFORMATION: synthetic

<400> SEQUENCE: 460

Gly Phe Thr Phe Thr Ser Tyr Ala
1               5

<210> SEQ ID NO 461
<211> LENGTH: 24
<212> TYPE: DNA
<213> ORGANISM: Artificial Sequence
<220> FEATURE:
<223> OTHER INFORMATION: synthetic

<400> SEQUENCE: 461
attagtggta gtggtggtag aaca                                          24

<210> SEQ ID NO 462
<211> LENGTH: 8
<212> TYPE: PRT
<213> ORGANISM: Artificial Sequence
<220> FEATURE:
<223> OTHER INFORMATION: synthetic

<400> SEQUENCE: 462

Ile Ser Gly Ser Gly Gly Arg Thr
1               5

<210> SEQ ID NO 463
<211> LENGTH: 57
<212> TYPE: DNA
<213> ORGANISM: Artificial Sequence
<220> FEATURE:
<223> OTHER INFORMATION: synthetic

<400> SEQUENCE: 463
gcgaagggaa caggccagca ggtggacctt tacaactact actatgcttt ggacgtc      57

<210> SEQ ID NO 464
<211> LENGTH: 19
<212> TYPE: PRT
<213> ORGANISM: Artificial Sequence
<220> FEATURE:
<223> OTHER INFORMATION: synthetic

<400> SEQUENCE: 464

Ala Lys Gly Thr Gly Gln Gln Val Asp Leu Tyr Asn Tyr Tyr Tyr Ala
1               5                   10                  15

Leu Asp Val

<210> SEQ ID NO 465
<211> LENGTH: 387
<212> TYPE: DNA
<213> ORGANISM: Artificial Sequence
<220> FEATURE:
<223> OTHER INFORMATION: synthetic

<400> SEQUENCE: 465
caggtgcagc tggtggagtc tgggggaggc gtggtccagc ctggaggtc cctgagactc     60 tcctgtgcag cgtctggatt caccttcagt tactatggca tgcactgggt ccgccaggct   120
ccaggcaagg ggctggagtg ggtggcagtt atatggtatg atggaagtaa taaacactat   180
gcagactccg tgaagggccg attcaccatc tccagagaca attccaagaa cacgctgtat   240

```
ctgcaaatga acagcctgag agccgacgac acggctgtct attactgtgc gagagataag    300
ggtataagtg gaattaaggg gggttcttac tactactact atgccatgga cgtctggggc    360
caagggacca cggtcaccgt ctcctca                                        387
```

```
<210> SEQ ID NO 466
<211> LENGTH: 129
<212> TYPE: PRT
<213> ORGANISM: Artificial Sequence
<220> FEATURE:
<223> OTHER INFORMATION: synthetic

<400> SEQUENCE: 466
```

```
Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Lys Gly Ile Ser Gly Ile Lys Gly Ser Tyr Tyr Tyr Tyr
            100                 105                 110

Tyr Tyr Ala Met Asp Val Trp Gly Gln Gly Thr Thr Val Thr Val Ser
        115                 120                 125

Ser
```

```
<210> SEQ ID NO 467
<211> LENGTH: 24
<212> TYPE: DNA
<213> ORGANISM: Artificial Sequence
<220> FEATURE:
<223> OTHER INFORMATION: synthetic

<400> SEQUENCE: 467
ggattcacct tcagttacta tggc                                            24
```

```
<210> SEQ ID NO 468
<211> LENGTH: 8
<212> TYPE: PRT
<213> ORGANISM: Artificial Sequence
<220> FEATURE:
<223> OTHER INFORMATION: synthetic

<400> SEQUENCE: 468

Gly Phe Thr Phe Ser Tyr Tyr Gly
1               5
```

```
<210> SEQ ID NO 469
<211> LENGTH: 24
<212> TYPE: DNA
<213> ORGANISM: Artificial Sequence
<220> FEATURE:
<223> OTHER INFORMATION: synthetic

<400> SEQUENCE: 469
atatggtatg atggaagtaa taaa                                            24
```

<210> SEQ ID NO 470
<211> LENGTH: 8
<212> TYPE: PRT
<213> ORGANISM: Artificial Sequence
<220> FEATURE:
<223> OTHER INFORMATION: synthetic

<400> SEQUENCE: 470

Ile Trp Tyr Asp Gly Ser Asn Lys
1               5

<210> SEQ ID NO 471
<211> LENGTH: 66
<212> TYPE: DNA
<213> ORGANISM: Artificial Sequence
<220> FEATURE:
<223> OTHER INFORMATION: synthetic

<400> SEQUENCE: 471
gcgagagata agggtataag tggaattaag gggggttctt actactacta ctatgccatg    60
gacgtc                                                               66

<210> SEQ ID NO 472
<211> LENGTH: 22
<212> TYPE: PRT
<213> ORGANISM: Artificial Sequence
<220> FEATURE:
<223> OTHER INFORMATION: synthetic

<400> SEQUENCE: 472

Ala Arg Asp Lys Gly Ile Ser Gly Ile Lys Gly Gly Ser Tyr Tyr Tyr
1               5                   10                  15

Tyr Tyr Ala Met Asp Val
            20

<210> SEQ ID NO 473
<211> LENGTH: 360
<212> TYPE: DNA
<213> ORGANISM: Artificial Sequence
<220> FEATURE:
<223> OTHER INFORMATION: synthetic

<400> SEQUENCE: 473
gaggtgcagc tggtggagtc tgggggaggc ttggtaaagc ctggggggtc ccttagactc    60
tcctgtgcag cctctggatt cactttcagt aacgcctgga tgacctgggt ccgccaggct   120
ccagggaagg ggctggagtg ggttggccgt attaaaaaca aaattgatgg tgggacaaca   180
gactacgctg cacccgtgaa aggcagattc accatctcaa gagatgattc aaaaaacacg   240
gtttatctgc aaatgaacag cctgaaaacc gaggacacac ccgttattta ctgttccacg   300
gtggactaca attggtactt cgatttctgg ggccgtggca ccctggtcac tgtctcctca   360

<210> SEQ ID NO 474
<211> LENGTH: 120
<212> TYPE: PRT
<213> ORGANISM: Artificial Sequence
<220> FEATURE:
<223> OTHER INFORMATION: synthetic

<400> SEQUENCE: 474

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala

```
                    20                  25                  30
Trp Met Thr Trp Val Arg Gln Ala Pro Gly Lys Gly Leu Glu Trp Val
            35                  40                  45

Gly Arg Ile Lys Asn Lys Ile Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Thr Val Asp Tyr Asn Trp Tyr Phe Asp Phe Trp Gly Arg
            100                 105                 110

Gly Thr Leu Val Thr Val Ser Ser
        115                 120
```

<210> SEQ ID NO 475
<211> LENGTH: 24
<212> TYPE: DNA
<213> ORGANISM: Artificial Sequence
<220> FEATURE:
<223> OTHER INFORMATION: synthetic

<400> SEQUENCE: 475
ggattcactt tcagtaacgc ctgg                                          24

<210> SEQ ID NO 476
<211> LENGTH: 8
<212> TYPE: PRT
<213> ORGANISM: Artificial Sequence
<220> FEATURE:
<223> OTHER INFORMATION: synthetic

<400> SEQUENCE: 476

Gly Phe Thr Phe Ser Asn Ala Trp
1               5

<210> SEQ ID NO 477
<211> LENGTH: 30
<212> TYPE: DNA
<213> ORGANISM: Artificial Sequence
<220> FEATURE:
<223> OTHER INFORMATION: synthetic

<400> SEQUENCE: 477
attaaaaaca aaattgatgg tgggacaaca                                    30

<210> SEQ ID NO 478
<211> LENGTH: 10
<212> TYPE: PRT
<213> ORGANISM: Artificial Sequence
<220> FEATURE:
<223> OTHER INFORMATION: synthetic

<400> SEQUENCE: 478

Ile Lys Asn Lys Ile Asp Gly Gly Thr Thr
1               5                   10

<210> SEQ ID NO 479
<211> LENGTH: 33
<212> TYPE: DNA
<213> ORGANISM: Artificial Sequence
<220> FEATURE:
<223> OTHER INFORMATION: synthetic

<400> SEQUENCE: 479

```
tccacggtgg actacaattg gtacttcgat ttc                                    33
```

<210> SEQ ID NO 480
<211> LENGTH: 11
<212> TYPE: PRT
<213> ORGANISM: Artificial Sequence
<220> FEATURE:
<223> OTHER INFORMATION: synthetic

<400> SEQUENCE: 480

```
Ser Thr Val Asp Tyr Asn Trp Tyr Phe Asp Phe
1               5                   10
```

<210> SEQ ID NO 481
<211> LENGTH: 387
<212> TYPE: DNA
<213> ORGANISM: Artificial Sequence
<220> FEATURE:
<223> OTHER INFORMATION: synthetic

<400> SEQUENCE: 481

```
caggtgcagc tggtggagtc tgggggaggc gtggtccagc ctgggaggtc cctgagactc        60
tcctgtgcag cgtctggatt caccttcagt ttctttggca tgcactgggt ccgccaggct       120
ccaggcaagg ggctggagtg ggtggcactt atatggtatg atggaactaa tgaaaactat       180
gcagactccg tgaagggccg attcaccatc tccagagaca attccaagtc cacgctgtat       240
ctgcaaatga acagtctgag agccgaggac acggctgttt actactgtgc gagagatagg       300
ggagtggcga catttacgag ggggaattac tactacaact acggtatgga cgtctggggc       360
caagggacca cggtcaccgt ctcctca                                           387
```

<210> SEQ ID NO 482
<211> LENGTH: 129
<212> TYPE: PRT
<213> ORGANISM: Artificial Sequence
<220> FEATURE:
<223> OTHER INFORMATION: synthetic

<400> SEQUENCE: 482

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Phe Phe
            20                  25                  30

Gly Met His Trp Val Arg Gln Ala Pro Gly Lys Gly Leu Glu Trp Val
        35                  40                  45

Ala Leu Ile Trp Tyr Asp Gly Thr Asn Glu Asn Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Ala Thr Phe Thr Arg Gly Asn Tyr Tyr Tyr
            100                 105                 110

Asn Tyr Gly Met Asp Val Trp Gly Gln Gly Thr Thr Val Thr Val Ser
        115                 120                 125

Ser
```

<210> SEQ ID NO 483
<211> LENGTH: 24

```
<212> TYPE: DNA
<213> ORGANISM: Artificial Sequence
<220> FEATURE:
<223> OTHER INFORMATION: synthetic

<400> SEQUENCE: 483
ggattcacct tcagtttctt tggc                                          24

<210> SEQ ID NO 484
<211> LENGTH: 8
<212> TYPE: PRT
<213> ORGANISM: Artificial Sequence
<220> FEATURE:
<223> OTHER INFORMATION: synthetic

<400> SEQUENCE: 484

Gly Phe Thr Phe Ser Phe Phe Gly
1               5

<210> SEQ ID NO 485
<211> LENGTH: 24
<212> TYPE: DNA
<213> ORGANISM: Artificial Sequence
<220> FEATURE:
<223> OTHER INFORMATION: synthetic

<400> SEQUENCE: 485
atatggtatg atggaactaa tgaa                                          24

<210> SEQ ID NO 486
<211> LENGTH: 8
<212> TYPE: PRT
<213> ORGANISM: Artificial Sequence
<220> FEATURE:
<223> OTHER INFORMATION: synthetic

<400> SEQUENCE: 486

Ile Trp Tyr Asp Gly Thr Asn Glu
1               5

<210> SEQ ID NO 487
<211> LENGTH: 66
<212> TYPE: DNA
<213> ORGANISM: Artificial Sequence
<220> FEATURE:
<223> OTHER INFORMATION: synthetic

<400> SEQUENCE: 487
gcgagagata ggggagtggc gacatttacg aggggaatt actactacaa ctacggtatg    60
gacgtc                                                              66

<210> SEQ ID NO 488
<211> LENGTH: 22
<212> TYPE: PRT
<213> ORGANISM: Artificial Sequence
<220> FEATURE:
<223> OTHER INFORMATION: synthetic

<400> SEQUENCE: 488

Ala Arg Asp Arg Gly Val Ala Thr Phe Thr Arg Gly Asn Tyr Tyr Tyr
1               5                   10                  15

Asn Tyr Gly Met Asp Val
            20

<210> SEQ ID NO 489
```

<211> LENGTH: 387
<212> TYPE: DNA
<213> ORGANISM: Artificial Sequence
<220> FEATURE:
<223> OTHER INFORMATION: synthetic

<400> SEQUENCE: 489

```
caggtgcagc tggtggagtc tgggggaggc gtggtccagc ctggagggtc cctgagactc    60
tcctgtgcag cgtctggatt caccttcagt ttctatggca tgcactgggt ccgccaggct   120
ccaggcaagg ggctggaggg ggtggcagtt atatggtatg atggaagtaa taaatactat   180
gcagactccg tgaagggccg attcaccata tccagagaca attccaagaa catgctgtat   240
ctacaaatga ccagcctgag agccgaggac acggctgtgt attactgtgc gagagattcg   300
ggtaaaactg gaactgggat aactgggtac tcctactact acggtatgga cgtctggggc   360
caagggacca cggtcaccgt ctcctca                                       387
```

<210> SEQ ID NO 490
<211> LENGTH: 129
<212> TYPE: PRT
<213> ORGANISM: Artificial Sequence
<220> FEATURE:
<223> OTHER INFORMATION: synthetic

<400> SEQUENCE: 490

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Phe Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Thr Ser Leu Arg Ala Glu Asp Thr Ala Val Tyr Tyr Cys
                85                  90                  95

Ala Arg Asp Ser Gly Lys Thr Gly Thr Gly Ile Thr Gly Tyr Ser Tyr
            100                 105                 110

Tyr Tyr Gly Met Asp Val Trp Gly Gln Gly Thr Thr Val Thr Val Ser
        115                 120                 125

Ser

<210> SEQ ID NO 491
<211> LENGTH: 24
<212> TYPE: DNA
<213> ORGANISM: Artificial Sequence
<220> FEATURE:
<223> OTHER INFORMATION: synthetic

<400> SEQUENCE: 491

```
ggattcacct tcagtttcta tggc                                           24
```

<210> SEQ ID NO 492
<211> LENGTH: 8
<212> TYPE: PRT
<213> ORGANISM: Artificial Sequence
<220> FEATURE:
<223> OTHER INFORMATION: synthetic

<400> SEQUENCE: 492

```
<210> SEQ ID NO 493
<211> LENGTH: 24
<212> TYPE: DNA
<213> ORGANISM: Artificial Sequence
<220> FEATURE:
<223> OTHER INFORMATION: synthetic

<400> SEQUENCE: 493
atatggtatg atggaagtaa taaa                                          24

<210> SEQ ID NO 494
<211> LENGTH: 8
<212> TYPE: PRT
<213> ORGANISM: Artificial Sequence
<220> FEATURE:
<223> OTHER INFORMATION: synthetic

<400> SEQUENCE: 494

Ile Trp Tyr Asp Gly Ser Asn Lys
1               5

<210> SEQ ID NO 495
<211> LENGTH: 66
<212> TYPE: DNA
<213> ORGANISM: Artificial Sequence
<220> FEATURE:
<223> OTHER INFORMATION: synthetic

<400> SEQUENCE: 495
gcgagagatt cgggtaaaac tggaactggg ataactgggt actcctacta ctacggtatg   60
gacgtc                                                              66

<210> SEQ ID NO 496
<211> LENGTH: 22
<212> TYPE: PRT
<213> ORGANISM: Artificial Sequence
<220> FEATURE:
<223> OTHER INFORMATION: synthetic

<400> SEQUENCE: 496

Ala Arg Asp Ser Gly Lys Thr Gly Thr Gly Ile Thr Gly Tyr Ser Tyr
1               5                   10                  15

Tyr Tyr Gly Met Asp Val
            20

<210> SEQ ID NO 497
<211> LENGTH: 354
<212> TYPE: DNA
<213> ORGANISM: Artificial Sequence
<220> FEATURE:
<223> OTHER INFORMATION: synthetic

<400> SEQUENCE: 497
cagctgcagc tgcaggagtc gggcccagga ctggtgaagc cttcggagac cctgtccctc   60
acctgcactg tctctggtgg ctccatcatc actaatagtt attactgggg ctggatccgc  120
cagcccccag ggaagggtct ggagtggatt ggtagtatct attatagtgg gaggacctac  180
tacaacccgt ccctcgagag tcgagtcacc atatccgtgg acacgtccaa gaaccagttc  240
tccctgaagt tgacctctgt gaccgccgca gacacggcta tattactg tgcgagggaa    300
```

Gly Phe Thr Phe Ser Phe Tyr Gly
1               5

```
gggatccgt cgctcgaccc ctggggccag ggaaccctgg tcaccgtctc ctca         354
```

<210> SEQ ID NO 498
<211> LENGTH: 118
<212> TYPE: PRT
<213> ORGANISM: Artificial Sequence
<220> FEATURE:
<223> OTHER INFORMATION: synthetic

<400> SEQUENCE: 498

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ile Thr Asn
            20                  25                  30
Ser Tyr Tyr Trp Gly Trp Ile Arg Gln Pro Pro Gly Lys Gly Leu Glu
        35                  40                  45
Trp Ile Gly Ser Ile Tyr Tyr Ser Gly Arg Thr Tyr Tyr Asn Pro Ser
    50                  55                  60
Leu Glu Ser Arg Val Thr Ile Ser Val Asp Thr Ser Lys Asn Gln Phe
65                  70                  75                  80
Ser Leu Lys Leu Thr Ser Val Thr Ala Ala Asp Thr Ala Ile Tyr Tyr
                85                  90                  95
Cys Ala Arg Glu Gly Asp Pro Ser Leu Asp Pro Trp Gly Gln Gly Thr
            100                 105                 110
Leu Val Thr Val Ser Ser
        115
```

<210> SEQ ID NO 499
<211> LENGTH: 30
<212> TYPE: DNA
<213> ORGANISM: Artificial Sequence
<220> FEATURE:
<223> OTHER INFORMATION: synthetic

<400> SEQUENCE: 499

```
ggtggctcca tcatcactaa tagttattac                                    30
```

<210> SEQ ID NO 500
<211> LENGTH: 10
<212> TYPE: PRT
<213> ORGANISM: Artificial Sequence
<220> FEATURE:
<223> OTHER INFORMATION: synthetic

<400> SEQUENCE: 500

```
Gly Gly Ser Ile Ile Thr Asn Ser Tyr Tyr
1               5                   10
```

<210> SEQ ID NO 501
<211> LENGTH: 21
<212> TYPE: DNA
<213> ORGANISM: Artificial Sequence
<220> FEATURE:
<223> OTHER INFORMATION: synthetic

<400> SEQUENCE: 501

```
atctattata gtgggaggac c                                             21
```

<210> SEQ ID NO 502
<211> LENGTH: 7
<212> TYPE: PRT
<213> ORGANISM: Artificial Sequence
<220> FEATURE:

<223> OTHER INFORMATION: synthetic

<400> SEQUENCE: 502

Ile Tyr Tyr Ser Gly Arg Thr
1               5

<210> SEQ ID NO 503
<211> LENGTH: 30
<212> TYPE: DNA
<213> ORGANISM: Artificial Sequence
<220> FEATURE:
<223> OTHER INFORMATION: synthetic

<400> SEQUENCE: 503
gcgagggaag gggatccgtc gctcgacccc                                        30

<210> SEQ ID NO 504
<211> LENGTH: 10
<212> TYPE: PRT
<213> ORGANISM: Artificial Sequence
<220> FEATURE:
<223> OTHER INFORMATION: synthetic

<400> SEQUENCE: 504

Ala Arg Glu Gly Asp Pro Ser Leu Asp Pro
1               5                   10

<210> SEQ ID NO 505
<211> LENGTH: 363
<212> TYPE: DNA
<213> ORGANISM: Artificial Sequence
<220> FEATURE:
<223> OTHER INFORMATION: synthetic

<400> SEQUENCE: 505
gaggtgcagc tggtggagtc tgggggagac ttggtacagc ctggggggtc cctgagactc        60
tcctgtgcag cctctggatt cacctttagc acctatgcca tgaactgggt ccgccaggct       120
ccagggaagg gctggagtg gtctcacat attagtggta gtggtggtaa ttcatactcc        180
gcagactccg tgaagggccg gttcaccatc tccagagaca attccaagaa cacgctatat       240
ctgcaaatga acagcctgcg agccgaggac acggccatat attactgttc gctggatata       300
atggctacag taggcggtct ctttgcctac tggggccagg gaaccctggt caccgtctcc       360
tca                                                                    363

<210> SEQ ID NO 506
<211> LENGTH: 121
<212> TYPE: PRT
<213> ORGANISM: Artificial Sequence
<220> FEATURE:
<223> OTHER INFORMATION: synthetic

<400> SEQUENCE: 506

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser His Ile Ser Gly Ser Gly Gly Asn Ser Tyr Ser Ala Asp Ser Val
    50                  55                  60

Lys Gly Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Ile Tyr Tyr Cys
                85                  90                  95
Ser Leu Asp Ile Met Ala Thr Val Gly Gly Leu Phe Ala Tyr Trp Gly
               100                 105                 110
Gln Gly Thr Leu Val Thr Val Ser Ser
           115                 120
```

<210> SEQ ID NO 507
<211> LENGTH: 24
<212> TYPE: DNA
<213> ORGANISM: Artificial Sequence
<220> FEATURE:
<223> OTHER INFORMATION: synthetic

<400> SEQUENCE: 507
ggattcacct ttagcaccta tgcc                                          24

<210> SEQ ID NO 508
<211> LENGTH: 8
<212> TYPE: PRT
<213> ORGANISM: Artificial Sequence
<220> FEATURE:
<223> OTHER INFORMATION: synthetic

<400> SEQUENCE: 508

Gly Phe Thr Phe Ser Thr Tyr Ala
1               5

<210> SEQ ID NO 509
<211> LENGTH: 24
<212> TYPE: DNA
<213> ORGANISM: Artificial Sequence
<220> FEATURE:
<223> OTHER INFORMATION: synthetic

<400> SEQUENCE: 509
attagtggta gtggtggtaa ttca                                          24

<210> SEQ ID NO 510
<211> LENGTH: 8
<212> TYPE: PRT
<213> ORGANISM: Artificial Sequence
<220> FEATURE:
<223> OTHER INFORMATION: synthetic

<400> SEQUENCE: 510

Ile Ser Gly Ser Gly Gly Asn Ser
1               5

<210> SEQ ID NO 511
<211> LENGTH: 42
<212> TYPE: DNA
<213> ORGANISM: Artificial Sequence
<220> FEATURE:
<223> OTHER INFORMATION: synthetic

<400> SEQUENCE: 511
tcgctggata taatggctac agtaggcggt ctctttgcct ac                      42

<210> SEQ ID NO 512
<211> LENGTH: 14
<212> TYPE: PRT
<213> ORGANISM: Artificial Sequence
<220> FEATURE:

<223> OTHER INFORMATION: synthetic

<400> SEQUENCE: 512

Ser Leu Asp Ile Met Ala Thr Val Gly Gly Leu Phe Ala Tyr
1               5                   10

<210> SEQ ID NO 513
<211> LENGTH: 393
<212> TYPE: DNA
<213> ORGANISM: Artificial Sequence
<220> FEATURE:
<223> OTHER INFORMATION: synthetic

<400> SEQUENCE: 513

```
caggtgcagc tggtggagtc tgggggaggc gtggtccagc ctggagggtc cctgagactc      60
tcctgtgtag cgtctggatt catcttcagt ttctatggca tgcactgggt ccgccaggct     120
ccagacaagg gctggagtg gtggcagtt atatggtatg atggaagtaa tgaatactat      180
gcagactccg tgaagggccg attcaccatc tccagagaca attccaagaa cacgctgtat     240
ctgcaaatga acagcctgag agccgaggac acggctgtgt attactgtgg gagagatcaa     300
ggtatttcgt attacgatat tttgactggt aattataact attactacgg tgtggacgtc     360
tggggccaag ggaccacggt caccgtctcc tca                                  393
```

<210> SEQ ID NO 514
<211> LENGTH: 131
<212> TYPE: PRT
<213> ORGANISM: Artificial Sequence
<220> FEATURE:
<223> OTHER INFORMATION: synthetic

<400> SEQUENCE: 514

Gln Val Gln Leu Val Glu Ser Gly Gly Gly Val Val Gln Pro Gly Arg
1               5                   10                  15

Ser Leu Arg Leu Ser Cys Val Ala Ser Gly Phe Ile Phe Ser Phe Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Asp Gln Gly Ile Ser Tyr Tyr Asp Ile Leu Thr Gly Asn Tyr
            100                 105                 110

Asn Tyr Tyr Tyr Gly Val Asp Val Trp Gly Gln Gly Thr Thr Val Thr
        115                 120                 125

Val Ser Ser
    130

<210> SEQ ID NO 515
<211> LENGTH: 24
<212> TYPE: DNA
<213> ORGANISM: Artificial Sequence
<220> FEATURE:
<223> OTHER INFORMATION: synthetic

<400> SEQUENCE: 515

```
ggattcatct tcagtttcta tggc                                             24
```

<210> SEQ ID NO 516
<211> LENGTH: 8
<212> TYPE: PRT
<213> ORGANISM: Artificial Sequence
<220> FEATURE:
<223> OTHER INFORMATION: synthetic

<400> SEQUENCE: 516

Gly Phe Ile Phe Ser Phe Tyr Gly
1               5

<210> SEQ ID NO 517
<211> LENGTH: 24
<212> TYPE: DNA
<213> ORGANISM: Artificial Sequence
<220> FEATURE:
<223> OTHER INFORMATION: synthetic

<400> SEQUENCE: 517
atatggtatg atggaagtaa tgaa                                           24

<210> SEQ ID NO 518
<211> LENGTH: 8
<212> TYPE: PRT
<213> ORGANISM: Artificial Sequence
<220> FEATURE:
<223> OTHER INFORMATION: synthetic

<400> SEQUENCE: 518

Ile Trp Tyr Asp Gly Ser Asn Glu
1               5

<210> SEQ ID NO 519
<211> LENGTH: 72
<212> TYPE: DNA
<213> ORGANISM: Artificial Sequence
<220> FEATURE:
<223> OTHER INFORMATION: synthetic

<400> SEQUENCE: 519
gggagagatc aaggtatttc gtattacgat attttgactg gtaattataa ctattactac    60
ggtgtggacg tc                                                        72

<210> SEQ ID NO 520
<211> LENGTH: 24
<212> TYPE: PRT
<213> ORGANISM: Artificial Sequence
<220> FEATURE:
<223> OTHER INFORMATION: synthetic

<400> SEQUENCE: 520

Gly Arg Asp Gln Gly Ile Ser Tyr Tyr Asp Ile Leu Thr Gly Asn Tyr
1               5                   10                  15

Asn Tyr Tyr Tyr Gly Val Asp Val
            20

<210> SEQ ID NO 521
<211> LENGTH: 324
<212> TYPE: DNA
<213> ORGANISM: Artificial Sequence
<220> FEATURE:
<223> OTHER INFORMATION: synthetic

<400> SEQUENCE: 521

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta ccccctccgat caccttcggc   300 caagggacac gactggagat taaa                                          324
```

```
<210> SEQ ID NO 522
<211> LENGTH: 108
<212> TYPE: PRT
<213> ORGANISM: Artificial Sequence
<220> FEATURE:
<223> OTHER INFORMATION: synthetic

<400> SEQUENCE: 522
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

```
<210> SEQ ID NO 523
<211> LENGTH: 18
<212> TYPE: DNA
<213> ORGANISM: Artificial Sequence
<220> FEATURE:
<223> OTHER INFORMATION: synthetic

<400> SEQUENCE: 523
cagagcatta gcagctat                                                  18

<210> SEQ ID NO 524
<211> LENGTH: 6
<212> TYPE: PRT
<213> ORGANISM: Artificial Sequence
<220> FEATURE:
<223> OTHER INFORMATION: synthetic

<400> SEQUENCE: 524
```

Gln Ser Ile Ser Ser Tyr
1               5

```
<210> SEQ ID NO 525
<211> LENGTH: 9
<212> TYPE: DNA
<213> ORGANISM: Artificial Sequence
<220> FEATURE:
<223> OTHER INFORMATION: synthetic

<400> SEQUENCE: 525 gctgcatcc                                                             9
```

<210> SEQ ID NO 526
<211> LENGTH: 3
<212> TYPE: PRT
<213> ORGANISM: Artificial Sequence
<220> FEATURE:
<223> OTHER INFORMATION: synthetic

<400> SEQUENCE: 526

Ala Ala Ser
1

<210> SEQ ID NO 527
<211> LENGTH: 30
<212> TYPE: DNA
<213> ORGANISM: Artificial Sequence
<220> FEATURE:
<223> OTHER INFORMATION: synthetic

<400> SEQUENCE: 527
caacagagtt acagtacccc tccgatcacc                                       30

<210> SEQ ID NO 528
<211> LENGTH: 10
<212> TYPE: PRT
<213> ORGANISM: Artificial Sequence
<220> FEATURE:
<223> OTHER INFORMATION: synthetic

<400> SEQUENCE: 528

Gln Gln Ser Tyr Ser Thr Pro Pro Ile Thr
1               5                   10

<210> SEQ ID NO 529
<211> LENGTH: 324
<212> TYPE: DNA
<213> ORGANISM: Artificial Sequence
<220> FEATURE:
<223> OTHER INFORMATION: synthetic

<400> SEQUENCE: 529
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccttg gacgttcggc     300
caagggacca aggtggaaat caaa                                            324

<210> SEQ ID NO 530
<211> LENGTH: 108
<212> TYPE: PRT
<213> ORGANISM: Artificial Sequence
<220> FEATURE:
<223> OTHER INFORMATION: synthetic

<400> SEQUENCE: 530

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys
            100                 105
```

<210> SEQ ID NO 531
<211> LENGTH: 21
<212> TYPE: DNA
<213> ORGANISM: Artificial Sequence
<220> FEATURE:
<223> OTHER INFORMATION: synthetic

<400> SEQUENCE: 531
cagagtgtta gcagcagcta c         21

<210> SEQ ID NO 532
<211> LENGTH: 7
<212> TYPE: PRT
<213> ORGANISM: Artificial Sequence
<220> FEATURE:
<223> OTHER INFORMATION: synthetic

<400> SEQUENCE: 532

```
Gln Ser Val Ser Ser Ser Tyr
1               5
```

<210> SEQ ID NO 533
<211> LENGTH: 9
<212> TYPE: DNA
<213> ORGANISM: Artificial Sequence
<220> FEATURE:
<223> OTHER INFORMATION: synthetic

<400> SEQUENCE: 533 ggtgcatcc         9

<210> SEQ ID NO 534
<211> LENGTH: 3
<212> TYPE: PRT
<213> ORGANISM: Artificial Sequence
<220> FEATURE:
<223> OTHER INFORMATION: synthetic

<400> SEQUENCE: 534

```
Gly Ala Ser
1
```

<210> SEQ ID NO 535
<211> LENGTH: 27
<212> TYPE: DNA
<213> ORGANISM: Artificial Sequence
<220> FEATURE:
<223> OTHER INFORMATION: synthetic

<400> SEQUENCE: 535
cagcagtatg gtagctcacc ttggacg         27

<210> SEQ ID NO 536
<211> LENGTH: 9
<212> TYPE: PRT

<210> SEQ ID NO 537
<211> LENGTH: 357
<212> TYPE: DNA
<213> ORGANISM: Artificial Sequence
<220> FEATURE:
<223> OTHER INFORMATION: synthetic

<400> SEQUENCE: 537

```
caggtgcagc tacagcagtg gggcgcagga ctgttgaagc cttcggagac cctgtccctc      60
acctgcgctg tctatggtgg gtccttcagt ggttactact ggaactggat ccgccagccc     120
ccagggaagg gctggagtg gttggggaa atcagtcata gaggaagcac caactacaac      180
ccgtccctca agagtcgagt caccatatca ctggacacgt ccaagaacca gttctccctg     240
aagctgacct ctgtgaccgc cgcggacacg gctgtgtatt actgttcgag agacgaggaa     300
ctggaattcc gtttctttga ctactggggc cagggaaccc tggtcaccgt ctcctca        357
```

<210> SEQ ID NO 538
<211> LENGTH: 119
<212> TYPE: PRT
<213> ORGANISM: Artificial Sequence
<220> FEATURE:
<223> OTHER INFORMATION: synthetic

<400> SEQUENCE: 538

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Val
        35                  40                  45

Gly Glu Ile Ser His Arg Gly Ser Thr Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Lys Leu Thr Ser Val Thr Ala Ala Asp Thr Ala Val Tyr Tyr Cys Ser
                85                  90                  95

Arg Asp Glu Glu Leu Glu Phe Arg Phe Phe Asp Tyr Trp Gly Gln Gly
            100                 105                 110

Thr Leu Val Thr Val Ser Ser
        115

<210> SEQ ID NO 539
<211> LENGTH: 24
<212> TYPE: DNA
<213> ORGANISM: Artificial Sequence
<220> FEATURE:
<223> OTHER INFORMATION: synthetic

<400> SEQUENCE: 539
ggtgggtcct tcagtggtta ctac                                             24

<210> SEQ ID NO 540

```
<211> LENGTH: 8
<212> TYPE: PRT
<213> ORGANISM: Artificial Sequence
<220> FEATURE:
<223> OTHER INFORMATION: synthetic

<400> SEQUENCE: 540

Gly Gly Ser Phe Ser Gly Tyr Tyr
1               5

<210> SEQ ID NO 541
<211> LENGTH: 21
<212> TYPE: DNA
<213> ORGANISM: Artificial Sequence
<220> FEATURE:
<223> OTHER INFORMATION: synthetic

<400> SEQUENCE: 541
atcagtcata gaggaagcac c                                              21

<210> SEQ ID NO 542
<211> LENGTH: 7
<212> TYPE: PRT
<213> ORGANISM: Artificial Sequence
<220> FEATURE:
<223> OTHER INFORMATION: synthetic

<400> SEQUENCE: 542

Ile Ser His Arg Gly Ser Thr
1               5

<210> SEQ ID NO 543
<211> LENGTH: 39
<212> TYPE: DNA
<213> ORGANISM: Artificial Sequence
<220> FEATURE:
<223> OTHER INFORMATION: synthetic

<400> SEQUENCE: 543
tcgagagacg aggaactgga attccgtttc tttgactac                           39

<210> SEQ ID NO 544
<211> LENGTH: 13
<212> TYPE: PRT
<213> ORGANISM: Artificial Sequence
<220> FEATURE:
<223> OTHER INFORMATION: synthetic

<400> SEQUENCE: 544

Ser Arg Asp Glu Glu Leu Glu Phe Arg Phe Phe Asp Tyr
1               5                   10

<210> SEQ ID NO 545
<211> LENGTH: 321
<212> TYPE: DNA
<213> ORGANISM: Artificial Sequence
<220> FEATURE:
<223> OTHER INFORMATION: synthetic

<400> SEQUENCE: 545
gaaattgtgt tgacacagtc tccagccacc ctgtctttgt ctccagggga aagagccacc    60
ctctcctgca gggccagtca gagtgttagc agctatttag cctggtacca acaaaaacct   120
ggccaggctc ccaggctcct cgtctatggt gcatccaaca gggccactgg catcccagcc   180
aggttcagtg gcagtgggtc tgggacagac ttcactctca ccatcagcag cctagagcct   240
```

```
gaagattttg catttattta ctgtcagcag cgtagcaact ggccgctcac tttcggcgga    300
gggaccaagg tggagatcaa a                                              321
```

<210> SEQ ID NO 546
<211> LENGTH: 107
<212> TYPE: PRT
<213> ORGANISM: Artificial Sequence
<220> FEATURE:
<223> OTHER INFORMATION: synthetic

<400> SEQUENCE: 546

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Val
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 547
<211> LENGTH: 18
<212> TYPE: DNA
<213> ORGANISM: Artificial Sequence
<220> FEATURE:
<223> OTHER INFORMATION: synthetic

<400> SEQUENCE: 547

```
cagagtgtta gcagctat                                                   18
```

<210> SEQ ID NO 548
<211> LENGTH: 6
<212> TYPE: PRT
<213> ORGANISM: Artificial Sequence
<220> FEATURE:
<223> OTHER INFORMATION: synthetic

<400> SEQUENCE: 548

```
Gln Ser Val Ser Ser Tyr
1               5
```

<210> SEQ ID NO 549
<211> LENGTH: 9
<212> TYPE: DNA
<213> ORGANISM: Artificial Sequence
<220> FEATURE:
<223> OTHER INFORMATION: synthetic

<400> SEQUENCE: 549

```
ggtgcatcc                                                              9
```

<210> SEQ ID NO 550
<211> LENGTH: 3
<212> TYPE: PRT
<213> ORGANISM: Artificial Sequence
<220> FEATURE:
<223> OTHER INFORMATION: synthetic

<400> SEQUENCE: 550

Gly Ala Ser
1

<210> SEQ ID NO 551
<211> LENGTH: 27
<212> TYPE: DNA
<213> ORGANISM: Artificial Sequence
<220> FEATURE:
<223> OTHER INFORMATION: synthetic

<400> SEQUENCE: 551
cagcagcgta gcaactggcc gctcact    27

<210> SEQ ID NO 552
<211> LENGTH: 9
<212> TYPE: PRT
<213> ORGANISM: Artificial Sequence
<220> FEATURE:
<223> OTHER INFORMATION: synthetic

<400> SEQUENCE: 552

Gln Gln Arg Ser Asn Trp Pro Leu Thr
1               5

<210> SEQ ID NO 553
<211> LENGTH: 372
<212> TYPE: DNA
<213> ORGANISM: Artificial Sequence
<220> FEATURE:
<223> OTHER INFORMATION: synthetic

<400> SEQUENCE: 553
gaggtgcagc tggtggagtc tgggggaggc ttggtacagc ctggggggtc cctgagactc    60
tcctgtgtag cctctggatt cacctttagc ctctatgcca tgacctgggt ccgccaggtt   120
ccagggaagg ggctggaatg ggtctcaact attagtggta gtggtggtgg cacatactac   180
acagactccg ttaagggccg gttcaccatc tccagagaca attccaagaa cacactgtat   240
ctgcaaatga acagcctgag agccgacgac acggccgttt tttactgtac gaaagagagt   300
acaactggaa cttactccta cttctacggt atggacgtct ggggccaagg gaccacggtc   360
accgtctcct ca   372

<210> SEQ ID NO 554
<211> LENGTH: 124
<212> TYPE: PRT
<213> ORGANISM: Artificial Sequence
<220> FEATURE:
<223> OTHER INFORMATION: synthetic

<400> SEQUENCE: 554

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Leu Tyr
            20                  25                  30

Ala Met Thr Trp Val Arg Gln Val Pro Gly Lys Gly Leu Glu Trp Val
        35                  40                  45

Ser Thr Ile Ser Gly Ser Gly Gly Gly Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Asp Asp Thr Ala Val Phe Tyr Cys
                85                  90                  95

Thr Lys Glu Ser Thr Thr Gly Thr Tyr Ser Tyr Phe Tyr Gly Met Asp
            100                 105                 110

Val Trp Gly Gln Gly Thr Thr Val Thr Val Ser Ser
        115                 120
```

<210> SEQ ID NO 555
<211> LENGTH: 24
<212> TYPE: DNA
<213> ORGANISM: Artificial Sequence
<220> FEATURE:
<223> OTHER INFORMATION: synthetic

<400> SEQUENCE: 555
ggattcacct ttagcctcta tgcc                                          24

<210> SEQ ID NO 556
<211> LENGTH: 8
<212> TYPE: PRT
<213> ORGANISM: Artificial Sequence
<220> FEATURE:
<223> OTHER INFORMATION: synthetic

<400> SEQUENCE: 556

```
Gly Phe Thr Phe Ser Leu Tyr Ala
1               5
```

<210> SEQ ID NO 557
<211> LENGTH: 24
<212> TYPE: DNA
<213> ORGANISM: Artificial Sequence
<220> FEATURE:
<223> OTHER INFORMATION: synthetic

<400> SEQUENCE: 557
attagtggta gtggtggtgg caca                                          24

<210> SEQ ID NO 558
<211> LENGTH: 8
<212> TYPE: PRT
<213> ORGANISM: Artificial Sequence
<220> FEATURE:
<223> OTHER INFORMATION: synthetic

<400> SEQUENCE: 558

```
Ile Ser Gly Ser Gly Gly Gly Thr
1               5
```

<210> SEQ ID NO 559
<211> LENGTH: 51
<212> TYPE: DNA
<213> ORGANISM: Artificial Sequence
<220> FEATURE:
<223> OTHER INFORMATION: synthetic

<400> SEQUENCE: 559
acgaaagaga gtacaactgg aacttactcc tacttctacg gtatggacgt c            51

<210> SEQ ID NO 560
<211> LENGTH: 17
<212> TYPE: PRT
<213> ORGANISM: Artificial Sequence
<220> FEATURE:
<223> OTHER INFORMATION: synthetic

<400> SEQUENCE: 560

Thr Lys Glu Ser Thr Thr Gly Thr Tyr Ser Tyr Phe Tyr Gly Met Asp
1               5                   10                  15
Val

<210> SEQ ID NO 561
<211> LENGTH: 321
<212> TYPE: DNA
<213> ORGANISM: Artificial Sequence
<220> FEATURE:
<223> OTHER INFORMATION: synthetic

<400> SEQUENCE: 561

```
gacatccaga tgacccagtc tccatcctcc ctgtctgcat ctgtaggaga cagagtcacc    60
atcacttgcc gggcaagtca gaccattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccctcagcgg tctccaacct   240
gaagattttg caacttacta ctgtcaacag agttacagta ccccgctcac tttcggcgga   300
gggaccaagg tggagatcaa a                                             321
```

<210> SEQ ID NO 562
<211> LENGTH: 107
<212> TYPE: PRT
<213> ORGANISM: Artificial Sequence
<220> FEATURE:
<223> OTHER INFORMATION: synthetic

<400> SEQUENCE: 562

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Leu Ser Gly Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 563
<211> LENGTH: 18
<212> TYPE: DNA
<213> ORGANISM: Artificial Sequence
<220> FEATURE:
<223> OTHER INFORMATION: synthetic

<400> SEQUENCE: 563

```
cagaccatta gcagctat                                                  18
```

<210> SEQ ID NO 564
<211> LENGTH: 6
<212> TYPE: PRT
<213> ORGANISM: Artificial Sequence
<220> FEATURE:

```
<223> OTHER INFORMATION: synthetic

<400> SEQUENCE: 564

Gln Thr Ile Ser Ser Tyr
1               5

<210> SEQ ID NO 565
<211> LENGTH: 9
<212> TYPE: DNA
<213> ORGANISM: Artificial Sequence
<220> FEATURE:
<223> OTHER INFORMATION: synthetic

<400> SEQUENCE: 565 gctgcatcc                                                                  9

<210> SEQ ID NO 566
<211> LENGTH: 3
<212> TYPE: PRT
<213> ORGANISM: Artificial Sequence
<220> FEATURE:
<223> OTHER INFORMATION: synthetic

<400> SEQUENCE: 566

Ala Ala Ser
1

<210> SEQ ID NO 567
<211> LENGTH: 27
<212> TYPE: DNA
<213> ORGANISM: Artificial Sequence
<220> FEATURE:
<223> OTHER INFORMATION: synthetic

<400> SEQUENCE: 567
caacagagtt acagtacccc gctcact                                             27

<210> SEQ ID NO 568
<211> LENGTH: 9
<212> TYPE: PRT
<213> ORGANISM: Artificial Sequence
<220> FEATURE:
<223> OTHER INFORMATION: synthetic

<400> SEQUENCE: 568

Gln Gln Ser Tyr Ser Thr Pro Leu Thr
1               5

<210> SEQ ID NO 569
<211> LENGTH: 327
<212> TYPE: PRT
<213> ORGANISM: Artificial Sequence
<220> FEATURE:
<223> OTHER INFORMATION: synthetic

<400> SEQUENCE: 569

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 570
<211> LENGTH: 326
<212> TYPE: PRT
<213> ORGANISM: Artificial Sequence
<220> FEATURE:
<223> OTHER INFORMATION: synthetic

<400> SEQUENCE: 570

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
            85                  90                  95

```
Arg Val Glu Ser Lys Tyr Gly Pro Pro Cys Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
                195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
                275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 571
<211> LENGTH: 326
<212> TYPE: PRT
<213> ORGANISM: Artificial Sequence
<220> FEATURE:
<223> OTHER INFORMATION: synthetic

<400> SEQUENCE: 571

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125
```

```
Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Pro Gly Lys
                325

<210> SEQ ID NO 572
<211> LENGTH: 326
<212> TYPE: PRT
<213> ORGANISM: Artificial Sequence
<220> FEATURE:
<223> OTHER INFORMATION: synthetic

<400> SEQUENCE: 572

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Gly Gly Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser Gln Glu Asp Pro Glu Val Gln Phe Asn Trp Tyr Val Asp Gly
145                 150                 155                 160
```

```
Val Glu Val His Asn Ala Lys Thr Lys Pro Arg Glu Glu Gln Phe Asn
            165                 170                 175

Ser Thr Tyr Arg Val Val Ser Val Leu Thr Val Leu His Gln Asp Trp
        180                 185                 190

Leu Asn Gly Lys Glu Tyr Lys Cys Lys Val Ser Asn Lys Gly Leu Pro
    195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 573
<211> LENGTH: 326
<212> TYPE: PRT
<213> ORGANISM: Artificial Sequence
<220> FEATURE:
<223> OTHER INFORMATION: synthetic

<400> SEQUENCE: 573

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190
```

```
Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Pro Gly Lys
                325

<210> SEQ ID NO 574
<211> LENGTH: 450
<212> TYPE: PRT
<213> ORGANISM: Artificial Sequence
<220> FEATURE:
<223> OTHER INFORMATION: aa 1-478: Human Lag3 (aa 29 through 450 of
      NP_002277.4) aa 451-478: myc-myc-hexahistidine tag

<400> SEQUENCE: 574

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220
```

```
Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
            245                 250                 255

Pro Ala Gly Val Gly Thr Arg Ser Phe Leu Thr Ala Lys Trp Thr Pro
        260                 265                 270

Pro Gly Gly Gly Pro Asp Leu Leu Val Thr Gly Asp Asn Gly Asp Phe
    275                 280                 285

Thr Leu Arg Leu Glu Asp Val Ser Gln Ala Gln Ala Gly Thr Tyr Thr
290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
            325                 330                 335

Gly Lys Leu Leu Cys Glu Val Thr Pro Val Ser Gly Gln Glu Arg Phe
        340                 345                 350

Val Trp Ser Ser Leu Asp Thr Pro Ser Gln Arg Ser Phe Ser Gly Pro
    355                 360                 365

Trp Leu Glu Ala Gln Glu Ala Gln Leu Leu Ser Gln Pro Trp Gln Cys
370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
            405                 410                 415

Leu Pro Ala Gly His Leu Glu Gln Lys Leu Ile Ser Glu Glu Asp Leu
        420                 425                 430

Gly Gly Glu Gln Lys Leu Ile Ser Glu Glu Asp Leu His His His His
    435                 440                 445

His His
    450

<210> SEQ ID NO 575
<211> LENGTH: 655
<212> TYPE: PRT
<213> ORGANISM: Artificial Sequence
<220> FEATURE:
<223> OTHER INFORMATION: aa 1-683: Human Lag3 (aa 29 through 450 of
      NP_002277.4) aa 451-683: mIgG2aFc

<400> SEQUENCE: 575

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
```

```
            115                 120                 125
Ala Leu Ser Cys Arg Leu Arg Leu Arg Leu Gly Gln Ala Ser Met Thr
130                 135                 140
Ala Ser Pro Pro Gly Ser Leu Arg Ala Ser Asp Trp Val Ile Leu Asn
145                 150                 155                 160
Cys Ser Phe Ser Arg Pro Asp Arg Pro Ala Ser Val His Trp Phe Arg
                165                 170                 175
Asn Arg Gly Gln Gly Arg Val Pro Val Arg Glu Ser Pro His His His
                180                 185                 190
Leu Ala Glu Ser Phe Leu Phe Leu Pro Gln Val Ser Pro Met Asp Ser
                195                 200                 205
Gly Pro Trp Gly Cys Ile Leu Thr Tyr Arg Asp Gly Phe Asn Val Ser
                210                 215                 220
Ile Met Tyr Asn Leu Thr Val Leu Gly Leu Glu Pro Pro Thr Pro Leu
225                 230                 235                 240
Thr Val Tyr Ala Gly Ala Gly Ser Arg Val Gly Leu Pro Cys Arg Leu
                245                 250                 255
Pro Ala Gly Val Gly Thr Arg Ser Phe Leu Thr Ala Lys Trp Thr Pro
                260                 265                 270
Pro Gly Gly Gly Pro Asp Leu Leu Val Thr Gly Asp Asn Gly Asp Phe
                275                 280                 285
Thr Leu Arg Leu Glu Asp Val Ser Gln Ala Gln Ala Gly Thr Tyr Thr
                290                 295                 300
Cys His Ile His Leu Gln Glu Gln Gln Leu Asn Ala Thr Val Thr Leu
305                 310                 315                 320
Ala Ile Ile Thr Val Thr Pro Lys Ser Phe Gly Ser Pro Gly Ser Leu
                325                 330                 335
Gly Lys Leu Leu Cys Glu Val Thr Pro Val Ser Gly Gln Glu Arg Phe
                340                 345                 350
Val Trp Ser Ser Leu Asp Thr Pro Ser Gln Arg Ser Phe Ser Gly Pro
                355                 360                 365
Trp Leu Glu Ala Gln Glu Ala Gln Leu Leu Ser Gln Pro Trp Gln Cys
                370                 375                 380
Gln Leu Tyr Gln Gly Glu Arg Leu Leu Gly Ala Ala Val Tyr Phe Thr
385                 390                 395                 400
Glu Leu Ser Ser Pro Gly Ala Gln Arg Ser Gly Arg Ala Pro Gly Ala
                405                 410                 415
Leu Pro Ala Gly His Leu Glu Pro Arg Gly Pro Thr Ile Lys Pro Cys
                420                 425                 430
Pro Pro Cys Lys Cys Pro Ala Pro Asn Leu Leu Gly Gly Pro Ser Val
                435                 440                 445
Phe Ile Phe Pro Pro Lys Ile Lys Asp Val Leu Met Ile Ser Leu Ser
                450                 455                 460
Pro Ile Val Thr Cys Val Val Asp Val Ser Glu Asp Asp Pro Asp
465                 470                 475                 480
Val Gln Ile Ser Trp Phe Val Asn Asn Val Glu Val His Thr Ala Gln
                485                 490                 495
Thr Gln Thr His Arg Glu Asp Tyr Asn Ser Thr Leu Arg Val Val Ser
                500                 505                 510
Ala Leu Pro Ile Gln His Gln Asp Trp Met Ser Gly Lys Glu Phe Lys
                515                 520                 525
Cys Lys Val Asn Asn Lys Asp Leu Pro Ala Pro Ile Glu Arg Thr Ile
                530                 535                 540
```

Ser Lys Pro Lys Gly Ser Val Arg Ala Pro Gln Val Tyr Val Leu Pro
545                 550                 555                 560

Pro Pro Glu Glu Glu Met Thr Lys Lys Gln Val Thr Leu Thr Cys Met
                565                 570                 575

Val Thr Asp Phe Met Pro Glu Asp Ile Tyr Val Glu Trp Thr Asn Asn
            580                 585                 590

Gly Lys Thr Glu Leu Asn Tyr Lys Asn Thr Glu Pro Val Leu Asp Ser
        595                 600                 605

Asp Gly Ser Tyr Phe Met Tyr Ser Lys Leu Arg Val Glu Lys Lys Asn
    610                 615                 620

Trp Val Glu Arg Asn Ser Tyr Ser Cys Ser Val Val His Glu Gly Leu
625                 630                 635                 640

His Asn His His Thr Thr Lys Ser Phe Ser Arg Thr Pro Gly Lys
                645                 650                 655

<210> SEQ ID NO 576
<211> LENGTH: 516
<212> TYPE: PRT
<213> ORGANISM: Artificial Sequence
<220> FEATURE:
<223> OTHER INFORMATION: aa 1-533 (aa 18 through 533 of cynomolgus
    XP_005570011.1 modified to replace amino acid at position 74 with
    a P based on Rhesus macaque XP_001108923.1

<400> SEQUENCE: 576

Ala Pro Val Lys Pro Pro Gln Pro Gly Ala Glu Ile Ser Val Val Trp
1               5                   10                  15

Ala Gln Glu Gly Ala Pro Ala Gln Leu Pro Cys Ser Pro Thr Ile Pro
            20                  25                  30

Leu Gln Asp Leu Ser Leu Leu Arg Arg Ala Gly Val Thr Trp Gln His
        35                  40                  45

Gln Pro Asp Ser Gly Pro Pro Ala Pro Ala Pro Gly His Pro Pro Val
    50                  55                  60

Pro Gly His Arg Pro Ala Ala Pro Tyr Ser Trp Gly Pro Arg Pro Arg
65                  70                  75                  80

Arg Tyr Thr Val Leu Ser Val Gly Pro Gly Gly Leu Arg Ser Gly Arg
                85                  90                  95

Leu Pro Leu Gln Pro Arg Val Gln Leu Asp Glu Arg Gly Arg Gln Arg
            100                 105                 110

Gly Asp Phe Ser Leu Trp Leu Arg Pro Ala Arg Arg Ala Asp Ala Gly
        115                 120                 125

Glu Tyr Arg Ala Thr Val His Leu Arg Asp Arg Ala Leu Ser Cys Arg
    130                 135                 140

Leu Arg Leu Arg Val Gly Gln Ala Ser Met Thr Ala Ser Pro Pro Gly
145                 150                 155                 160

Ser Leu Arg Thr Ser Asp Trp Val Ile Leu Asn Cys Ser Phe Ser Arg
                165                 170                 175

Pro Asp Arg Pro Ala Ser Val His Trp Phe Arg Ser Arg Gly Gln Gly
            180                 185                 190

Arg Val Pro Val Gln Gly Ser Pro His His Leu Ala Glu Ser Phe
    195                 200                 205

Leu Phe Leu Pro His Val Gly Pro Met Asp Ser Gly Leu Trp Gly Cys
    210                 215                 220

Ile Leu Thr Tyr Arg Asp Gly Phe Asn Val Ser Ile Met Tyr Asn Leu
225                 230                 235                 240

-continued

Thr Val Leu Gly Leu Glu Pro Ala Thr Pro Leu Thr Val Tyr Ala Gly
                245                 250                 255

Ala Gly Ser Arg Val Glu Leu Pro Cys Arg Leu Pro Pro Ala Val Gly
            260                 265                 270

Thr Gln Ser Phe Leu Thr Ala Lys Trp Ala Pro Pro Gly Gly Gly Pro
        275                 280                 285

Asp Leu Leu Val Ala Gly Asp Asn Gly Asp Phe Thr Leu Arg Leu Glu
    290                 295                 300

Asp Val Ser Gln Ala Gln Ala Gly Thr Tyr Ile Cys His Ile Arg Leu
305                 310                 315                 320

Gln Gly Gln Gln Leu Asn Ala Thr Val Thr Leu Ala Ile Ile Thr Val
                325                 330                 335

Thr Pro Lys Ser Phe Gly Ser Pro Gly Ser Leu Gly Lys Leu Leu Cys
            340                 345                 350

Glu Val Thr Pro Ala Ser Gly Gln Glu His Phe Val Trp Ser Pro Leu
        355                 360                 365

Asn Thr Pro Ser Gln Arg Ser Phe Ser Gly Pro Trp Leu Glu Ala Gln
    370                 375                 380

Glu Ala Gln Leu Leu Ser Gln Pro Trp Gln Cys Gln Leu His Gln Gly
385                 390                 395                 400

Glu Arg Leu Leu Gly Ala Ala Val Tyr Phe Thr Glu Leu Ser Ser Pro
                405                 410                 415

Gly Ala Gln Arg Ser Gly Arg Ala Pro Gly Ala Leu Arg Ala Gly His
            420                 425                 430

Leu Pro Leu Phe Leu Ile Leu Gly Val Leu Phe Leu Leu Leu Leu Val
        435                 440                 445

Thr Gly Ala Phe Gly Phe His Leu Trp Arg Arg Gln Trp Arg Pro Arg
    450                 455                 460

Arg Phe Ser Ala Leu Glu Gln Gly Ile His Pro Pro Gln Ala Gln Ser
465                 470                 475                 480

Lys Ile Glu Glu Leu Glu Gln Glu Pro Glu Leu Glu Pro Glu Pro Glu
                485                 490                 495

Leu Glu Arg Glu Leu Gly Pro Glu Pro Glu Pro Gly Pro Glu Pro Glu
            500                 505                 510

Pro Glu Gln Leu
        515

<210> SEQ ID NO 577
<211> LENGTH: 449
<212> TYPE: PRT
<213> ORGANISM: Artificial Sequence
<220> FEATURE:
<223> OTHER INFORMATION: synthetic

<400> SEQUENCE: 577

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
            85                  90                  95

Ala Ser Val Ala Thr Ser Gly Asp Phe Asp Tyr Tyr Gly Met Asp Val
           100                 105                 110

Trp Gly Gln Gly Thr Thr Val Thr Val Ser Ser Ala Ser Thr Lys Gly
           115                 120                 125

Pro Ser Val Phe Pro Leu Ala Pro Cys Ser Arg Ser Thr Ser Glu Ser
           130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
           180                 185                 190

Thr Val Pro Ser Ser Ser Leu Gly Thr Lys Thr Tyr Thr Cys Asn Val
           195                 200                 205

Asp His Lys Pro Ser Asn Thr Lys Val Asp Lys Arg Val Glu Ser Lys
           210                 215                 220

Tyr Gly Pro Pro Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
           260                 265                 270

Pro Glu Val Gln Phe Asn Trp Tyr Val Asp Gly Val Glu Val His Asn
           275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
           340                 345                 350

Leu Pro Pro Ser Gln Glu Glu Met Thr Lys Asn Gln Val Ser Leu Thr
           355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
           420                 425                 430

Ala Leu His Asn His Tyr Thr Gln Lys Ser Leu Ser Leu Ser Leu Gly
           435                 440                 445

Lys

<210> SEQ ID NO 578
<211> LENGTH: 214
<212> TYPE: PRT
<213> ORGANISM: Artificial Sequence
<220> FEATURE:
<223> OTHER INFORMATION: synthetic -continued

<400> SEQUENCE: 578

Glu Ile Val Leu Thr Gln Ser Pro Ala Thr Leu Ser Leu Ser Pro Gly
1               5                   10                  15

Glu Arg Thr Thr Leu Ser Cys Arg Ala Ser Gln Arg Ile Ser Thr Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Gly Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 579
<211> LENGTH: 450
<212> TYPE: PRT
<213> ORGANISM: Artificial Sequence
<220> FEATURE:
<223> OTHER INFORMATION: synthetic

<400> SEQUENCE: 579

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Ser Val Ala Thr Ser Gly Asp Phe Asp Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser

```
                 130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
                210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
450

<210> SEQ ID NO 580
<211> LENGTH: 445
<212> TYPE: PRT
<213> ORGANISM: Artificial Sequence
<220> FEATURE:
<223> OTHER INFORMATION: synthetic

<400> SEQUENCE: 580

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Asn Trp Ile Arg Gln Pro Pro Gly Lys Gly Leu Glu Trp Val
```

```
              35                  40                  45
Gly Glu Ile Ser His Arg Gly Ser Thr Asn Tyr Asn Pro Ser Leu Lys
 50                  55                  60

Ser Arg Val Thr Ile Ser Leu Asp Thr Ser Lys Asn Gln Phe Ser Leu
 65                  70                  75                  80

Lys Leu Thr Ser Val Thr Ala Ala Asp Thr Ala Val Tyr Tyr Cys Ser
                 85                  90                  95

Arg Asp Glu Glu Leu Glu Phe Arg Phe Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 581
```

<211> LENGTH: 214
<212> TYPE: PRT
<213> ORGANISM: Artificial Sequence
<220> FEATURE:
<223> OTHER INFORMATION: synthetic

<400> SEQUENCE: 581

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Val
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 582
<211> LENGTH: 525
<212> TYPE: PRT
<213> ORGANISM: Artificial Sequence
<220> FEATURE:
<223> OTHER INFORMATION: synthetic

<400> SEQUENCE: 582

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly

```
               100                 105                    110
Arg Leu Pro Leu Gln Pro Arg Val Gln Leu Asp Glu Arg Gly Arg Gln
            115                 120                 125
Arg Gly Asp Phe Ser Leu Trp Leu Arg Pro Ala Arg Ala Asp Ala
            130                 135                 140
Gly Glu Tyr Arg Ala Ala Val His Leu Arg Asp Arg Ala Leu Ser Cys
145                 150                 155                 160
Arg Leu Arg Leu Arg Leu Gly Gln Ala Ser Met Thr Ala Ser Pro Pro
                165                 170                 175
Gly Ser Leu Arg Ala Ser Asp Trp Val Ile Leu Asn Cys Ser Phe Ser
            180                 185                 190
Arg Pro Asp Arg Pro Ala Ser Val His Trp Phe Arg Asn Arg Gly Gln
            195                 200                 205
Gly Arg Val Pro Val Arg Glu Ser Pro His His Leu Ala Glu Ser
210                 215                 220
Phe Leu Phe Leu Pro Gln Val Ser Pro Met Asp Ser Gly Pro Trp Gly
225                 230                 235                 240
Cys Ile Leu Thr Tyr Arg Asp Gly Phe Asn Val Ser Ile Met Tyr Asn
                245                 250                 255
Leu Thr Val Leu Gly Leu Glu Pro Pro Thr Pro Leu Thr Val Tyr Ala
                260                 265                 270
Gly Ala Gly Ser Arg Val Gly Leu Pro Cys Arg Leu Pro Ala Gly Val
            275                 280                 285
Gly Thr Arg Ser Phe Leu Thr Ala Lys Trp Thr Pro Pro Gly Gly Gly
            290                 295                 300
Pro Asp Leu Leu Val Thr Gly Asp Asn Gly Asp Phe Thr Leu Arg Leu
305                 310                 315                 320
Glu Asp Val Ser Gln Ala Gln Ala Gly Thr Tyr Thr Cys His Ile His
                325                 330                 335
Leu Gln Glu Gln Gln Leu Asn Ala Thr Val Thr Leu Ala Ile Ile Thr
                340                 345                 350
Val Thr Pro Lys Ser Phe Gly Ser Pro Gly Ser Leu Gly Lys Leu Leu
            355                 360                 365
Cys Glu Val Thr Pro Val Ser Gly Gln Glu Arg Phe Val Trp Ser Ser
370                 375                 380
Leu Asp Thr Pro Ser Gln Arg Ser Phe Ser Gly Pro Trp Leu Glu Ala
385                 390                 395                 400
Gln Glu Ala Gln Leu Leu Ser Gln Pro Trp Gln Cys Gln Leu Tyr Gln
                405                 410                 415
Gly Glu Arg Leu Leu Gly Ala Ala Val Tyr Phe Thr Glu Leu Ser Ser
            420                 425                 430
Pro Gly Ala Gln Arg Ser Gly Arg Ala Pro Gly Ala Leu Pro Ala Gly
            435                 440                 445
His Leu Leu Leu Phe Leu Ile Leu Gly Val Leu Ser Leu Leu Leu Leu
            450                 455                 460
Val Thr Gly Ala Phe Gly Phe His Leu Trp Arg Arg Gln Trp Arg Pro
465                 470                 475                 480
Arg Arg Phe Ser Ala Leu Glu Gln Gly Ile His Pro Pro Gln Ala Gln
                485                 490                 495
Ser Lys Ile Glu Glu Leu Glu Gln Glu Pro Glu Pro Glu Pro
                500                 505                 510
Glu Pro Glu Pro Glu Pro Glu Pro Glu Pro Glu Gln Leu
            515                 520                 525
```

<210> SEQ ID NO 583
<211> LENGTH: 15
<212> TYPE: PRT
<213> ORGANISM: Artificial Sequence
<220> FEATURE:
<223> OTHER INFORMATION: synthetic

<400> SEQUENCE: 583

Glu Asn Pro Val Val His Phe Phe Lys Asn Ile Val Thr Pro Arg
1               5                   10                  15

<210> SEQ ID NO 584
<211> LENGTH: 17
<212> TYPE: DNA
<213> ORGANISM: Artificial Sequence
<220> FEATURE:
<223> OTHER INFORMATION: synthetic

<400> SEQUENCE: 584
agcagctctg ccctcat                                                    17

<210> SEQ ID NO 585
<211> LENGTH: 22
<212> TYPE: DNA
<213> ORGANISM: Artificial Sequence
<220> FEATURE:
<223> OTHER INFORMATION: synthetic

<400> SEQUENCE: 585
gctctggctg gtcttcagta tg                                              22

<210> SEQ ID NO 586
<211> LENGTH: 22
<212> TYPE: DNA
<213> ORGANISM: Artificial Sequence
<220> FEATURE:
<223> OTHER INFORMATION: synthetic

<400> SEQUENCE: 586
ttgccgtatg gttggtttga ac                                              22

<210> SEQ ID NO 587
<211> LENGTH: 665
<212> TYPE: PRT
<213> ORGANISM: Artificial Sequence
<220> FEATURE:
<223> OTHER INFORMATION: hLAG3.Fc

<400> SEQUENCE: 587

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
        50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu

```
                100                 105                 110
Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
        130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
        210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
        290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
        370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Ile Glu Gly Arg
            420                 425                 430

Met Asp Pro Lys Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
        450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525
```

```
Gln Asp Trp Leu Asn Gly Lys Glu Tyr Lys Cys Lys Val Ser Asn Lys
        530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
        595                 600                 605

Tyr Lys Thr Thr Pro Pro Val Leu Asp Ser Asp Gly Ser Phe Phe Leu
    610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Lys
            660                 665

<210> SEQ ID NO 588
<211> LENGTH: 422
<212> TYPE: PRT
<213> ORGANISM: Artificial Sequence
<220> FEATURE:
<223> OTHER INFORMATION: hLAG3 extracellular domain P18627

<400> SEQUENCE: 588

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220
```

```
Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu
            420

<210> SEQ ID NO 589
<211> LENGTH: 44
<212> TYPE: PRT
<213> ORGANISM: Artificial Sequence
<220> FEATURE:
<223> OTHER INFORMATION: hLAG3 epitope

<400> SEQUENCE: 589

Leu Arg Arg Ala Gly Val Thr Trp Gln His Gln Pro Asp Ser Gly Pro
1               5                   10                  15

Pro Ala Ala Ala Pro Gly His Pro Leu Ala Pro Gly Pro His Pro Ala
                20                  25                  30

Ala Pro Ser Ser Trp Gly Pro Arg Pro Arg Arg Tyr
            35                  40
```